(12) United States Patent
Rodriguez et al.

(10) Patent No.: US 7,348,310 B2
(45) Date of Patent: Mar. 25, 2008

(54) SYNTHETIC METHODS FOR APLIDINE AND NEW ANTITUMORAL DERIVATIVES, METHODS OF MAKING AND USING THEM

(75) Inventors: Ignacio Rodriguez, Madrid (ES); Concepción Polanco, Madrid (ES); Felix Cuevas, Tres Cantos (ES); Paloma Mendez, Madrid (ES); Carmen Cuevas, Madrid (ES); Pilar Gallego, Tres Cantos (ES); Simon Munt, Madrid (ES); Ignacio Manzanares, Madrid (ES)

(73) Assignee: Pharma Mar, S.A., Madrid (ES)

( * ) Notice: Subject to any disclaimer, the term of this patent is extended or adjusted under 35 U.S.C. 154(b) by 0 days.

(21) Appl. No.: 10/312,341

(22) PCT Filed: Jul. 2, 2001

(86) PCT No.: PCT/GB01/02901

§ 371 (c)(1),
(2), (4) Date: Jul. 28, 2003

(87) PCT Pub. No.: WO02/02596

PCT Pub. Date: Jan. 10, 2002

(65) Prior Publication Data

US 2004/0097413 A1    May 20, 2004

(30) Foreign Application Priority Data

Jun. 30, 2000  (GB) ................................. 0016148.9
Feb. 15, 2001  (GB) ................................. 0103750.6

(51) Int. Cl.
*C07K 11/00*  (2006.01)

(52) U.S. Cl. .................... 514/11; 530/323; 530/329; 530/331; 530/337

(58) Field of Classification Search ............. 530/323, 530/329, 331, 337; 514/11, 17, 18
See application file for complete search history.

(56) References Cited

U.S. PATENT DOCUMENTS

| | | | |
|---|---|---|---|
| 4,493,796 A | 1/1985 | Rinehart, Jr. ............... 530/317 |
| 4,670,262 A | 6/1987 | Battelli et al. .............. 424/649 |
| 5,294,603 A | 3/1994 | Rinehart ..................... 514/10 |
| 5,462,726 A | 10/1995 | Lodge ........................ 514/558 |
| 5,834,586 A | 11/1998 | Rinehart et al. ............ 530/322 |
| 5,883,135 A | 3/1999 | Gyory et al. ............... 514/724 |
| 6,030,943 A | 2/2000 | Crumb et al. .................. 514/9 |
| 6,034,058 A | 3/2000 | Rinehart et al. ............. 514/11 |
| 6,080,877 A | 6/2000 | Swindell et al. ............ 549/510 |
| 6,153,731 A | 11/2000 | Rinehart et al. ............ 530/345 |
| 6,156,724 A | 12/2000 | Rinehart et al. ............. 514/10 |
| 6,509,315 B1 * | 1/2003 | Joullie et al. ................ 514/10 |
| 6,610,699 B2 | 8/2003 | Cavazza et al. ............ 514/283 |
| 6,710,029 B1 | 3/2004 | Rinehart et al. .............. 514/9 |
| 6,890,904 B1 | 5/2005 | Wallner et al. | |
| 7,064,105 B2 * | 6/2006 | Joullie et al. ................ 514/10 |

FOREIGN PATENT DOCUMENTS

| | | |
|---|---|---|
| EP | 0 048 149 A1 | 3/1982 |
| EP | 0 393 883 | 10/1990 |
| ES | 2 102 322 | 7/1997 |
| WO | WO 91/04985 | 4/1991 |
| WO | WO 93/00362 | 1/1993 |
| WO | WO 98/17275 | 4/1998 |
| WO | WO 98/17302 | 4/1998 |
| WO | WO 99/42125 | 8/1999 |
| WO | WO 00/06134 | 2/2000 |
| WO | WO 00/71135 | 11/2000 |
| WO | WO 01/35974 | 5/2001 |
| WO | WO 01/76616 | 10/2001 |
| WO | WO 02/02596 | 1/2002 |

(Continued)

OTHER PUBLICATIONS

Mayer et al. Synthesis of New Didemnin B Analogs for Investigations of Structure/ Biological Activity Relationships. Journal of Organic Chemistry. 1994, vol. 59, No. 18, pp. 5192-5205.*

(Continued)

*Primary Examiner*—Jeffrey Edwin Russel
(74) *Attorney, Agent, or Firm*—Fish & Richardson P.C.

(57) ABSTRACT

The invention relates to aplidine derivatives of the general formula:

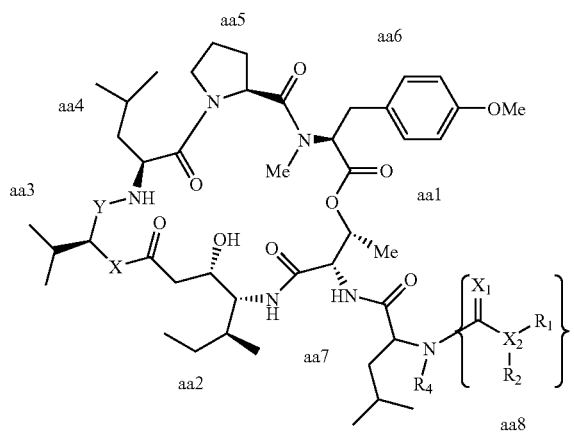

which are useful for the treatment of tumors.

41 Claims, No Drawings

FOREIGN PATENT DOCUMENTS

| WO | WO 02/30441 | 4/2002 |
|---|---|---|
| WO | WO 02/030441 | 4/2002 |
| WO | WO 03/033013 | 4/2003 |
| WO | WO 2004/080421 A2 | 9/2004 |

OTHER PUBLICATIONS

Ady-Vago, N. et al., "L-Carnitine as a Protector Against Aplidine Induced Skeletal Muscle Toxicity", *Proceedings of the American Association for Cancer Research*, vol. 42, pp. 545 (Mar. 2001).

Bergeron, Raymond J. et al., "Antineoplastic and Antiherpetic Activity of Spermidine Catecholamide Iron Chelators", *Biochemical and Biophysical Research Communications*, vol. 121, No. 3, pp. 848-854 (1994).

Broggini, M. et al., "Aplidine Blocks VEGF Secretion and VEGF/VEGF-RI Autocrine Loop in a Human Leukemic Cell Line", *11th NCI-EORTC-AACR on New Drugs in Cancer Therapy*, Amsterdam (2000), Abstract 21.

Chapa, A.M. et al., "Influence of Intravenous L-Carnitine Administration in Sheep Preceding an Oral Urea Drench[1,2]", *Journal of Animal Science*, vol. 76, No. 11, pp. 2930-2937 (1998).

Depenbrock, H. et al., "In vitro activity of aplidine, a new marine-derived anti-cancer compound, on freshly explanted clonogenic human tumor cells and haematopoietic precursor cells", *British Journal of Cancer*, vol. 78, No. 6, pp. 739-744 (1998).

Erba, E. et al., "Cell cycle phases perturbations induced by new natural marine compounds", *Annals of Oncology*, vol. 7, Supplement 1, #283, pp. 82 (1996).

Faircloth, G. et al., "Aplidine (APL) is a novel marine-derived depsipeptide with in vivo antitumor activity", *Proceedings of the American Association for Cancer Research*, vol. 39, #1551, pp. 227 (1998).

Faircloth, G. et al., "Dehydrodidemin B (DDB) a new marine derived anti-cancer agent (MDA) with activity against experimental tumor models" and "Biological activity of thiocoraline. A new depsipeptide from a marine micromonospora", *Annals of Oncology*, vol. 7, Supplement 1, #111 and #112, pp. 34 (1996).

Faircloth, G. et al., "Preclinical characterization of Aplidine (APD), a new marine anticancer depsipeptice (MADEP)", *Proceedings of the American Association for Cancer Research*, vol. 38, #692, pp. 103 (1997).

Faircloth, G. et al., "Preclinical development of aplidine, a novel marine-derived agent with potent antitumor activity", *Annals of Oncology*, vol. 9, Supplement 2, #129, pp. 34 (1998).

Faircloth, G. et al., "Schedule-dependency of aplidine, a marine depsipeptide with antitumor activity", *Proceedings of the American Association for Cancer Research*, vol. 40, #2612, pp. 394-395 (1999).

Geldof, Albert A. et al., "Cytotoxicity and neurocytotoxicity of new marine anticancer agents evaluated using in vitro assays", *Cancer Chemother. Pharmacol.*, vol. 44, pp. 312-318 (1999).

Genin, Michael J. et al., "Synthesis and Crystal Structure of a Peptidomimetic Containing the (R)-4, 4-Spiro Lactam Type-II β-Turn Mimic", *Journal of Organic Chemistry*, vol. 58, No. 8, pp. 2334-2337 (1993).

Gomez-Fabre, P.M. et al., "Polamine contents of human breast cancer cells treated with the cytotoxic agents chlorpheniramine and dehydrodidemnin B", *Cancer Letters*, vol. 113, Nos. 1, 2, pp. 141-144 (1997).

Jimeno et al., "A Correlation of Selective Antitumor Activities of the Marine-Derived Compound Aplidine Using Different Models", *10th NCI-EORTC-AACR Symposium on Molecular Targets and Cancer Therapeutics*, Washington (1999), Abstract 311.

Jou, Gemma et al., "Total Synthesis of Dehydrodidemnin B. Use of Uronium and Phosphonium Salt Coupling Reagents in Peptide Synthesis in Solution", *Journal of Organic Chemistry*, vol. 62, No. 2, pp. 354-366 (1997).

Lobo, C. et al., "Effect of Dehydrodidemnin B on Human Colon Carcinoma Cell Lines", *Anticancer Research*, vol. 17, No. 1A, pp. 333-336 (1997).

Luber-Narod, J. et al., "In Vitro Safety Profile of Aplidine, A Marine Natural Product with Chemotherapeutic Potential", *Proceedings of the AACR*, vol. 42, Abstract 374, Mar. 2001.

Mastbergen, S.C. et al., "Cytotoxicity and neurocytotoxicity of aplidine, a new marine anticancer agent evaluated using in vitro assays", *Annals of Oncology*, vol. 9, Supplement 2, #131 (1998).

Montgomery, D.W. et al., "Didemnin B Alters the Specific Binding of Prolactin to Human Lymphocytes and Decreases the Circulating Level of Prolactin in Mice", *Federal Proceedings*, vol. 44, No. 3, pp. 634, #1311 (1985).

Montgomery, David W. et al., "Didemnin B: A New Immunosuppressive Cyclic Peptide with Potent Activity In Vitro and In Vivo[1]", *Transplantation*, vol. 40, No. 1, pp. 49-56 (1985).

Nuijen, B. et al., "Pharmaceutical development of anticancer agents derived from marine sources", *Anti-Cancer Drugs*, vol. 11, pp. 793-811 (2000).

Raymond, Eric et al., "Preliminary Results of a Phase I and Pharmacokinetic Study of Aplidine Given as a 24-hour Infusion Every 2 Weeks in Patients With Solid Tumors and Non Hodgkin's Lymphomas", Proceedings of the American Association for Cancer Research, vol. 41, #3886 (2000).

Rinehart, K., "Didemnin and its Biological Properties", *Escom.*, pp. 626-631 (1987).

Rinehart, Kenneth L. et al., "Biologically Active Peptides and Their Mass Spectra", *Pure and Applied Chemistry*, vol. 54, No. 12, pp. 2409-2424 (1982).

Rinehart, Kenneth L. et al., "Didemnins and Tunichlorin: Novel Natural Products from the Marine Tunicate Trididemnum Solidum[1]", *Journal of Natural Products*, vol. 51, No. 1, pp. 1-21 (1988).

Rinehart, Kenneth L. et al., "Total Synthesis of Didemnins A, B and C[1,2]", *Journal of the American Chemical Society*, vol. 109, No. 22, pp. 6846-6848 (1987).

Rinehart, Kenneth L., Jr. et al., "Antiviral and antitumor compounds from tunicates[1,2]" *Federation Proceedings*, vol. 42, No. 1, pp. 87-90 (1983).

Rinehart, Kenneth L., Jr. et al., "Didemnins: Antiviral and Antitumor Depsipeptides from a Caribbean Tunicate", *Science*, vol. 212, No. 4497, pp. 933-935 (1981).

Rinehart, Kenneth L., Jr. et al., "Structure of the Didemnins, Antiviral and Cytotoxic Depsipeptides from a Caribbean Tunicate[1]", *Journal of the American Chemistry Society*, vol. 103, No. 7, pp. 1857-1859 (1981).

Sakai, Ryuichi et al., "Structure—Activity Relationships of the Didemnins[1,2]", *Journal of Medicinal Chemistry*, vol. 39, No. 14, pp. 2819-2834 (1996).

Seebach, Dieter et al., "Alkylation of Amino Acids without Loss of Optical Activity: Preparation of α-Substituted Proline Derivatives. A Case of Self-Reproduction of Chirality[1,2]", *Journal of the American Chemical Society*, vol. 105, No. 16, pp. 5390-5398 (1983).

Urdiales, Jose L. et al., "Antiproliferative effect of dehydrodidemnin B (DDB), a depsipeptide isolated from Mediterranean tunicates", *Cancer Letters*, vol. 102, Nos. 1,2, pp. 31-37 (1996).

Vervoort, Helene et al., "Tamandarins A and B: New Cytotoxic Depsipeptides from a Brazilian Ascidian of the Family Didemnidae", *The Journal of Organic Chemistry*, vol. 65, No. 3, pp. 782-792 (2000).

Rinehart et al., "Total Synthesis of Didemnins A, B, and C[1,2]" *J. Am. Chem. Soc.*, 109, 6846-6848 (1987).

Chauhan, D. et al., "Multiple Myeloma Cell Adhesion-Induced Interleukin-6 Expression in Bone Marrow Stromal Cells Involves Activation of NF-κB," *Blood*, 87(3):1104-1112 (1996).

"Didemnin B," *Drugs of the Future*, 20(1):77 (1995).

Faircloth, G. et al., "Marine (MA) Depsipeptides (DEP) with Activity (A) against Solid Tumours (ST) Models," *Proceedings 8th ECCO Congress*, 31A (Suppl. 5):S29, Abstract No. 122 (1995).

Faircloth, G. et al., "Preclinical Development of Aplidine, a Novel Marine-Derived Agent with Potent Antitumor Activity," *Annals of Oncology*, 9 (Suppl. 2):34, Abstract No. 129 (1998).

Giovanella, B.C. et al., "Correlation Between Response to Chemotherapy of Human Tumors in Patients and in Nude Mice," *Cancer*, 52(7):1146-1152 (1983).

Hideshima, T. et al., "The Proteasome Inhibitor PS-341Inhibits Growth, Induces Apoptosis, and Overcomes Drug Resistance in Human Multiple Myeloma Cells," *Cancer Res.*, 61:3071-3076 (2001).

Jimeno, J. et al., "Translational Studies Supporting the Clinical Development of Aplidine (APL) in Pediatric Leukemia," *Annals of Oncology*, 13 (Suppl. 5):19, Abstract No. 65P (2002).

Mitsiades, C.S. et al., "TRAIL/Apo2L Ligand Selectively Induces Apoptosis and Overcomes Drug Resistance in Multiple Myeloma: Therapeutic Applications," *Blood*, 98(3):795-804 (2001).

Mitsiades, C.S. et al., "Activation of NF-kappaB and Upregulation of Intracellular Anti-Apoptotic Proteins via the IGF-1/Akt Signaling in Human Multiple Myeloma Cells: Therapeutic Implications," *Oncogene*, 21(37):5673-5683 (2002).

Mitsiades, N. et al., "Molecular Sequelae of Proteasome Inhibition in Human Multiple Myeloma Cells," *Proc Natl Acad Sci USA*, 99(22):14374-14379 (2002).

Mitsiades, N. et al., "The Proteasome Inhibitor PS-341 Potentiates Sensitivity of Multiple Myeloma Cells to Conventional Chemotherapeutic Agents: Therapeutic Applications," *Blood*, 101(6):2377-2380 (2003).

Mitsiades, N. et al., "Molecular Sequelae of Histone Deacetylase Inhibition in Human Malignant B Cells," *Blood*, 101(10):4055-4062 (2003).

Palangie, T. et al., "Dose-Intense Salvage Therapy After Neoadjuvant Chemotherapy: Feasibility and Preliminary Results," *Cancer Chemother. Pharmacol.*, 44 (Suppl.):S24-S25 (1999).

Uchiyama, H. et al., "Adhesion of Human Myeloma-Derived Cell Lines to Bone Marrow Stromal Cells Stimulates Interleukin-6 Secretion," *Blood*, 82(12):3712-3720 (1993).

Weiss, R. et al., "A Phase II Trial of Didemnin B in Myeloma," *Investigational New Drugs*, 12(1):41-43 (1994).

Hudes, G.R., "Phase II trial of 96-hour paclitaxel plus oral estramustine phosphate in metastatic hormone-refractory prostate cancer", *J. Clin Oncol.*, 15(9):3156-63 (1997).

Matsuoka, M., "Comparison of the effects of l-carnitine, d-carnitine and acetyl-l-carnitine on the neurotoxicity of ammonia", *Biochemical Pharmacology*, (46(1):159-164 (1993).

Mead Johnson Oncology Products, Taxol (Paclitaxel) Injection Labeling Revision (Apr. 9, 1998).

Rinehart, K., "Antitumor compounds from tunicates", *Medicinal Research Reviews*, 20(1):1-27; *Wiley Interactive Science Journal*, Pub. online Dec. 22, 1999.

Virmani, M.A., "Protective action of l-carnitine and acetyl-l-carntine on the neurotoxicity evoked by mitochondiral uncoupling or inhibitors", *Pharmacological Research*, 32(6):383-389 (1995).

Cecil Textbook of Medicine (Bennett, J.C. and Plum, F., eds.) 20th Edition, vol. 1, pp. 1004-1010 (1996).

Draetta et al., "Section V. Topics in Biology—Cell Cycle Control and Cancer", *Annual Reports in Medicinal Chemistry*, Chapter 25, pp. 241-248, 1996.

Geldof et al., "Cytotoxicity and Neurocytotoxicity of New Marine Anticancer Agents Evaluated Using in Vitro Assays", *Cancer Chemother. Pharmacol.*; 44 321-318, (1999).

Hansen et al., "Continuous 5-Fluorouracil (5FU) Infusion in Carcinoma of the Pancreas: A Phase II Study", *Am. J. Med. Sci.*, 295:91-93, (1988).

Robert S. Kerbel, "What is the Optimal Rodent Model for Anti-Tumor Drug Testing?", *Cancer and Metastasis Reviews*, 17: 301-304, (1999).

"Note for Guidance on Evaluation of Anticancer Medicinal Products in Man", *The European Agency for the Evaluation of Medicinal Products*, EMEA, London, England, CPMP/EWP/205/95 rev. 1 corr, 14 pages, (2001).

Raymond et al., 25th Congress of the European Society of Medicinal Oncology, Hamburg, Germany, Oct. 13-17, 2000, reported in the *Annals of Oncology*, vol. 11, Suppl. 4, Abstract 610PD, (2000).

Urdiales et al., "Antiproliferative Effect of Dehydrodidemnin B (DDB), a Depsipeptide Isolated from Mediterranean Tunicates", *Cancer Letters*, 102:31-37, (1996).

Van-Boxtel et al., "*Drug Benefits and Risks: International Textbook of Clinical Pharmacology*", Chapter 9, pp. 91-102, (2001).

DeVita, Jr., Vincent T, Samuel Hellman, and Steven A Rosenberg, eds. *Cancer: Principles and Practice of Oncology*, "Section 3—Cancer of the Pancreas", Lippincott Williams & Wilkins, 7th Ed., 7 pages, (2005).

O'Neil, Maryadele J., Ann Smith and Patricia E. Heckelman, eds. *The Merck Index—An Encyclopedia of Chemicals, Drugs, and Biologicals*, Merck & Co., Inc., 13th Ed., p. 1791, (2001).

Tempero, Margaret, et al., *Clincial Practice Guidelines in Oncology—v.2.2006*—"Pancreatic Adenocarcinoma" National Comprehensive Cancer Network, http://www.neen.org/professionals/physician_gls/PDF/pancreatic.pdf, 41 pages, (2006).

U.S. National Cancer Institute, U.S. National Institutes of Health, www.cancer.gov, "FactSheet", 6 pages, http://www.cancer.gov/cancertopics/factsheet/information/clinical-trials (2006).

U.S. National Center Institute, U.S. National Institutes of Health, www.cancer.gov., "Pancreatic Cancer (PDQ®): Treatment", 3 pages, http://www.cancer.gov/cancertopics/pdq/treatment/pancreatic/healthprofessional, (2006).

* cited by examiner

SYNTHETIC METHODS FOR APLIDINE AND NEW ANTITUMORAL DERIVATIVES, METHODS OF MAKING AND USING THEM

The present invention relates to synthetic methods for aplidine and new antitumoral derivatives, methods of making and using them.

BACKGROUND OF THE INVENTION

Aplidine has a cyclic structure with a sidechain, as follows:

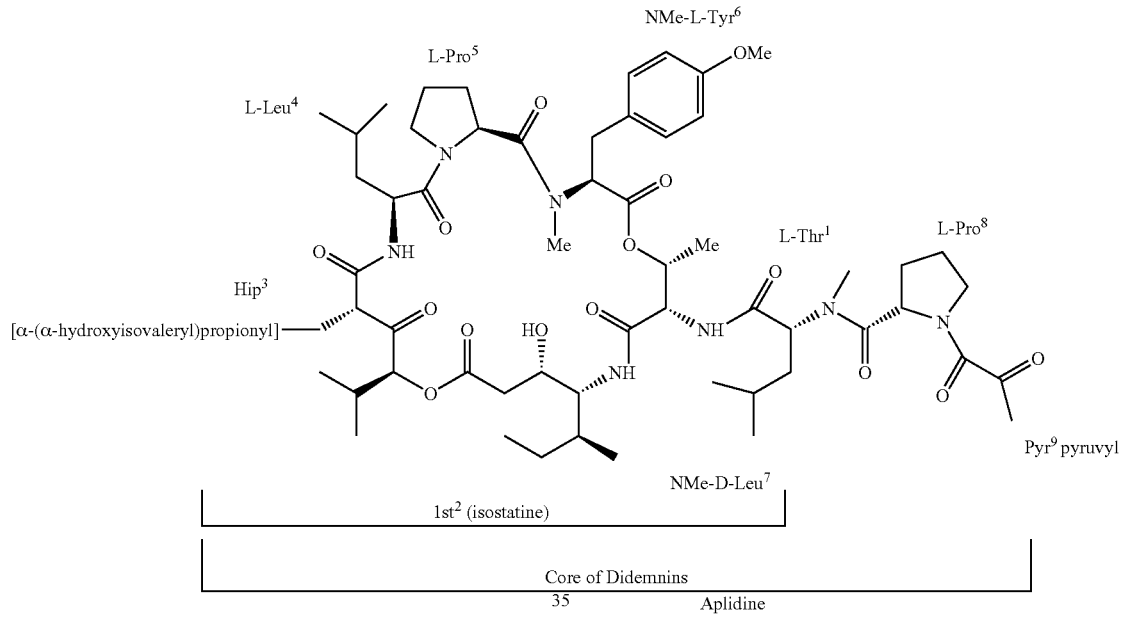

Aplidine

The didemnins form a class of cyclic depsipeptides which have been isolated from various species of the *Tridemnum* genus (Rinehart, Jr. et al. *J., Am. Chem. Soc,* 103, 1857-59 (1981), Rinehart, Jr. et al. *Science,* 212, 933-935 (1981) with potent antitumoral and antiviral activities. Among them, aplidine is one of the most antitumoral active natural didemnins. Description of the isolation and antitumoral activity of Aplidine is provided in U.S. Pat. No. 5,834,586 patent.

A number of synthetic or natural analogs of Aplidine have been described (Rinehart, Jr. et al. *J. Med. Chem,* 1996, 39, 2819-2834) that include different modifications in the side chain, but preserving the same macrocyclic structure.

Recently have been described a related structure of didemnins called Tamandarins (Fenical, W et al., *J. Org. Chem.,* 2000, 65, 782-792) which were isolated from an unidentified ascidian of the family didemnidae. These molecules were found to differ only by the presence of hydroxyisovaleric acid ($Hiv^3$), instead of the hydroxyisovalerylpropionic acid ($Hip^3$). They have been described as highly active antiviral, antitumor and immunosuppresive peptides.

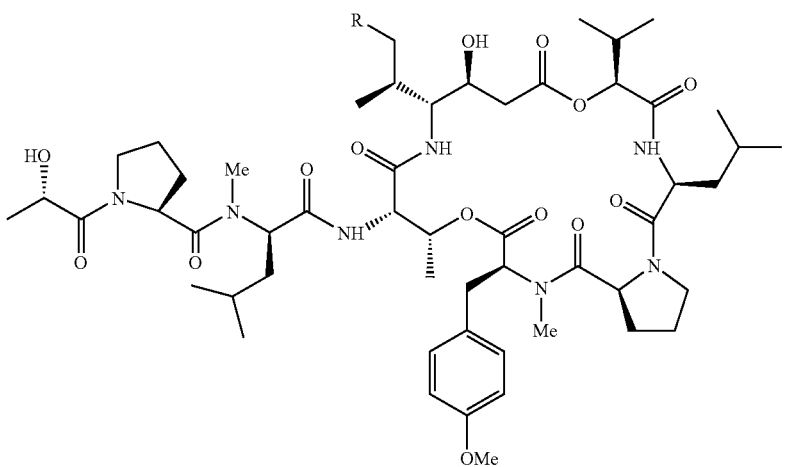

TAMANDARINE A: R = CH$_3$
TAMANDARINE B: R = H

SUMMARY OF THE INVENTION

The present invention relates to the compounds described herein, termed aplidine derivatives for use in medicine, in particular in the treatment of tumours. The invention also relates to pharmaceutical preparations comprising them for treatment of tumours, for example, solid tumours, and use of the compound in the preparation of a medicament for the treatment of tumours. Treatment of solid tumours such as bladder, breast, colon, gastric, liver, nscl, ovary, pancreas, pharynx, prostate, renal, scl, retinoblastoma, melanoma, fibrosarcoma, chondrosarcoma, or osteosarcoma, or treatment of leukemia/lymphomas such as ALL (Promyelocytic leukemia), ALL (Acute lymphobalstic), CML (Chronic myelogenous), ALL (B-cell), leukemia (Hairy B-cell), leukemia (plasma cell), lymphoma (T cell), lymphoma (cutaneous T cell), lymphoma (undifferentiated), lymphoma (Burkitts B cell), lymphoma (histiocytic), lymphoma (B cell), lymphoma (Burkitts ascites) is particularly preferred.

Examples of pharmaceutical compositions of the invention include any solid (for example tablets, pills, capsules, granules) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

Suitably, the compound may be conjugated to a carrier protein or another suitable agent for delivery into the animal or human body. Conjugation may occur directly between a carrier and the compound, or indirectly via a suitable linker.

Administration of the compound or compositions of the present invention may be by any suitable method, such as intravenous infusion, oral preparations, intraperitoneal and intravenous administration. We prefer that infusion times of up to 24 hours are used, more preferably 2-12 hours, with 2-6 hours most preferred. Short infusion times which allow treatment to be carried out without an overnight stay in hospital are especially desirable. However, infusion may be 12 to 24 hours or even longer if required. Infusion may be carried out at suitable intervals of say 2 to 4 weeks. Pharmaceutical compositions containing compounds of the invention may be delivered by liposome or nanosphere encapsulation, in sustained release formulations or by other standard delivery means.

The correct dosage of the compound will vary according to the particular formulation, the mode of application, and the particular situs, host and cancer or tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds of this invention may be used with other drugs to provide a combination therapy. The other drugs may form part of the same composition, or be provided as a separate composition for administration at the same time or a different time. The identity of the other drug is not particularly limited, and suitable candidates include:

a) drugs with antimitotic effects, especially those which target cytoskeletal elements including microtubule modulators such as taxane drugs (such as taxol, paclitaxel, taxotere, docetaxel), podophylotoxins or vinca alkaloids (vincristine, vinblastine);
b) antimetabolite drugs such as 5-fluorouracil, cytarabine, gemcitabine, purine analogues such as pentostatin, methotrexate);
c) allylating agents such as nitrogen mustards (such as cyclophosphamide or ifosphamide);
d) drugs which target DNA such as the antracycline drugs adriamycin, doxorubicin, pharmorubicin or epirubicin;
e) drugs which target topoisomerases, such as etoposide;
f) hormones and hormone agonists or antagonists such as estrogens, antiestrogens (tamoxifen and related compounds) and androgens, futamide, leuprorelin, goserelin, cyprotrone or octreotide;
g) drugs which target signal transduction in tumour cells including antibody derivatives such as herceptin;
h) alkylating drugs such as platinum drugs (cis-platin, carbonplatin, oxaliplatin, paraplatin) or nitrosoureas;
i) drugs potentially affecting metastasis of tumours such as matrix metalloproteinase inhibitors;
j) gene therapy and antisense agents;
k) antibody therapeutics; and
l) other bioactive compounds of marine origin, notably the ecteinascidins such as ET-743.

In one aspect, the present invention relates to compounds of the formula:

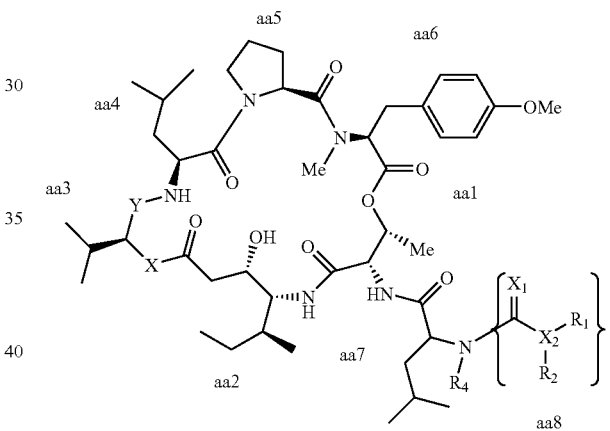

wherein:

X is independently —$CR_2$—, —O—, —S—, or —NR—, in which R is independently H or an organic group selected from an alkyl group, an alkenyl group, an aryl group, an aralkyl group, and their substituted derivatives substituted with one or more of a heterocyclic group, an alkoxy group, an hydroxy group, a mercapto group, an optionally protected amino group, a guanidino group, or a halogen group;

X is independently —$C(R)_2$—, —O—, —S—, or —NR—, in which R is independently H or an organic group selected from an alkyl group, an alkenyl group, an aryl group, an aralkyl group, and their substituted derivatives substituted with one or more of a heterocyclic group, an alkoxy group, an hydroxy group, a mercapto group, an optionally protected amino group, a guanidino group, or a halogen group;

$X_1$ is O or S;

$R_1$, $R_2$ and $R_4$ are each independently H or an organic group selected from an amido group RCONH— or an acyl group RCO— where R is as defined, an alkyl group, an alkenyl group, an aryl group, an aralkyl group, and substituted derivatives substituted with one or more of a heterocyclic group, an alkoxy group, an hydroxy group, a mercapto group, an optionally protected amino group, a guanidino group, or a halogen group, and $R_1$ or $R_2$ when $X_2$ is N, and $R_4$, can further be —$SO_2R$, where R is as defined;

or $R_1$ and $R_2$ with $X_2$ may form an optionally N-substituted proline, the N-substituted proline aa8 being of formula

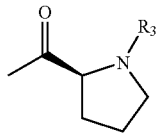

where $R_3$ is independently H or an organic group selected from a group $RSO_2$— or an acyl group RCO—, where R is as defined, or $R_3$ is an alkyl group, an alkenyl group, an aryl group, an aralkyl group, and substituted derivatives substituted with one or more of a carbonyl group, an hydroxy group, a mercapto group, an optionally protected amino group, a guanidino group, or a halogen group;

or $R_1$ and $R_2$ with $X_2$ may form a cycloalkyl, aryl or heterocyclic group, optionally substituted with one or more groups $R_3$;

or $R_1$, $R_2$, $X_2$, $R_4$ and the nitrogen bearing $R_4$ may form an oxadiazaspiroalkane N-substituted with $R_5$, where $R_5$ is independently H or an organic group selected from a group $RSO_2$— or an acyl group RCO where R is as defined, an alkyl group, an aryl group, an aralkyl group, and substituted derivatives substituted with one or more of a carbonyl group, an alkoxy group, an hydroxy group, a mercapto group, an amino group, a guanidino group, or a halogen group;

or aa8 is replaced by an organic group selected from a group $RSO_2$— or an acyl group RCO where R is as defined, an alkyl group, an aryl group, an aralkyl group, and substituted derivatives substituted with one or more of a carbonyl group, an alkoxy group, an hydroxy group, a mercapto group, an amino group, a guanidino group, or a halogen group;

and pharmaceutically acceptable salts thereof.

Preferred compounds include those wherein X is —NR—, in which R is as defined. More preferably, X is —NH— or —NMe-, and most preferably X is —NH—.

Further preferred compounds include those wherein X is —O—.

The group Y is preferably —COR'CO—, where R' is an alkyl group, especially where R' is —CHCH$_3$—.

Further preferred compounds include those wherein Y is —CO—.

In view of these preferences, a preferred class of compounds is that wherein X is —NH— or —O— and Y is —COCHCH$_3$CO— or —CO—.

Preferably $R_4$ is methyl.

Preferably $X_1$ is =O.

Preferably $X_2R_1$ is an optionally substituted aralkyloxy group, such as a benzyloxy group.

Other preferred compounds include those wherein $X_2R_1$ is an optionally substituted amino group, more preferably those wherein $X_2R_1$ is a group —$NHR_1$, where $R_1$ is an optionally substituted alkyl group, alkenyl group, aryl group, or aralkyl group, especially an alkyl group or an aryl group, such as a phenyl group or a butyl group.

Further preferred compounds comprise those wherein $X_2R_1$ is an optionally substituted alkyl group, especially where $X_2R_1$ is a propyl group, isopropyl group, pentyl group or biotin group.

A group of preferred compounds is those wherein —C(=$X_2$)$R_1R_2$ form an optionally substituted amino acid acyl group. Suitably the optionally substituted amino acid acyl group is optionally substituted proline or optionally substituted glycine or optionally substituted valine, and more especially the optionally substituted proline is optionally substituted norvaline-proline, optionally substituted alanine-proline, Boc-proline, optionally substituted alkyl-proline, or the optionally substituted glycine is heterocyclic-substituted glycine, or the optionally substituted valine is valine, Boc-valine, or alkyl-valine. Preferably the optionally substituted proline is norvaline-proline, Z-norvaline-proline, alanine-proline, Z-alanine-proline, Boc-alanine-proline, isobutyrylproline or optionally protected D-lactylproline, or the heterocyclic-substituted glycine is coumarinyl-glycine, or the optionally substituted valine is valine, Boc-valine, or isobutyrylvaline.

A further group of preferred compounds includes those wherein $X_1$ is S and $X_2R_1$ is a group —$NHR_1$, where $R_1$ is an optionally substituted alkyl group, alkenyl group, aryl group, or aralkyl group. $R_1$ is preferably an alkyl group or an aryl group, more preferably a phenyl group or a butyl group.

$R_1$ and $R_2$ with $X_2$ can form a heterocyclic group, optionally substituted with one or more groups $R_3$. For example, the heterocyclic group can be coumarin.

Preferred compounds include those wherein aa8 is replaced by an organic group $RSO_2$—, where R is as defined, such as methyl.

$R_1$, $R_2$, $X_2$, $R_4$ and the nitrogen bearing $R_4$ can form an oxadiazaspiroalkane N-substituted with $R_5$, where $R_5$ is H. The N-substituted oxadiazaspiroalkane is preferably 6-oxa-1,7-diazaspiro[4,4]nonane.

Examples of compounds according to this invention include:
3-[Aip]-Z-didemnin A,
8-[Phenylurea]-didemnin A,
8-[Butylurea]-didemnin A,
3-[val]-8-[isobutyryl]-aplidine,
9-[norvaline]-aplidine,
3-[Hiv]-9-[Isobutyryl]-aplidine,
3-[Val]-9-[Isobutyryl]-aplidine,
3-[hiv]-8-[isobutyryl]-didemnin A,
3-[Hiv]9-[Ala]-aplidine,
3-[Hiv]-9-[Nva]-aplidine,
8-[Phenylthiourea]-didemnin A,
8-[Coumarin]-didemnin A,
8-[Butylthiourea]-didemnin A,
3-[Hiv]-9-[D-Lac]-aplidine,
8-[Methylsulphonyl]-didemnin A,
3-[val]-Z-didemnin A,
3-[Hiv]-8-[Val]-didemnin A,
3-[Hiv]-8-[butyryl]-aplidine,
3-[val]-didemnin A,
3-[Hiv]-didemnin A,
Z-Didemnin A,
9-[Z-Nva]-aplidine,
3-[Hiv]-9-[Z-ala]-aplidine,
8-[Gly]-9-[Coumarin]-didemnin A,
8-[Biotin]-didemnin A,
3-[Hiv]-7,8-[Spiro]-9-[Boc]-aplidine,
3-[Hiv]-Z-didemnin A,
3-[Hiv]-9-[Z-Nva]-aplidine,
7,8-[Spiro]-9-[pyr]-aplidine, 3-[Hiv]-9-[lac(OTBDMS)]-aplidine,
3-[Hiv]-9-[Boc-Ala]-Eplidine,
7,8-[Spiro]-9-[Boc]-aplidine,
3-[Hiv]-8-[Boc-Val]-aplidine,
8-[Val]-9-[Isobutyryl]-didemnin A,
3-[Hiv]-8-[hexanoyl]-didemnin A,
3-[Val]-9-[Lac(OTBDMS)]-aplidine,
3-[Aip]-didemnin A,
3-[Hiv]-9-[D-Lac(OTBDMS)]-aplidine,
7,8-[Spiro]-9-[Isobutyryl]-aplidine,
3-[Hiv]-7,8-[Spiro]-9-[Pyr]-aplidine,
3-[Hiv]-7,8-[Spiro]-9-[Isobutyryl]-aplidine,
3-[Hiv]-7,8-[Spiro]-9-[Acryloyl]-aplidine, or
[Aip]$^3$-aplidine.

In a related aspect, the present invention is directed to compounds having the following formulae:

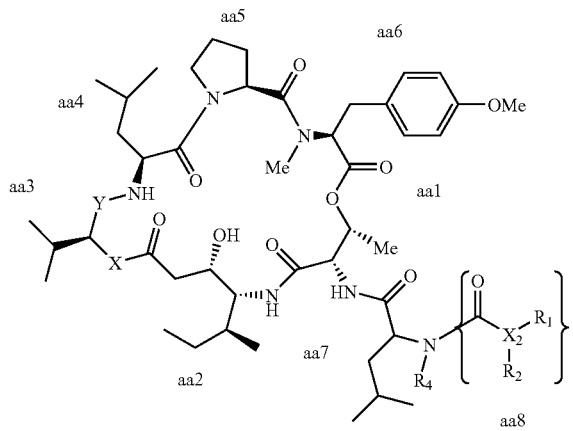

Formula I

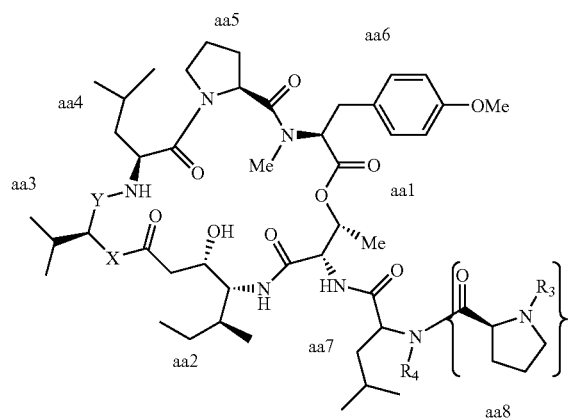

Formula II and related structures.

In one particularly preferred embodiment, the present invention provides a synthetic route to the formation of aa3 [Hiv]$^3$ or [Val]$^3$ or [Aip]$^3$, as a part of a series of exceedingly potent and rare antitumor agents which scheduled slated for clinical trials when adequate quantities become available, and its simplest isomers, where amino acid residues are permuted. This process is enantio- and stereocontrolled and fast, taking advantages of the standard methods of solution-phase synthetic methodology The preferred embodiment of the present invention is represented in formula I, wherein aa3 are independently α-amino acids of L or D configuration. If applies X is independently —C(R)$_2$—, O, S, or NR; where R is independently H or an organic group selected from the group consisting of an alkyl group, an aryl group, an aralkyl group, and their substituted derivatives with an hydroxy group, a mercapto group, an amino group, a guanidino group, a halogeno group. Where R most preferably have from 1 to about 12 carbon atoms, more preferably 1 to about 8 carbon atoms, still more preferably 1 to about 6 carbon atoms, and most preferably 1, 2, 3 or 4 carbon atoms. Methyl, ethyl and propyl including isopropyl are particularly preferred alkyl groups in the compounds of the present invention, Where aa3 most preferably is α-(α'-hydroxyisovaleryl)propionyl (Hip), (X=O, Y=—COCHCH$_3$CO—)-serie A, or α-(α'-aminoisovaleryl)propionyl (Aip) (X=NH, Y=—COCHCH$_3$CO—)-serie N, or valine (X=NH, Y=—CO—)-serie V, or α-hydroxyisovaleryl (X=—O—, Y=—CO—)-serie H, or N-methylvaline (X=NMe, Y=—CO—)-serie M. Wherein aa8 are independently α-amino acids of L or D configuration, if applies; wherein X$_2$ is independently CR, O, S, or N; where R is independently H or an organic group selected from the group consisting of an alkyl group, an alkenyl group, an aryl group, an aralkyl group, and their substituted derivatives with an hydroxy group, a mercapto group, an amino group, a guanidino group, a halogeno group, wherein R$_1$, R$_2$, R$_3$ and R$_4$ are each independently H or an organic group selected from the group consisting of an alkyl group, an aryl group, an aralkyl group, and their substituted derivatives with an hydroxy group, a mercapto group, an amino group, a guanidino group, a halogen group. Aa8 also can be a proline residue as in formula II. Where R$_3$ is independently H or an organic group selected from the group consisting of an alkyl group, an aryl group, an aralkyl group, and their substituted derivatives with an hydroxy group, a mercapto group, an amino group, a guanidino group, a halogen group.

Where R$_3$ most preferably can be pyruvic acid, aralkyloxycarbonyl group or aminoacid or peptides. Alkyl groups preferably have from 1 to about 12 carbon atoms, more preferably 1 to about 8 carbon atoms, still more preferably 1 to about 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members. Preferred aminoacids are protected or non protected D or L glycine, valine, leucine, isoleucine, phenylalanine, tyrosine, tryptophan, methionine, cysteine, aspartate, asparagine, glutamic acid, glutamine, lysine, arginine, proline, serine, threonine, histidine and hydroxyproline. Preferred peptides can be formed with the above mentioned aminoacids.

Besides, aa8 and $R_4$ can be linked through derivatives of a 6-oxo-1,7-diazaspiro[4,4]-nonane structure:

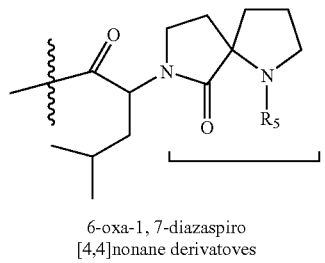

6-oxa-1, 7-diazaspiro [4,4]nonane derivatoves where $R_5$ most preferably can be pyruvic acid, aralkykoxycarbonyl group or aminoacid or peptides. Alkyl groups preferably have from 1 to about 12 carbon atoms, more preferably 1 to about 8 carbon atoms, still more preferably 1 to about 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members. Preferred aminoacids are protected or non protected D or L glycine, valine, leucine, isoleucine, phenylalanine, tyrosine, tryptophan, methionine, cysteine, aspartate, asparagine, glutamic acid, glutamine, lysine, arginine, proline, serine, threonine, histidine and hydroxyproline. Preferred peptides can be formed with the above mentioned aminoacids.

As used herein, the term "organic group" means a hydrocarbon group that is classified as an aliphatic group, cyclic group, or combination of aliphatic and cyclic groups (e.g., aralkyl groups). In the context of the present invention, the term "aliphatic group" means a saturated or unsaturated linear or branched hydrocarbon. This term is used to encompass alkyl, alkenyl, and alkynyl groups, for example. The term "alkyl group" means a saturated linear or branched hydrocarbon group including, for example, methyl, ethyl, isopropyl, isobutyl, t-butyl, heptyl, dodecyl, octadecyl, amyl, 2-ethylhexyl, 2-methylbutyl, 5-methylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group. The term "heterocycyclic group" means a closed ring hydrocarbon in which one or more of the atoms in the ring is an element other than carbon (e,g., nitrogen, oxygen, sulfur, etc.).

Preferred alkoxy groups in the compounds of the present invention include groups having one or more oxygen linkages and from 1 to about 12 carbon atoms, more preferably from 1 to about 8 carbon atoms, and still more preferably 1 to about 6 carbon atoms, and most preferably 1, 2, 3 or 4 carbon atoms.

Suitable heteroaromatic groups in the compounds of the present invention contain one, two or three heteroatoms selected from N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyj, indolyl, benzofuranyl and benzothiazol. Suitable heteroalicyclic groups in the compounds of the present invention contain one, two or three heteroatoms selected from N, O or S atoms and include, e.g., tetrahydrofuranyl, tetrahydropyranyl, piperidinyl, morpholino and pyrrolindinyl groups.

Suitable carbocyclic aryl groups in the compounds of the present invention include single and multiple ring compounds, including multiple ring compounds that contain separate and/or fused aryl groups. Typical carbocyclic aryl groups contain 1 to 3 separate or fused rings and from 6 to about 18 carbon ring atoms, Specifically preferred carbocyclic arykl groups include phenyl including substituted phenyl, such as 2-substituted phenyl, 3-substituted phenyl, 2,3-substituted phenyl, 2,5-substituted phenyl, 2,3,5-substituted and 2,4,5-substituted phenyl, including where one or more of the phenyl substituents is an electron-withdrawing group such as halogen, cyano, nitro, alkanoyl, sulfinyl, sulfonyl and the like; naphthyl including 1-naphthyl and 2-naphthyl; biphenyl; phenanthryl; and anthracyl.

Optionally protected amino groups can be protected using groups known for this purpose. Suitable protecting groups for amines include carbamates, amides, and other protecting groups, such as alkyl, arylayl, supho- or halo-arylalkyl, haloalkyl, alkylsilylalkyl, arylalkyl, cycloalkylalkyl, alkylarylalkyl, heterocyclylalkyl, nitroarylalkyl, acylaminoalkyl, nitroaryldithioarylalkyl, dicycloalkylcarboxamidoalkyl, cycloalkyl, alkenyl, axylalkenyl, nitroarylalkenyl, heterocyclylalkenyl, heterocyclyl, hydroxyheterocyclyl, alkyldithio, alkoxy- or halo- or alkylsulphinyl arylalkyl, hetercyclylacyl, and other carbamates, and alkanoyl, haloalkanoyl, aryalkanoyl, alkenoyl, heterocyclylacyl, aroyl, arylaroyl, haloaroyl, nitroaroyl, and other amides, as well as alkyl, alkenyl, alkylsilylalkoxyalkyl, alkoxyalkyl, cyanoalkyl, heterocyclyl, alkoxyarylalkyl, cycloalkyl, nitroaryl, arylalkyl, alkoxy- or hydroxyarylalkyl, and many other groups. Such groups may optionally be substituted with the previously mentioned substituent groups.

References herein to substituted groups in the compounds of the present invention refer to the specified moiety that may be substituted at one or more available positions by one or more suitable groups, e.g., halogen such as fluoro, chloro, bromo and iodide; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms, alkylsulfinyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or 1 to about 6 carbon atoms; carbocyclic aryl having 6 or more carbons, particularly phenyl (e.g., R being a substituted or unsubstituted biphenyl moiety); and aralkyl such as benzyl.

As is well understood in this technical area, a large degree of substitution is not only tolerated, but is often advisable. Substitution is anticipated on the compounds of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, or S atoms, for example, in the chain as well as carbonyl group or other conventional substitution. Where the term "moiety" is used to describe a chemical compound or substituent, only a unsubstituted chemical material is intended to be included. For example, the phrase "alkyl group" is intended to include not only pure open chain saturated hydrocarbon alkyl substituents, such as methyl, ethyl, propyl, isobutyl, and the like, but also alkyl substituents bearing further substituents known in the art, such as hydroxy, alkoxy, amino, carboxyl, carboxamido, halogen atoms, cyano, nitro, alkylsulfonyl, etc. Thus, "alkyl group" includes ether groups, haloalkyls, alcohols, thiols, carboxyl, amines, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, isobutyl, and the like.

In a further aspects of this invention, there are provided synthetic methods.

A method is provided of making a didemnin fragment having the structure

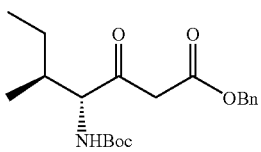

the method comprising coupling Boc-D-allo-Ileu-OH with the lithium enolate of benzyl acetate.

The carbonyl group of a didemnin fragment of formula;

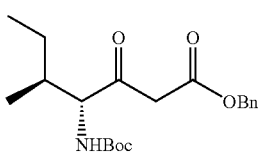

can be reduced to yield a didemnin fragment having the structure

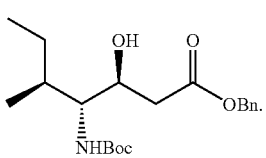

The hydroxy group of a compound of formula:

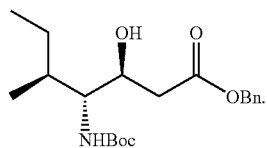

can be protected to yield a didemnin fragment having the structure

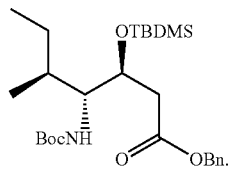

Further deprotection of the benzyl ester group yields a didemnin fragment having the structure

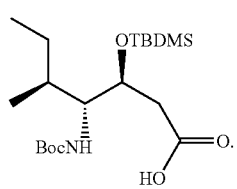

A further method of this invention for making a didemnin fragment comprises coupling a first reactant having the structure

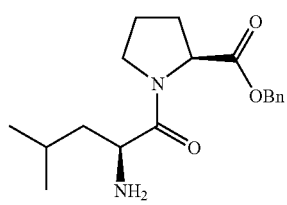

and a second reactant having the structure

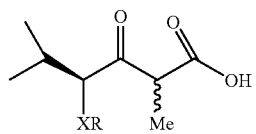

to yield a didemnin fragment having the structure

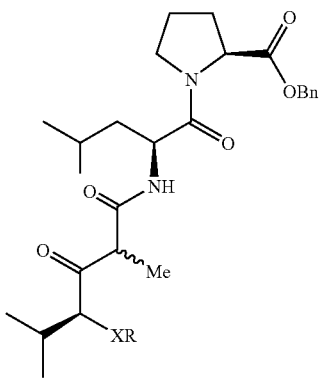

wherein X is selected from the group consisting of —O— and —NH—; where R is an amine protecting group; and where R is a hydroxy protecting group. Suitably X is —O— and R is tert-butyldinethylsilyl; or X is —NH— and R is Boc.

Another method of this invention for making a didemnin fragment comprises coupling a first reactant having the structure

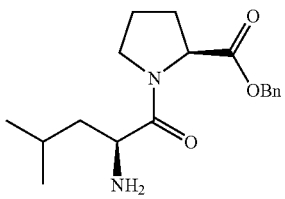

and a second reactant having the structure

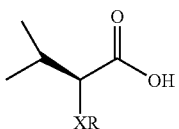

to yield a didemnin fragment having the structure

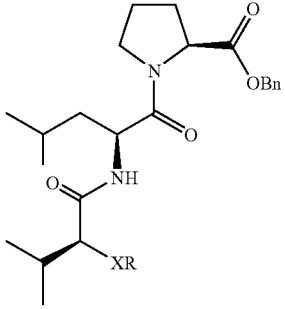

wherein X is selected from the group consisting of —O—, —NMe, and —NH—; where R is an amine protecting group; and where R is H. Suitably X is —O— and R is H.; or X is —NH— and R is Boc; or X is —NMe- and R is Boc.

A method of this invention comprises hydrolyzing the didemnin fragment of formula:

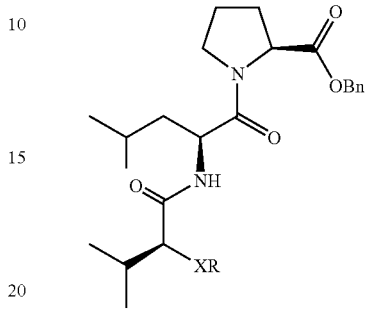

to yield a didemnin fragment having the structure

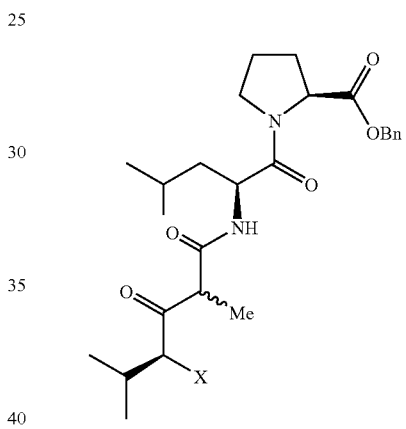

wherein X is selected from the group consisting of —OH, and —NH$_2$

Another method involves hydrolyzing the didemnin fragment

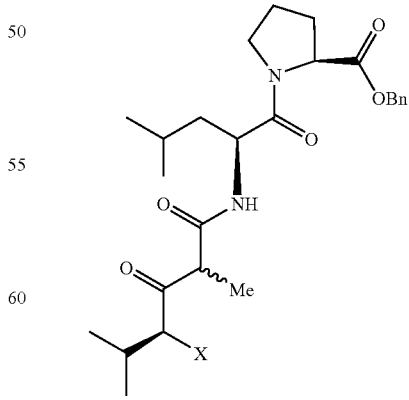

to yield a didemnin fragment having the structure

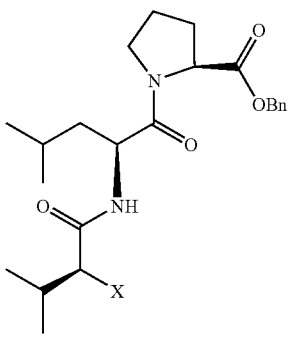

wherein X is selected from the group consisting of —NH₂ and —NHMe.

A further method is provided of making a didemnin fragment, the method comprising coupling a first reactant having the structure

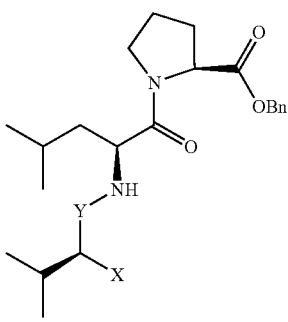

and a second reactant having the structure

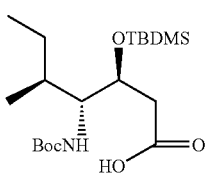

to yield a didemnin fragment having the structure

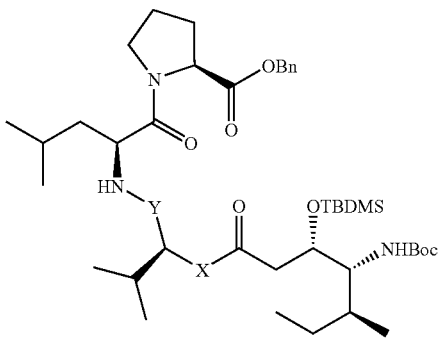

wherein X is selected from the group consisting of —O—, —NMe, and —NH—; where Y is —(COCHCH₃)$_n$CO—; where n is 0 or 1.

A method comprises comprising hydrolyzing the didemnin fragment

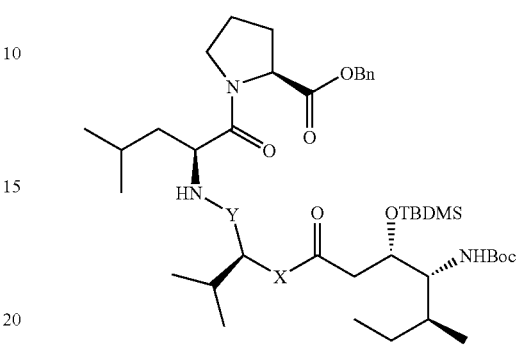

to yield a didemnin fragment having the structure

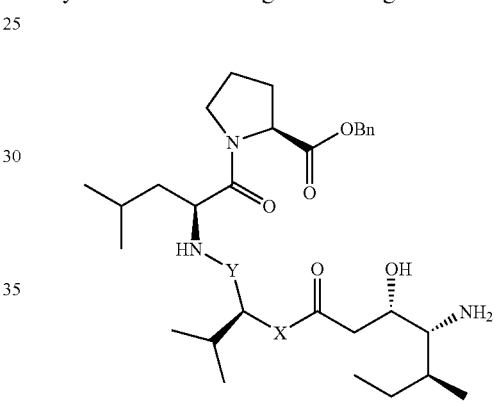

wherein X is selected from the group consisting of —O—, and —NH—; where Y is —(COCHCH₃)$_n$CO—; where n is 0 or 1.

Another method of making a didemnin fragment is provided by this invention, the method comprising coupling a first reactant having the structure

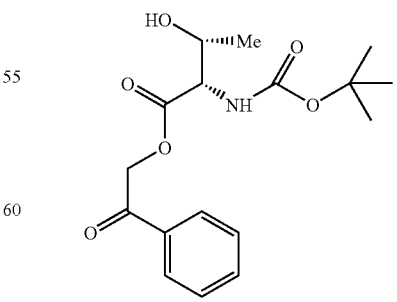

and a second reactant having the structure

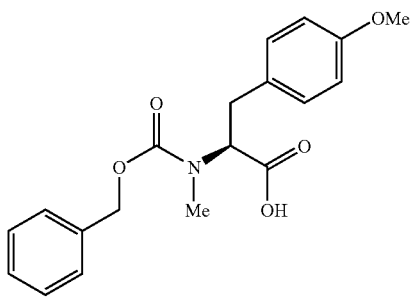

to yield a didemnin fragment having the structure

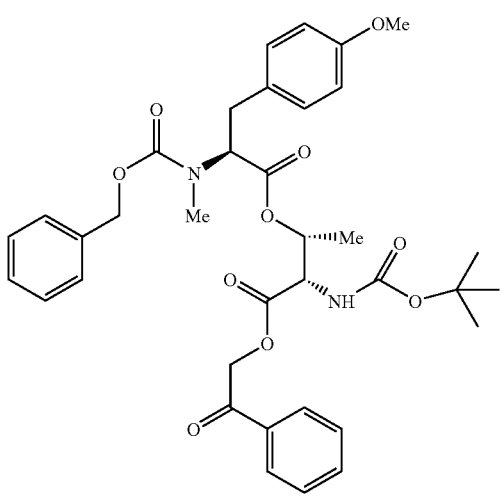

A method of this invention involves deprotection of the benzyl ester group of the didemnin fragment of formula

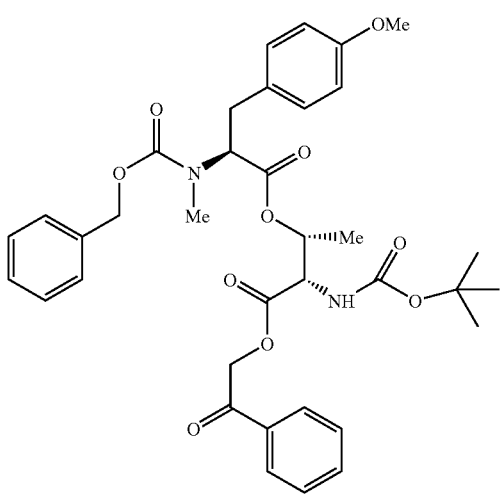

to yield a didemnin fragment having the structure

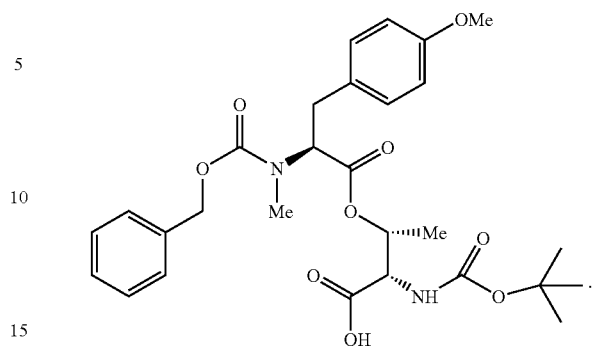

According to this invention, a method of making a didemnin fragment comprises coupling a first reactant having the structure

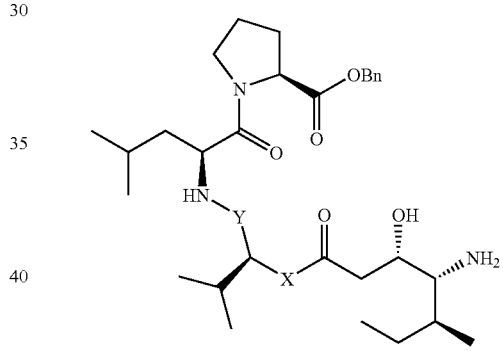

and a second reactant having the structure

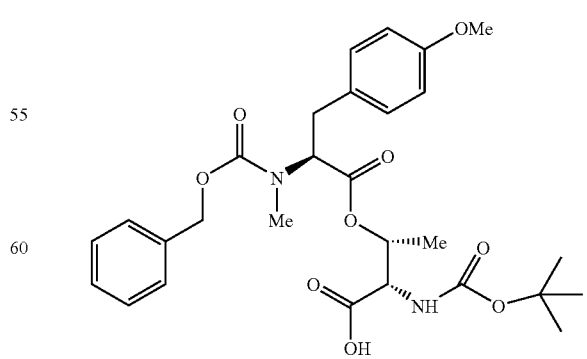

to yield a didemnin fragment having the structure

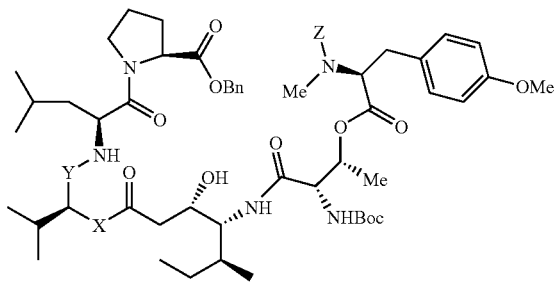

wherein X is selected from the group consisting of —O—, and —NH—; where Y is —(COCHCH$_3$)$_n$CO—; where n is 0 or 1.

A method comprises deprotection of the didemnin fragment

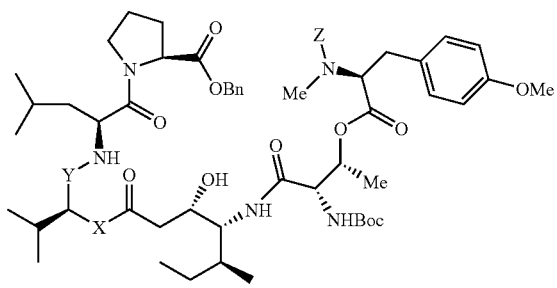

to yield a didemnin fragment having the structure

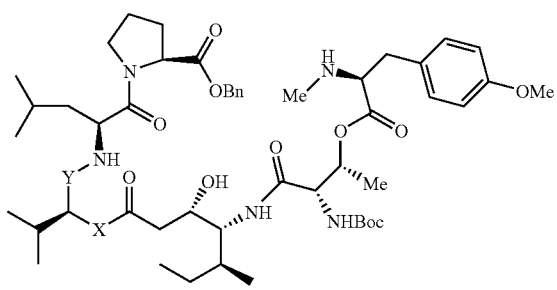

wherein X is selected from the group consisting of —O—, and —NH—; where Y is —(COCHCH$_3$)$_n$CO—; where n is 0 or 1.

A further method of this invention for making a didemnin fragment comprises the cyclizing the fragment of formula:

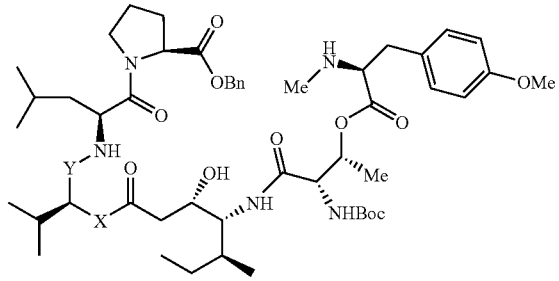

to yield a didemnin analog having the structure

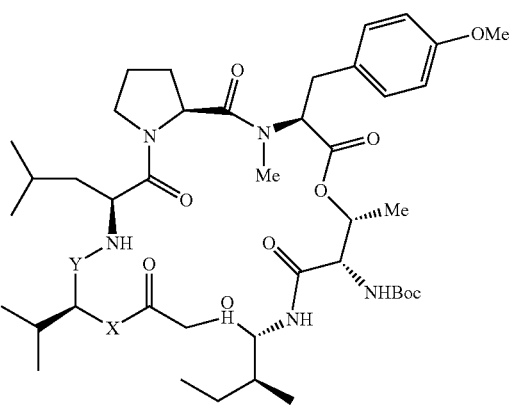

wherein X is selected from the group consisting of —O—, and —NH—; where Y is —(COCHCH$_3$)$_n$CO—; where n is 0 or 1.

A method involves hydrolyzing the didemnin analog

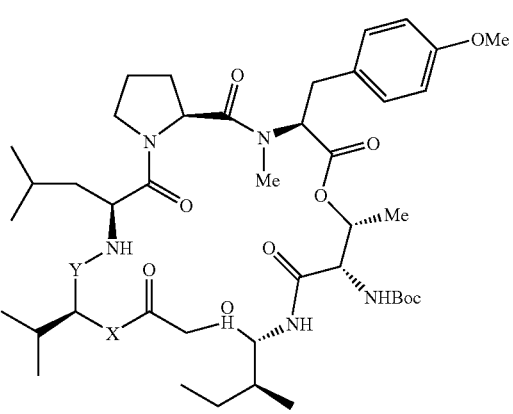

to yield a didemnin analog having the structure

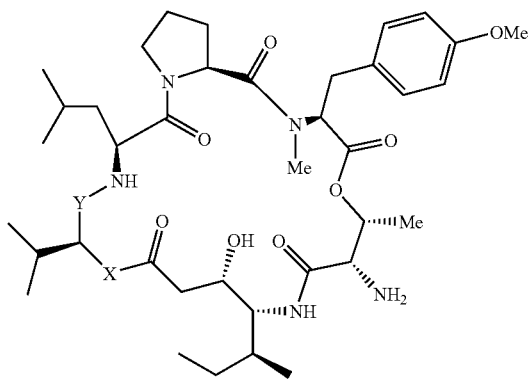

wherein X is selected from the group consisting of —O—, and —NH—; where Y is —(COCHCH₃)ₙCO—; where n is 0 or 1.

A method is further provided of making a didemnin analog, the method comprising coupling a first reactant having the structure

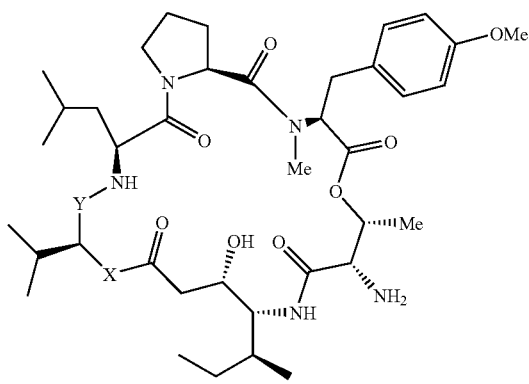

and a second reactant having the structure

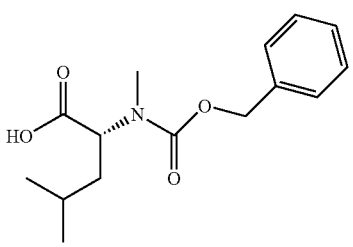

to yield a didemnin analog having the structure

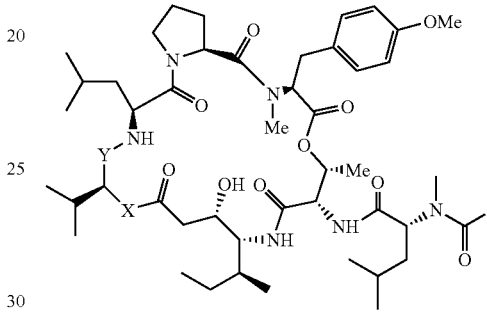

wherein X is selected from the group consisting of —O—, and —NH—; where Y is —(COCHCH₃)ₙCO—; where n is 0 or 1.

Another method comprises deprotection the didemnin fragment of formula:

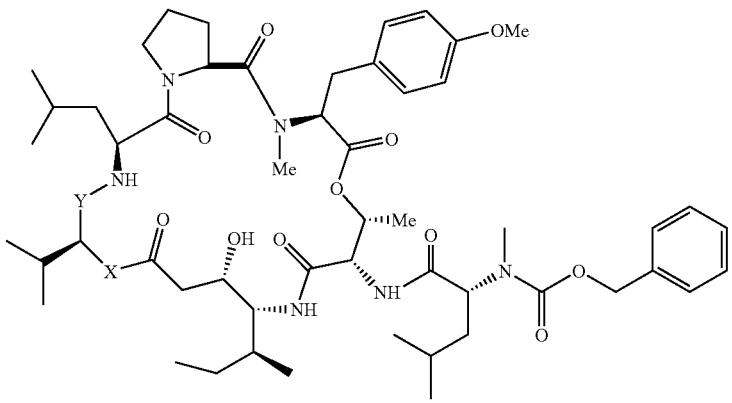

to yield a didemnin fragment having the structure

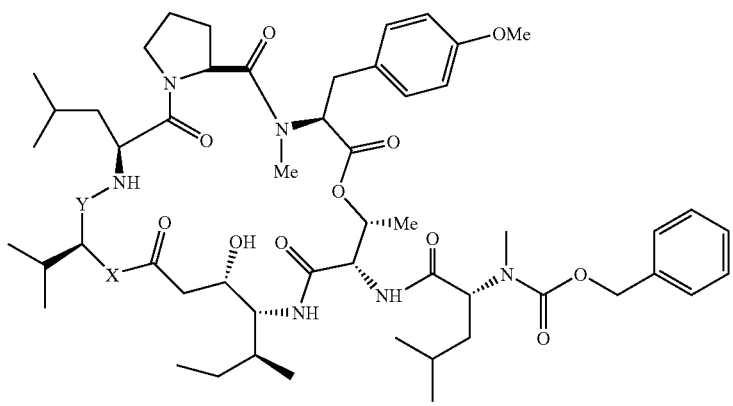

wherein X is selected from the group consisting of —O—, and —NH—; where Y is —(COCHCH$_3$)$_n$CO—; where n is 0 or 1.

A method of making a didemnin fragment comprises the coupling of the fragment having the structure

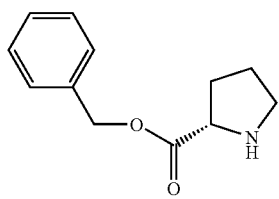

and a second reactant having the structure

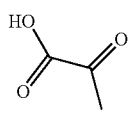

to yield a didemnin fragment having the structure

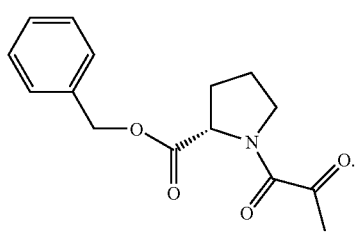

A further method comprises deprotection the didemnin fragment of formula:

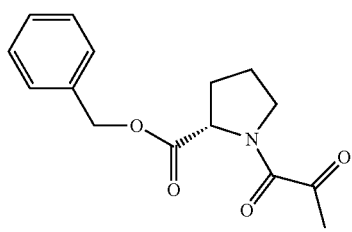

to yield a didemnin fragment having the structure

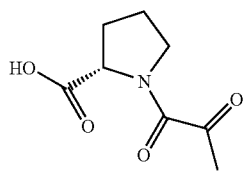

A method of this invention for making a didemnin analog comprises the coupling of the didemnin analog of formula:

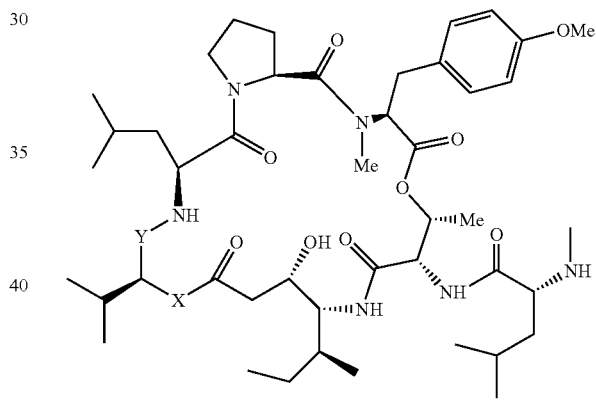

with the fragment

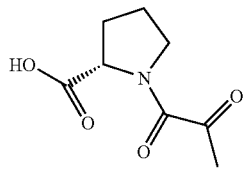

to yield the didemnin analog having the structure

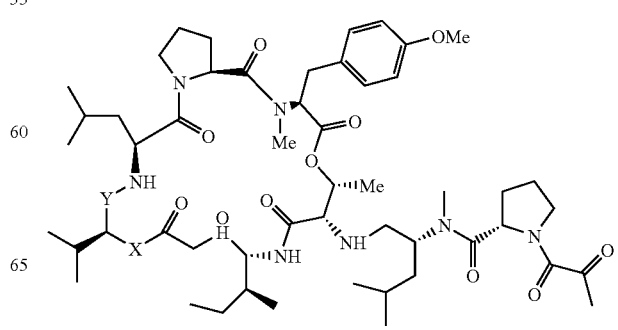

wherein X is selected from the group consisting of —O—, and —NH—; where Y is —(COCHCH₃)ₙCO—; where n is 0 or 1.

A method of making a didemnin analog comprises the coupling of the didemnin analog having the structure

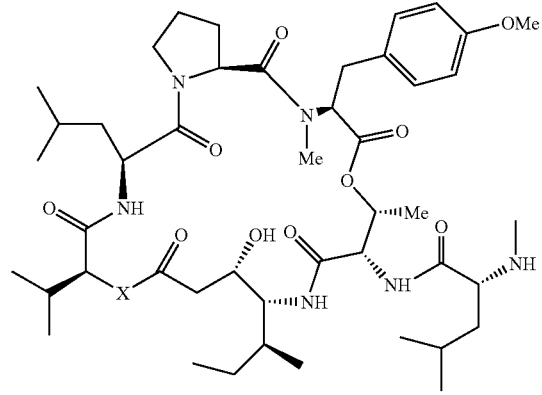

and the fragment having the structure

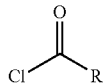

to yield the didemnin analog having the structure

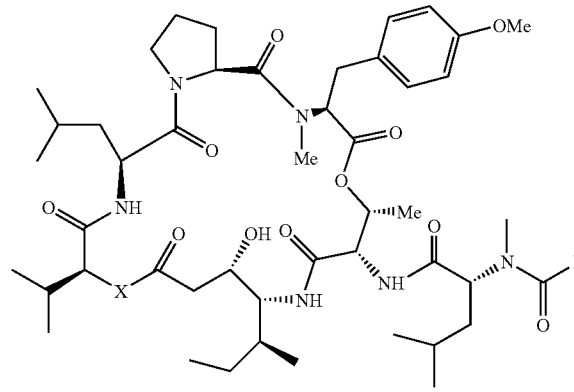

wherein X is selected from the group consisting of —O—, and —NH—, and R is i-Propyl; wherein X is —O— and R is n-Propyl, and R is n-Pentyl A method of this invention for making a didemnin analog comprises the coupling of the didemnin analog having the structure

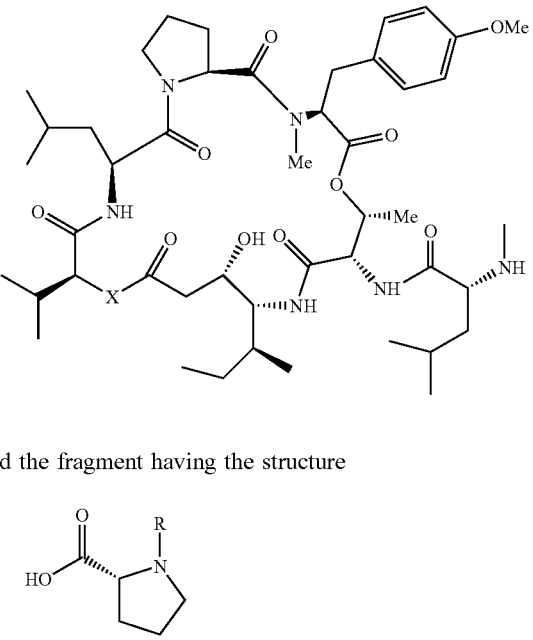

and the fragment having the structure

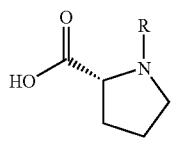

to yield the didemnin analog having the structure

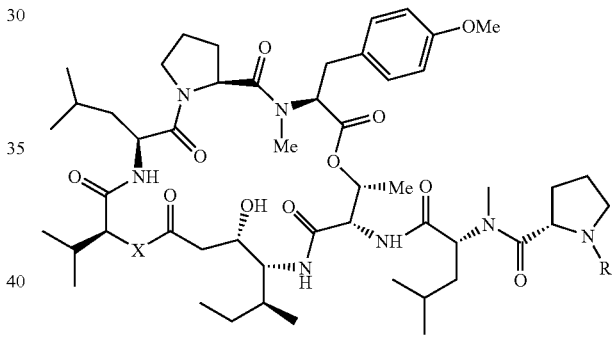

wherein:

X = O, NH

R = 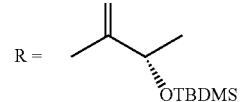

X = O

R = 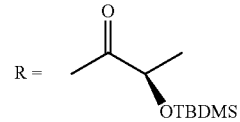

X = O

R = 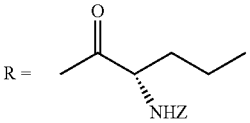

X = O

R = 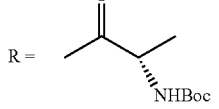

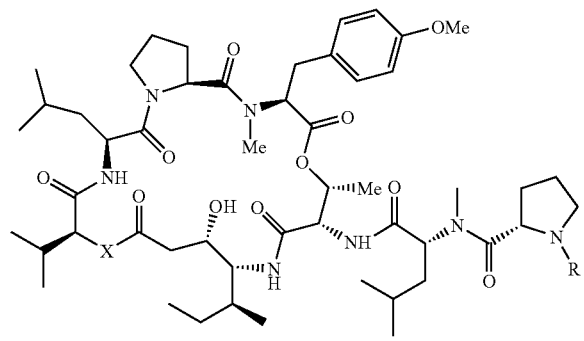
wherein:
X = O
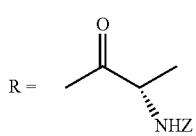
X = O    R = —CO—OtBu.
A method of this invention involves deprotection the didemnin analog
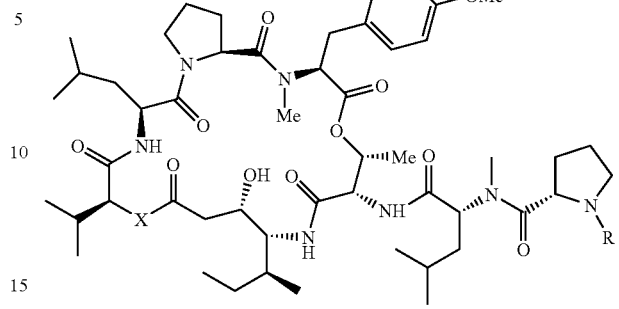
wherein
X = O, NH
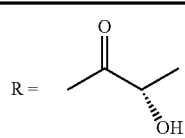
X = O
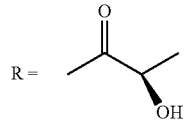
X = O
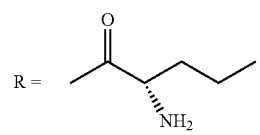
X = O
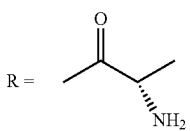
X = O    R = H.
A method of making a didemnin analog is provided comprising the coupling of the didemnin analog having the structure
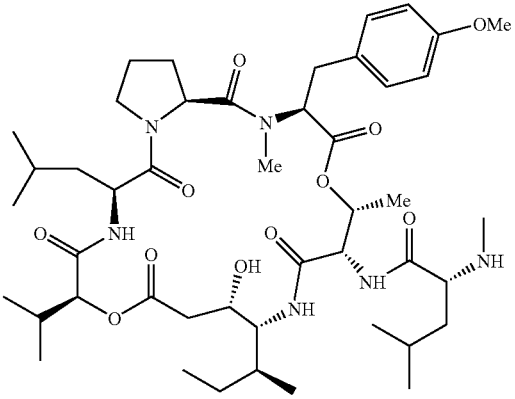
and the fragment having the structure
to yield a didemnin fragment having the structure
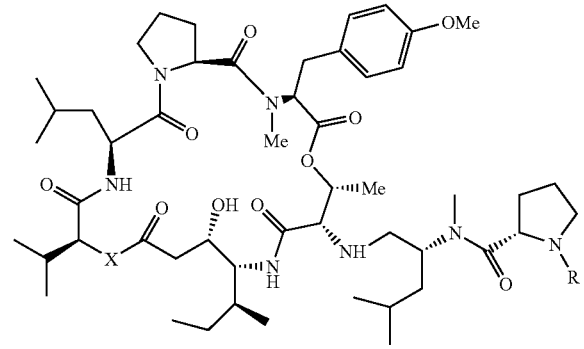

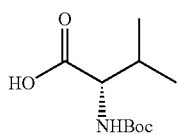

to yield the didemnin analog having the structure

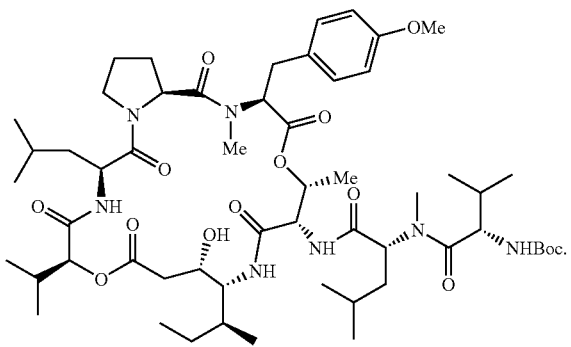

A method further comprises deprotection the didemnin analog

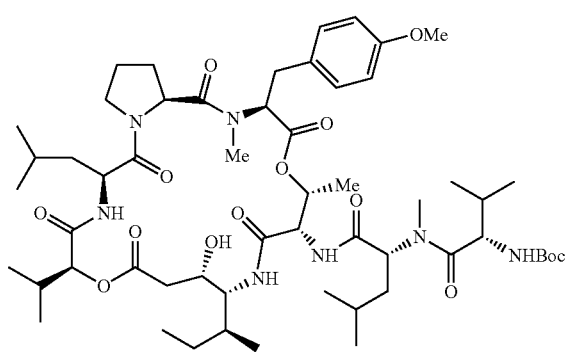

to yield a didemnin analog having the structure

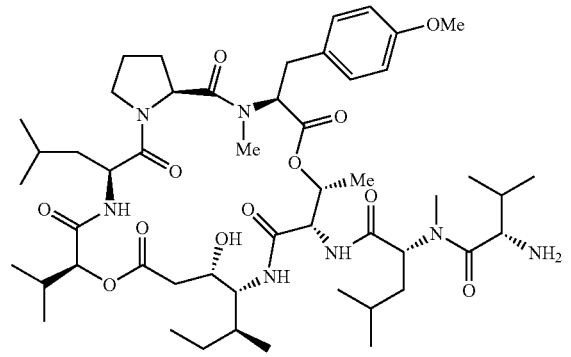

A method is provided of making a didemnin analog comprising the coupling of the didemnin analog

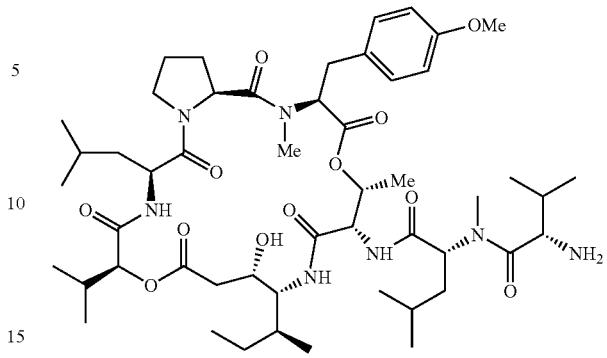

and isobutyryl chloride to yield the didemnin analog having the structure

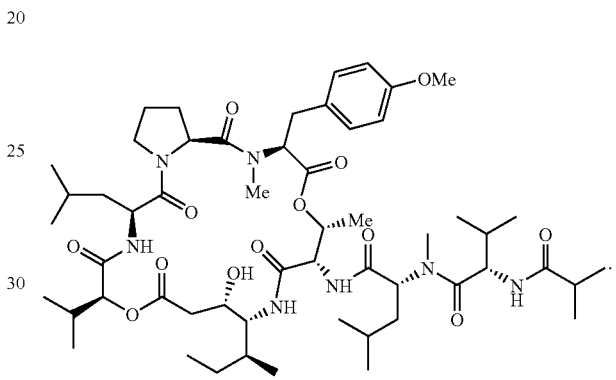

A method of making a didemnin analog is provided comprising the coupling of the didemnin analog having the structure

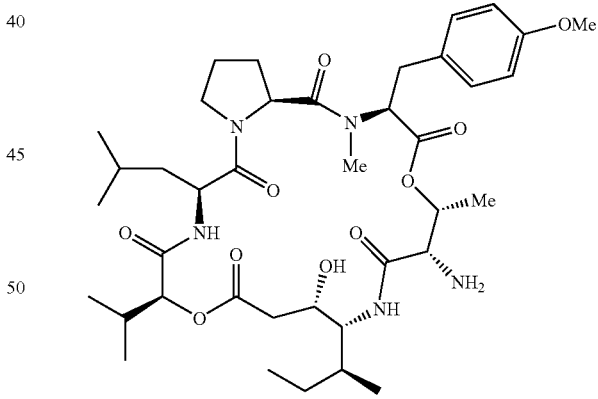

the fragment having the structure

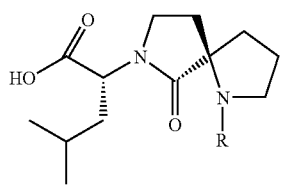

to yield the didemnin analog having the structure

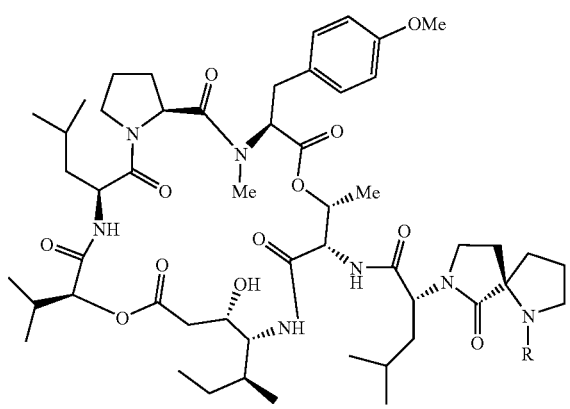

wherein R is Boc, isobutyryl, pyruvyl, or acryloyl.

A method of making a didemnin analog comprises the coupling of the didemnin analog having the structure

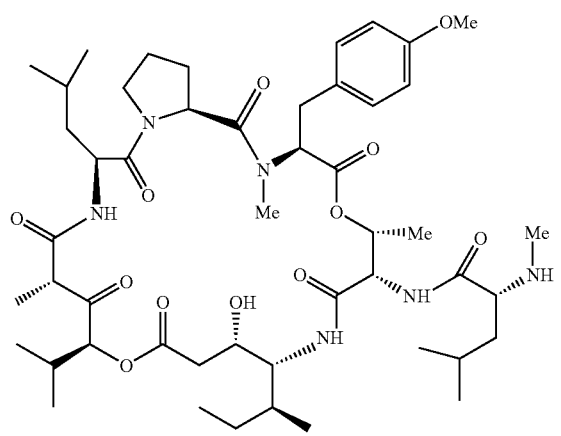

and the fragment having the structure

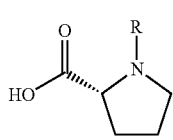

to yield a didemnin analog having the structure

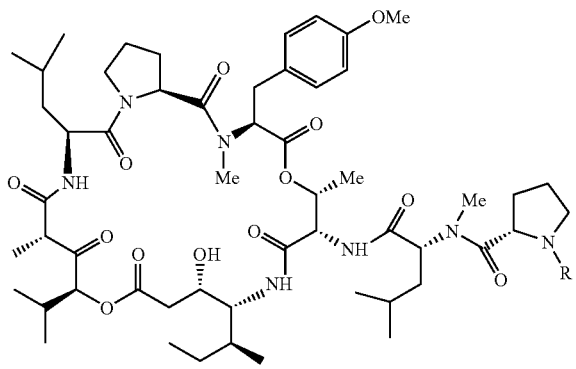

wherein R is SO$_2$Me, or Z-Nva.

A method is provided by this invention comprising deprotection the didemnin analog

to yield a didemnin analog having the structure

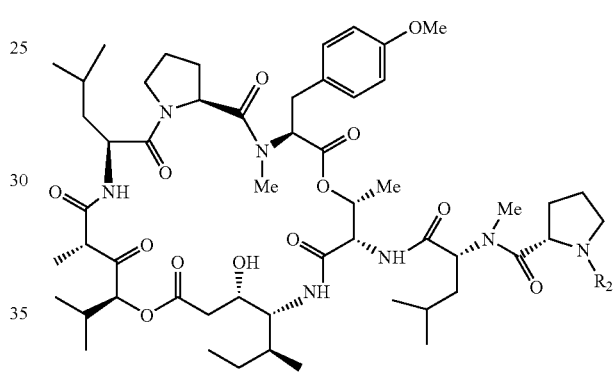

wherein R$_2$ is Nva.

A method of making a didemnin analog is part of this invention, comprising the coupling of the didemnin analog having the structure

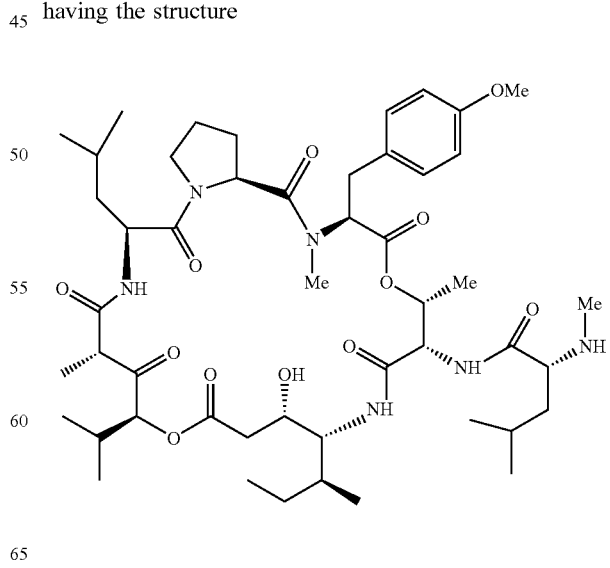

and the fragment having the structure

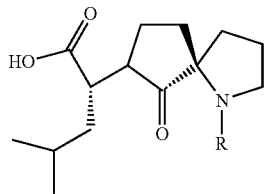
to yield the didemnin analog having the structure
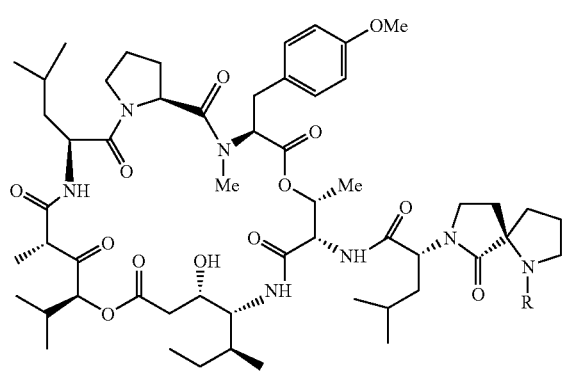
wherein R is Boc, isobutyryl, or pyruvyl.
A method of making a didemnin analog comprises the coupling of the didemnin analog having the structure
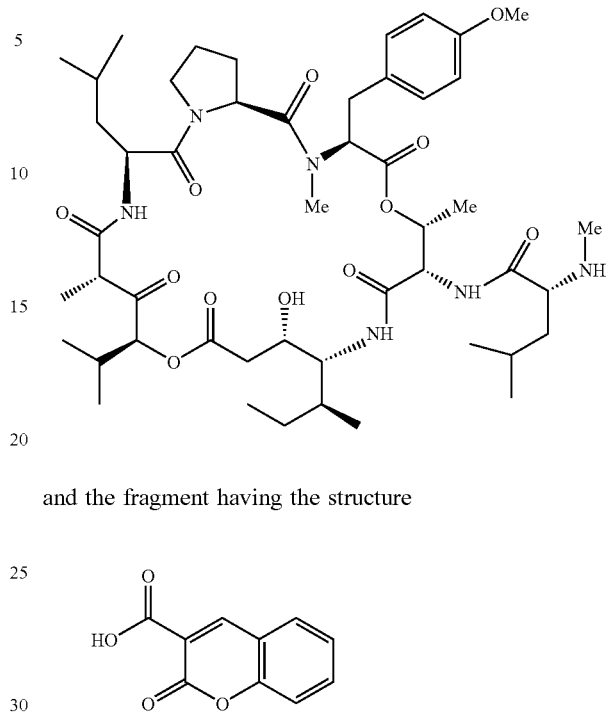
and the fragment having the structure
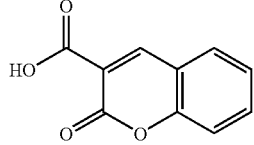
to yield the didemnin analog having the structure
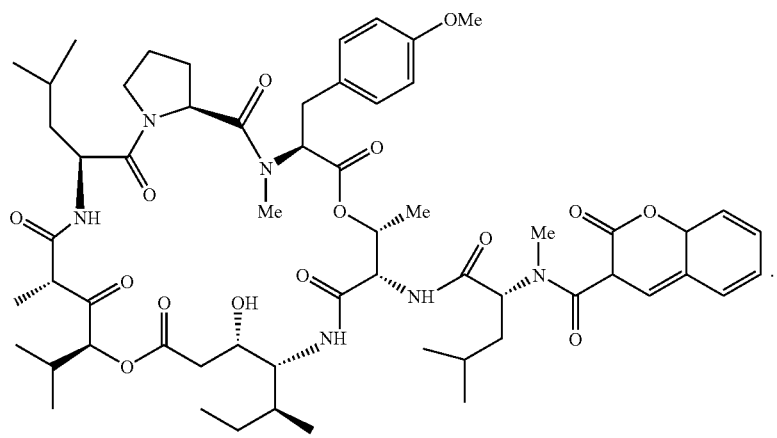

A method of making a didemnin analog is provided comprising the coupling of the didemnin analog having the structure
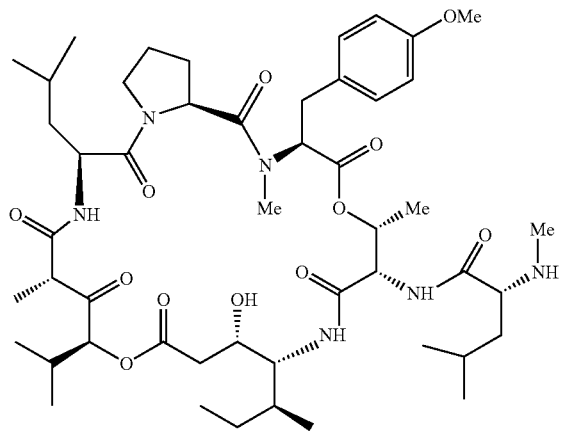
and the fragment having the structure
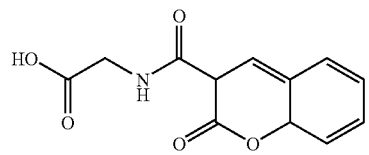
to yield the didemnin analog having the structure
A method of making a didemnin analog comprising the coupling of the didemnin analog having the structure
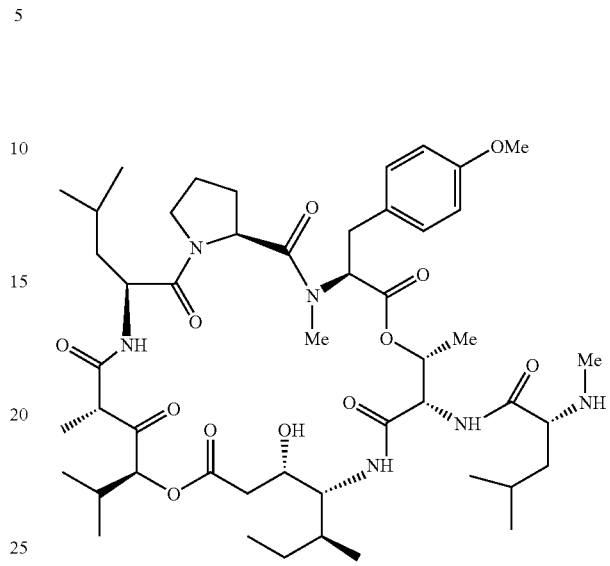
and the fragment having the structure
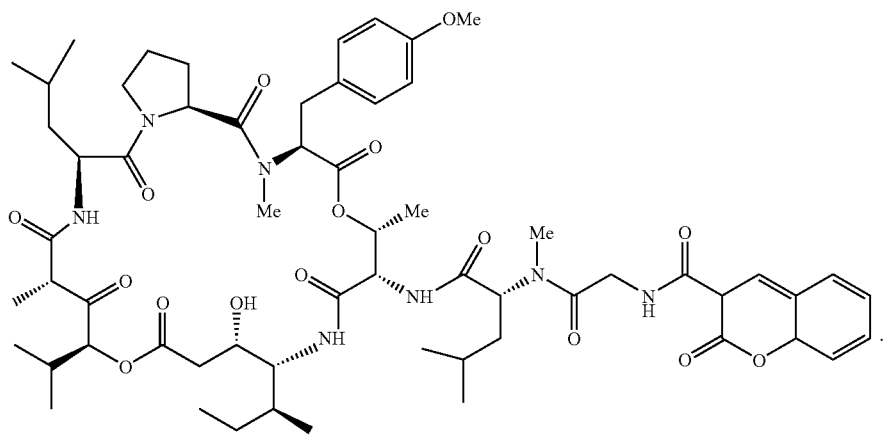

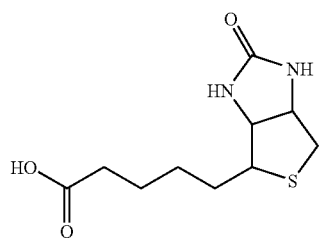
to yield the didemnin analog having the structure
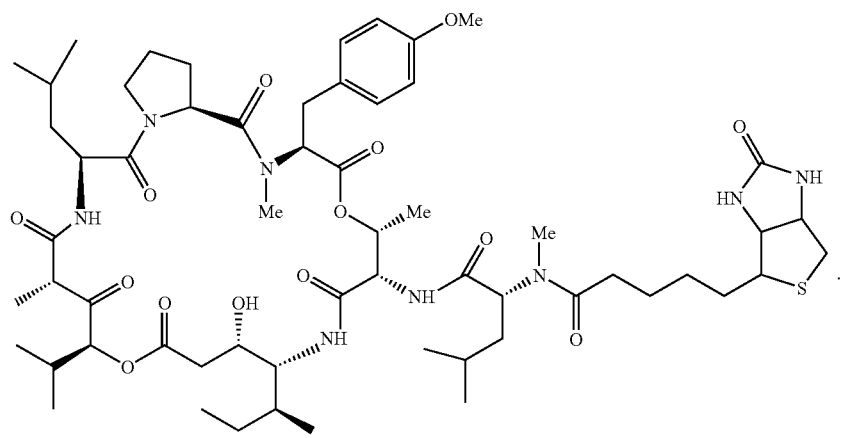
A method of making a didemnin analog is provided comprising the coupling of the didemnin analog having the structure
and methylsulphonyl chloride, to yield the didemnin analog having the structure
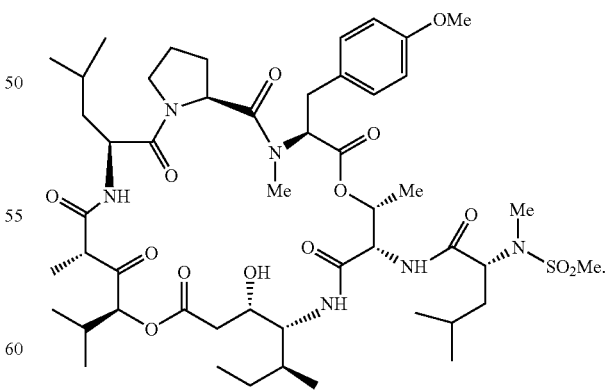
A method of making a didemnin analog comprises the coupling of the didemnin analog having the structure

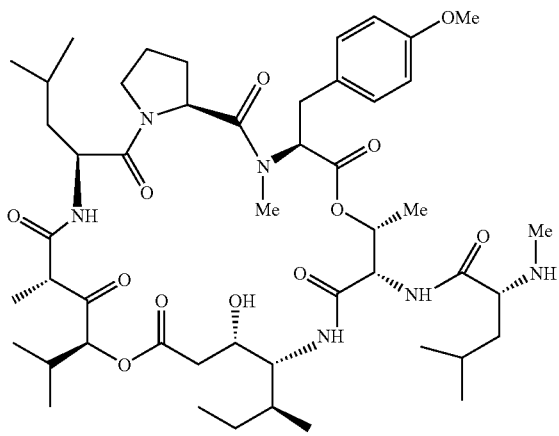

and the fragment having the structure

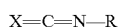

to yield the didemnin analog having the structure

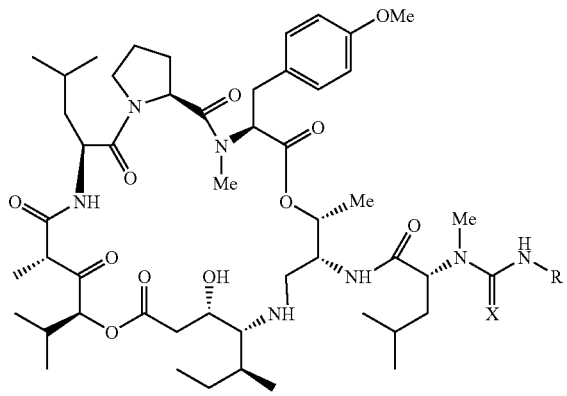

wherein X is O, and S; wherein R is butyl, and phenyl.

It will be appreciated that these methods are all illustrative of the present invention and can be modified as desired. In particular, different protecting groups can be adopted for protection of amino groups or hydroxy groups. Different reagents can be employed to introduce intended groups. The substituents may be varied as desired, with particular regard to the general formula for the compounds of this invention, and the examples of preferred meanings. The modified methods are part of this invention.

To the extent that it may be necessary to ensure that this description includes all of the disclosure in our priority applications, and to ensure entitlement to the full extent to the priority dates, we hereby incorporate by reference the content of our GB 0016148.9 and GB 0103750.6.

DETAILED DESCRIPTION OF THE PREFERRED EMBODIMENTS

The compounds of the present invention can be prepared synthetically. The methods described here for the synthesis of aplidine and derivatives can also be used for the synthesis of a broad range of didemnins.

The structures of some of the compounds are shown in Chart I below:

Chart I

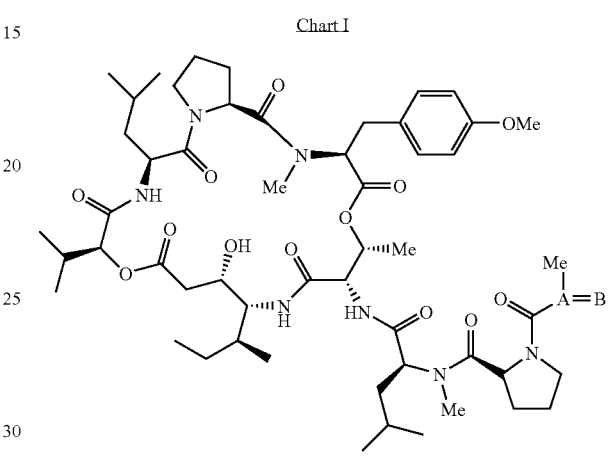

[Hiv]$^3$-aplidine (I), A = C, B = O
Tamandarin A (IV), A = CH (conformation S), B = OH

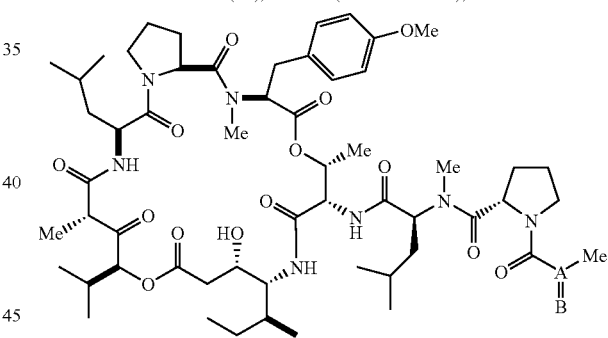

Aplidine (II), A = C, B = O
Didemnin B (III), A = CH (conf. S), B = OH

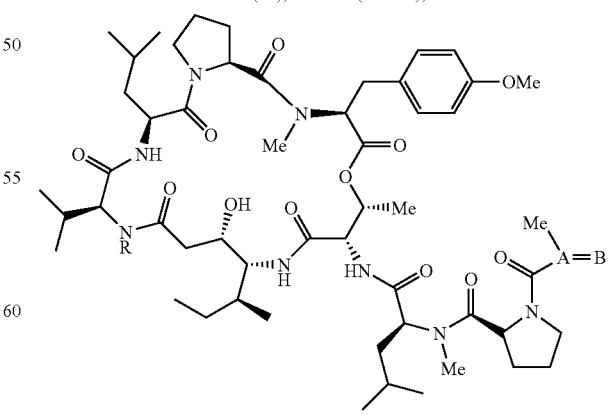

[Val]$^3$-aplidine (V), A = C, B = O, R = H
[MeVal]$^3$-aplidine (IV), A = C, B = O, R = Me

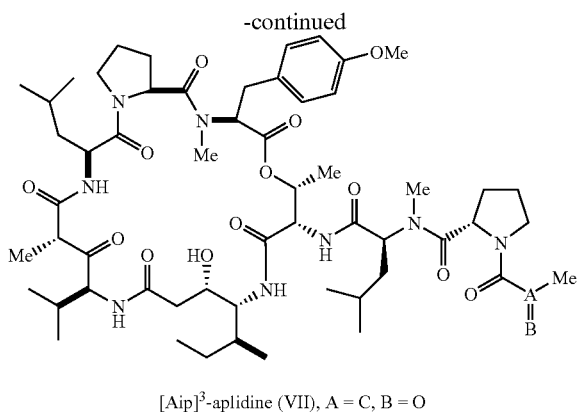

[Aip]³-aplidine (VII), A = C, B = O

Aa3-aplidine derivatives are synthetic cyclic depsipeptides similar in structure to aplidine (compound II) (aa3=Hip, also known as dehydrodidemnin B) which is a natural didemnin isolated from the ascidian *Aplidium albicans* (Chart I). The molecules prepared differs by the presence of hydroxyisovaleric acid (Hiv) (compound I), or valine (compound V) or methyl valine (compound VI) or α-(α'-aminoisovaleryl)propionyl (Aip) (compound VII) instead of the hydroxy-isovalerylpropionic (Hip) (II) unit which is present in all other naturally occurring didemnin congeners. The similarity between these two structures has also been found recently between didemnin B (compound III), the most well-known member of this class of depsipeptides, and a new isolated cyclic depsipeptide from an unidentified Brazilian ascidian of the family Didemnidae: Tamandarine A (compound IV). Compounds I, V, VI and VII are non natural didemnin derivatives.

The structural homology between III and IV is also reflected in their respective biological activity. Comparing both compounds, IV retains similar levels of in vitro antitumor activity in clonogenic assays as well as protein biosynthesis inhibition properties, and it has been shown to be somewhat more active in vitro than III against pancreatic carcinoma. However, compound IV does not show any tumor type specificity whatsoever in NCl 60 cell panel. Didemnin B proved to be toxic at doses near those required for therapeutic applications and it is likely that IV is a broad spectrum toxin rather than a selective agent.

[Hiv]³-aplidine (I) otherwise exhibits the same benefits found in aplidine (II) with respect to didemnin B (III), in that is more specific against solid tumors like colon, chondrosarcoma and osteosarcoma in the MTS assay. [Val]³-aplidine (V) and [MeVal]³-aplidine (VI) are otherwise new compounds which exhibit a high level of in vitro antitumor activity. Finally, compounds V, VI and VII are likely to result, with respect to the parent aplidine, in an increase in hydrogen bonding at the active site, and thus, provide more active compounds. In addition the presence of the amide bond replacing the ester bond may improve the stability of the cyclodepsipeptide core.

We report here the first total synthesis of the different series of aplidine derivatives. By way of example the retrosynthetic analysis is shown in Chart II.

The key steps include an efficient macrocyclization of linear precursors 6, and a practical stereoselective synthesis of Ist-aa3-Leu-Pro unit (A1), and the right fragment D1. Final coupling of the macrocycle 4 with different side chains affords aa3-aa8-aplidine and derivatives. The robustness of this synthetic methodology has been proved successfully in developing a practical synthesis of aplidine II (aa3=Hip).

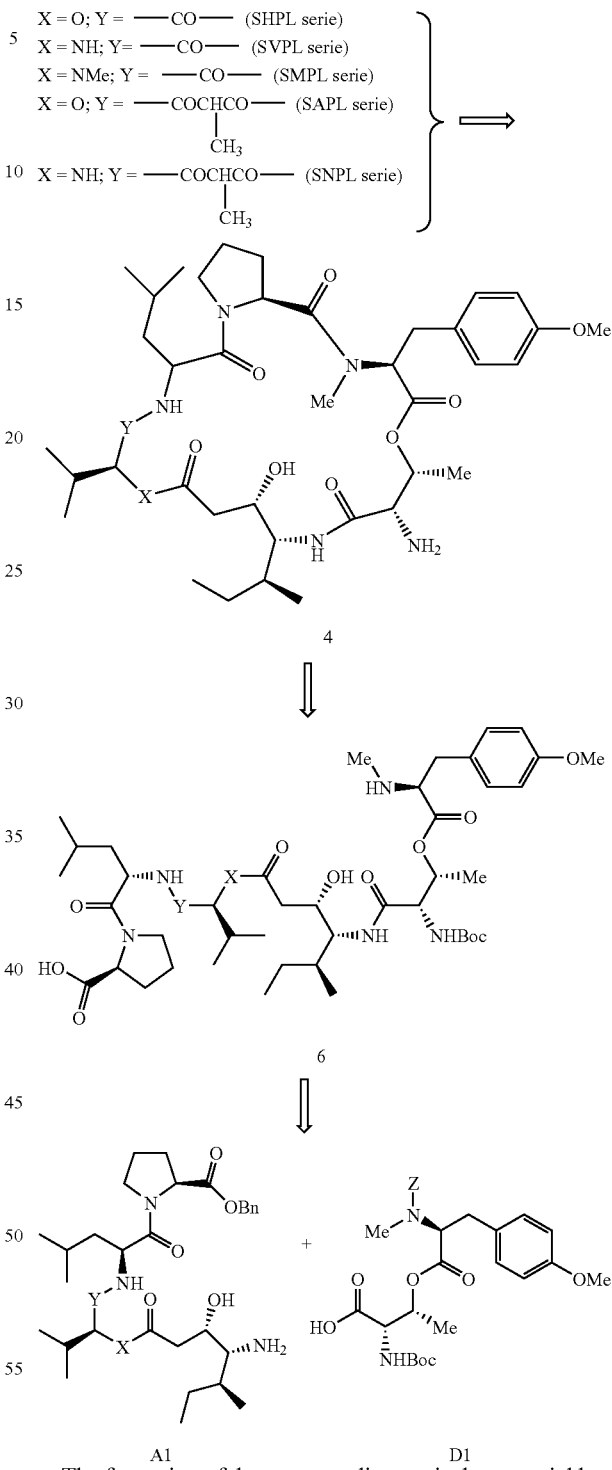

The formation of the macrocyclic core is the essential key step in all series. Successful cyclization at all of the four possible amide bonds has been achieved in previous syntheses of the didemnins. However, in the present work, the bond linking N(Me)-O(Me)-Tyr and Pro was selected as the point for macrocyclization based on previous work developed during the total synthesis of aplidine II (G. Jou, I. Gonzalez, F. Albericio, P. LLoyd-Williams, E. Giralt., *J. Org. Chem.* 1997, 62, 354-366 and patent ES-2102322).

Scheme 1

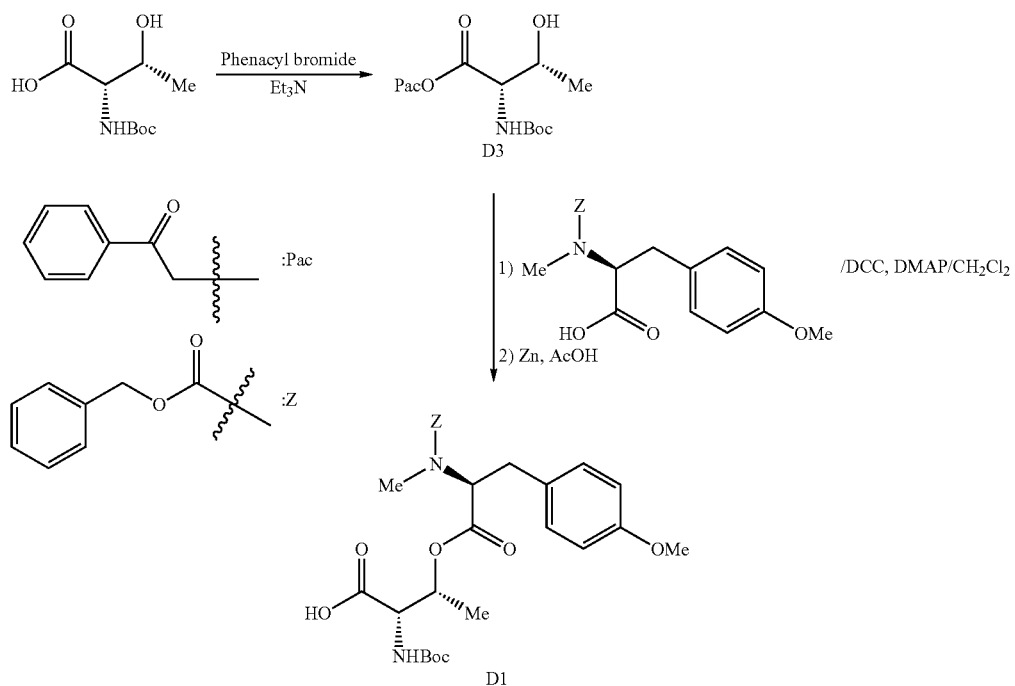

The macrocyclic core of the target molecule is disconnected into Ist-aa3-Leu-Pro tetrapeptide left unit A1 and the dipeptide Boc-Thr-(Z-NMe-OMe-Tyr)-OH D1.

Synthesis of the dipeptide right fragment D1 has been already described. However the synthesis outlined in Scheme 1 allows the preparation of this intermediate on a kilogram scale. The acid function of Boc-Thr(OH)-OH was protected with phenacyl bromide to gave directly alcohol D3, which was esterified with Z-N(Me)-O(Me)-Tyr-OH using DCC in the presence of DMAP giving D2. Removal of the phenacyl group with Zn in acetic acid afforded cleanly fragment D1.

The formation of precursor A1 is outlined in Scheme 2 for the different series. For the SHPL, SVPL and SMPL series, the first coupling step between Leu-Pro-OBzl (A5) and commercially available acid (B1) gave directly alcohol A3 ready for the next reaction with isostatine (C1). For the synthesis of SAPL and SNPL series, the route differs to that previously described in that B1 is a β-ketoester synthesized from α-(α'-hydroxyiso-valeryl)propionic and α-(α'-aminoisovaleryl)propionic acid respectively. The synthesis of the fragment B2 (SAPL and SNPL series) is outlined in scheme 3. Hydrogenolisis from B2 to B1 is achieved just before the (one pot) coupling reaction with A5.

Scheme 2

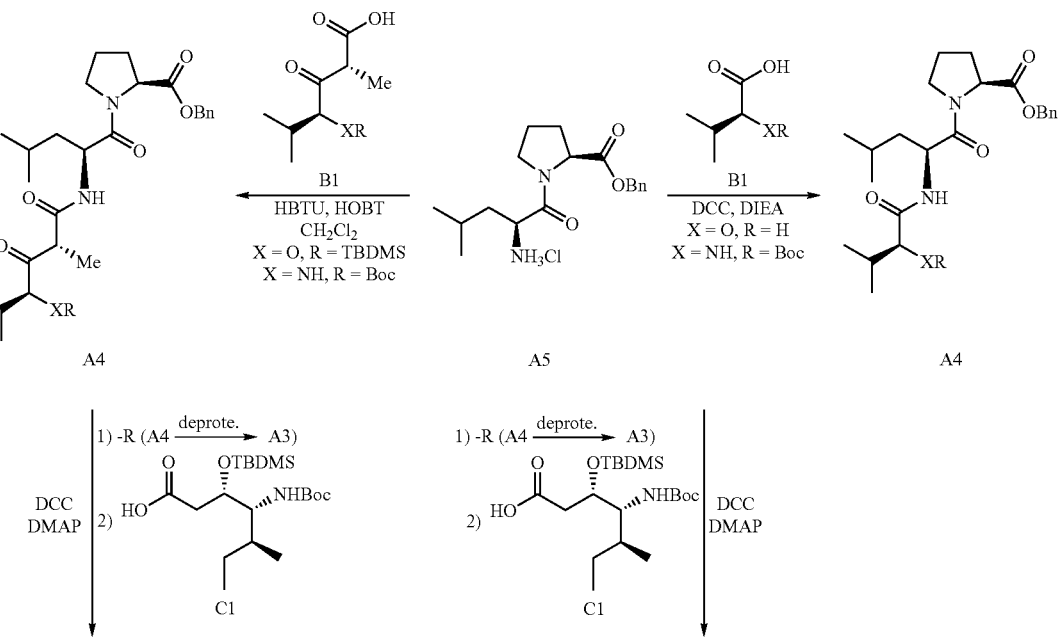

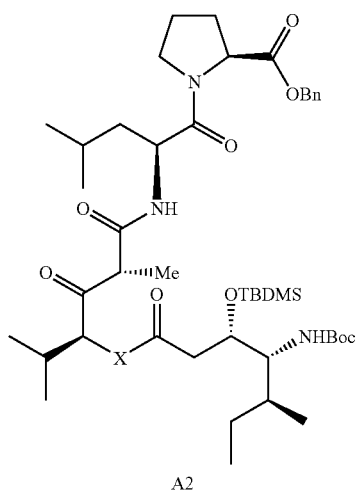
A2
↓ HCl (g)
  Dioxane
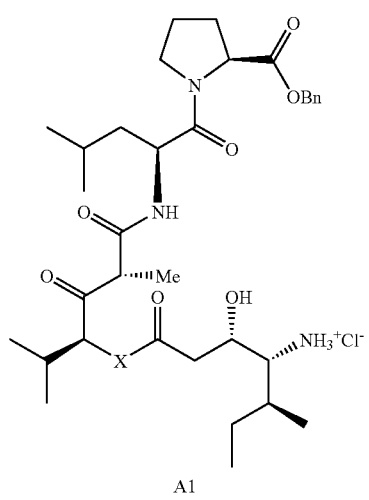
A1
SAPLA1 serie, X = O
SNPLA1 serie, X = NH
Scheme 3
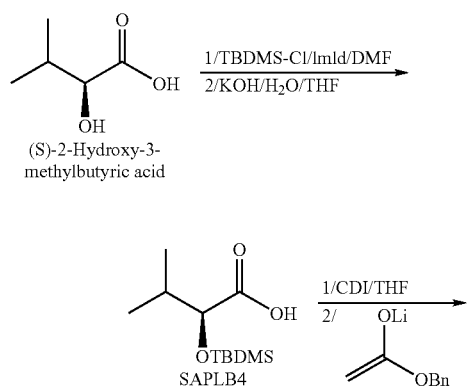
-continued
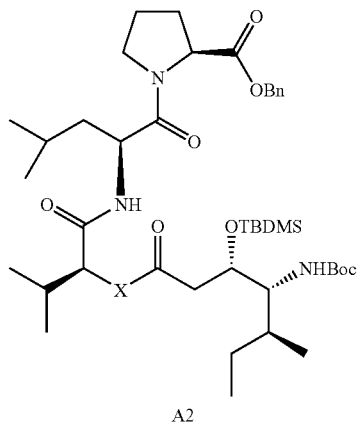
A2
↓ HCl (g)
  Dioxane
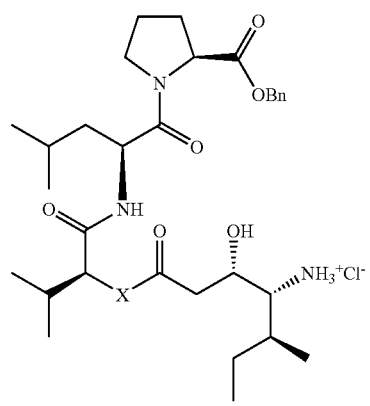
A1
SHPLA1 serie, X = O
SVPLA1 serie, X = NH
SMPLA1 serie, X = NMe
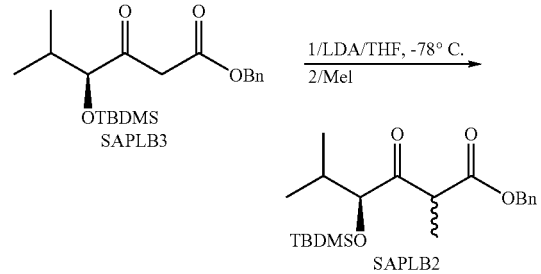
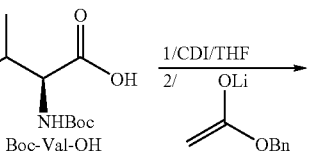

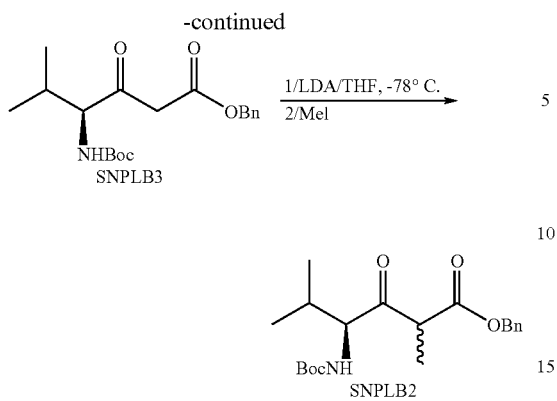

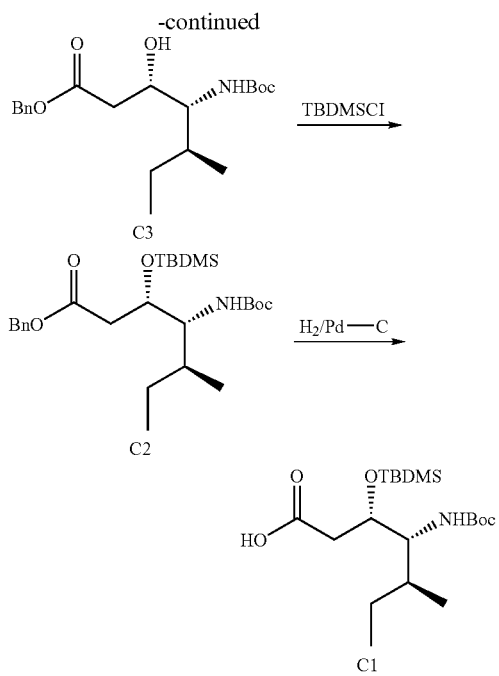

The preparation of the entire fragment A1 rely on the availability of the isostatine portion which has been prepared from the non proteinogenic amino protected Boc-D-alloisoleucine (C5) on large quantities. The synthetic route for the preparation of C1 is outlined in Scheme 4.

Activation of the carboxylic functionality of Boc-D-allo-Ile with carbonyldiimidazol followed by condensation with the lithium enolate of the benzyl acetate, gave the β-ketoester (C4). Stereoselective reduction with KBH$_4$ in methanol gave C3. Protection of the secondary hydroxyl group as the TBDMS ether (C2) and hydrogenolysis of the resulting benzyl ester afforded isostatine (C1).

Scheme 4

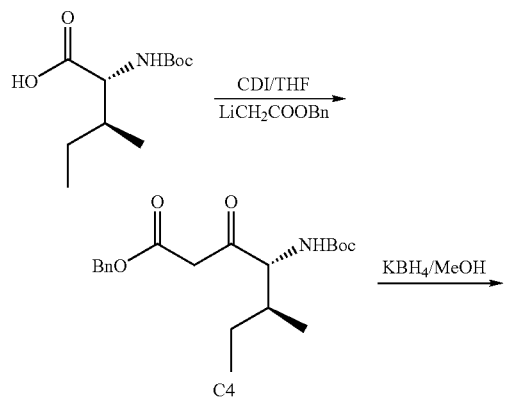

Subsequent steps yielding compounds I, II, V, and VII are depicted in scheme 5.

Coupling of fragments A1 and D1 with HBTU/HOBt afforded the linear precursor type 7. Hydrogenolysis of Cbz and Benzyl protecting groups proceeds out cleanly and smoothly with Pd(OH)$_2$ to give 6. Macrocyclization step using HATU/HOAt afforded intermediate 5 in good yield (75%). Hydrogen chloride in dioxane was used to cleave Boc protecting group affording amine 4. This compound was coupled with Z-NMe-D-Leu-OH to give 3, which was subjected to hydrogenolysis with Pd—C. The resulting compound 2 was coupled with Pyr-Pro-OH side chain using DIPCDI to afford the corresponding compounds.

Interestingly, precursors of type 2 which are analogs in all aspects mentioned earlier, to didemnin A have served as starting building blocks for the synthesis of some interesting congeners, since the N-terminus, a free secondary amino group, offers a site to attach various acyl groups to the cyclic depsipeptide.

Scheme 5

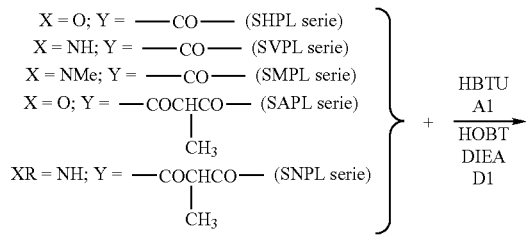

-continued
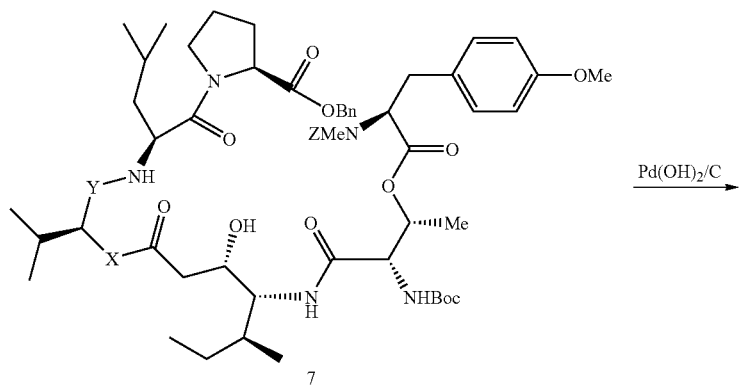
7
Pd(OH)₂/C →
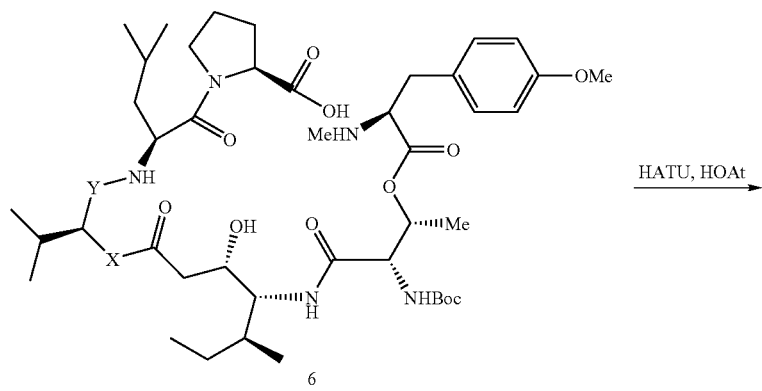
6
HATU, HOAt →
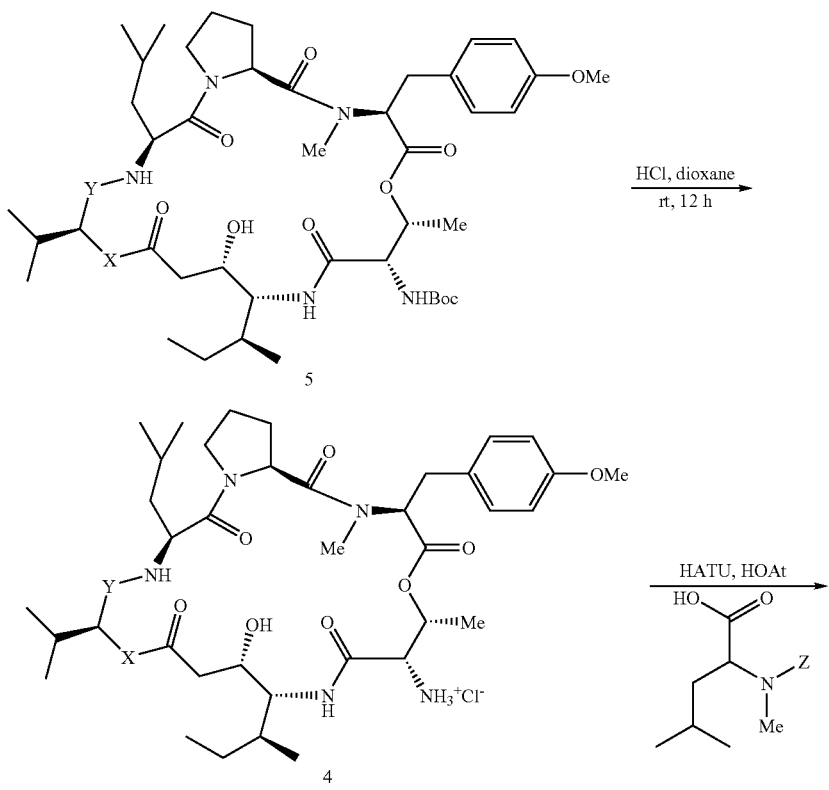
5
HCl, dioxane
rt, 12 h →
4
HATU, HOAt →

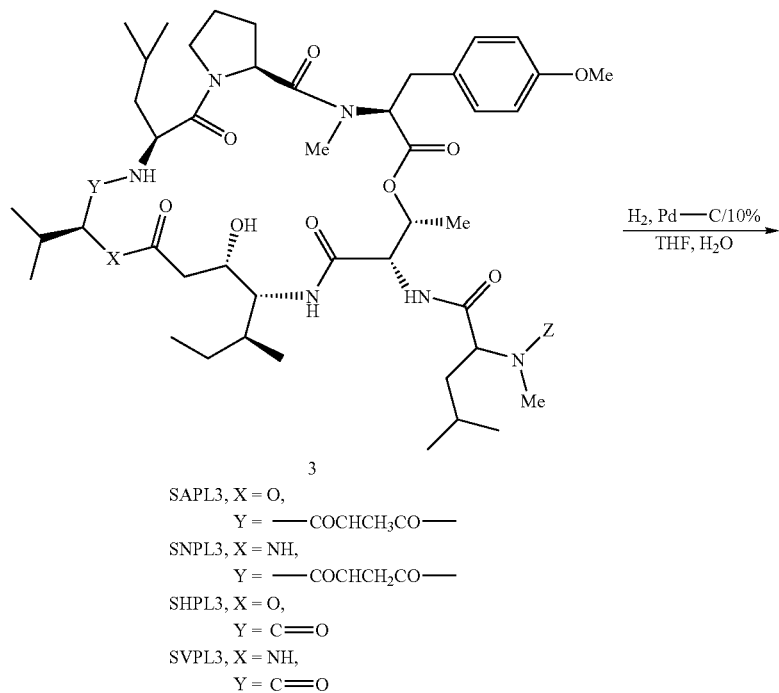
3
SAPL3, X = O,
 Y = —COCHCH₃CO—
SNPL3, X = NH,
 Y = —COCHCH₂CO—
SHPL3, X = O,
 Y = C=O
SVPL3, X = NH,
 Y = C=O
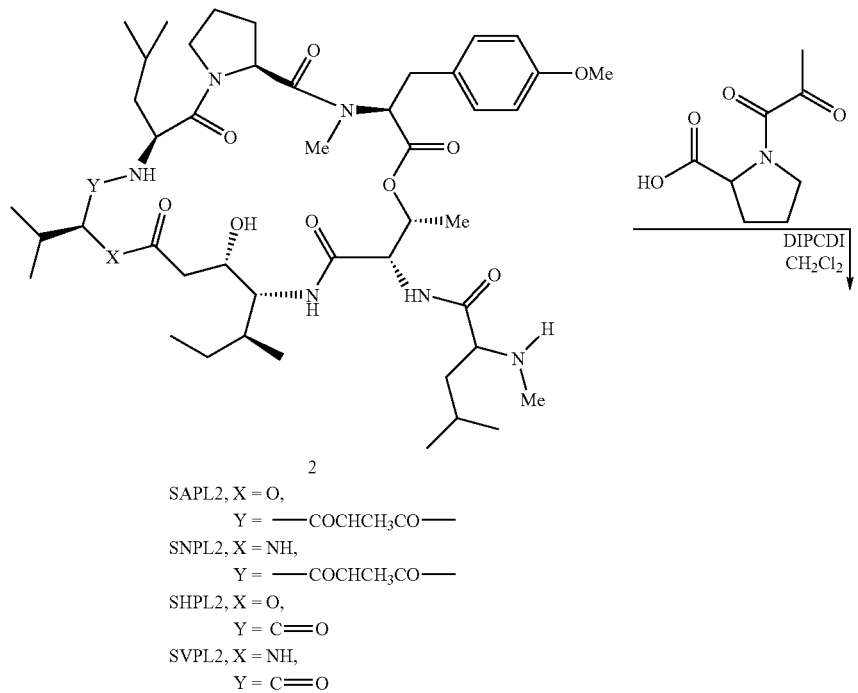
2
SAPL2, X = O,
 Y = —COCHCH₃CO—
SNPL2, X = NH,
 Y = —COCHCH₃CO—
SHPL2, X = O,
 Y = C=O
SVPL2, X = NH,
 Y = C=O

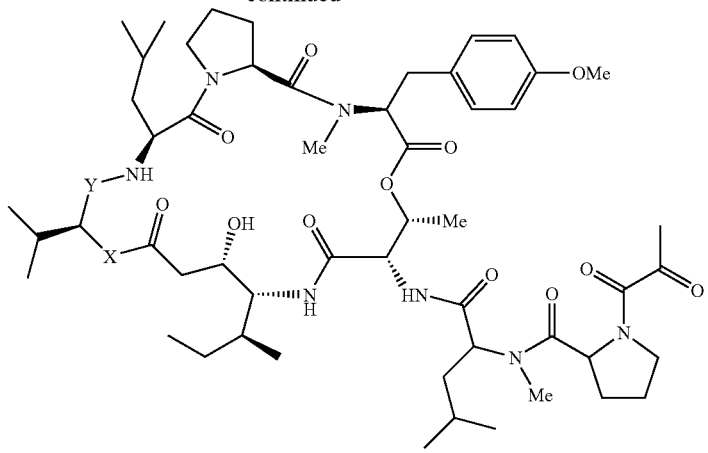

I, II, V, VII
I (SHPL1), X = O,
   Y = C=O
II (SAPL1), X = O,
   Y = —COCHCH₃CO—
V (SVPL1), X = NH,
   Y = C=O
VII (SNPL1), X = NH,
   Y = —COCHCH₃CO—

In an earlier study (Rinehart et al *J. Med. Chem*, 1996, 39, 2819-2834) acyl derivatives of didemnin A (dA) 3 were have also found active as the parent compounds 2. For the aa3 series we found also activity in compounds 3

TABLE 1

Cytotoxicity of [aa3]-aplidine Congeners IC$_{50}$(Molar)

| Compound/Serie | P388 | A549 | HT29 | MEL28 | DU145 |
|---|---|---|---|---|---|
| Aplidine (II)/SAPL1 | 1.80E−10 | 1.80E−10 | 4.50E−10 | 4.50E−10 | |
| [Hiv]³-aplidine(I)/SHPL1 | 4.74E−10 | 4.74E−10 | 4.74E−10 | 4.74E−10 | |
| [Val]³-aplidine(V)/SVPL1 | 1.13E−10 | 1.13E−10 | 1.13E−10 | 1.13E−10 | |
| [Alp]³-aplidine(VII)/SNPL1 | | 9.01E−10 | 9.01E−10 | | |

Methodology: after Berjeron et al, Biochem and Bioph Res. Comm., 1984, 121, 3, 848-854.

P388=Murine lymphoma. A549=human lung carcinoma. HT-29=human colon carcinoma. MEL-28=human melanoma. DU145=human prostate carcinoma

TABLE 2

IC$_{50}$ (Molar) values for the Aplidine Family

| | Line | Didemnin B 9LSAPL1 III | Aplidine SAPL1 II | [Hiv]³-Aplidine SHPL1 I |
|---|---|---|---|---|
| Solid Tumors | | | | |
| Bladder | 5637 | 2.50E−08 | 3.59E−08 | 9.02E−08 |
| Breast | MX-1 | 1.54E−06 | 1.67E−07 | N/A |
| Colon | HT-29 | 8.07E−08 | 6.87E−07 | 1.02E−08 |
| Gastric | Hs746t | 6.60E−09 | 2.52E−08 | 7.16E−08 |
| Liver | SK-HEP-1 | 9.21E−08 | 9.44E−08 | 2.65E−07 |
| NSCL | A549 | 1.21E−04 | 2.40E−05 | N/A |
| Ovary | SK-OV-3 | 1.63E−07 | 7.20E−08 | — |
| Pancreas | PANC-1 | 1.52E−10 | 1.7E−07 | — |
| Pharynx | FADU | 9.79E−08 | 7.29E−08 | 3.71E−08 |

TABLE 2-continued

IC$_{50}$ (Molar) values for the Aplidine Family

| Line | | Didemnin B 9LSAPL1 III | Aplidine SAPL1 II | [Hiv]$^3$-Aplidine SHPL1 I |
|---|---|---|---|---|
| Prostate | PC-3 | 9.00E−08 | 5.13-07 | — |
| Prostate | DU-145 | — | — | N/A |
| Prostate | LNCAP | — | — | 1.46E−08 |
| Renal | 786-O | 2.90E−07 | 8.31E−08 | — |
| SCL | NCI-H187 | — | — | N/A |
| Retinoblastoma | Y-79 | — | — | — |
| Melanoma | Mel-28 | — | — | 4.86E−07 |
| Fibrosarcoma | SW 694 | 3.28E−06 | 1.49E−06 | N/A |
| Chondrosarcoma | CHSA | — | — | 3.45E−09 |
| Osteosarcoma | OSA-FH | — | — | 5.89E−09 |
| Leukemias/Lymphomas | | | | |
| ALL (Promyelocytic leukemia) | HL-60 | 1.44E−07 | 7.89E−08 | N/A |
| ALL (Acute lymphobalstic) | Molt 3 | 5.45E−07 | 5.95E−07 | 1.77E−08 |
| CML (Chronic myelogenous) | K562 | 3.31E−06 | 5.72E−07 | 5.21E−07 |
| ALL (B-cell) | CCRF-SB | 6.55E−07 | 4.72E−07 | — |
| Leukemia (Hairy B-cell) | Mo-B | — | — | — |
| Leukemia (Plasma cell) | ARH-77 | — | 1.78E−07 | — |
| Lymphoma (T cell) | H9 | 2.13E−07 | 5.25E−07 | N/A |
| Lymphoma (Cutaneous T cell) | Hut 78 | 3.56E−08 | 4.47E−08 | — |
| Lymphoma (undifferentiated) | MC116 | 8.84E−09 | 9.21E−07 | 3.82E−07 |
| Lymphoma (Burkitts B cell) | RAMOS | — | — | — |
| Lymphoma (Histiocytic) | U-937 | 1.87E−07 | 5.62E−07 | — |
| Lymphoma (B cell) | MoB | — | — | — |
| Lymphoma (Burkitts ascites) | P3HR1 | 5.58E−08 | 5.34E−08 | — |
| Methodology: | | MTT | MTT | MTS (new) |

N/A = not active

Compounds prepared herein are shown in Schemes 5 and 6. These compounds include N$^\alpha$-propionyl-[aa]$^3$-dA, N$^\alpha$-butyryl-[aa]$^3$-dA, N$^\alpha$-isobutryl-[aa]$^3$-dA, and N$^\alpha$-pentanoyl-[aa]$^3$-dA.

Analogs which have two acyl subunits after the N-terminus of the aa3-dA core were prepared to examine the structural factors contributing to the specificity to certain tumors. The diacyl compounds isobutyryl Pro-OH, O-isobutyryl-Lac-Pro-OH, N-Benzyl-Ala-Pro-OH were prepared and condensed with type 2 compounds by the DIPCDI method to obtain respectively, after deprotection and purification, [aa]-$^3$[isobutyryl]$^9$-aplidine, [O-isobutyryl-Lac]$^9$-aplidine, [Ala]$^9$-aplidine.

Preferred Aplidine derivatives: Compounds from Series: H, V

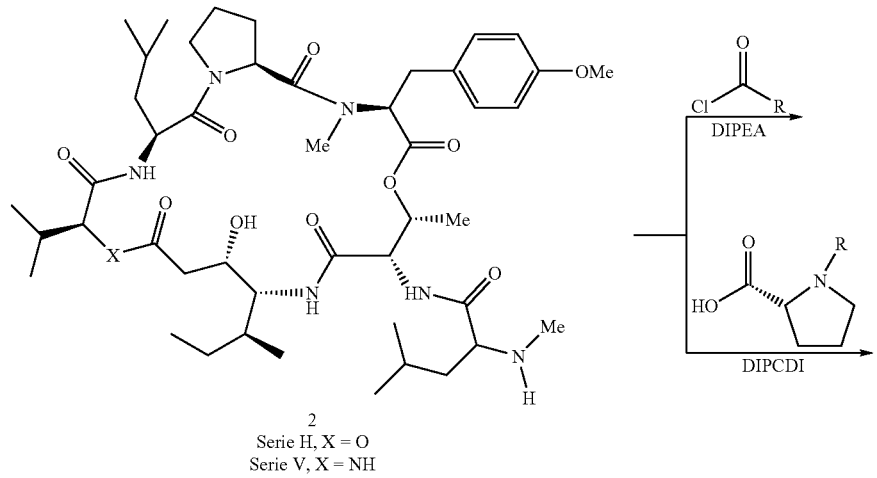

2
Serie H, X = O
Serie V, X = NH

-continued
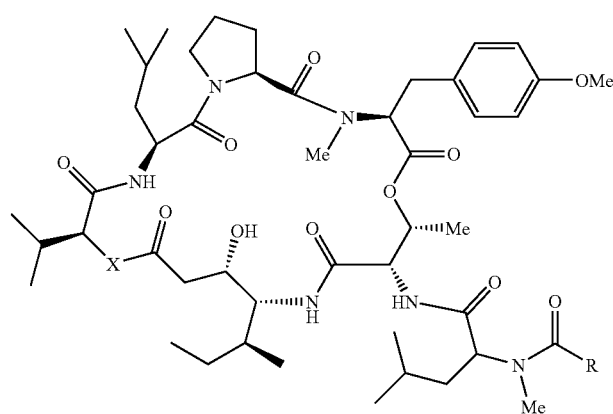
8ISHPL1, X = O, R = iPr
8BSHPL1, X = O, R = nPr
8HSHPL1, X= O, R = nPentyl
8ISVPL1, X = NH, R = iPr
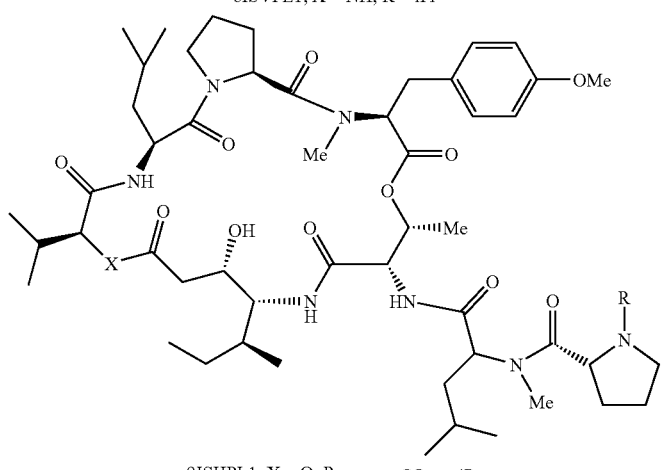
9ISHPL1, X = O, R = —CO—iPr
9ISVPL1, X = NH, R = —CO—iPr
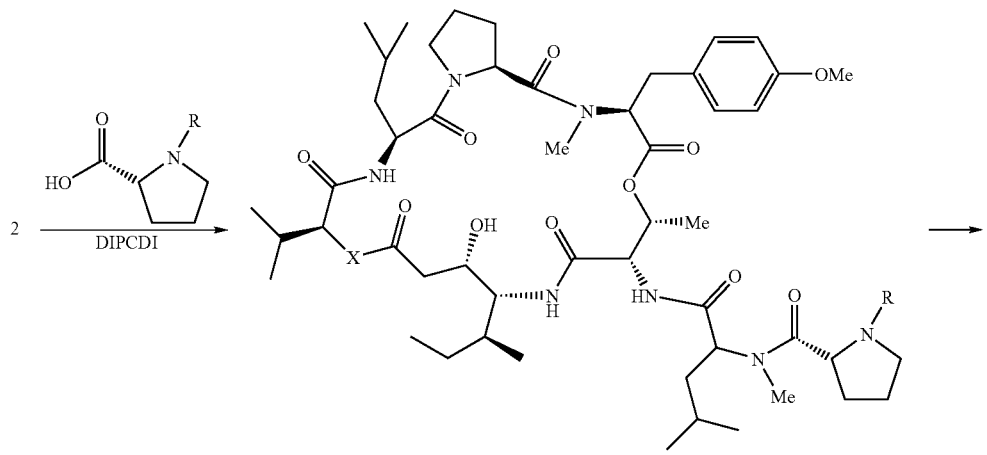

-continued
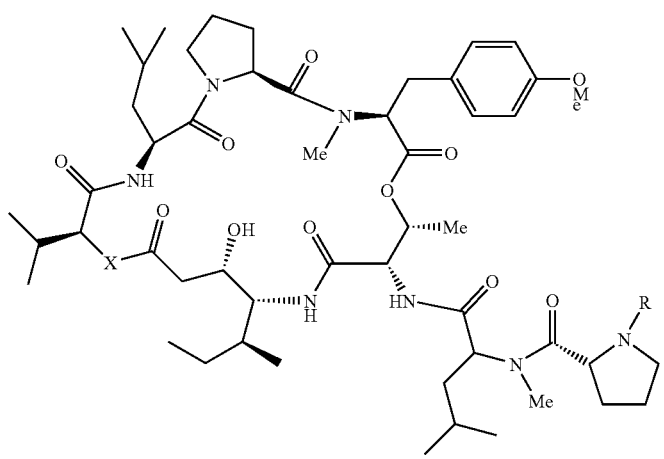
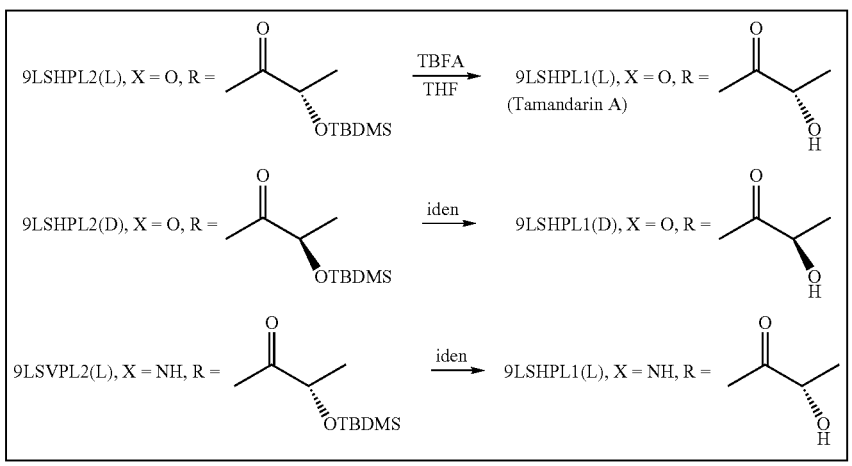
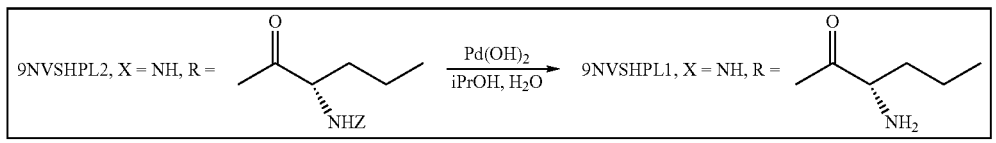
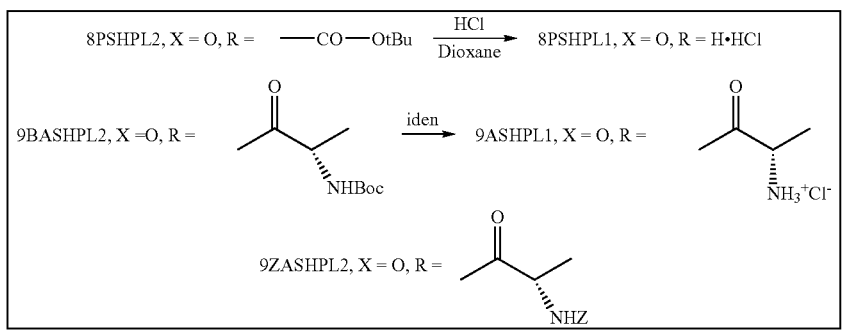

-continued
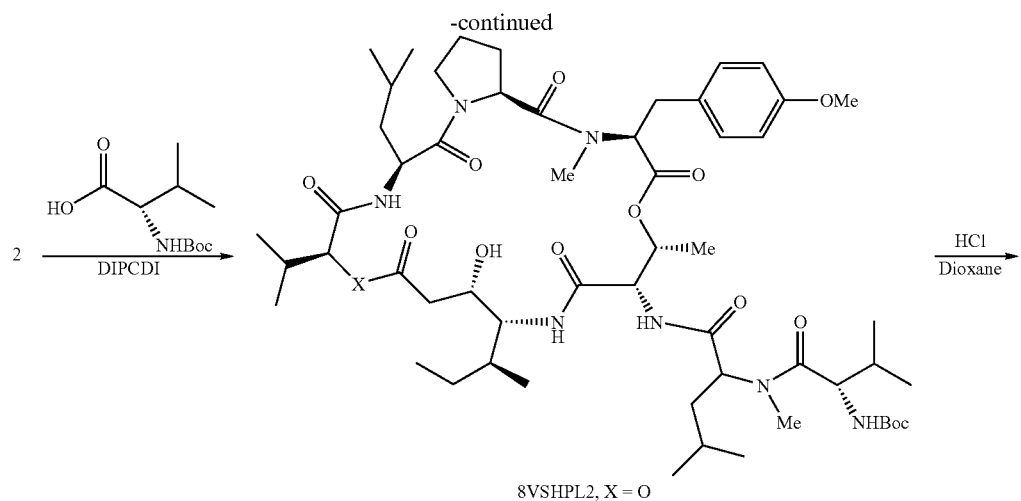
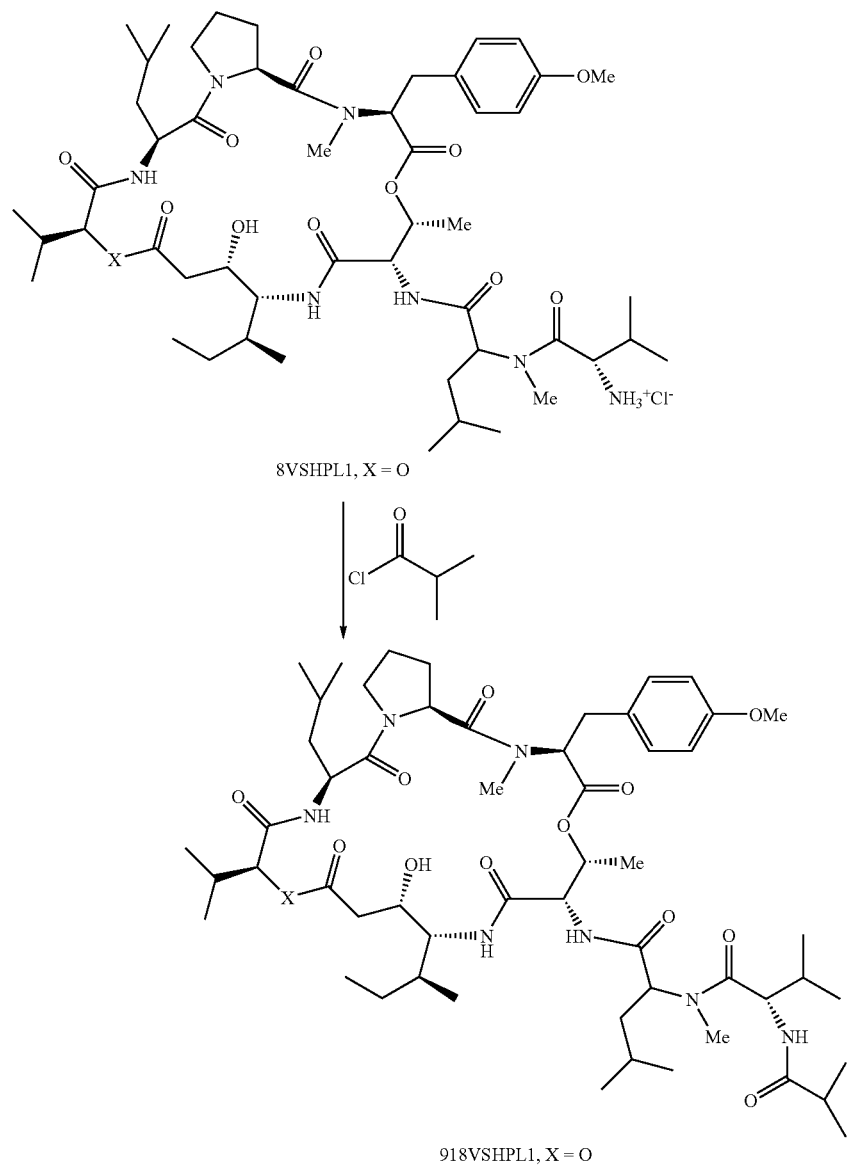

Spirocompounds were also linked to form active compounds:
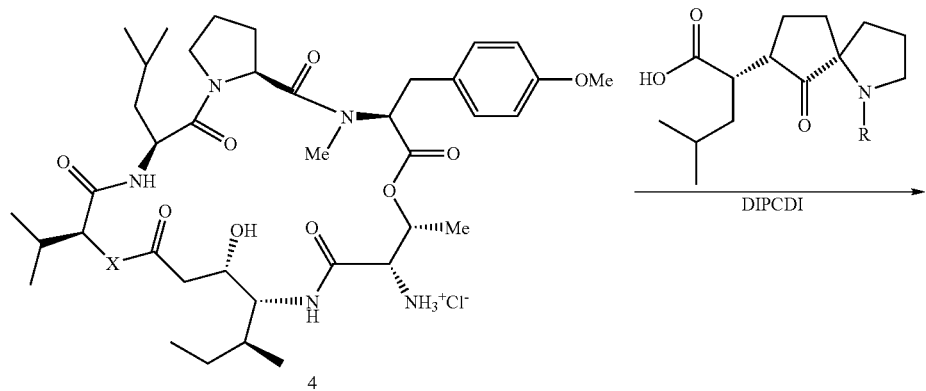
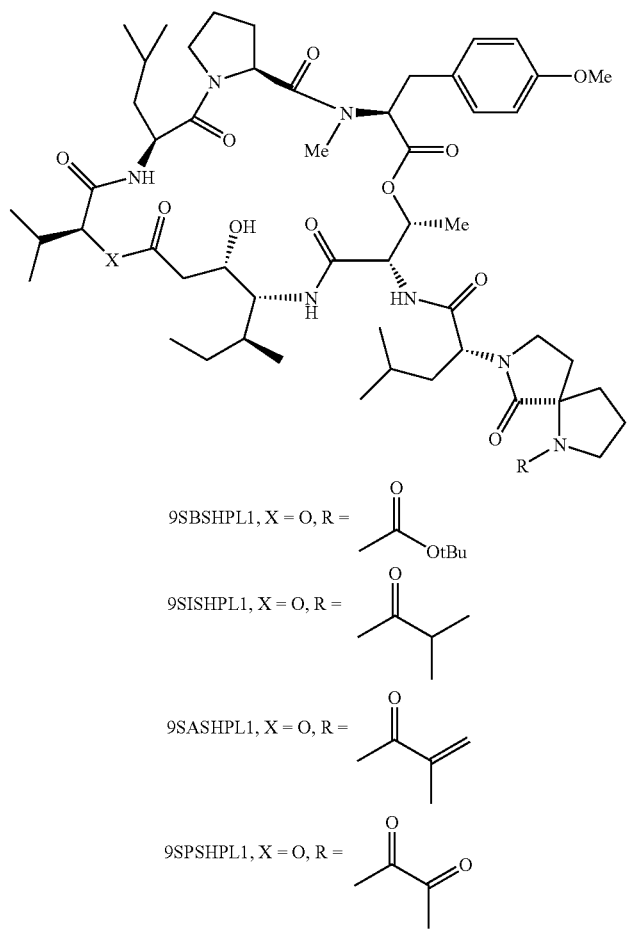

The spirocyclic fragments synthesis is outlined in scheme 7. The synthesis started from the previously reported compound 8. Ref: a) Seebach, D. et al. *J. Am. Chem. Soc.* 1983, 105, 5390-5398. b) Genin, M. J. et al. *J. Org. Chem.* 1993, 58, 2334-2337.
Scheme 7
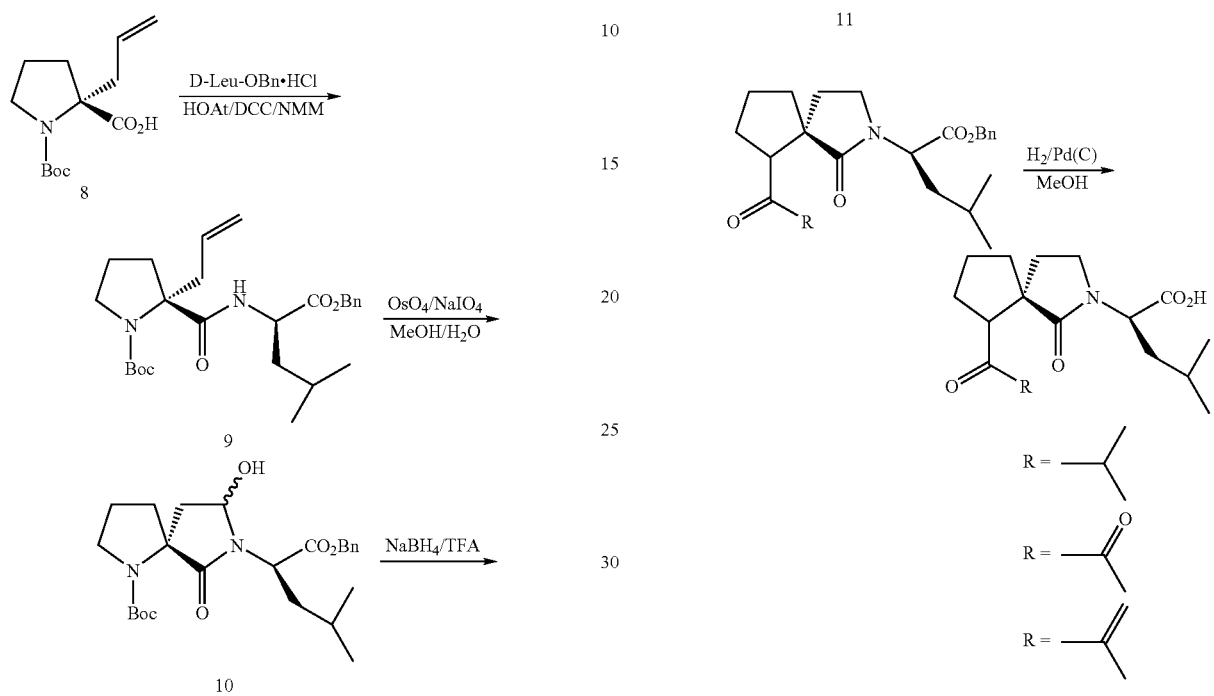
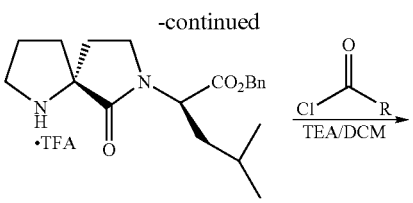
Preferred Aplidin derivatives: Compounds from Seri A
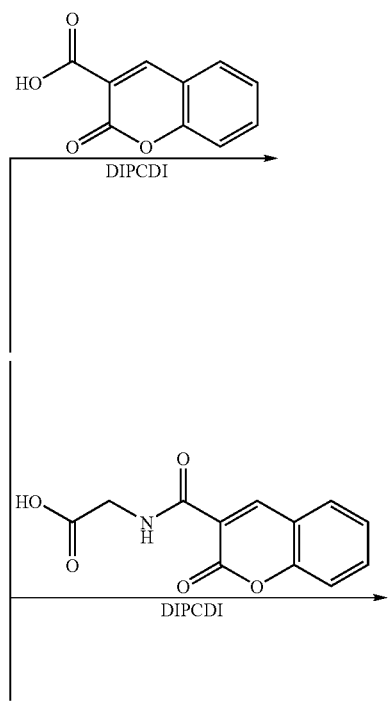

-continued
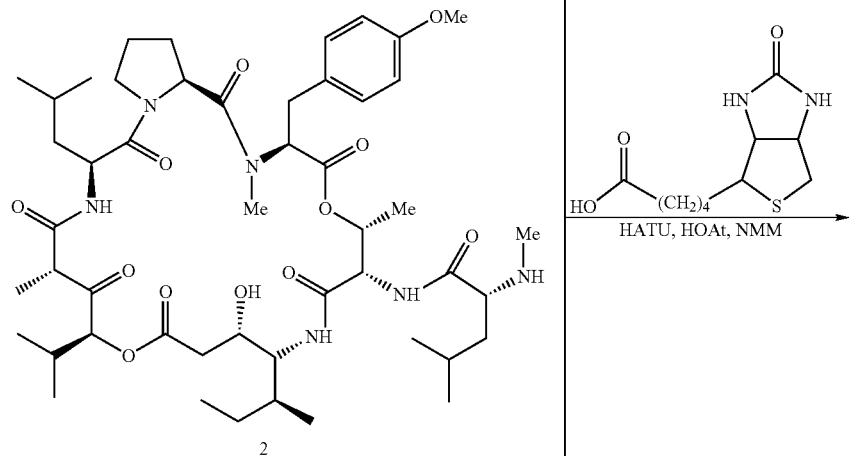
| DIPCDI |
| MeSO₂Cl |
X=C=N—R
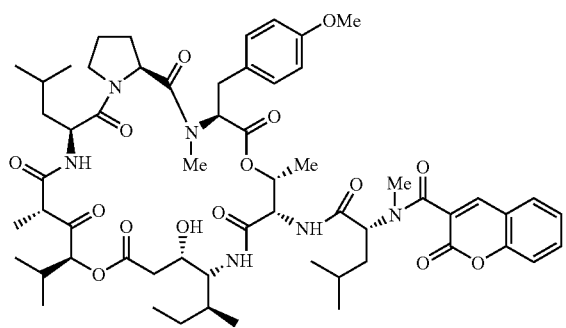
8CAPL1

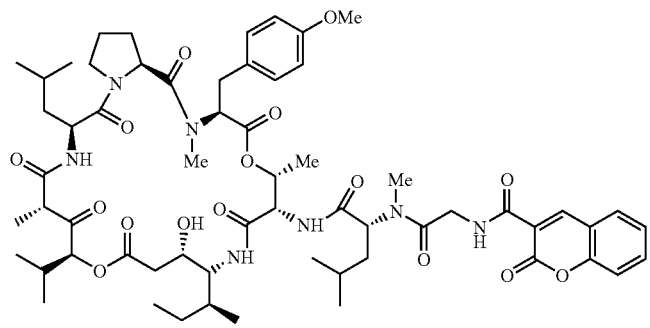
8G9CAPL1
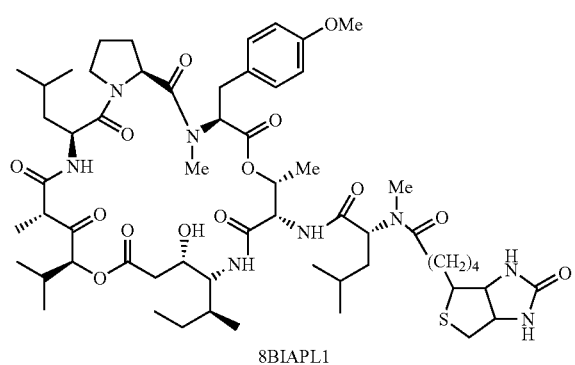
8BIAPL1
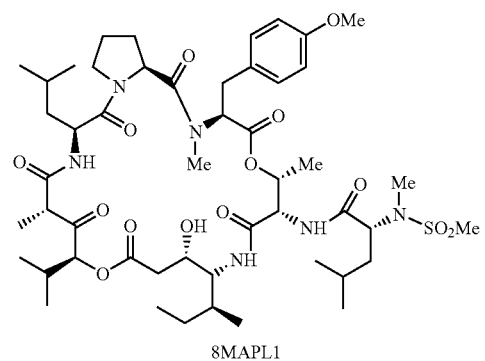
8MAPL1
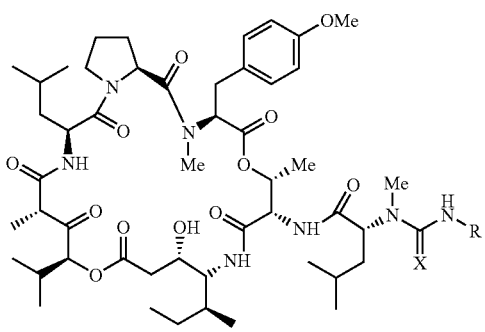
8PUAPL1, X = O, R = Ph
8BUAPL1, X = O, R = Bu
8PTAPL1, X = S, R = Ph
8BTAPL1, X = S, R = Bu

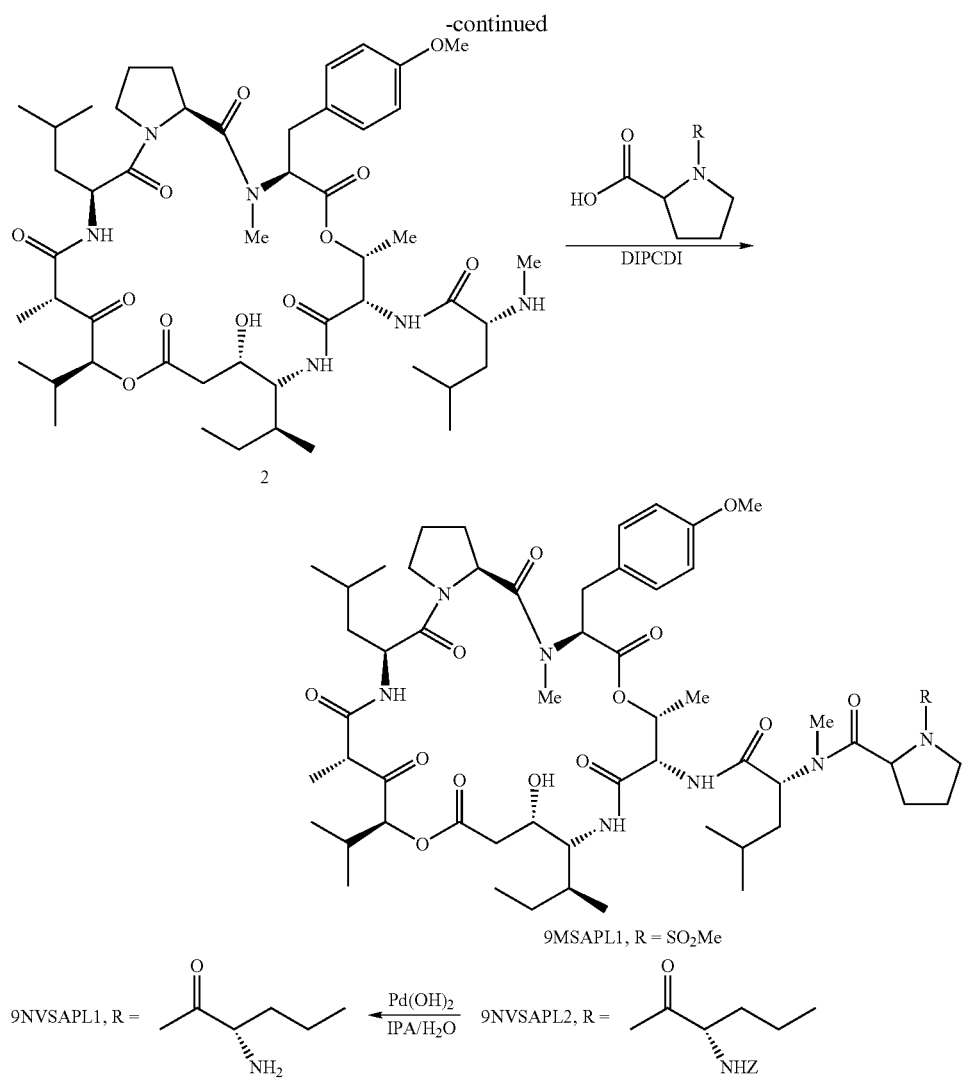
Spiro compounds also linked as in the previous series to give active compounds:
Scheme 8
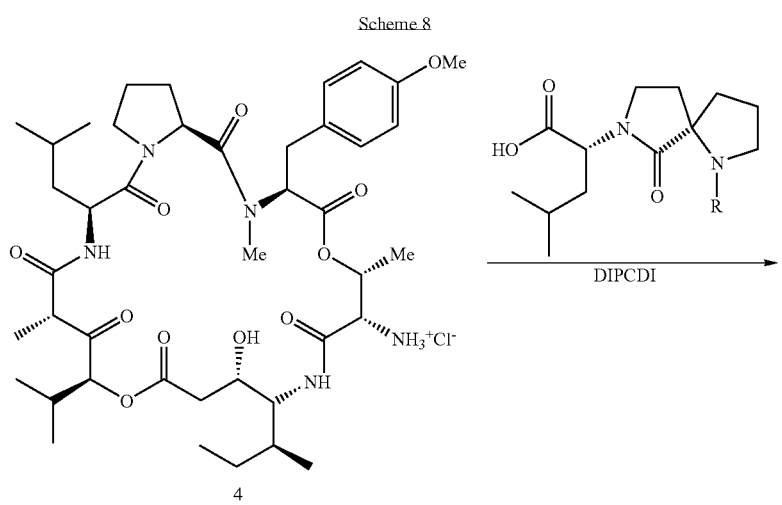

-continued

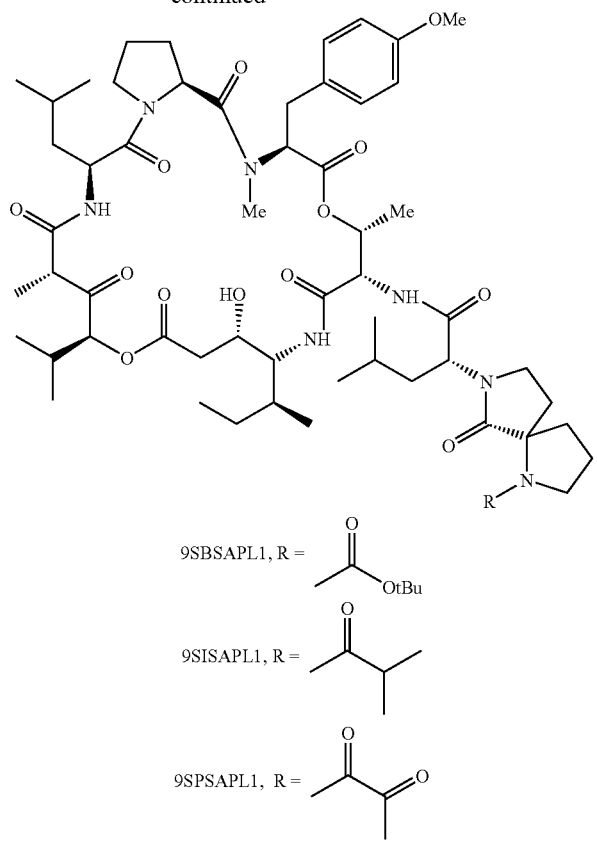

9SBSAPL1, R = (acetyl-OtBu group)

9SISAPL1, R = (isobutyryl group)

9SPSAPL1, R = (pyruvoyl group)

TABLE 3

Cytoxicity of aplidine derivatives IC$_{50}$ (Molar)

| Serie | Description | MolW | P388 | A549 |
|---|---|---|---|---|
| SNPL3 | 3-[Aip]-Z-didemnin A | 1076 | | 9.29E−11 |
| 8PUSAPL1 | 8-[Phenylurea]-didemnin A | 1062 | | 9.42E−11 |
| 8BUSAPL1 | 8-[Butylurea]-didemnin A | 1042 | | 9.59E−11 |
| 8ISVPL1 | 3-[val]-8-[isobutyryl]-aplidine | 956 | | 1.05E−10 |
| 9NVSAPL1 | 9-[norvaline]-aplidine | 1139 | | 4.39E−10 |
| 9ISHPL1 | 3-[Hiv]-9-[Isobutyryl]-aplidine | 1054 | | 4.74E−10 |
| 9ISVPL1 | 3-[Val]-9-[Isobutyryl]-aplidine | 1053 | | 4.75E−10 |
| 8ISHPL1 | 3-[hiv]-8-[isobutyryl]-didemnin A | 957 | | 5.22E−10 |
| 9ASHPL1 | 3-[Hiv]-9-[Ala]-aplidine | 1091 | | 9.16E−10 |
| 8PSHPL2 | 3-[Hiv]-8-[Boc-Pro]-didemnin A | 1084 | | 9.22E−10 |
| 9NVSHPL1 | 3-[Hiv]-9-[Nva]-aplidine | 1083 | | 9.23E−10 |
| 8PTSAPL1 | 8-[Phenylthiourea]-didemnin A | 1078 | | 9.27E−10 |
| 8CSAPL1 | 8-[Coumarin]-didemnin A | 1062 | | 9.41E−10 |
| 8BTSAPL1 | 8-[Butylthiourea]-didemnin A | 1058 | | 9.45E−10 |
| 9LSHPL1(L) | 3-[Hiv]-9-[L-Lac]-aplidine (Tamandarine A) | 1056 | | 9.47E−10 |
| 9LSHPL1(D) | 3-[Hiv-9-[D-Lac]-aplidine | 1056 | | 9.47E−10 |
| 9LSVPL1(L) | 3-[Val]-9-[Lac]-aplidine | 1055 | | 9.48E−10 |
| 8MSAPL1 | 8-[Methyl-sulphonyl]-didemnin A | 1021 | | 9.79E−10 |
| SVPL3 | 3-[val]-Z-didemnin A | 1020 | 9.8E−10 | 9.8E−10 |
| 8PSHPL1 | 3-[Hiv]-8-[Pro]-didemnin A | 984 | | 1.01E−09 |
| 8VSHPL1 | 3-[Hiv]-8-[Val]-didemnin A | 986 | | 1.01E−09 |
| 8BSHPL1 | 3-[Hiv]-8-[butyryl]-aplidine | 957 | | 1.04E−09 |
| SVPL2 | 3-[val]-didemnin A | 886 | 1.1E−09 | 1.13E−09 |
| SHPL2 | 3-[Hiv]-didemnin A | 886 | 1.1E−09 | 1.13E−09 |
| SAPL3 | Z-Didemnin A | 1077 | 9.3E−09 | 2.32E−09 |
| 9NVSAPL2 | 9-[Z-Nva]-aplidine | 1273 | 7.9E−09 | 3.93E−09 |
| 9ZASHPL2 | 3-[Hiv]-9-[Z-ala]-aplidine | 1189 | | 4.21E−09 |
| SAPL2 | Didemnin A | 943 | 5.30E−09 | 4.24E−09 |
| 8G9CSAPL1 | 8-[Gly]-9-[Coumarin]-didemnin A | 1172 | | 4.26E−09 |
| 8BISAPL1 | 8-[Biotin]-didemnin A | 1169 | | 4.27E−09 |
| 9SBSHPL1 | 3-[Hiv]-7,8-[Spiro]-9-[Boc]-aplidine | 1096 | | 4.56E−09 |

TABLE 3-continued

Cytoxicity of aplidine derivatives IC$_{50}$ (Molar)

| | | | | |
|---|---|---|---|---|
| SHPL3 | 3-[Hiv]-Z-didemnin A | 1021 | 4.9E−09 | 4.9E−09 |
| 9NVSHPL2 | 3-[Hiv]-9-[Z-Nva]-aplidine | 1217 | | 8.22E−09 |
| 9SPSAPL1 | 7,8-[Spiro]-9-[pyr]-aplidine | 1122 | | 8.55E−09 |
| 9LSHPL2(L) | 3-[Hiv]-9-[lac(OTBDMS)]-aplidine | 1170 | | 8.55E−09 |
| 9BASHPL2 | 3-[Hiv]-9-[Boc-Ala]-aplidine | 1155 | | 8.65E−09 |
| 9SBSAPL1 | 7,8-[Spiro]-9-[Boc]-aplidine | 1152 | | 8.68E−09 |
| 8VSHPL2 | 3-[Hiv]-8-[Boc-Val]-aplidine | 1086 | | 9.21E−09 |
| 8V9ISHPL1 | 8-[Val]-9-[Isobutiryl]-didemnin A | 1056 | | 9.46E−09 |
| 8HSHPL1 | 3-[Hiv]-8-[hexanoyl]-didemnin A | 985 | | 1.01E−08 |
| 9LSVPL2(L) | 3-[Val]-9-[Lac(OTBDMS)]-aplidine | 1169 | | 1.02E−08 |
| SNPL2 | 3-[Aip]-didemnin A | 942 | | 1.06E−08 |
| 9LSHPL2(D) | 3-[Hiv]-9-[D-Lac(OTBDMS)]-aplidine | 1170 | | 8.55E−08 |
| 9SISAPL1 | 7,8-[Spiro]-9-[Isobutyryl]-aplidine | 1122 | | 8.91E−08 |
| 9SPSHPL1 | 3-[Hiv]-7,8-[Spiro]-9-[Pyr]-aplidine | 1066 | | 9.38E−08 |
| 9SISHPL1 | 3-[Hiv]-7,8-[Spiro]-9-[Isobutyryl]-aplidine | 1066 | | 9.38E−08 |
| 9SASHPL1 | 3-[Hiv]-7,8-[Spiro]-9-[Acriloyl]-aplidine | 1064 | | 9.39E−08 |

| Serie | Description | HT29 | MEL28 | DU145 |
|---|---|---|---|---|
| SNPL3 | 3-[Aip]-Z-didemnin A | 9.29E−11 | | |
| 8PUSAPL1 | 8-[Phenylurea]-didemnin A | 9.42E−11 | | |
| 8BUSAPL1 | 8-[Butylurea]-didemnin A | 9.59E−11 | | |
| 8ISVPL1 | 3-[val]-9-[isobutyryl)-aplidine | 1.05E−10 | | |
| 9NVSAPL1 | 9-[norvaline]-aplidine | 4.39E−10 | | |
| 9ISHPL1 | 3-[Hiv]-9-[Isobutyryl]-aplidine | 4.74E−10 | | |
| 9ISVPL1 | 3-[Val]-9-[Isobutyryl]-aplidine | 4.75E−10 | | |
| 8ISHPL1 | 3-[hiv]-8-[isobutyryl]-didemnin A | 5.22E−10 | | |
| 9ASHPL1 | 3-[Hiv]-9-[Ala]-aplidine | 9.16E−10 | | |
| 8PSHPL2 | 3-[Hiv]-8-[Boc-Pro]-didemnin A | 9.22E−10 | | |
| 9NVSHPL1 | 3-[Hiv]-9-[Nva]-aplidine | 9.23E−10 | | |
| 8PTSAPL1 | 8-[Phenylthiourea]-didemnin A | 9.27E−10 | | |
| 8CSAPL1 | 8-[Coumarin]-didemnin A | 9.41E−10 | | |
| 8BTSAPL1 | 8-[Butylthiourea]-didemnin A | 9.45E−10 | | |
| 9LSHPL1(L) | 3-[Hiv]-9-[L-Lac]-aplidine (Tamandarine A) | 9.47E−10 | | |
| 9LSHPL1(D) | 3-[Hiv]-9-[D-Lac]-aplidine | 9.47E−10 | | |
| 9LSVPL1(L) | 3-[Val]-9-[Lac]-aplidine | 9.48E−10 | | |
| 8MSAPL1 | 8-[Methysulphonyl]-didemnin A | 9.79E−10 | | |
| SVPL3 | 3-[val]-Z-didemnin A | 9.8E−10 | 9.8E−10 | 9.8E−10 |
| 8PSHPL1 | 3-[Hiv]-8-[Pro]-didemnin A | 1.01E−09 | | |
| 8VSHPL1 | 3-[Hiv]-8-[Val]-didemnin A | 1.01E−09 | | |
| 8BSHPL1 | 3-[Hiv]-8-[butyryl]-aplidine | 1.04E−09 | | |
| SVPL2 | 3-[val]-didemnin A | 1.13E−09 | 1.13E−09 | 1.13E−09 |
| SHPL2 | 3-[Hiv]-didemnin A | 1.13E−09 | 1.13E−09 | |
| SPAL3 | Z-Didemnin A | 4.64E−09 | 4.64E−09 | |
| 9NVSAPL2 | 9-[Z-Nva]-aplidine | 3.93E−09 | 3.93E−09 | 3.93E−09 |
| 9ZASHPL2 | 3-[Hiv]-9-[Z-ala]-aplidin | 4.21E−09 | | |
| SAPL2 | Didemnin A | 8.48E−09 | 1.13E−09 | |
| 8G9CSAPL1 | 8-[Gly]-9-[Coumarin]-didemnin A | 4.26E−09 | | |
| 8BISAPL1 | 8-[Biotin]-didemnin A | 4.27E−09 | | |
| 9SBSHPL1 | 3-[Hiv]-7,8-[Spiro]-9-[Boc]-aplidine | 4.56E−09 | | |
| SHPL3 | 3-[Hiv]-Z-didemnin A | 4.9E−09 | 4.9E−09 | 4.9E−09 |
| 9NVSHPL2 | 3-[Hiv]-9-[Z-Nva]-aplidine | 8.22E−09 | | |
| 9SPSAPL1 | 7,8-[Spiro]-9-[pyr]-aplidine | 8.9E−09 | | |
| 9LSHPL2(L) | 3-[Hiv]-9-[lac(OTBDMS)]-aplidine | 8.55E−09 | | |
| 9BASHPL2 | 3-[Hiv]-9-[Boc-Ala]-aplidine | 8.65E−09 | | |
| 9SBSAPL1 | 7,8-[Spiro]-9-[Boc]-aplidine | 8.68E−09 | | |
| 8VSHPL2 | 3-[Hiv]-8-[Boc-Val]-aplidine | 9.21E−09 | | |
| 8V9ISHPL1 | 8-[Val]-9-[Isobutiryl]-didemnin A | 9.46E−09 | | |
| 8HSHPL1 | 3-[Hiv]-8-[hexanoyl]-didemnin A | 1.01E−08 | | |
| 9LSVPL2(L) | 3-[Val]-9-[Lac(OTBDMS)]-aplidine | 8.55E−09 | | |
| SNPL2 | 3-[Aip]-didemnin A | 1.06E−08 | | |
| 9LSHPL2(D) | 3-[Hiv]-9-[D-Lac(OTBDMS)]-aplidine | 8.55E−08 | | |

TABLE 3-continued

Cytoxicity of aplidine derivatives IC$_{50}$ (Molar)

| | | |
|---|---|---|
| 9SISAPL1 | 7,8-[Spiro]-9-[Isobutyryl]-aplidine | 8.91E–08 |
| 9SPSHPL1 | 3-[Hiv]-7,8-[Spiro]-9-[Pyr]-aplidine | 9.38E–08 |
| 9SISHPL1 | 3-[Hiv]-7,8-[Spiro]-9-[Isobutyryl]-aplidine | 9.38E–08 |
| 9SASHPL1 | 3-[Hiv]-7,8-[Spiro]-9-[Acriloyl]-aplidine | 9.39E–08 |

Spiro = [(5R)-1-(substituent at 9)-7-[(1R)-1-carboxy-3-methylbutyl]-6-oxo-1,7-diazaspiro[4.4]nonane]$^{7\text{-}9}$
(1)This compound has been described in the literature: Joc Org. Chem. 2000, 65, 782-792. Their synthesis was published before their discovery (I): Org. Lett., 2000, vol 0, No. 0, A-D
Methodology: after Berjeron et al, Biochem and Bioph Res. Comm., 1984, 121, 3, 848-854
388 = Murine lymphoma.
A549 = human lung carcinoma.
HT-29 = human colon carcinoma.
MEL-28 = human melanoma.
DU145 = human prostate carcinoma List of Abbreviations

| Miscellaneous | |
|---|---|
| AA | Amino acid |
| Ist | Isostatine |
| Hip | Hydroxyisovalerylpropionic acid |
| Hiv | Hydroxyisovaleric acid |
| Aip | Aminoisovalerylpropionic acid |
| Lac | Lactic acid |
| LC | Liquid Chromatography |
| HPLC | High Performance Liquid Chromatography |
| TLC | Thin Layer Cromatography |
| M.p. | Melting point |
| R$_t$ | Retention time |
| Quant. | Quantitative yield |
| ESI-MS | Electrospray Ionization Mass Spectra |
| Protecting groups | |
| Bn | Benzyl |
| Boc | tert-Butyloxycarbonyl |
| TBDMS | tert-Butyldimethylsilyl |
| Z | Benzyloxycarbonyl |
| Pac | Phenyl acetic |
| Solvents | |
| THF | Tetrahydrofurane |
| Hex | Hexane |
| ACN | Acetonitrile |
| DCM | Dichlorometane |
| EtOAc | Ethyl acetate |
| DMF | Dimethylformamide |
| MTBE | Methyl tertbutyl ether |
| Et$_2$O | Diethyl ether |
| t-BuOH | tert-Butanol |
| TFA | Trifluoroacetic acid |
| MeOH | Methanol |
| EtOH | Ethanol |
| IPA | Isopropanol |
| Reagents | |
| CDI | 1,1'-Carbonyldiimidazole |
| HOBt | 1-Hydroxybenzotriazole |
| HBTU | N-[(1H-Benzotriazol-1-yl)(dimethylamino)methylene]-N-methanaminium hexafluorophosphate N-oxide |
| BOP-Cl | Bis(2-oxo-3-oxazolidinyl)phosphinic chloride |
| HATU | N-[(dimethylamino)-1H-1,2,3,-triazolo[4,5-b]pyridin-1-ylmethylene]-N-methyl-methanaminium hexafluorophosphate N-oxide |
| HOAt | 1-Hydroxy-7-aza-benzotriazole |
| DCC | Dicyclohexylcarbodiimide |
| DIPCDI | N,N'-Diisopropylcarbodiimide |
| TBAF | Tetrabutylammonium fluoride |
| AcOH | Acetic acid |
| p-TsOH | p-toluensulphonic acid |
| DMAP | 4-Dimethylamino pyridine |
| NMM | N-Methyl morpholine |
| DIPEA | Diisopropylethylamine |
| TEA | Triethylamine |
| TFA | Trifluoroacetic acid |

General Procedure

All manipulations were conducted under an inert atmosphere of argon. All solvents were reagent grade (used in work-ups) or HPLC grade (used as reaction and or as purification solvent). Anhydrous solvents were used directly as supplied by the manufacturer. Tetrahydrofuran was freshly distilled prior to use to remove stabilizer. All other reagents were commercial compounds of the highest purity available. Analytical thin-layer chromatography (TLC) was performed on Merck silica gel aluminum sheets (60, F254) precoated with a fluorescent indicator. Visualization was effected using ultraviolet light (254 nm), phosphomolybdic acid (5% w/v) in 95% ethanol, or vainilline. Proton and carbon magnetic resonance spectra ($^1$H, $^{13}$C-NMR) were recorded on a Varian-300 (300 MHz) Fourier transform spectrometer, and chemical shifts were expressed in parts per million (ppm) relative to CHCl$_3$ as an internal reference (7.26 ppm for $^1$H and 77.0 for $^{13}$C). Multiplicities are designated as singlet (s), doublet (d), doublet of doublets (dd), doublet of triplets (dt), triplet (t), quartet (q) multiplet (m), and broad singlet (bs), and coupling constants (J) were expressed in Hz. Optical rotations (in degrees) were measured with a Jasco P1020 polarimeter. Electrospray ionization mass spectra (ESI-MS) were obtained on a Hewlett Packard Series 1100 MSD. Elemental. Flash column chromatography was carried out on E. Merck silica gel 60 (240-400 mesh) or RP C18 (40-63 □m) using the solvent systems listed under individual experiments.

The following procedures describe the synthesis of intermediates obtained toward aplidine (SAPL), [Aiv]$^3$-aplidine (SNPL), [Hiv]$^3$-aplidine (SHPL), [Val]$^3$-aplidine (SVPL), and [MeVal]$^3$-aplidine (SMPL).

EXAMPLE 1

Synthesis of Benzyl (4R,5S)-4-(tert-Butoxycarbonylamino)-5-Methyl-3-oxoheptanoate (C4)

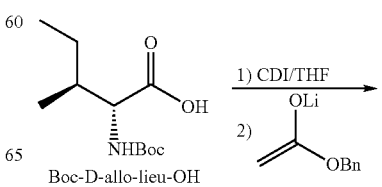

Boc-D-allo-Ileu-OH

-continued

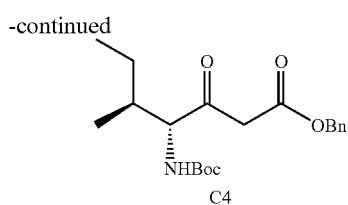
C4

To a solution of Boc-D-alloIle-OH (15.26 g, 65.9 mmol) in dry THF (200 ml) at 0° C. under argon, was added CDI (16.04 g, 98.96 mmol). After 15 min, the mixture was allowed to warm to room temperature, and stirred over a period of 16 h. The resulting solution was cooled to −78° C., and added via cannula to a well stirred solution of benzyl lithium enolate cooled at −78° C. (625 ml, 0.37 M), [prepared by adding dropwise a solution of benzyl acetate (33.34 ml), in THF (165 ml) to a solution of lithium diisopropylamide (0.36M) in THF/hex 3:1 (642 ml) at −78° C.]. The temperature should be kept <−75° C. The reaction mixture was stirred at −78° C. for 60 min. Then, it was allowed to come to −10° C. (30 min), recooled to −78° C. and quenched with saturated aq. ammonium chloride (200 ml), then extracted with DCM (3×500 ml) at room temperature. The combined extracts were washed successively with aq sat. NaHCO$_3$ (500 ml) and brine (200 ml). Drying (Na$_2$SO$_4$) followed by removal of solvent gave an oil, which was coated on silica C18 and loaded to the top of a LC-RPC18 [Lichroprep RPC-18 (40-60 microns) column. Elution using a gradient ACN-H$_2$O (60 to 100% ACN)] yielded the product C4 as a colourless oil (16.7 g, 70%). $[\alpha]^{20}_D$ −20.0 (c 1, CHCl$_3$), TLC: Rf=0.32 (Merck, RP-C18, ACN-H$_2$O 7:3).

$^1$H NMR (300 MHz, CDCl$_3$) δ 0.77 (d, 3H), 0.94 (t, 3H), 1.25 (s, 9H), 1.60 (m, 1H), 1.90 (m, 2H), 3.58 (s, 2H), 4.47 (dd, 1H), 5.00 (d, 1H), 5.18 (s, 2H), 7.35 (bs, 5H).

EXAMPLE 2

Synthesis of (3S,4R,5S)-N-(tert-Butoxycarbonyl)isostatine Benzyl Ester (C3)

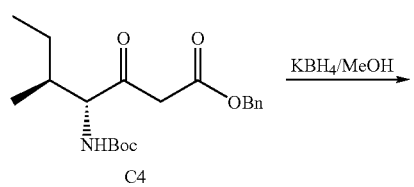

C4 (16.7 g, 45.9 mmol) was dissolved in methanol (690 ml) at 0° C. Potassium Borohydride (7.43 g, 137.8 mmol) was added to the stirred solution and after 30 nm the reaction was quenched with aq HCl (0.1 N) to pH 4, and extracted with DCM (300 ml). The extract was washed successively with aq NaHCO$_3$ (100 ml, sat) and brine (100 ml). Drying (Na$_2$SO$_4$) followed by removal of solvent afforded alcohol C3 (15.7 g, 93%) as a colourless oil. Rf=0.45 (hex-EtOAc 2:1); $[\alpha]_D$=−9.5 (c 0.76, CHCl$_3$); Rf=0.45 (EtOAc-Hex 1:2).

$^1$H NMR (300 MHz, CDCl$_3$) δ 0.81 (d, 3H), 0.90 (t, 3H), 1.20 (m, 1H), 1.36 (m, 1H), 1.40 (s, 9H), 1.90 (m, 1H), 2.55 (dd, 1H), 2.70 (dd, 1H), 3.20 (d, 1H), 3.61 (m, 1H), 3.90 (m, 1H), 4.40 (d, 1H), 5.18 (s, 2H), 7.40 (bs, 5H).

EXAMPLE 3

Synthesis of Boc-(3S,4R,5S)-Ist(TBDMS)-OBn (C2)

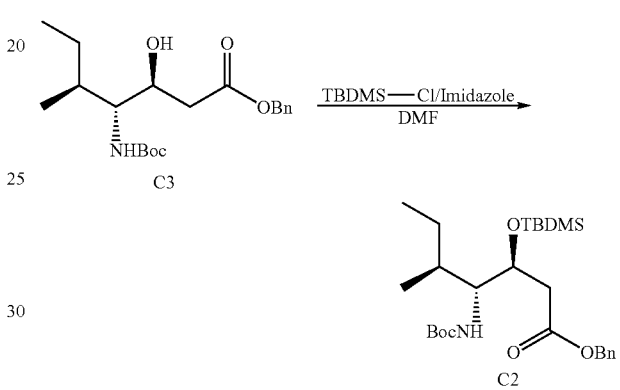

To a solution of C3 (15.7 g, 42.9 mmol) in dry DMF (65 ml) at 0° C., imidazol (8.77 g, 128.8 mmol), OMAP (1.57 g, 12.81 mmol), and TBDMS-Cl (19.42 g, 128.8 mmol) were added. The reaction mixture was allowed to warm to room temperature overnight, then it was partitioned between Et$_2$O (200 ml) and successively with aq HCl (100 ml, 0.1 N), aq NaHCO$_3$ (100 ml, sat) and brine (50 ml). After drying (Na$_2$SO$_4$) and solvent removal, the residue was purified by flash LC (silica gel, hex) to yield C2 (19.96 g, 97%).

$[\alpha]_D$=10.6 (c 1.01, CHCl$_3$); Rf=0.73 (EtOAc-Hex 1:2).

$^1$H NMR (300 MHz, CDCl$_3$) δ 0.15 (s, 6H), 0.82 (s, 9H), 0.85 (d, 3H), 0.89 (t, 3H), 1.18 (m, 1H), 1.35 (m, 1H), 1.41 (s, 9H), 1.77 (m, 1H), 2.45 (dd, 1H), 2.60 (dd, 1H), 3.62 (m, 1H), 4.20 (m, 1H), 4.40 (d, 1H), 5.05 (d, 1H), 5.15 (d, 1H), 7.40 (bs, 5H).

EXAMPLE 4

Synthesis of Boc-(3S,4R,5S)-Ist(TBDMS)-OH (C1)

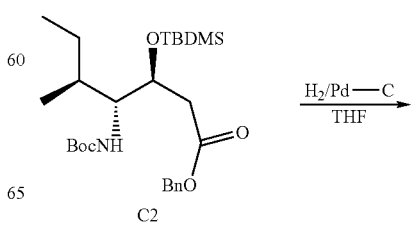

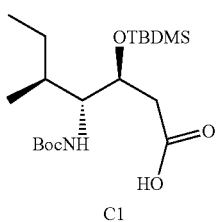

C1

To a solution of C2 (10.48 g, 21.8 mmol) in THF (110 ml), degassed and purged with argon, was added Pd/C 10% (2.096 g, 20% by weight). The mixture was stirred under $H_2$ (1 atm) for 16 h, then filtered over a 0.45 mm teflon filter and concentrated at reduced pressure to give 7.8 g of a colorless oil. Colorless crystals (6 g, 70%) were obtained after crystallization in ACN at −20° C. $[\alpha]^{20}_D$ 1.8 (c 0.594, DCM) [Lit. $[\alpha]_D$ 1.74 (c 2.64, CHCl$_3$). *Synthesis*, 1991, 2941; Rf=0.45 (Merck HPTLC, RP-C18, ACN-H$_2$O 8:2).

$^1$H NMR (300 MHz, CDCl$_3$) δ 0.18 (s, 6H), 0.82 (s, 9H), 0.85 (d, 3H), 0.89 (t, 3H), 1.10-1.20 (m, 2H), 1.42 (s, 9H), 1.80 (m, 1H), 2.50 (m, 2H), 3.58 (m, 1H), 4.11 (m, 1H).

EXAMPLE 5

Synthesis of (2S)-2-tert-Butyl(dimethyl)silyloxy-3-methylbutyric Acid (SAPLB4)

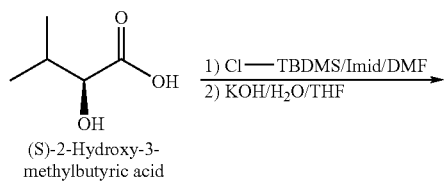

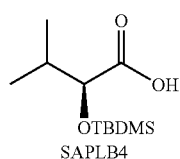

SAPLB4

To a stirred solution of (S)-2-hydroxy-3-methylbutyric acid (21.12 g, 181.9 mmol) in DMF (91 ml) at 0° C. under argon were added Imidazol (27.24 g, 400.11 mmol) and DMAP (6.94 g, 54.56 mmol). After 5 min, tert-Butyldimethylchlorosilane (60.31 g, 400.11 mmol) was added. The mixture was allowed to warm to 23° C. and stirred overnight. The crude reaction mixture was partitioned between EtO (250 ml) and aq HCl (250 ml, 0.1N). The organic phase was washed successively with aq. NaHCO$_3$ (250 ml, sat), and brine (250 ml), dried (Na$_2$SO$_4$), filtered and concentrated at reduced pressure to afford the bissilylated product as a pale yellow oil. A solution of this product in THF (100 ml) was added dropwise (10 min) to a cooled (0° C.) solution of KOH (30.47 g, 543 mmol) in THF/H$_2$O (543 ml: 181 ml), After 40 min the reaction mixture was partitioned between H$_2$O (300 ml) and Et$_2$O (500 ml), The aqueous phase was partitioned between cold (0° C.) aq HCl (200 ml, 3N) and EtOAc (5×250 ml). The combined organic extracts were dred (Na$_2$SO$_4$) filtered and concentrated under reduced pressure to afford SAPLB4 as a pale yellow oil (38.38 g, 91%).

$^1$H NMR (300 MHz, CDCl$_3$) δ 0.02 (m, 6H), 0.90 (m, 15H), 2.08 (m, 1H), 4.06 (d, 1H).

EXAMPLE 6

Synthesis of Benzyl (4S)-4-tert-Butyl(dimethyl)silyloxy-5-Methyl-3-oxohexanoate (SAPLB3)

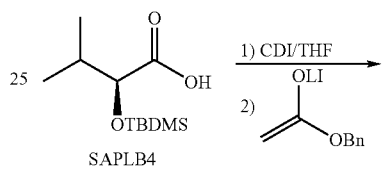

SAPLB4

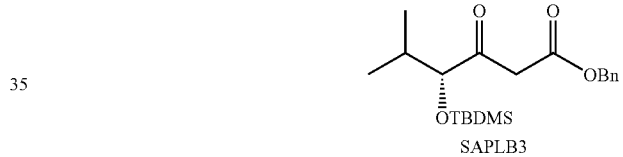

SAPLB3

To a solution of (S)-2-(tertButyldimethylsilyloxy)-3-methylbutyric acid (15.31 g, 65.9 mmol) in dry THF (200 ml) at 0° C. under argon, was added CDI (16.04 g, 98.96 mmol). After 15 min, the mixture was allowed to warm to room temperature, and stirred over a period of 16 h. The resulting solution was cooled to −78° C., and added via cannula to a well stirred solution cooled at −78° C of benzyl lithium enolate (625 ml, 0.37 M), [prepared by adding dropwise a solution of benzyl acetate (33.34 ml), in THF (165 ml) to a solution of lithium diisopropylamide (0.36M) in THF/hex 3:1 (642 ml) at −78° C.]. The temperature should be kept <−75° C. The reaction mixture was stirred at −78° C. for 60 min. Then, it was allowed to come to −10° C. (30 min), recooled to −78° C. and quenched with aq. ammonium chloride (200 ml, sat), then extracted with DCM (3×500 ml) at room temperature, The combined extracts were washed successively with aq NaHCO$_3$ (500 ml, sat) and brine (200 ml). Drying (Na$_2$SO$_4$) followed by removal of solvent gave an oil, which was coated on silica C18 and loaded to the top of a LC-RPC18 [Lichroprep RPC-18 (40-60 microns), column. Elution using a grad. ACN-H$_2$O (60 to 100% ACN)] yielded SAPLB3 as a colourless oil (16.1 g, 70%). $[\alpha]_D$ −25 (c 0.5, MCOH); Rf=0.32 (Merck, RP-C18, ACN-H$_2$O7:3).

$^1$H NMR (300 MHz, CDCl$_3$) δ 0.02 (m, 6H), 0.92 (m, 15H), 1.92 (m, 1H), 3.63 (s, 2H), 3.80 (s, 2H), 3.38 (d, 1H), 5.17 (d, 1H), 5.20 (d, 1H), 7.35 (bs, 5H).

EXAMPLE 7

Synthesis of Benzyl (4S)-4-tert-Butoxycarbonylamino-5-Methyl-3-oxohexanoate (SNPLB3)

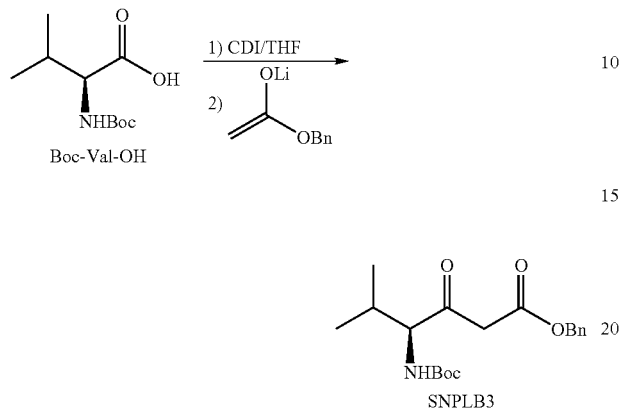

Following the procedure obtained for the synthesis of SAPLB3 from Boc-Val-OH (10 g, 46.0 mmol), the title compound was obtained after purification by flash LC (silica gel, gradient hex-EtOAc 10:1 to 5:1) as an oil (6.9 g, 43%).

$^1$H NMR (300 MHz, CDCl$_3$) δ 0.77 (d, J=7, 3H), 0.98 (d, J=7, 3H), 1.44 (s, 9H), 2.22 (m, 1H), 3.58 (s, 2H), 4.31 (m, 1H), 5.03 (m, 1H), 5.18 (s, 2H), 7.34 (bs, 5H). ESI-MS Calcd for C$_{19}$H$_{27}$NO$_5$: 349.19. Found (m/z): 372.1 (M+Na)$^+$.

EXAMPLE 8

Synthesis of Benzyl (2RS,4S)-4-tert-butyl(dimethyl)silyloxy-2,5-dimethyl-3-oxohexanoate (SAPLB2)

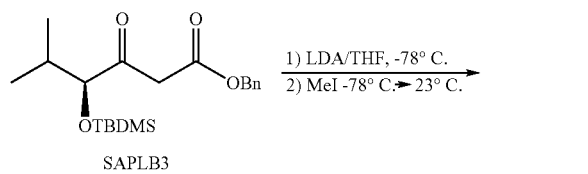

The ester SAPLB3 (15.12 g, 41.49 mmol) in dry THF (43 ml) was added dropwise to a solution of lithium diisopropylamine at −78° C. [prepared by adding butyllithium (1.6 M solution in hex; 31.12 ml, 49.79 mmol) dropwise to diisopropylamine (7.26 ml, 51.86 mmol) in dry THF (83 ml) under Ar at −78° C. for 30 min.] The mixture was stirred for 0.5 h and then, Iodomethane was added (52.11 ml, 829.8 mmol). The mixture was allowed to warm to 23° C. and then, stirring continues for 24 h. Additional Iodomethane was added (2.67 ml, 42 mmol) and the mixture was stirred 24 h further or until dissaparence of starting material. The mixture was then partitioned between aq. NH$_4$Cl (50 ml, sat) and EtOAc (2×200 ml). The organic layer was washed successively with aq. NaHCO$_3$ (100 ml, sat), brine (100 ml), dried (Na$_2$SO$_4$), filtered and concentrated to give a yellow oil (12 g). Pure product (SAPLB2) was obtained after purification by LC-silica gradient hex-Et$_2$O 100:0 to 100:2 as a diastereomeric mixture of epiners at C2 (10 g, 63%).

$^1$H NMR (300 MHz, CDCl$_3$) δ 0.01 (s, 3H), 0.02 (s, 3H), 0.91 (m, 15H), 1.30 (d, 3H), 2.01 (m, H), 4.01 (m, 1H), 5.10 (d, 1H), 5.15 (d, 1H), 7.34 (bs, 5H).

EXAMPLE 9

Synthesis of Benzyl (2RS,4S)-4-tert-butoxycarbonylamino-2,5-dimethyl-3-oxohexanoate (SNPLB2)

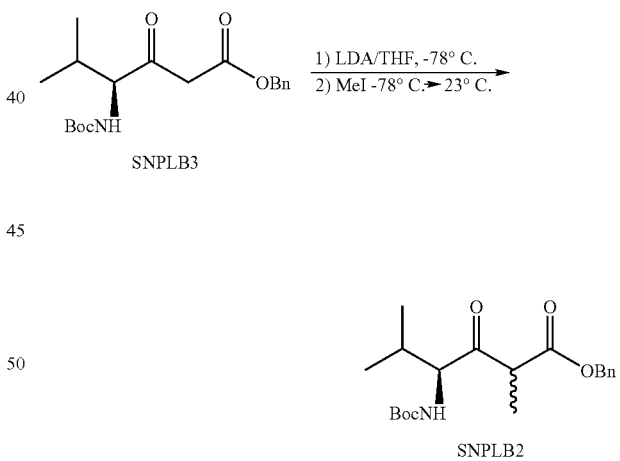

Following the procedure obtained for the synthesis of SAPLB2, starting from SNPLB3 (10 g, 46.0 mmol), the title compound was obtained after purification by flash LC (silica gel, gradient hex-EtOAc 10:1 to 5:1) as a diastereomeric mixture (1:1) of epimers at C2 (4.4 g, 62%). Rf=0.4 and 0.37 (silica, Hex/EtOAc 3:1).

$^1$H NMR (300 MHz, CDCl$_3$) δ 0.72 (m, 3H), 0.86 (m, 3H), 1.37 (m, 3H), 1.44 (s, 9H), 2.22 (m, 1H), 3.79 (m, 1H), 4.43 (m, 1H), 5.02 (m, 1H), 5.16 (m, 2H), 7.34 (m, 5H). ESI-MS Calcd for C$_{20}$H$_{29}$NO$_5$: 363.20. Found (m/z): 364.1 (M+H)$^+$.

EXAMPLE 10

Synthesis of Leu-Pro-OBn as Chlorhydrate Salt (A5)

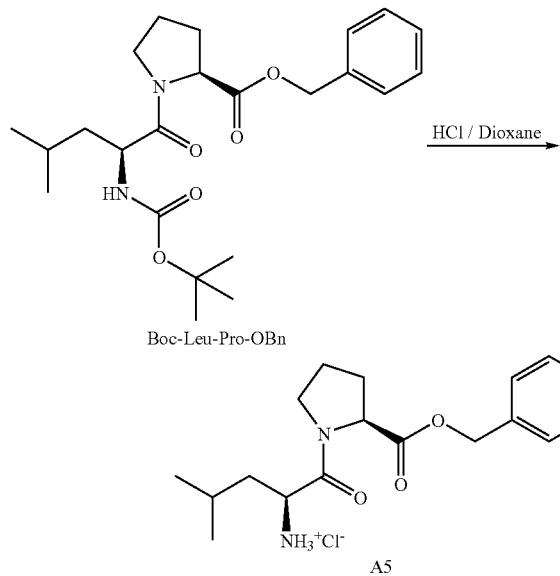

Boc-Leu-Pro-OBn

A5

To a flask containing Boc-Leu-Pro-OBn (113.8 g, 272 mmol) a solution of hydrogen chloride in dioxane (209 ml, 5.3 N) was added and the stirring was continued for 5 h or until total conversion by TLC (disappearance of starting material; Rf=0.47 (hex-EtOAc 2:1, silica). The solution was concentrated under reduced pressure and the resulting oil was chased with $CHCl_3$ (3×50 ml), $CHCl_3$-MTBE (30 ml-50 ml), MTBE (50 ml) and hex (50 ml). The residue was dried under vacuum (16 h) to remove residual HCl, to give the title compound as a white solid. A5 (96.4 g, 100%) was used directly without further purification in the next step. $[\alpha]_D^{22}$-85.21 (c=1, $CHCl_3$).

$^1$NMR (300 MHz, $CDCl_3$) δ 0.92 (d, J=7.1, 3H), 0.96 (d, J=7.1, 3H), 1.55 (m, 1H), 1.82-2.14 (m, 5H), 2.26 (m, 1H), 3.42 (m, 1H), 3.90 (m, 1H), 4.32 (bs, 1H), 4.64 (m, 1H), 5.01 (d, J=11.5, 1H), 5.16 (d, J=11.5, 1H), 7.34 (m, 5H), 8.40 (bs, 3H). ESI-MS Calcd for $C_{18}H_{26}N_2O_3$: 318.19. Found (m/z), 319.2 (M+H)$^+$.

EXAMPLE 11

Synthesis of TBDMS-Hip-Leu-Pro-OBn (SAPLA4)

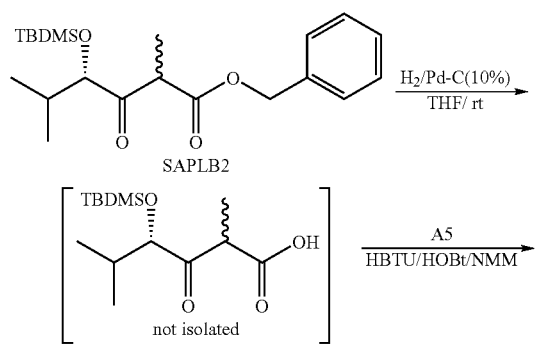

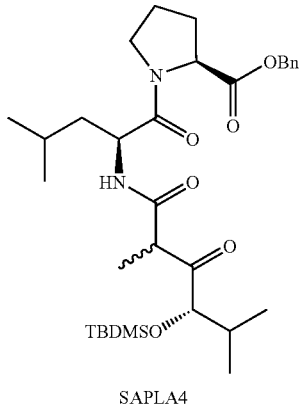

SAPLA4

To a flask containing a degassed solution of SAPLB2 (20 g, 52.88 mmol) in THF anh. (158 ml), provided with gas inlet-outlet tubes, was added 10% Pd/C (6.0 g, 30% by wt.) under Ar. Then, a stream of hydrogen is passed through for 8 h or until complete conversion by TLC (disappearance of starting material). The resulting mixture was bubbled with Ar to displace hydrogen, and filtered under Ar in a sintered glass funnel through a sort pad of celite, to a cooled flask (-5° C.) containing HOBt (7.17 g, 52.88 mmol) and HBTU (21.0 g, 55.53 mmol). Additional THF (158 ml) was added to wash the celite. To the mixture (at -5° C.) were added NMM (5.8 ml, 52.88 mmol) and after 5 min a cooled (-5° C.) solution containing: A5 (31.96 g, 89.81 mmol), NMM (16 ml, 145 mmol) and DMF (120 ml), fresh prepared. The reaction mixture was allowed to warm to rt and stirred for 14 h. The crude reaction was filtered and the solvent removed under reduced pressure. To the residual solution of DMF, EtOAc (300 ml) was added and washed successively with aq HCl (200 ml, 0.1 N), aq. $NaHCO_3$ (200 ml, sat.) and rinsed with brine (300 ml). The organic phase was dried ($Na_2SO_4$) filtered and concentrated. The resulting material was coated with silica (EtOAc as solvent), and chromatographed on silica gel eluting with a gradient EtOAc:hex 1:5 to 1:1 to yield SAPLA4 (26.8 g, 78%) as a thick colourless oil. This product is a 1:1 mixture of diastereomers, Rf=0.5 (silica, Hex/EtOAc 1:1, dark blue/vanillin).

IR (film, DCM) 3295, 3060 and 3040, 2957, 2934, 2880, 2858, 1736, 1634, 1528, 1454, 1387, 1252, 1171, 1070 cm$^{-1}$.

$^1$H NMR (300 MHz, $CDCl_3$) δ 0.01 (s, 3H), 0.03 (s, 3H), 0.85-0.97 (m, 12H), 0.92 (s, 9H), 0.93 (s, 9H), 1.33 (d, J=7.0, 3H), 1.37 (d, J=7.0, 3H), 2.40-2.65 (m, 3H), 1.92-2.28 (m, 4H), 3.64-3.76 (m, 1H), 4.69-4.82 (m, 1H), 5.05 (d, J=11.8, 1H), 5.20 (d, J=11.8, 2H), 6.73 (d, J=8.9, 1H), 6.98 (d, J=9.0, 1H), 7.34 (bs, 5H). $^{13}$C NMR (75 MHz, $CDCl_3$) δ -5.24, -4.81, 15.70, 17.43, 17.57, 18.84, 21.48, 21.61, 18.05, 23.28, 24.43, 24.55, 24.76, 25.68, 28.87, 31.36, 31.77, 41.27, 41.67, 48.68, 48.55, 48.89, 58.71, 66.84, 83.84, 83.29, 128.09, 128.47, 135.40, 169.24, 170.67, 170.89, 171.16, 171.20, 209.11, 211.62. m/z (FAB) 611.5 [(M+Na)$^+$, 15], 589.5 [(M+H)$^+$, 100]; m/z (FABHRMS) 589.369 045, $C_{32}H_{52}N_2O_6Si$ requires (M+H)$^+$, 589.367 291

EXAMPLE 12

Synthesis of Boc-Aip-Leu-Pro-OBn (SNPLA4)

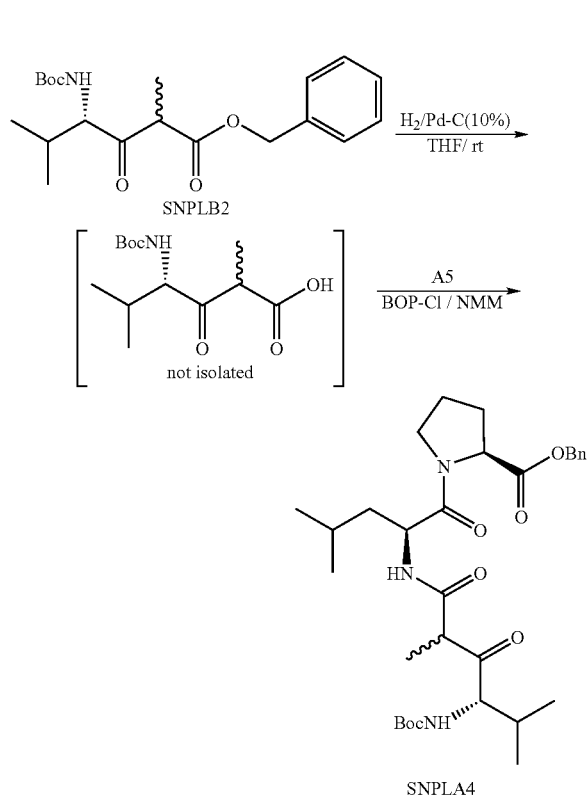

To a degassed solution of SNPLB2 (2.3 g, 6.32 mmol) in dry THF (30 ml) was added 10% Pd/C (0.74 g, 16% by wt.) and then hydrogenated at atmospheric pressure for 5 h. 30 min or until complete conversion by TLC (disappearance of starting material). The resulting mixture was filtered through a sort pad of celite and additional THF (20 ml) was added to wash the celite. To the filtered solution (at −5° C.) were added BOP-Cl (1.77 g, 6.96 mmol) and NMM (765 μl, 6.91 mmol) and after 30 min a cooled (−5° C.) solution containing: A5 (3.15 g, 8.85 mmol), NMM (1.88 ml, 8.84 mmol) and DMF (14 ml) prepared 10 ml before. The reaction mixture was allowed to warm to rt and stirred for 17 h. The crude reaction was filtered and the solid washed with EtOAc (100 ml). The combined organic solutions was successively washed with aq KHSO$_4$ (50 ml, 10%), aq. NaHCO$_3$ (50 ml, sat.) and brine (50 ml). The organic phase was dried (Na$_2$SO$_4$) filtered and concentrated in vacuo, and the resulting material was chromatographed on silica gel eluting with a gradient EtOAc:hex 1:4 to 1:1 to yield SNPLA4 (750 mg, 20%) as a white solid. This product is a mixture of diastereomers. Rf=0.26 and 0.17 (silica, Hex/EtOAc 1:1).

$^1$H NMR (300 MHz, CDCl$_3$) δ 0.74-1.04 (m, 12H), 1.31-1.70 (m, 6H), 1.43 (s, 9H), 2.01 (m, 3H), 2.22 (m, 2H), 3.60 (m, 2H), 3.77 (m, 1H), 4.40 (m, 1H), 4.58 (m, 1H), 4.69 (m, 1H), 5.14 (m, 2H), 6.75 (d, J=8.7, 1H), 7.04 (d, J=7.8, 1H), 7.34 (bs, 5H). $^{13}$C NMR (75 MHz, CDCl$_3$) δ 16.74, 16.91, 20.22, 21.94, 23.53, 24.80, 25.06, 28.48, 29.14, 41.29, 41.41, 46.98, 49.45, 49.64, 51.26, 59.06, 63.70, 64.27, 67.08, 79.86, 80.10, 128.32, 128.48, 128.74, 135.74, 156.28, 169.15, 169.32, 171.18, 171.91. ESI-MS Calcd for C$_{31}$H$_{47}$N$_3$O$_7$: 573.34. Found (m/z): 574.4 [(M+H)]$^+$.

EXAMPLE 13

Synthesis of Hiv-Leu-Pro-OBn (SHPLA4)

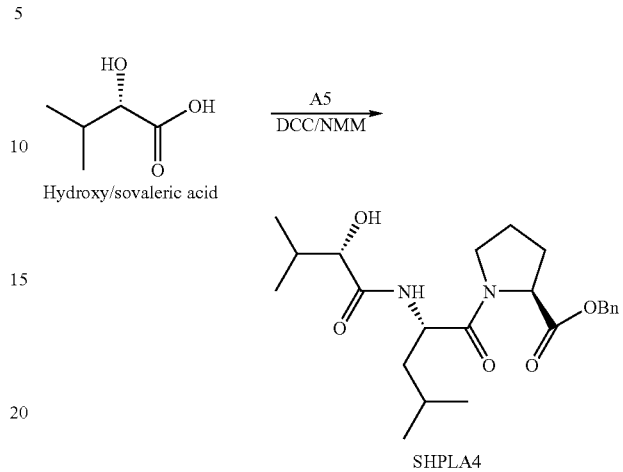

To a flask containing A5 (2.06 g, 4.78 mmol) in DCM (5 ml) at 0° C., NMM (506 mg, 5.01 mmol) was added with stirring. After 15 min (2S)-2-hydroxy-3-methylbutanoic acid (hydroxyisovaleric acid) (487 mg, 4.78 mmol) and DCC (986 mg, 4.78 mmol) were added in portions. The reaction mixture was allowed to warm to 23° C. and stirred for 14 h. The suspension was diluted with CHCl$_3$ (25 ml) and partitioned between aq HCl (10 ml, 1N), aq NaHCO$_3$ (10 ml, sat) and brine (10 ml) dried (Na$_2$SO$_4$) and concentrated under reduced pressure. The residue was purified by flash LC (silica gel, gradient hex-EtOAc 1:1 to 1:3) to give SHPLA4 (1.13 g, 80%) as a white solid. Rf=0.46 (hex-EtOAc 1:2).

$^1$H NMR (300 MHz, CDCl$_3$) δ 0.81 (d, J=7.0, 3H) 0.92 (m, 6H), 0.97 (d, J=7.0, 3H), 1.42 (m, 1H), 1.63 (m, 2H), 2.00 (m, 3H), 2.19 (m, 2H), 3.60 (m, 1H), 3.85 (m, 1H), 3.88 (d, J=4.8, 1H), 4.46 (m, 1H), 4.80 (m, 1H), 5.06 (d, J=12.3, 1H), 5.14 (d, J=12.3, 1H), 7.32 (m, 5H), 7.41 (d, J=8.4, 1H). $^{13}$C NMR (75 MHz, CDCl$_3$) δ 15.32, 19.08, 21.38, 23.11, 24.41, 24.69, 28.77, 31.31, 40.54, 46.81, 48.20, 58.82, 66.69, 75.76, 127.93, 128.14, 128.37, 135.28, 171.39, 171.95, 173.94.

EXAMPLE 14

Synthesis of Bac-Val-Leu-Pro-OBn (SVPLA4)

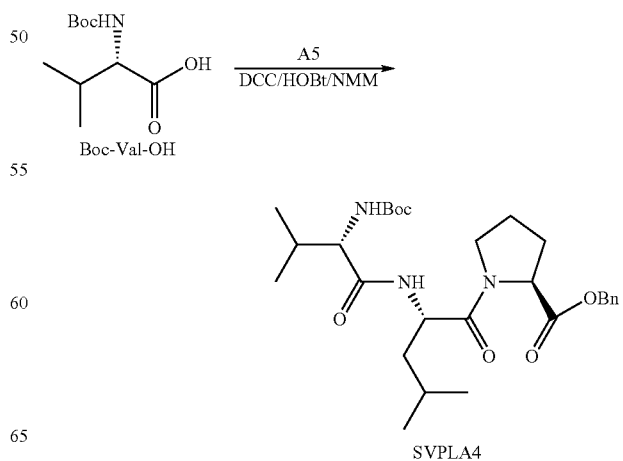

To a flask containing Boc-Valine-OH (652 mg, 3 mmol) in DCM (6 ml) at 0° C. was added NMM (0.35 ml, 3.15 mmol). After stirring for 15 min, A5 (1.065 g, 3 mmol), HOBt (405 mg, 3.0 mmol) and DCC (650 mg, 3.15 mmol) were added in portions, The reaction mixture was allowed to warm to 23° C. and stirred for 14 h. The suspension was diluted with DCM (25 ml) and washed successively with aq $KHSO_4$ (2×10 ml, 10%), aq $NaHCO_3$ (2×10 ml, sat) and brine (10 ml) dried over $Na_2SO_4$ filtered and concentrated under reduced pressure. The residue was purified by flash LC (silica, gradient hex-EtOAc 2:1 to 1:1) to give SVPLA4 (1.48 g, 93%) as a white solid. Rf=0.57 (hex-EtOAc 1:2).

$^1$H NMR (300 MHz, $CDCl_3$) δ 0.83-0.95 (m, 12H), 1.2-1.4 (m, 1H), 1.42 (s, 9H), 1.40-1.51 (m, 1H), 1.60-1.75 (m, 1H), 1.82-2.20 (m, 5H), 3.50-3.60 (m, 1H), 3.74-3.78 (m, 1H), 3.91-3.96 (m, 1H), 4.52-4.57 (s, 1H), 4.75-4.77 (m, 1H), 5.04 (bs, 1H), 5.05 (d, J=12.3, 1H), 5.17 (d, J=12.3, 1H), 6.60 (d, J=8.4, 1H), 7.26-7.35 (m, 5H). $^{13}$C NMR (75 MHz, $CDCl_3$) δ 7.61, 19.19, 21.66, 23.23, 24.43, 24.78, 24.87, 25.55, 28.20, 28.87, 30.91, 33.86, 41.68, 46.73, 48.86, 58.77, 59.74, 66.82, 79.66, 128.08, 128.21, 128.46, 135.47, 155.66, 170.83, 171.33, 171.60. ESI-MS Calcd for $C_{28}H_{43}N_3O_6$: 517.32. Found (m/z): 518.2 [(M+H)]$^+$.

EXAMPLE 15

Synthesis of Boc-Me-Val-Leu-Pro-OBn (SMPLA4)

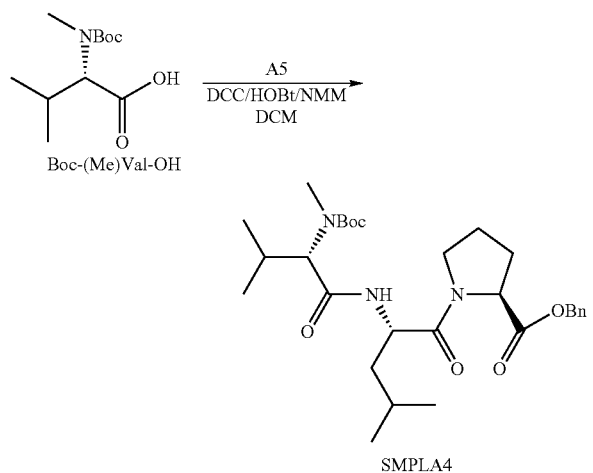

Following the procedure described for the synthesis of SVPLA4, starting from A5 (1.07 mg, 3.00 mmol) and Boc-(Me)Val-OH (694 mg, 3.00 mmol), the title compound was obtained as a white solid (1.39 g, 87%) after purification by flash LC (silica gel, gradient hex-EtOAc 2:1 to 1:1). Rf=0.51 (Hex-EtOAc 1:2).

$^1$H NMR (300 MHz, $CDCl_3$) δ 0.83-0.91 (m, 12H), 1.45 (s, 9H), 1.93-2.03 (m, 4H), 2.18-2.22 (m, 2H), 2.76 (s, 3H), 3.40-3.50 (m, 2H) 3.55-3.62 (m, 1H), 3.75-3.85 (m, 1H), 4.00-4.10 (m, 1H), 4.50-4.60 (m, 1H), 4.70-4.82 (m, 1H), 5.07 (d, J=11.2, 1H), 5.24 (d, J=11.2, 1H), 6.20 (m, 0.5H), 6.50 (m, 0.5H), 7.26-7.35 (m, 5H). $^{13}$C NMR (75 MHz, $CDCl_3$) δ 18.43, 19.77, 21.53, 23.23, 24.47, 24.77, 25.89, 25.30, 28.85, 41.25, 46.67, 48.51, 58.75, 64.05, 66.79, 128.06, 128.18, 128.44, 135.49, 170.12, 170.80, 171.66. ESI-MS Calcd for $C_{29}H_{45}N_3O_6$: 531.33. Found (m/z): 532.3 (M+H)$^+$.

EXAMPLE 16

Synthesis of Hip-Leu-Pro-OBn (SAPLA3)

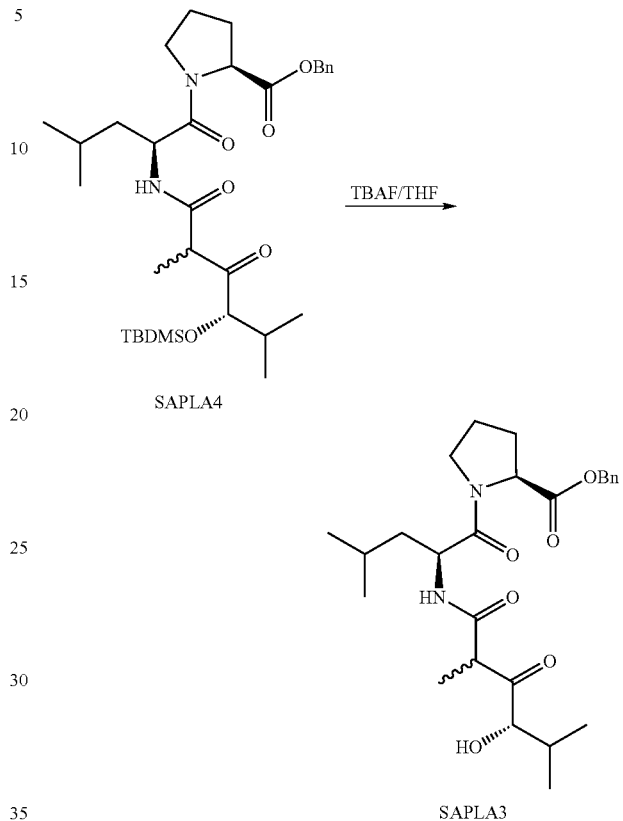

To a flask containing SAPLA4 (15.86 g 26.97 mmol) a clear colorless solution of tetrabutylammonium fluoride 1M in THFF (80.9 ml, 80.9 mmol) was added and the mixture was stirred vigorously at r.t. for 15 min (or total conversion by TLC), The reaction was quenched by addition of $H_2O$ (4 ml) and silica gel (50 g). The crude material was concentrated and purified by flash LC (silica gel, grad hex:EtOAc 2:1 to 1:1) to yield SAPLA3 (12.2 g, 95%) as a white solid (mixture of diastereomers). Rf=0.36 and 0.29 (silica, hex: $CHCl_3$:IPA; 1:5:1).

IR (film, DCM) v 3450-3293, 3060 and 3040, 2961, 2946, 2883, 2852, 1746, 1632, 1533, 1454, 1357, 1387, 1265, 1173, 1095, 1045, 1018 cm$^{-1}$. $^1$H NMR (500 MHz, $CDCl_3$) δ 0.71 (d, J=6.8, 3H), 0.81 (d, J=6.6, 3H), 0.88 (d, J=6.5, 3H), 0.91 (d, J=6.5, 3H), 0.94 (d, J=6.5, 3H), 0.99 (d, J=7.1, 3H), 1.07 (d, J=6.5, 3H), 1.36 (d, 6.5, 3H), 1.43-1.52 (m, 2H), 1.60-1.66 (m, 1H), 1.93-2.10 (m, 3H), 2.12-2.23 (m, 2H), 3.53-3.58 (m, 1H), 3.65 (q, J=7.1, 1H), 3.67-3.73 (m, 1H), 3.89 (q, J=7.1, 1H), 3.96 (d, J=4.2, 1H), 4.22 (d, J=4.1, 1H), 4.54-4.56 (m, 1H), 4.58-4.62 (m, 1), 4.69-4.73 (m, 1H), 5.1 (d, J=12.1, 1H), 5.18 (d, J=12.1, 1H), 6.57 (d, J=8.5, 1H), 6.63 (d, J=8.5, 1H), 7.28-7.38 (m, 5H). $^{13}$C NMR (75 MHz, $CDCl_3$) δ 14.06, 14.26, 15.85, 16.48, 20.07, 20.53, 22.02, 22.25, 25.37, 25.46, 29.45, 29.53, 31.59, 32.09, 41.13, 42.29, 49.93, 50.91, 51.02, 59.52, 67.60, 81.02, 128.78, 1.29.2, 169.48, 171.58, 172.17, 209.76. m/z (FAB) 497.4 [(M+Na)$^+$, 12], 475.5 [(M+H)$^+$, 100]. m/z (FABHRMS) 497.263 162, $C_{26}H_{38}N_2O_6$ requires (M+Na)$^+$497.262 757. Anal. Calcd for $C_{26}H_{38}N_2O_6$: C, 65.82; H, 8.02; N, 5.91. Found: C, 65.97; H, 8.18; N, 5.76.

EXAMPLE 17

Synthesis of Aip-Leu-Pro-OBn (SNPLA3)

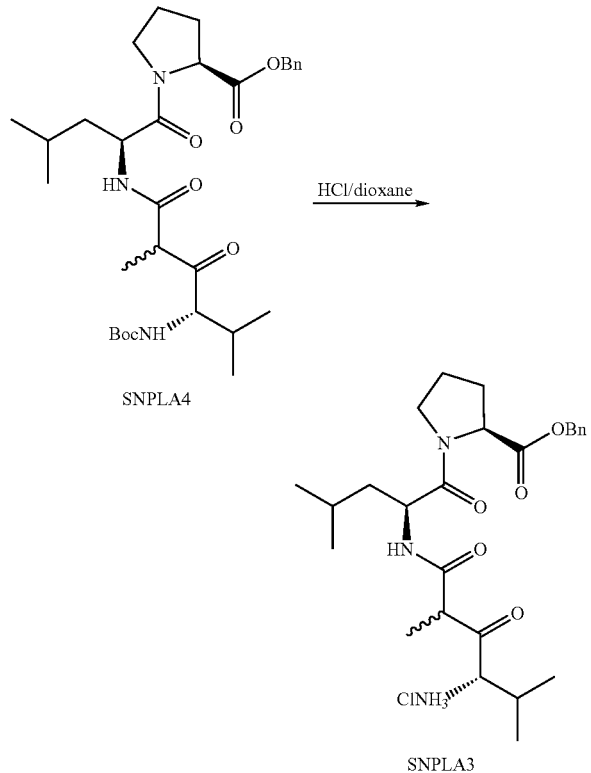

To a solution of SNPLA4 (750 mg, 1.30 mmol) in dioxane (15 ml, anh), a solution of hydrogen chloride in dioxane (39 ml, 5.3 N) was added and the mixture was stirred for 5 hours or until total conversion by TLC (disappearance of starting material). The solution was concentrated under reduced pressure and the resulting oil was chased with $CHCl_3$ (15 ml), MTBE (15 ml) and hex (15 ml). The residue was dried under vacuum to remove residual HCl, to give a foamy solid. SNPLA3 (660 mg, quant.) was used directly in next step with no further purification.

ESI-MS Calcd for $C_{26}H_{39}N_3O_5$; 473.29. Found 474.2 $(M+H)^+$.

EXAMPLE 18

Synthesis of Val-Leu-Pro-OBn (SVPLA3)

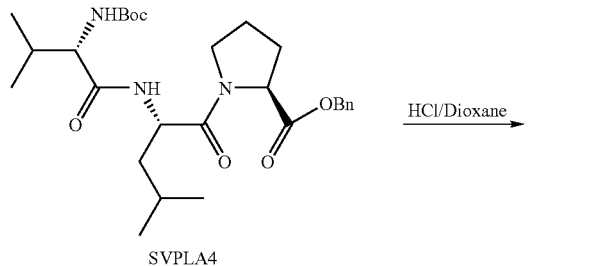

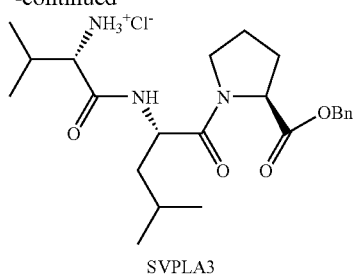

To a flask containing SVPLA4 (215 mg, 0.41 mmol) a solution of hydrogen chloride in dioxane (1.5 ml, 5.3 N) was added and the mixture was stirred for 5 hours or until total conversion by TLC. The solution was concentrated under reduced pressure and the resulting oil was chased with $CHCl_3$ (5 ml), MTBE (5 ml) and hex (5 ml). The residue was dried under vacuum to remove residual HCl, to give a foamy solid of SVPLA3 (185 mg, quant.) was used directly in next step with no further purification.

$^1$H NMR (300 MHz, $CDCl_3$) δ 0.86-0.90 (m, 6H), 1.04 (d, J=6.3, 3H), 1.12 (d, J=6.3, 3H), 1.45-1.55 (m, 1H), 1.60-1.80 (m, 2H), 1.82-2.11 (m, 2H), 2.11-2.25 (m, 1H), 2.25-2.40 (m, 1H), 3.50-3.70 (m, 1H), 3.80-3.95 (m, 2H), 4.52-4.57 (s, 1H), 4.70-4.85 (m, 1H), 5.05 (d, J=12, 1H), 5.20 (d, J=12.3, 1H), 7.27-7.37 (m, 5H), 7.91 (m, 1H), 8.62 (bs, 2H). $^{13}$C NMR (75 MHz, $CDCl_3$) δ 18.57, 18.79, 21.83, 23.11, 24.50, 24.67, 24.90, 25.34, 28.92, 30.23, 33.25, 40.40, 47.04, 49.46, 49.94, 59.26, 60.02, 66.88, 128.16, 128.27, 128.51, 135.48, 167.54, 170.80, 171.94.

EXAMPLE 19

Synthesis of (Me)Val-Leu-Pro-OBn (SMPLA3)

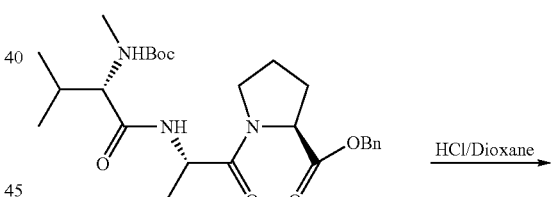

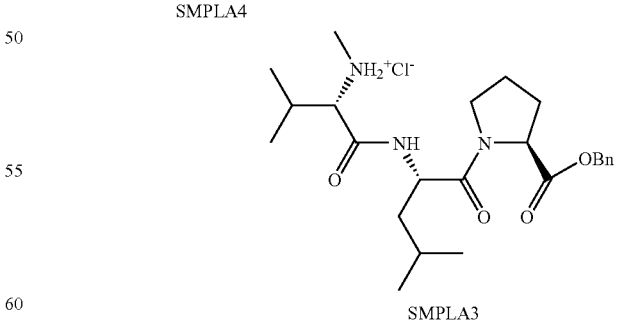

Following the procedure described for the synthesis of SVPLA3, starting from SMPLA4 (940 mg, 1.94 mmol) the title compound (828 mg, quant.) was obtained as a white solid. This product was used directly in next step with no further purification.

¹H NMR (300 MHz, CDCl₃) δ 0.93 (d, J=6.3, 6H), 1.07 (d, J=6.3, 3H), 1.21 (d, J=6.3, 3H), 1.47 (m, 1H), 1.73 (m, 2H), 2.00 (m, 3H), 2.23 (m, 1H), 2.52 (m, 1H), 2.83 (bs, 3H), 3.56-3.65 (m, 2H), 3.77 (m, 1H), 4.59 (m, 1H), 4.66 (m, 1H), 5.07 (d, J=12.3, 1H), 5.19 (d, J=12.3, 1H), 7.27-7.38 (m, 5H), 7.90 (m, 1H), 9.11 (m, 0.5H), 9.61 (m, 0.5H). ¹³C NMR (75 MHz, CDCl₃) δ 13.98, 18.37, 19.57, 21.33, 22.52, 23.16, 24.74, 28.77, 29.78, 31.54, 32.54, 39.87, 46.75, 50.09, 58.91, 66.85, 122.12, 128.06, 128.24, 128.47, 135.43, 166.22, 170.73, 171.54. ESI-MS Calcd for C₂₄H₃₈ClN₃O₄: 431.2. Found (m/z): 432.2 (M+H)⁺.

EXAMPLE 20

Synthesis of Boc-Ist(TBDMS)-Hip-Leu-Pro-On (SAPLA2)

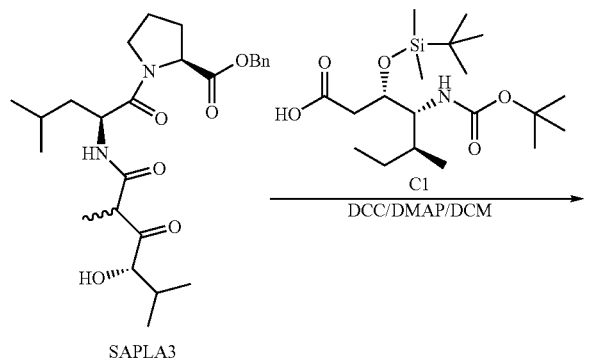

To a solution of SAPLA3 (12.2 g, 25.44 mmol) in anh. DCM (75 ml) at −5° C. under Ar, DMAP (0.932 g, 7.6 mmol), C1 (11.89 g, 30.53 mmol) and DCC (6.613 g, 32.05 mmol) were added in portions, while maintaining the temperature <−5° C. (ice-salt bath). The reaction mixture was stirred for 14 h at −5° C. and then, filtered and concentrated. The crude material was chased with ACN, cooled (−10° C.), filtered and concentrated again. The resulting material was dissolved in EtOAc (400 ml) and washed sequentially with aq. KHSO₄ (2×200 ml, 10%), brine (200 ml), aq. NaHCO₃ (200 ml, sat.) and rinsed with brine (200 ml). The organic phase was dried (Na₂SO₄), filtered and concentrated at reduced pressure to afford a colourless oil which was chromatographed on silica gel eluting with a gradient of Hex-EtOAc 3:1 to 2:1, to yield SAPLA2 (19.35 g, 90%) as a white foam (mixture of diastereomers).

IR (film, DCM) ν 3365-3200, 3069, 3038, 2959, 2930, 2882, 2857, 1746, 1688, 1640, 1533, 1456, 1389, 1258, 1171, 1086 cm⁻¹. ¹H NMR (500 MHz, CDCl₃) δ 0.01 (s, 3H), 0.03 (s, 3H), 0.05 (s, 3H), 0.07 (s, 3H), 0.77-1.03 (m, 18H), 0.84 (s, 9H), 0.85 (s, 9H), 1.33 (d, J=7.4, 3H), 1.32-1.36 (m, 2H), 1.49 (d, J=7.5, 3H), 1.38-1.62 (m, 3H), 1.42 (s, 9H), 1.44 (s, 9H), 1.51-1.77 (m, 1H), 1.88-2.37 (m, 3H), 2.17-2.33 (m, 2H), 2.47-2.74 (m, 2H), 3.34-3.72 (m, 1H), 3.72-3.82 (m, 1H), 3.99-4.40 (m, 1H), 4.03-4.16 (m, 1H), 4.49 (d, J=10.3, 1H), 4.54-4.59 (m, 1H), 4.63-4.70 (m, 2H), 4.75 (d, J=4.5, 1H), 4.77-4.81 (m, 1H), 4.95-5.19 (m, 2H), 5.22 (d, J=5.2, 1H), 5.32 (d, J=10.5, 1H), 6.38 (d, J=10.9, 1H), 6.71 (d, J=7.4, 1H), 6.76 (d, J=8.4, 1H), 8.60 (d, J=9.5, 1H). ¹³C NMR (75 MHz, CDCl₃) δ −5.05, −4.49, 11.83, 12.03, 13.01, 13.51, 13.83, 14.08, 16.92, 17.10, 17.85, 19.14, 19.65, 21.57, 22.09, 22.96, 23.28, 24.36, 24.60, 24.85, 25.73, 26.97, 27.33, 28.35, 28.46, 28.93, 29.09, 29.65, 34.12, 34.16, 40.45, 40.85, 41.18, 42.20, 46.74, 46.16, 47.99, 48.34, 48.90, 49.42, 57.62, 58.81, 58.96, 60.46, 66.62, 66.88, 68.18, 69.69, 78.98, 79.24, 79.84, 82.95, 128.08-128.49, 135.48 135.61, 155.85, 158.27, 157.44, 168.40, 169.07, 170.65, 170.86, 171.42 171.79, 203.09, 205.97. m/z (FAB) 846.6 [(M+H)⁺, 15], 746.6 (100); m/z (FABHRMS) 868.516 630, C₄₅H₇₅N₃O₁₀Si requires (M+Na)⁺868.511 930.

EXAMPLE 21

Synthesis of Boc-Ist(TBDMS)-Aip-Leu-Pro-OBn (SNPLA2)

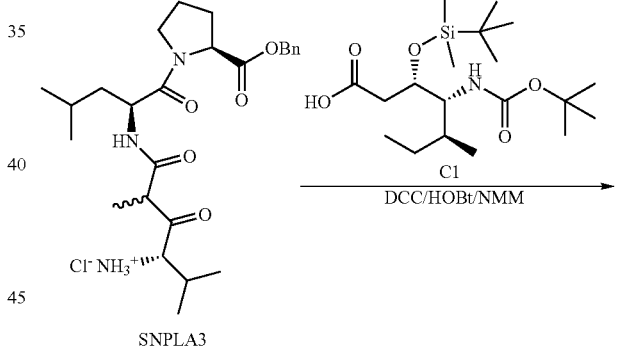

To a flask containing SNPLA3 (chlorhydrate) (660 mg, 1.12 mmol) in DCM (15 ml, anh) at 0° C., NMM (0.19 ml) was added. After 15 min, C1 (632 mg, 1.62 mmol), HOBt (266 mg, 1.73 mmol), and DCC (331 mg, 1.60 mmol) were added in portions. The flask was allowed to warm to room temperature and stirring was continued overnight. Crude reaction mixture was partitioned between DCM (50 ml) and aq KHSO$_4$ (2×20 ml, 10%), The organic phase was washed successively with aq. NaHCO$_3$ (2×20 ml, sat) and brine (20 ml), dried (Na$_2$SO$_4$), filtered and concentrated under reduced pressure. The resulting white solid was purified by flash LC (silica gel, gradient hex-EtOAc 4:1 to 1:1) to afford the title compound as a white solid (700 mg, 73%, mixture of diastereomers).

$^1$H NMR (300 MHz, CDCl$_3$) δ 0.05 (s, 3H), 0.08 (s, 3H), 0.09 (s, 3H), 0.68-1.05 (18H, m), 0.87 (9H, s), 1.05-1.85 (12H, m), 1.42 (9H, s), 1.85-2.10 (3H, m), 2.11-2.31 (2H, m), 2.32-2.46 (2H, m), 2.47-2.60 (m, 2H), 3.34-3.90 (2H, m), 3.93-4.30 (2H, m), 4.50-4.89 (6H, m), 4.90-5.12 (2H, m), 5.07 (d, J=12.2, 2H), 5.18 (d, J=12.2, 2H), 5.60 (1H, d, J=9.7), 5.67 (1H, d, J=10.2), 5.89 (1H, d, J=11.2), 6.56 (1H, d, J=7.3), 6.70 (1H, d, J=8.3), 6.76 (1H, d, J=6.8), 6.94 (d, J=6.8, 1H), 7.01-7.19 (m, 1H), 7.32 (bs, 5H), 8.17 (1H, d, J=7.8), 8.28 (d, J=7.8, 1H). ESI-MS Calcd for C$_{45}$H$_{79}$N$_4$O$_9$Si: 844.54. Found (m/z): 845.5 (M+H)$^+$.

EXAMPLE 22

Synthesis of Boc-Ist(TBDMS)-Hiv-Leu-Pro-OBn (SHPLA2)

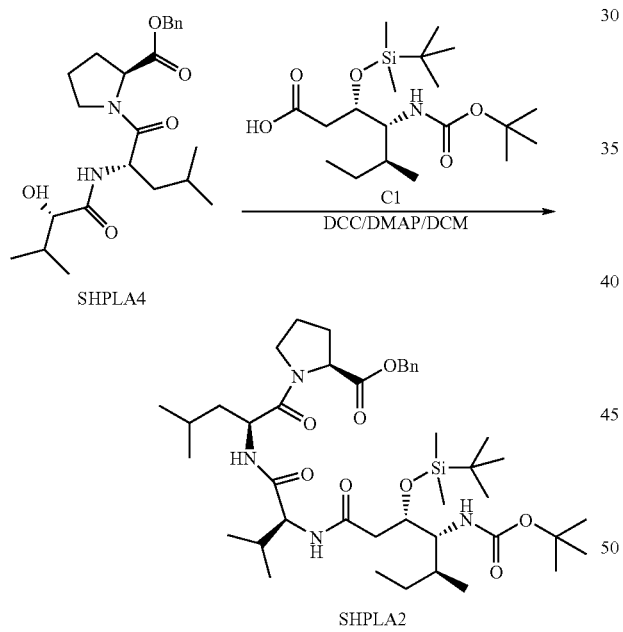

SHPLA4

SHPLA2

Following the procedure described for the synthesis of SAPLA2, starting from SHPLA4 (850 mg, 2.0 mmol) and C1 (935 mg, 2.4 mmol) the title compound was obtained (1.53 g, 97%) after purification by flesh LC (silica, gradient hex-FtOAc 3:1 to 2:1). Rf=0.63 (hex-EtOAc 2:1).

$^1$H NMR (300 MHz, CDCl$_3$) mixture of BocNH rotamers: δ 0.04 (s, 3H), 0.06 (s, 3H), 0.88 (s, 9H), 0.78-1.04 (m, 18H), 1.10-2.80 (m, 11H), 1.44 (s, 9H), 1.46 (s, 9H), 3.57 (m, 2H), 3.74 (m, 1H), 3.85 (m, 1H), 4.03 (m, 1H), 4.23 (d, J=4.8, 1H), 4.48 (m, 1H), 4.85 (m, 1H), 4.90 (d, J=10, 1H), 5.05 (m, 1H), 5.20 (d, J=10, 1H), 5.23 (d, J=10, 1H), 6.64 (d, J=6.4, 1H), 6.88 (d, J=8.6, 1H), 7.32 (m, 5H), 8.54 (d, J=8.3, 1H). $^{13}$C NMR (75 MHz, CDCl$_3$) δ −5.14, −4.58, 11.84, 12.97, 17.78, 17.92, 18.98, 21.05, 23.11, 23.49, 25.61, 26.92, 28.36, 28.70, 30.12, 33.68, 38.72, 42.86, 46.51, 48.18, 58.67, 60.24, 66.52, 71.14, 79.40, 82.66, 127.96, 128.01, 128.33, 135.36, 157.30, 169.92, 171.10, 171.69, 171.97. ESI-MS: Calcd for C$_{42}$H$_{71}$N$_3$O$_9$: 789.50. Found 790.5 (M+H)$^+$.

EXAMPLE 23

Synthesis of Boc-Ist(TBDMS)-Val-Leu-Pro-OBn (SVPLA2)

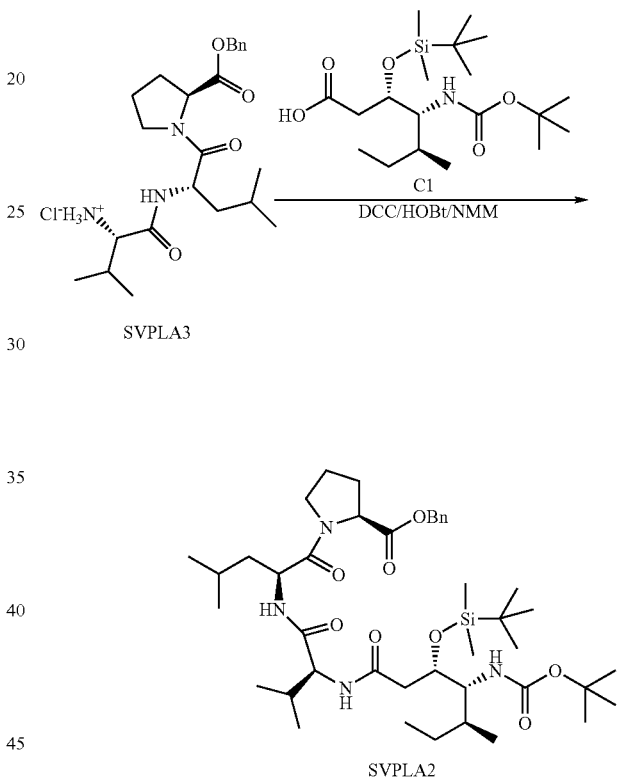

SVPLA3

SVPLA2

Following the procedure described for the synthesis of SNPLA2, starting from SVPLA3 (chlorhydrate) (1.2 g, 2.64 mmol), C1 (1.23 g, 3.17 mmol), DCC (654 mg, 3.17 mmol), HOBt (464 mg, 3.43 mmol), NMM (0.35 ml) and DCM (6 ml). The title compound was obtained as a white solid (1.87 g, 89%) after purification by flash LC (silica gel, gradient hex-EtOAc 3:1 to 2:1).

$^1$H NMR (500 MHz, CDCl$_3$) δ 0.07 (bs, 6H), 0.81-0.96 (m, 27H), 1.11-1.38 (m, 3H), 1.39-1.47 (bs, 7H), 1.51 (bs, 3H), 1.58-1.70 (m, 3H), 1.70-1.84 (m, 1H), 1.86-2.60 (m, 4H), 2.28-2.58 (m, 2H), 3.58-3.62 (m, 1H), 3.62-3.73 (m, 1H), 3.73-3.90 (m, 1H), 4.05-4.12 (m, 1H), 4.13-4.19 (m, 1H), 4.19-4.23 (m, 1H), 4.49-4.54 (m, 1H), 4.77-5.06 (m, 2H), 5.18 (d, J=12.3, 1H), 5.55 (bs, 1H), 6.44-6.61 (m, 2H), 7.30-7.35 (m, 5H), 7.94-7.98 (m, 1H). ESI-MS Calcd for C$_{42}$H$_{72}$N$_4$O$_8$Si: 788.51. Found (m/z): 789.5 (M+H)$^+$.

EXAMPLE 24

Synthesis of Boc-Ist(TBDMS)-(Me)Val-Leu-Pro-OBn (SMPLA2)

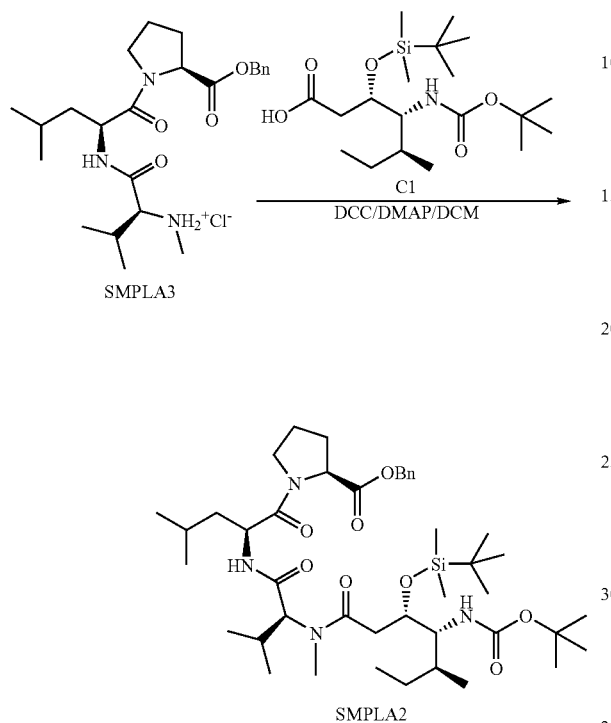

To a flask containing SMPLA3 (chlorhydrate) (176 mg, 0.38 mmol), in DCM (2 ml, anh) at 0° C., NMM (41 μl, 0.38 mmol) was added. After 15 min, C1 (176 mg, 0.46 mmol), and DCC (93 mg, 0.46 mmol) were added in portions. The flask was allowed to warm to room temperature and stirring was continued overnight. The reaction mixture was partitioned between DCM (10 ml) and aq KHSO$_4$ (2×5 ml, 10%). The organic phase was washed successively with aq. NaHCO$_3$ (2×5 ml, sat), brine (5 ml), dried (Na$_2$SO$_4$), filtered and concentrated under reduced pressure. The resulting white solid was purified by flash LC (silica, gradient Hex-EtOAc 3:1 to 2:1) to give SMPLA2 (127 mg, 42%) as a white solid. Rf=0.51 (Hex-EtOAc 1:1).

$^1$H NMR (300 MHz, CDCl$_3$) δ −0.08 (s, 3H), 0.05 (s, 3H), 0.75-0.86 (m, 27H), 1.00-1.43 (m, 1H), 1.52-1.65 (m, 1H), 1.68-1.80 (m, 1H), 1.83-2.01 (m, 3H), 2.08-2.24 (m, 2H), 2.40 (m, 2H), 2.87 (s, 3H), 3.50-3.57 (m, 3H), 3.71-3.76 (m, 1H), 4.29 (m, 1H), 4.47-4.63 (m, 4H), 5.01 (d, J=12.9, 1H), 5.11 (d, J=12.9, 1H), 6.41 (d, J=7.8, 0.5H), 6.62 (d, J=7.8, 1H), 7.01 (d, J=7.8, 0.5H), 7.23-7.28 (m, 5H). $^{13}$C NMR (75 MHz, CDCl$_3$) δ 11.56, 13.57, 13.98, 17.83, 18.87, 19.46, 21.77, 22.94, 23.11, 24.50, 24.71, 24.80, 25.64, 25.76, 25.97, 27.29, 28.18, 28.75, 30.40, 34.18, 39.28, 40.85, 46.58, 48.61, 57.03, 58.65, 62.26, 66.63, 69.21, 78.72, 127.92, 128.05, 128.11, 128.33, 135.42, 155.91, 169.76, 170.48, 171.56, 172.01. ESI-MS Calcd for C$_{43}$H$_{74}$N$_4$O$_8$Si: 802.53. Found (m/z): 825.5 (M+Na)$^+$.

EXAMPLE 25

Synthesis of Ist-Hip-Leu-Pro-OBn (SAPLA1)

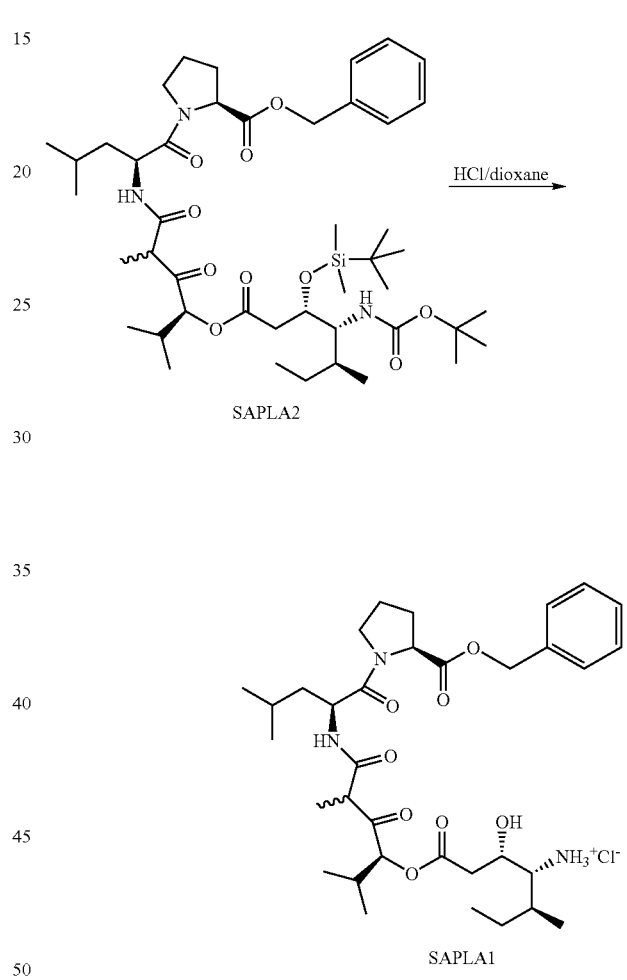

To a solution containing SAPLA2 (19.32 g, 22.8 mmol) in anh. dioxane (78 ml), a solution of hydrochloric acid in anhydrous dioxane (4.2 N, 220 ml, 924 mmol) was added. The resulting solution was stirred at 21° C. for 4.30 h or until complete disappearance of the starting material (TLC). Then, the solution was concentrated under reduced pressure. The residue was dissolved in DCM (25 ml) and concentrated to remove residual HCl. The resulting residue was dried under vacuum until complete elimination of free HCl (3 h) to give 17.3 g of SAPLA1 (15.1 g, quant) as a white foam (mixture of diasteromers).

EXAMPLE 26

Synthesis of Ist-Aip-Leu-Pro-OBn (SNPLA1)

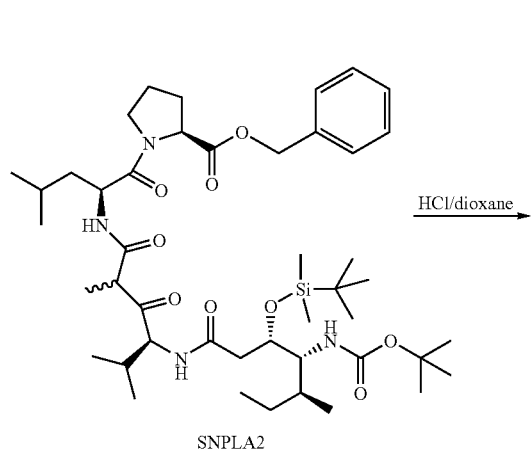

Following the procedure described for synthesis of SAPLA1, starting from SNPLA2 (700 mg, 0.82 mmol), the title compound was obtained as a white solid (545 mg, quant.) after precipitation with Et₂O (mixture of diasteromers).

¹H NMR (300 MHz, CDCl₃) δ 0.86-1.04 (m, 18H), 1.02-1.22 (m, 3H), 1.23-1.3 (m, 5H), 1.60-1.80 (m, 2H), 1.82-2.01 (m, 3H), 2.24 (m, 2H), 2.40-2.5 (m, 2H), 3.24 (m, 1H), 3.45 (m, 1H), 3.60 (m, 1H), 3.70-4.05 (m, 2H), 4.46 (m, 2H), 4.47-4.75 (m, 2H), 5.10 (bs, 2H), 7.34 (bs, 5H), 7.98 (bs, 1H), 8.10 (bs, 1H). ESI-MS Calcd for $C_{34}H_{54}N_4O_7$: 630.40. Found (m/z); 631.4 (M+H)⁺.

EXAMPLE 27

Synthesis of Ist-Hiv-Leu-Pro-OBn (SHPLA1)

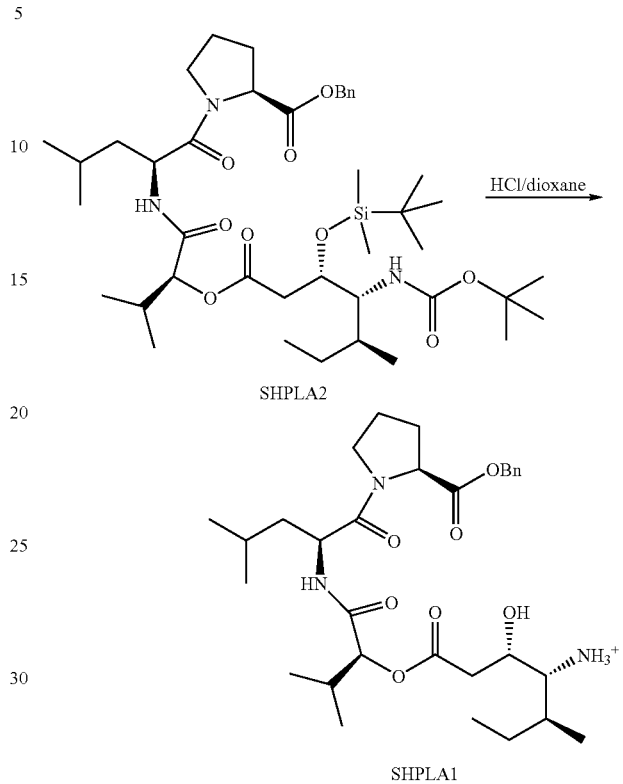

Following the procedure described for synthesis of SAPLA1, starting from SHPLA2 (1.53 g, 1.94 mmol), the title compound (1.12 g, quant.) was obtained as a white solid after precipitation with Et₂O.

¹H NMR (300 MHz, CDCl₃) δ 0.86-1.04 (m, 18H), 1.10-1.22 (m, 3H), 1.42 (m, 2H), 1.70 (m, 2H), 1.97 (m, 3H), 2.24 (m, 2H), 2.83 (m, 1H), 2.97 (m, 1H), 3.34 (m, 1H), 3.61 (m, 1H), 3.75 (m, 1H), 3.90 (m, 1H), 4.56 (m, 2H), 4.75 (m, 1H), 5.04 (d, J=11, 1H), 5.18 (d, J=11, 1H), 7.34 (bs, 5H), 8.21 (bs, 3H). ESI-MS Calcd for $C_{31}H_{49}N_3O_7$: 575.36. Found (m/z): 576.3 (M+H)⁺.

EXAMPLE 28

Synthesis of Ist-Val-Leu-Pro-OBn (SVPLA1)

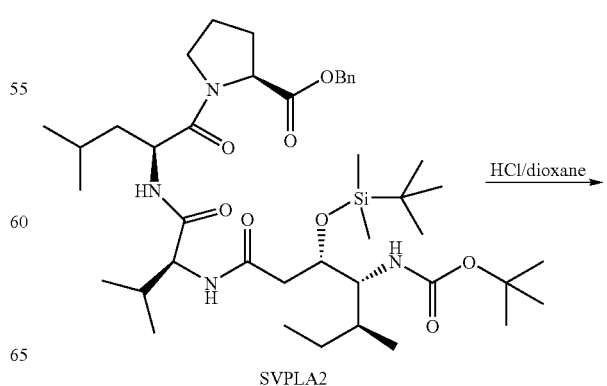

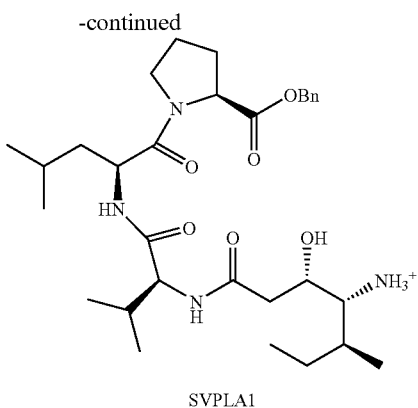

SVPLA1

Following the procedure described for synthesis of SAPLA1, starting from SVPLA2 (1.87 g, 2.36 mmol), the title compound (1.40 g, quant.) was obtained as a white solid after precipitation with Et$_2$O.

$^1$H NMR (300 MHz, CDCl$_3$) δ 0.82-1.01 (m, 15H), 1.01-1.10 (m, 3H), 1.20-1.79 (m, 5H), 1.81-2.05 (m, 4H), 2.05-2.15 (m, 2H), 2.50-2.68 (m, 2H), 2.82-3.1 (m, 1H), 3.20-3.35 (m, 1H), 3.50-3.70 (m, 1H), 3.80-3.90 (m, 1H), 4.18-4.30 (m, 1H), 4.35-4.45 (m, 1H), 4.45-4.55 (m, 1H), 4.60-4.70 (m, 1H), 5.02 (d, J=12.3, 1H), 5.15 (d, J=12.3, 1H), 7.28-7.38 (m, 5H), 7.5 (bs, 1H), 7.9 (bs, 3H), 8.15 (bs, 1H). $^{13}$C NMR (75 MHz, CDCl$_3$) δ 10.81, 14.67, 18.29, 19.32, 21.48, 23.14, 24.48, 24.76, 25.81, 30.29, 33.41, 40.31, 46.96, 49.35, 59.14, 59.94, 60.67, 66.94, 128.11, 128.32, 128.54, 135.32, 171.58, 171.74, 171.80, 172.57. ESI-MS Calcd for C$_{31}$H$_{50}$N$_4$O$_6$: 574.35. Found (m/z): 575.3 (M+H4)$^+$.

EXAMPLE 29

N-tert-Butyloxycarbonylthreonine Phenacyl Ester (D3)

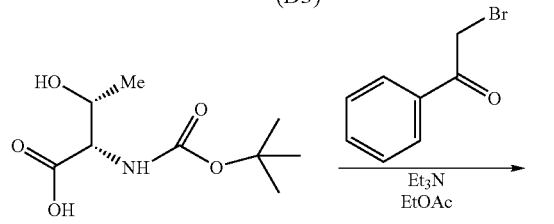

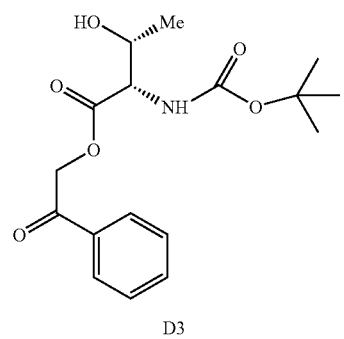

D3

To a stirred suspension of Boc-Thr-OH (21.91 g, 0.1 mol) in EtOAc (200 ml) at 0° C., TEA (14 ml, 0.1 mol) and bromoacetophenone (19.0 g, 0.1 mol) were added. The reaction mixture was allowed to warm to 20° C., stirred for 2 days and then diluted with EtOAc (500 ml). After washing successively with aq HCl (200 ml, 0.1 N), H$_2$O (100 ml), aq NaBCO$_3$ (200 ml, 1 N) and brine (200 ml), drying (Na$_2$SO$_4$), filtered and concentrated in vacuo, the residue was triturated with Et$_2$O and filtered. The resulting solid was dried in the dark to yield D3 (28.6 g, 85%). Rf=0.55 (hex-EtOAc 1:1, silica); M.p.=114.2° C.; [α]$_D^{22}$ −29.4 (c 2, EtOAc).

$^1$H NMR (300 MHz, CDCl$_3$): δ=1.31 (d, J=6.6, 3H), 1.46 (s, 9H), 3.77 (br d, OH), 4.44 (dd, J=9.6, 1H), 4.6 (q, 1H), 5.34 (d, J=16.5, 1H) 5.37 (br d, OH) 5.68 (d, J=16.8, 1H), 7.51 (t, 2H), 7.65 (t, 1H), 7.92 (dd, 2H).

EXAMPLE 30

N-Benzyloxycarbonyl-N,O-Dimethyl-L-tyrosine (E1)

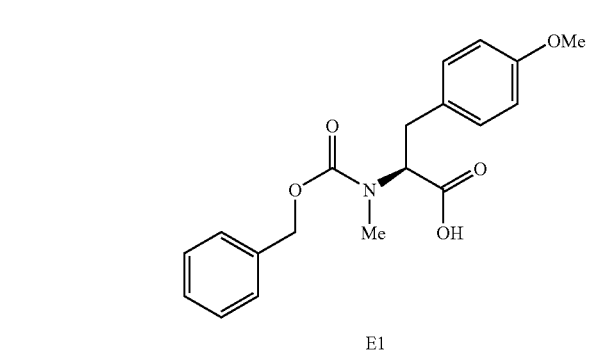

To a stirred solution of Z-Tyr-OH (63.24 g, 200 mmol) in THF (900 ml) at 0° C. was added finely powdered KOH (112.72 g, 2 mol) in portions, followed by the addition of tetrabutylammonium hydrogen sulfate (6.36 g, 10% by weight). Then, dimethyl sulfate (127.2 ml, 1.33 mol) was added dropwise over 30 min, while maintaining the reaction mixture below 4° C. The reaction was stirred for an additional 30 min and H$_2$O (950 ml) was added, After stirring 5 h at 0° C., the reaction was diluted with ether (1500 ml), the aqueous layer was separated, and the organic layer was extracted with aq NaHCO$_3$ (2×500 ml, sat). The combined aqueous layers were acidified to pH 1 with aq 1M KHSO$_4$, and extracted with EtOAc (5×500 ml). The organic layers were combined, dried (Na$_2$SO$_4$), filtered and concentrated. The residue was precipitated with ethyl ether and filtered to give E1 as a white solid (53.85 g, 78%).

[α]$_D^{22}$ −57.16 (c 2.23 CHCl$_3$) (lit [α]$_D$ −48 (c=2.23 CHCl$_3$). *JACS,* 112.21, 1990).

EXAMPLE 31

O-(Benzyloxycarbonyl-N,O-dimethyl-L-tyrosyl)N-tert-Butyloxycarbonyl-L-threonine Phenacyl Ester (D2)

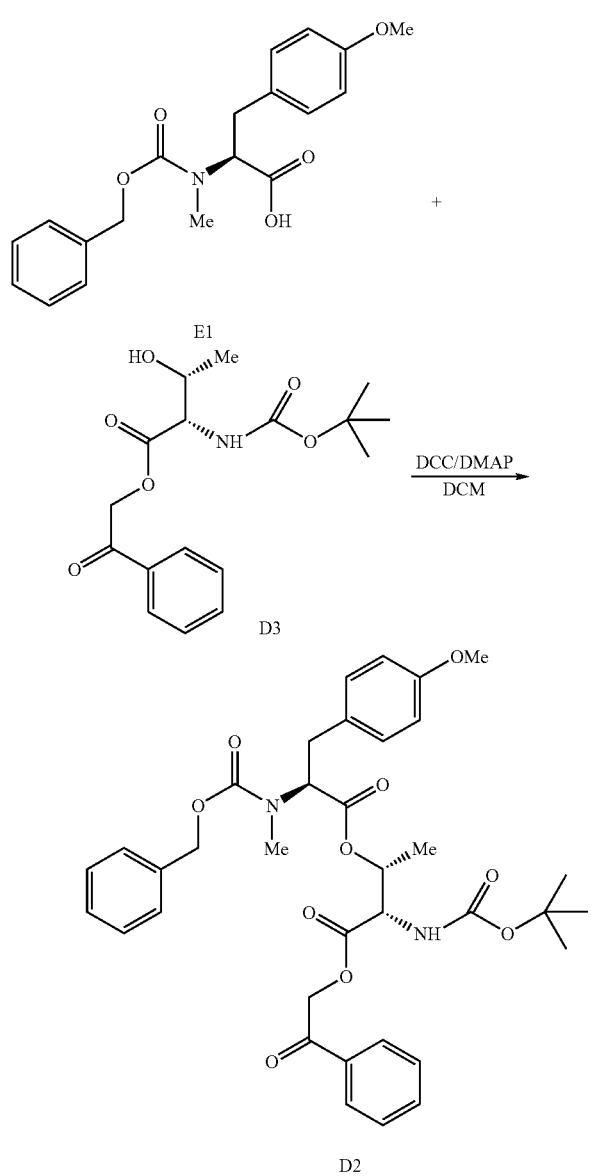

To a solution of D3 (33.72 g, 100 mmol) in DCM at 0° C., DMAP (3.66 g, 30 mmol), and E1 (34.33 g, 100 mmol) were added. After stirring 10 min at 0° C., DCC (22.7 g, 110 mmol) was added. The reaction mixture was allowed to warm to room temperature and stirred overnight. Then the mixture was filtered and the filtrate concentrated to dryness. The residue was chased with ACN (100 ml), filtered again and the filtrate was concentrated. The residue was dissolved in EtOAc (200 ml) and partitioned successively between aq KHSO$_4$ (100 ml, 10%), aq NaHCO$_3$ (100 ml, sat.) and brine (100 ml), The organic phase was dried (Na$_2$SO$_4$), filtered and concentrated. The residue was purified by flash LC (silica gel, grad EtOAc-Hex 1:4 to 1:2) to yield D2 (65.5 g, 98%). [α]$_D^{22}$ –39.56 (c 1.06 CHCl$_3$); Rf=0.55 (EtOAc:Hex 1:1).

EXAMPLE 32

O-(Benzyloxycarbonyl-N,O-dimethyl-L-tyrosyl)-N-tert-Butyloxycarbonyl-L-threonine (D1)

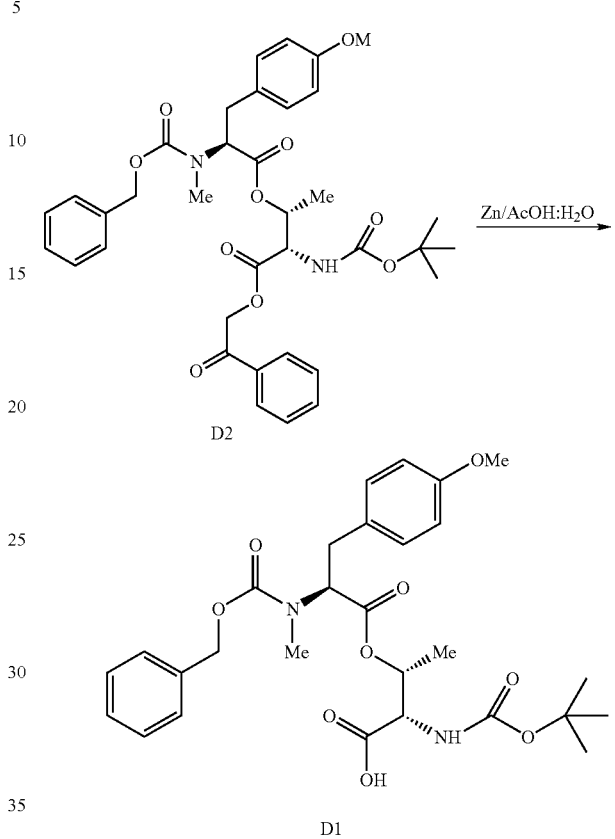

To a homogeneous solution of D2 (24.49 g, 38.4 mmol) in aq AcOH (211 ml, 90%) at 0° C., powdered Zn was added (18.65 g, 288.3 mmol). The resulting mixture was stirred at 0° C. for 3 h until disappearance of the starting material (followed by TLC), The reaction mixture was filtered over celite and washing with EtOAc (200 ml). The filtrate was concentrated at reduced pressure and the residue was chased with Et$_2$O (200 ml) and filtered. The filtrate was successively partitioned between aq KHSO$_4$(100 ml, 10%) and brine (100 ml). The organic phase was dried (Na$_2$SO$_4$) and concentrated to give an oil which was purified by flash LC (Lichroprep RPC18, ACN:H$_2$O 1:1 (800 ml, then 7.3 (600 ml)] to yield D1 (15.53 g, 74%) as a white solid. [α]$_D^{24}$ –27.6 (c 2.187, DCM); lit [α]$_D$ –20.5 (c 2, DCM), *JOC*, 62, 2, 1997. Rf=0.58 [ACN/H$_2$O (7:3)].

IR (film, DCM) ν 3400, 3050, 2900, 1715, 1613, 1514, 1456, 1402, 1368, 1248, 1165, 1061, 1036 cm$^{-1}$. $^1$H NMR (200 MHz, CDCl$_3$) δ 1.29 (d, J=6.5, 3H), 1.45 (s, 9H), 2.74 (s, 3H), 2.75 (s, 3H), 2.76-3.31 (m, 2H), 3.77 (s, 3H), 4.42-4.52 (m, 1H), 4.66-4.83 (m, 1H), 5.01-5.16 (m, 2H), 5.30-5.53 (m, 2H), 6.72-6.81 (m, 2H), 6.95-7.09 (m, 2H), 7.35 (bs, 5H). $^{13}$C NMR (75 MHz, CDCl$_3$) δ 16.44, 16.82, 28.23, 31.71, 31.97, 33.82, 33.68, 55.14, 56.87, 56.75, 60.39, 60.58, 67.51, 67.76, 71.83, 72.47, 80.40, 113.91, 127.59, 128.69, 129.77, 136.42, 156.00, 156.19, 156.71, 158.31, 159.47, 169.78. m/z (FAB) 567.1 [(M+Na)$^+$, 46], 545.1 [(M+H)$^+$, 7], 445.1 (100); m/z (FABHRMS) 567.233 280, C$_{28}$H$_{35}$N$_2$O$_9$ requires (M+Na)$^{30}$ 567.231 851.

EXAMPLE 33
Synthesis of Bac-Thr(Z-N(Mel-O(Me)-Tyr)-Ist-Hip-Leu-Pro-OBn (SAPL7)

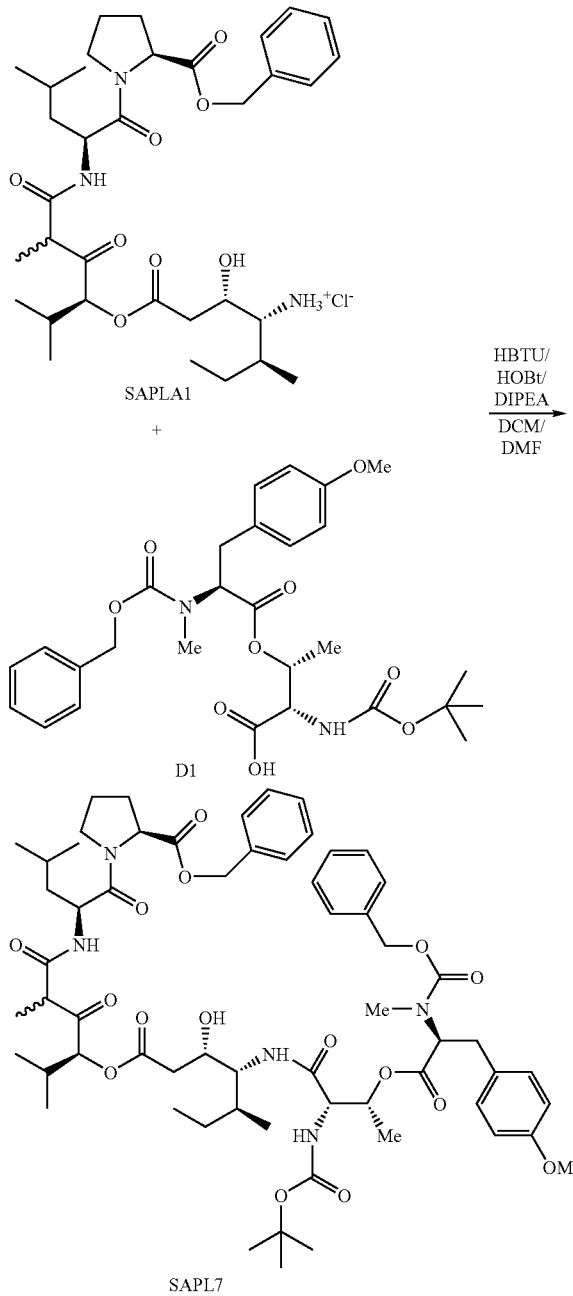

To flask containing HBTU (9.079 g, 23.9 mmol), HOBt (3.490 g, 22.8 mmol), SAPLA1 (15.258 g, 22.8 mmol) and D1 (12.417 g, 22.8 mmol), a solution of a DCM (296 mL) and anh DMP (148 mL) were cannulated under Ar at −5° C. After 5 min of stirring, DIPEA (15.9 mL, 91.2 mmol) was added dropwise by syringe, while maintaining the temperature <−5° C. The resulting reaction mixture was stirred for 21 h at −5° C., MTBE (300 mL) and KHSO₄ (200 mL, 10%) were added, and the resulting mixture was filtered off and concentrated up to 300 mL. Additional MTBE (200 mL) was added, the layers were separated, and the organic phase was treated sequentially with aq. KHSO₄ (200 ml, 10%), brine (200 ml), aq. NaHSO₄ (200 ml, sat.) and rinse with brine (200 ml). The organic phase was dried (Na₂SO₄) and con centrated under reduced pressure to afford a yellow oil (30 g). The oil was dissolved in MTBE and treated with hex while stirring. Solid precipitated and more hex was added. The solid was filtered to yield SAPL7 (18.33 g, 69% yield) as a white solid. This product is a mixture of two diastereomers. Rf=0.80 and 0.59 (hex:EtOAc 1:2).

IR (film, DCM) ν 3350, 2961, 2927, 2893, 1744, 1688, 1638, 1514, 1454, 1368, 1304, 1248, 1171, 1067, 1036 cm$^{-1}$. $^1$H NMR (500 MHz, CDCl₃) δ 0.74-0.92 (m, 18H), 1.05-1.15 (m, 2H), 1.18-1.20 (m, 2H), 1.23 (d, J=6.8, 3H), 1.25 (d, J=6.8, 3H), 1.29 (d, J=6.9, 3H), 1.42 (s, 9H), 1.45 (s, 9H), 1.50-1.66 (m, 3H), 1.89-2.02 (m, 4H), 2.17-2.25 (m, 2H), 2.37-2.42 (m, 1H), 2.81 (s, 3H), 2.88 (s, 3H), 2.91 (s, 3H), 2.95 (s, 3H), 2.84-2.93 (m, 2H), 3.17-3.25 (m, 1H), 3.53-3.59 (m, 1H), 3.75 (s, 3H), 3.88-3.98 (m, 4H), 4.49 (d, J=3.1, 1H), 4.51 (d, J=3.1, 1H), 4.53-4.57 (m, 1H), 4.68-4.72 (m, 1H), 4.96-4.99 (m, 1H), 5.02-5.33 (m, 4H), 5.02 (d, J=3.2, 1H), 5.23 (d, J=3.1, 1H), 5.26-5.33 (m, 1H), 5.47 (d, J=9.5, 1H), 6.74 (d, J=7.8, 2H), 6.77 (d, J=7.7, 2H), 7.08 (d, J=7.7, 2H), 7.17 (d, J=7.5, 1H), 7.21 (d, J=9.5, 1H), 7.23-7.36 (m, 10H), 7.75 (d, J=7.9, 1H), 7.79 (d, J=8.2, 1H). $^{13}$C NMR (75 MHz, CDCl₃) δ 11.95, 13.27, 15.16, 16.47, 17.33, 18.79, 21.28, 23.65, 24.65, 24.72, 27.09, 28.08, 28.93, 31.20, 31.32, 33.62, 33.98, 38.38, 41.01, 47.12, 49.38, 54.96, 55.17, 57.89, 58.83, 60.01, 60.16, 67.18, 71.05, 71.32, 8034, 81.24, 113.89, 127.51, 128.59, 129.69, 129.77, 135.52, 136.77, 156.93, 158.27, 169.87, 170.62, 171.15, 171.85, 172.39, 204.88. m/z(FAB) 1181.2 [(M+Na)⁺, 20], 1159.2 [(M+H)⁺, 80], 1059.2 (100). Anal. Calcd for C₆₂H₈₇N₅O₁₆; C, 64.30; H, 7.52; N, 6.05. Found: C, 64.14; H, 7.66; N, 5.95

EXAMPLE 34
Synthesis of Boc-Thr(Z-N(Me)-O(Me)-Tyr)-Ist-Aip-Leu-Pro-OBn (SNPL7)

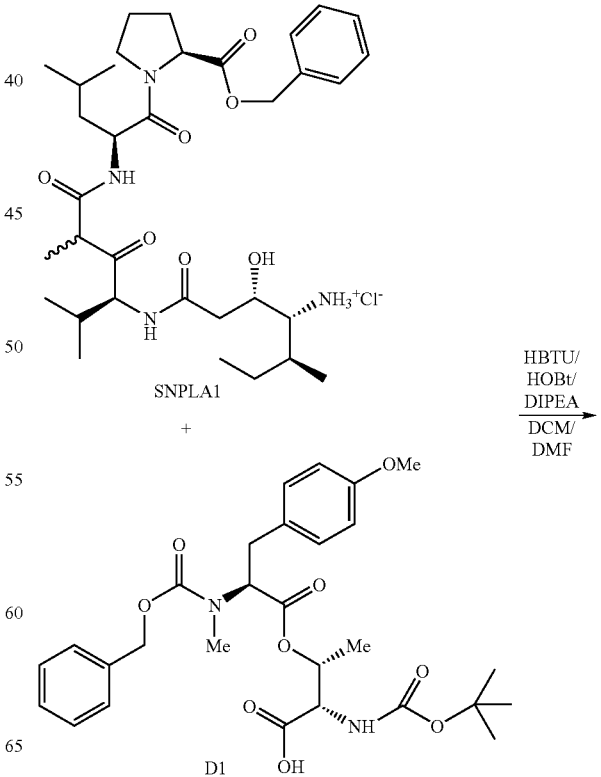

107

-continued

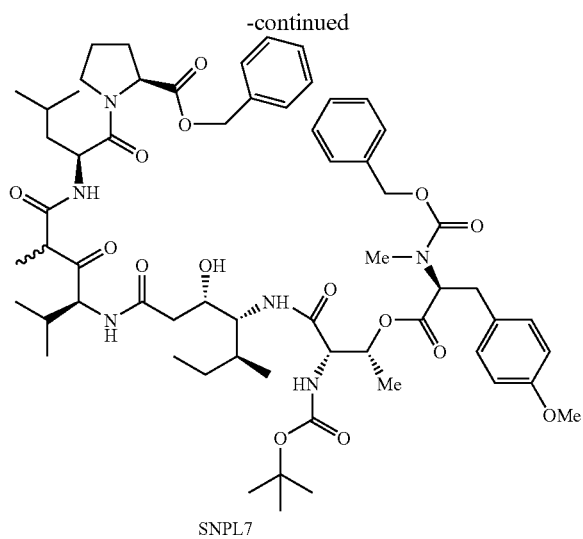

SNPL7

Following the procedure described for synthesis of SAPL7, starting from SNPLA1 (150 mg, 0.22 mmol) and D1 (122 mg, 0.22 mmol), the title compound was obtained as a white solid (130 mg, 51%) after purification by flash LC (silica gel, gradient hex-EtOAc 2:1 to 1:3) (mixture of diastereomers).

$^1$H NMR (300 MHz, CDCl$_3$) δ 0.74-1.03 (m, 18H), 1.16-1.37 (m, 10H), 1.45 (s, 9H), 1.68 (m, 3H), 1.99 (m, 4H), 2.22 (m, 2H), 2.48 (m, 1H), 2.82 (s, 3H), 2.84-3.10 (m, 2H), 3.19 (m, 1H), 3.51-3.69 (m, 2H), 3.75 (s, 3H), 3.72-4.02 (m, 3H), 4.18 (m, 1H), 4.50-4.73 (m, 4H), 5.00-5.27 (m, 5H), 5.49 (m, 2H), 6.54 (d, J=9.2, 1H), 6.78 (d, J=6.8, 2H), 7.02 (d, J=6.8, 2H), 7.18 (m, 1H), 7.23-7.36 (m, 10H), 7.52 (d, J=6.8, 1H). ESI-MS Calcd for C$_{62}$H$_{88}$N$_6$O$_{15}$: 1156.63. Found 1158.3 (M+H)$^+$.

EXAMPLE 35

Synthesis of Boc-Thr(Z-N(Me)-O(Me)-Tyr-Ist-Hiv-Leu-Pro-OBn (SHPL7)

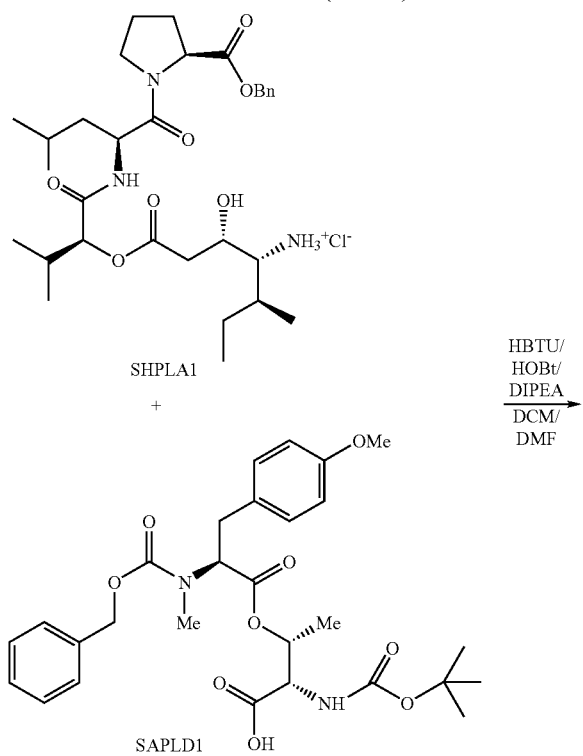

108

-continued

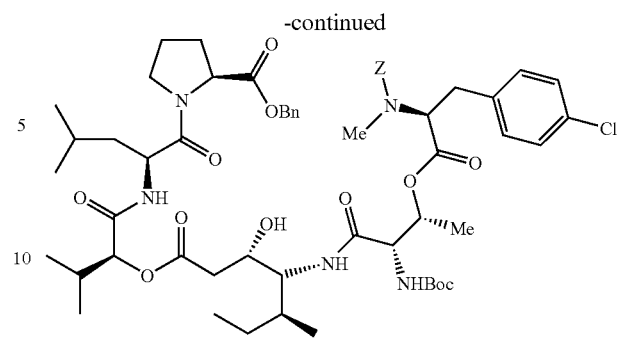

SHPL7

Following the procedure described for synthesis of SAPL7, starting from SHPLA1 (1.12 g, 1.94 mmol) and SAPLD1 (544.6 mg, 1.94 mmol), the title compound (1.045 g, 61%) was obtained as a white solid after purification by flash LC (silica gel, gradient hex-EtOAc 1:1 to 1:2). Rf=0.46 (hex-EtOAc 1:2).

$^1$H NMR (300 MHz, CDCl$_3$) δ 0.74-1.02 (m, 18H), 1.20 (m, 5H), 1.40 (m, 3H), 1.46 (s, 9H), 1.62 (m, 2H), 1.82-2.20 (m, 3H), 2.20 (m, 2H), 2.50 (m, 1H), 2.78 (s, 3H), 2.90 (m, 1H), 3.20 (m, 1H), 3.58 (m, 1H), 3.67 (s, 3H), 3.79 (m, 1H), 3.88 (m, 1H), 4.06 (m, 2H), 4.40 (m, 2H), 4.82 (m, 2H), 4.94 (m, 1H), 4.98 (m, 1H), 5.08 (m, 1H), 5.28 (m, 3H), 5.56 (d, J=6.2, 1H), 6.84 (d, J=8.3, 2H), 6.98 (d, J=6.5, 1H), 7.07 (d, J=8.3, 2H), 7.34 (m, 10H), 7.52 (d, J=6.2, 1H). $^{13}$C NMR (75 MHz, CDCl$_3$) δ 11.27, 13.77, 13.95, 16.75, 17.46, 18.31, 20.78, 20.96, 23.09, 24.35, 24.53, 26.74, 27.93, 28.63, 30.17, 33.76, 39.06, 40.01, 46.69, 48.17, 54.89, 57.04, 57.68, 58.65, 60.20, 60.60, 66.74, 67.08, 68.31, 70.30, 78.49, 79.90, 113.62, 127.36, 127.70, 128.14, 128.18, 128.31, 129.64, 135.19, 136.31, 155.86, 156.61, 158.09, 169.77, 170.70, 171.06, 171.17, 171.78. ESI-MS Calcd for C$_{59}$H$_{83}$N$_5$O$_{15}$: 1101.59. Found 1102.7 (M+H)$^+$.

EXAMPLE 36

Synthesis of Boc-Thr(Z-N(Me)-O(Me)-Tyr-Ist-Val-Leu-Pro-Bn (SVPL7)

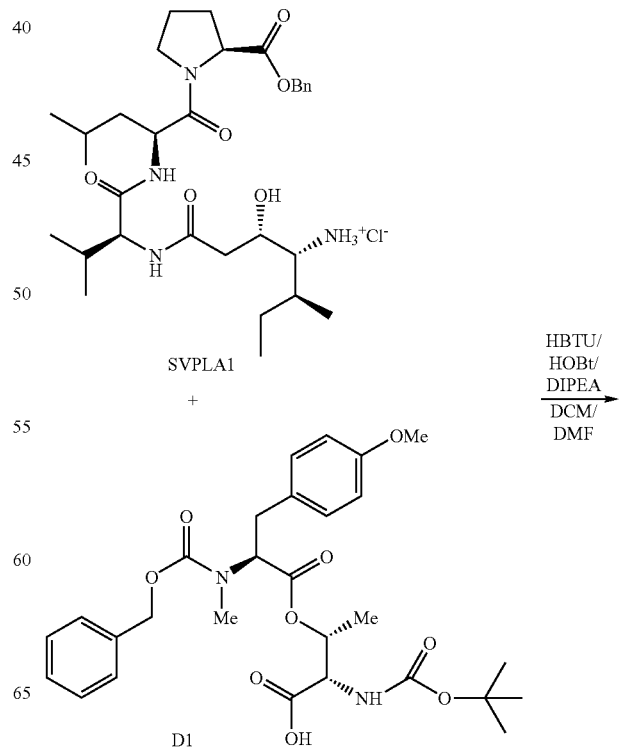

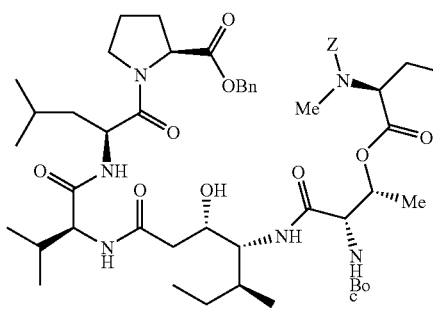

SVPL7

Following the procedure described for synthesis of SAPL7, starting from SVPLA1 (1.44 g, 2.37 mmol) and D1 (1.29 g, 2.37 mmol), the title compound (1.96 g, 75%) was obtained as a white solid after purification by ash LC (silica gel, gradient hex-EtOAc 2:1 to 1:3). Rf=0.56 (EtOAc).

$^1$H NMR (300 MHz, CDCl$_3$): δ 0.83-0.95 (m, 15H), 1.0-1.22 (m, 4H), 1.23-1.44 (m, 9H), 1.60-1.65 (m, 1H), 1.87-2.01 (m, 4H), 2.09-2.20 (m, 3H), 2.77 (bs, 8H), 2.84-3.01 (m, 1H), 3.17-3.24 (m, 1H), 3.51-3.60 (m, 1H), 3.73 (s, 3H), 3.80-3.90 (m, 2H), 4.03-4.15 (m, 1H), 4.25-4.40 (m, 2H), 4.40-4.52 (m, 1H), 4.70-4.80 (m, 2H), 5.00-5.26 (m, 4H), 5.34-5.36 (m, 1H), 5.58 (m, 1H), 6.75 (d, 2H, J=7.8), 6.96-7.09 (m, 1H), 7.04 (d, 2H, J=8.1), 7.04-7.12 (m, 1H), 7.16-7.20 (m, 1H), 7.18-7.30 (m, 10H). $^{13}$C NMR (75 MHz, CDCl$_3$) δ 11.43, 13.63, 17.17, 18.35, 19.21, 21.40, 23.23, 24.49, 24.67, 26.87, 28.10, 28.79, 30.48, 32.11, 33.84, 38.47, 40.37, 41.22, 46.80, 48.61, 55.04, 56.88, 57.95, 58.75, 59.25, 60.82, 66.87, 67.33, 69.40, 70.50, 76.44, 80.45, 113.58, 127.51, 127.74, 127.88, 128.10, 128.25, 128.33, 128.46, 128.72, 129.64, 129.77, 135.35, 136.37, 156.77, 158.29, 169.83, 170.57, 171.3, 171.4, 172.81. ESI-MS Calcd for $C_{59}H_{84}N_6O_{14}$: 1100.60. Found (m/z): 1101.7 (M+H)$^+$.

EXAMPLE 37

Synthesis of Boc-Thr(N(Me)-O(Me)-Tyr)-Ist-Hip-Leu-Pro-OH (SAPL6)

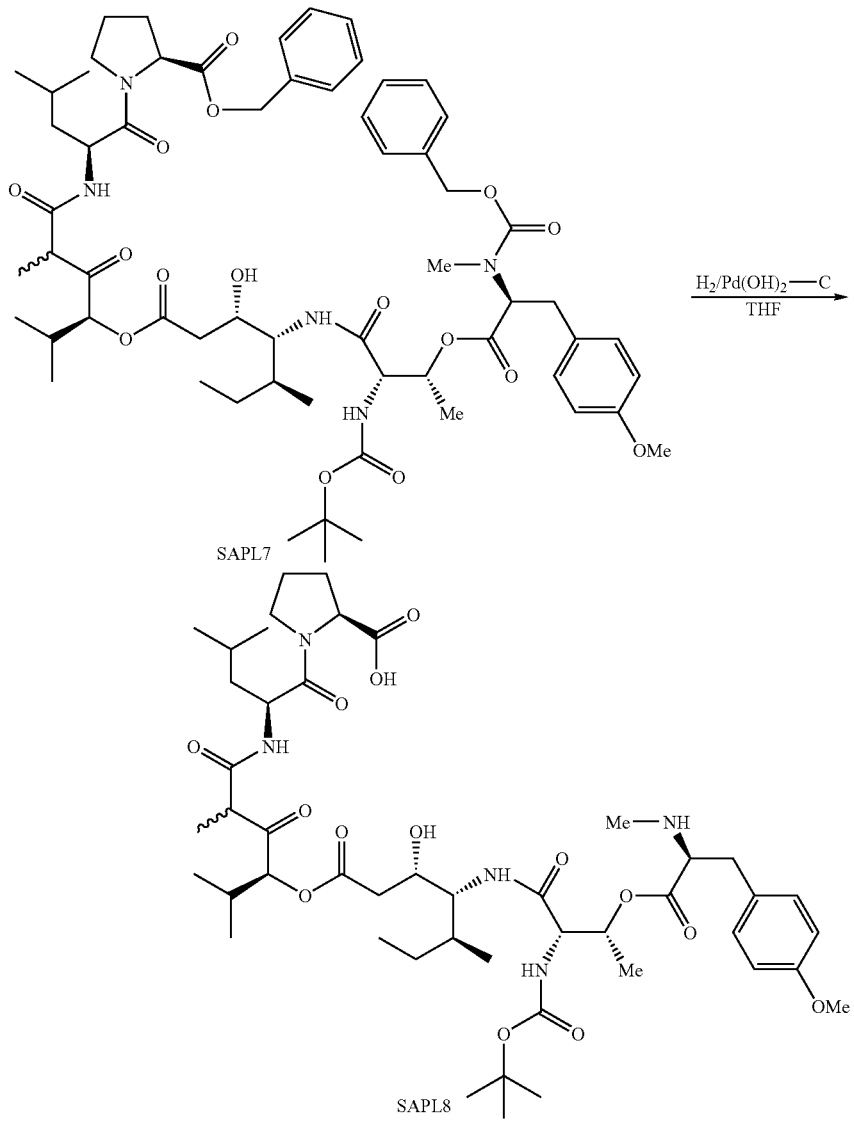

To a solution of SAPL7 (18.33 g, 15.8 mmol) in THF (free of stabilizer, 500 mL) degassed and purged with argon, Pd(OH)$_2$—C (20% Pd, 7.33 g, 40% w/w). The mixture was stirred under H$_2$ (1 atm) for 20 h, then filtered over a 0.45 μm teflon filter and concentrated under reduced pressure to give a white solid. Toluene (30 mL) was added, and concentrated again under reduced pressure and high vacuo to give SAPL6 (14.78 g, quant) as a white solid.

$^1$H NMR (500 MHz, CDCl$_3$) δ 0.79-1.08 (m, 18H), 1.09-1.18 (m, 3H), 1.26 (bs, 3H), 1.29 (d, J=7.1, 3H), 1.47 (s, 9H), 1.50-1.66 (m, 3H), 1.84-1.94 (m, 1H), 1.90-2.28 (m, 4H), 2.35-2.50 (m, 4H), 2.30-2.35 (m, 1H), 2.44-3.18 (m, 4H), 2.60 (m, 3H), 3.53-3.61 (m, 1H), 3.77 (s, 3H), 3.88-4.07 (m, 4H), 4.12-4.72 (m, 4H), 5.18-5.24 (m, 1H), 5.24 (bs, 1H), 6.84 (d, J=7.9, 2H), 7.08 (d, J=8.0, 2H), 7.13 (d, J=8.2, 1H), 7.18 (d, J=8.2, 1H), 7.62-7.68 (bs, 1H). m/z (FAB) 972.7 [(M+K)$^+$, 33], 934.9 (M)$^+$, 100).

EXAMPLE 38

Synthesis of Boc-Thr(N(Me)-O(Me)-Tyr-Ist-Aip-Leu-Pro-OH (SNPL6)

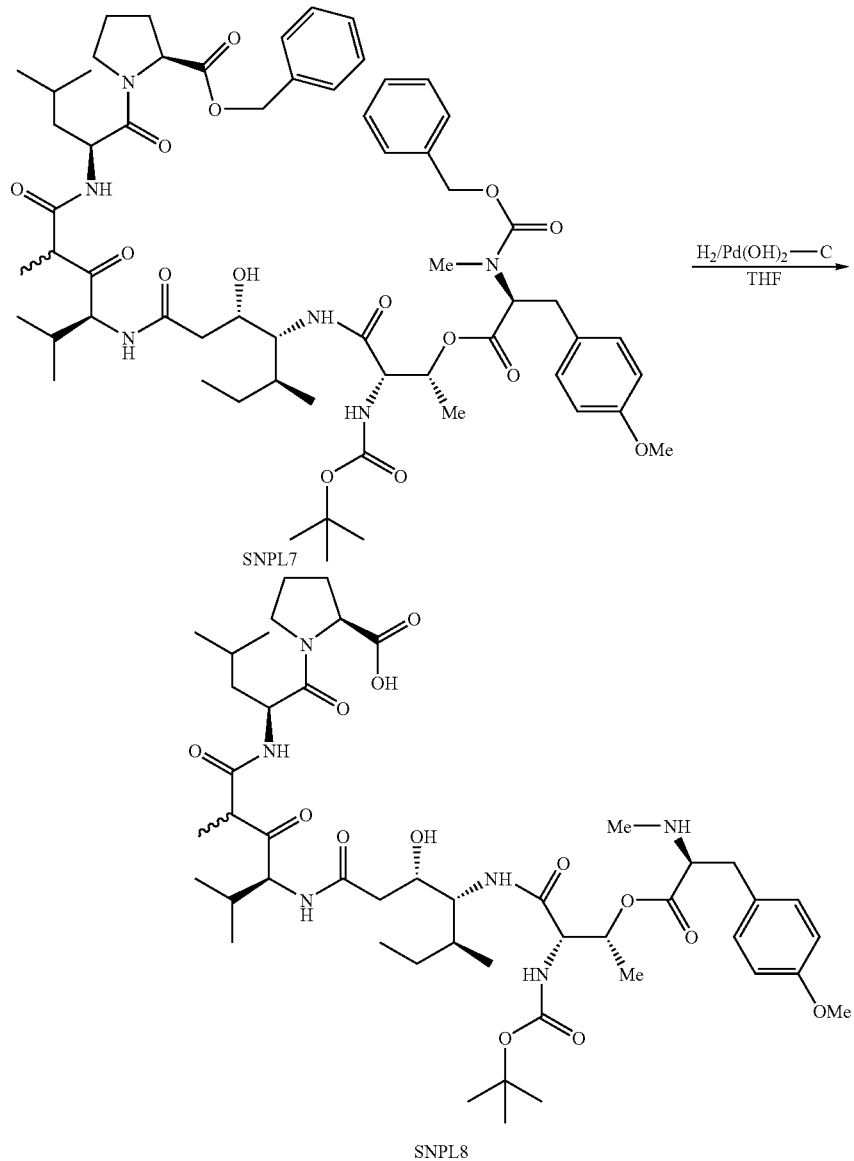

To a solution of SNPL7 (130 mg, 0.11 mmol) in a mixture IPA:H$_2$O (2:1, 4 ml:2 ml) degassed and purged with argon) Pd(OH)$_2$—C (20% Pd, 45 mg, 35% w/w). The mixture was stirred under H$_2$ (1 atm) for 20 h, then filtered over a 0.45 μm teflon filter and concentrated under reduced pressure to give a white solid. IPA (10 ml) was added, and concentrated again under reduced pressure and high vacuo to give SNPL6 (100 mg, quant) as a white solid.

ESI-MS Calcd for C$_{47}$H$_{76}$N$_6$O$_{13}$: 932.55. Found 934.0 (M+H)$^+$.

EXAMPLE 39
Synthesis of Boc-Thr(N(Me)-O(Me)-Tyr)-Ist-Hiv-Leu-Pro-OH (SHPL6)
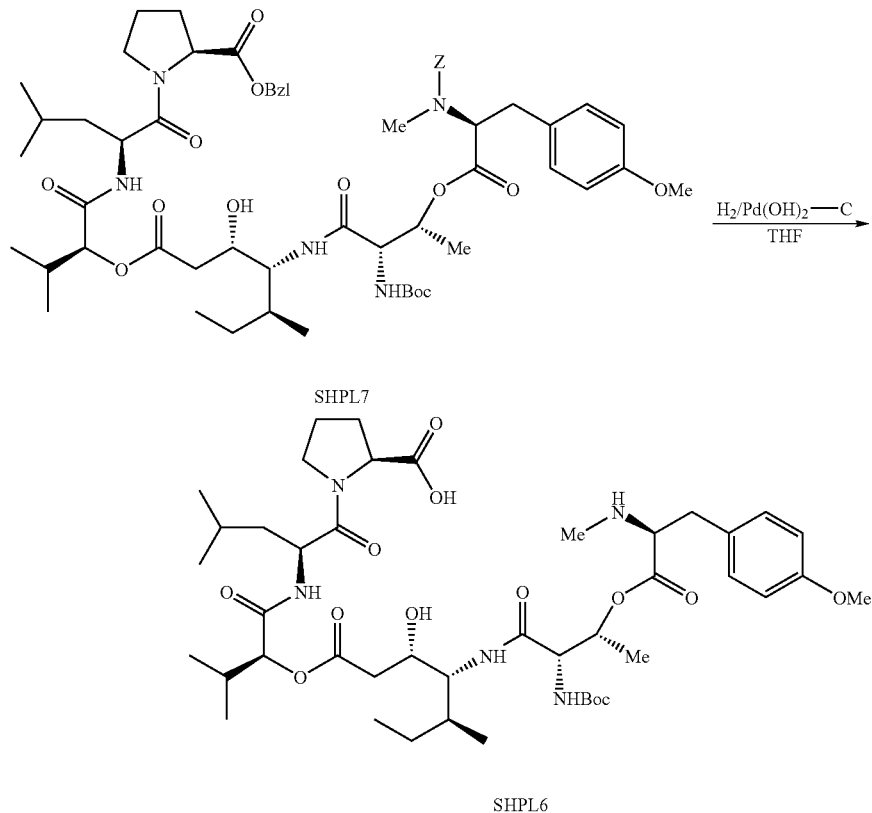
Following the procedure described for synthesis of SAPL6, starting from SHPL7 (1.045 g, 0.95 mmol). The title compound (825 g, 99%) was obtained as a white solid.
ESI-MS Calcd for $C_{44}H_{71}N_5O_{13}$: 877.50. Found 878.5 $(M+H)^+$.
EXAMPLE 40
Synthesis of Boc-Thr(N(Me)-O(Me)-Tyr)-Ist-Val-Leu-Pro-OH (SVPL6)
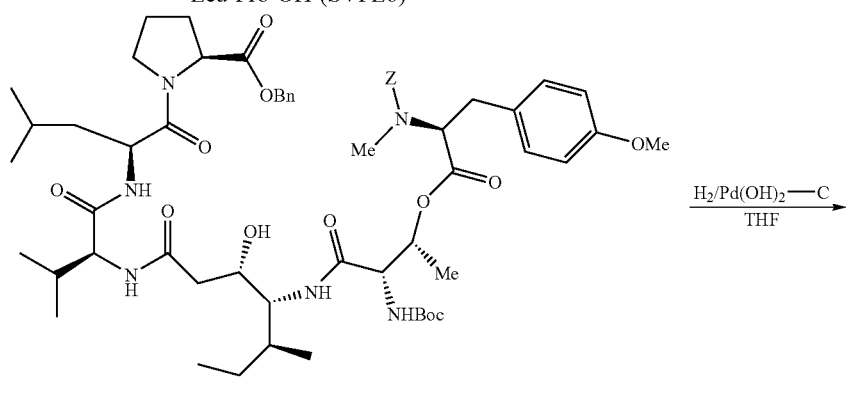

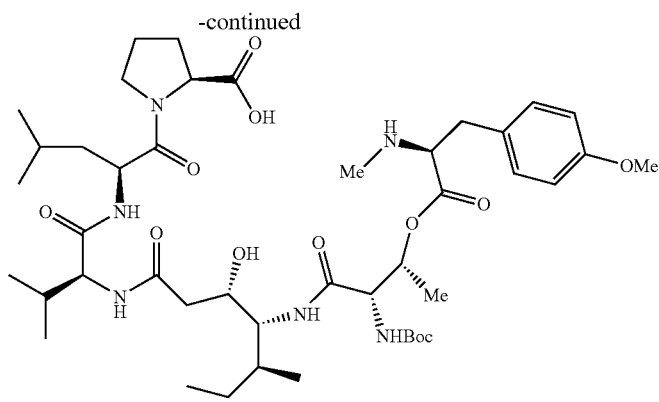
SVPL6
Following the procedure described for synthesis of SAPL6, starting from SVPL7 (250 mg, 0.23 mmol). The title compound (195 mg, 97%) was obtained as a white solid.
ESI-MS Calcd for $C_{44}H_{72}N_6O_{12}$: 876.56. Found (m/z): 877.5 $(M+H)^+$.
EXAMPLE 41
Synthesis of Cyclo-N(Me)-O(Me)Tyr-O-(Boc-Thr)-Ist-Hip-Leu-Pro (SAPL5)
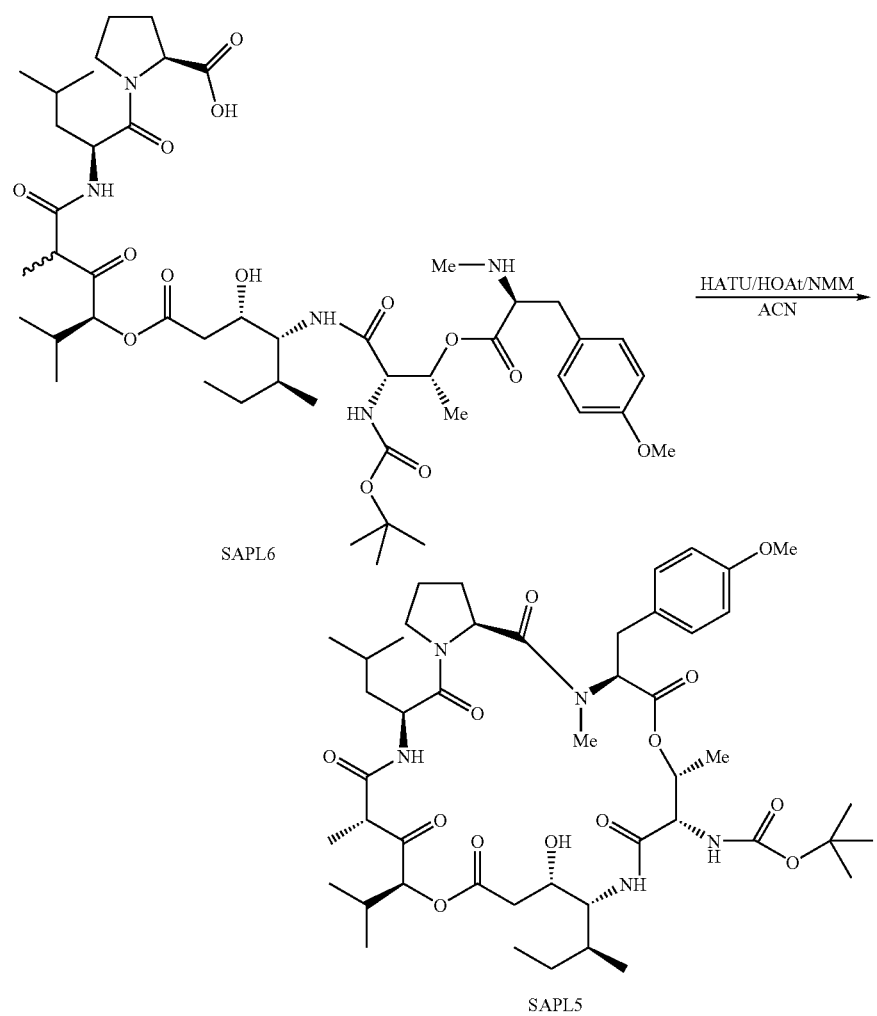

In a cooled (−5° C.) 5 L reactor fitted with mechanical stirrer containing ACN (3.2 L), HATU (14.436 g, 37.9 mmol) and HOAt (5.254 g, 38.6 mmol) were added under Ar while stirring. SAPL6 (14.77 g, 15.8 mmol) dissolved in ACN (500 ml) was added. NMM (3.65 ml, 33.18 mmol) was added dropwise by syringe while maintaining the temperature below −5° C. The resulting reaction mixture was allowed to reach room temperature and was stirred for 20 h. The solvent was evaporated under reduced pressure. The crude was chased with EtOAc (500 ml) and the solution was filtered off to remove precipitate. The solution was washed successively with aq. $KHSO_4$ (2×500 ml), brine (500 ml), aq. $NaHCO_3$ (500 ml, sat.) and rinse with brine (500 ml). The organic phase was dried ($Na_2SO_4$) and concentrated under reduced pressure to afford a yellow solid (17.52 g) that was purified by flash (silica gel, grad hex:EtOAc 3:1 to 1:1) to give SAPL5 (9.83 g, 68%) as a white solid. Rf=0.60 (Hex:EtOAc 1:3). $[\alpha]_D$ −209.4 (c 0.3, $CHCl_3$).

IR (film, DCM) ν 3343, 2961, 2927, 2893, 1734, 1640, 1514, 1454, 1368, 1302, 1248, 1167, 1018 $cm^{-1}$. $^1H$ NMR (500 MHz, $CDCl_3$) δ 0.78 (d, J=7.1, 3H), 0.85 (d, J=7.0, 3H), 0.87 (d, J=7.0, 3H), 0.89-0.93 (m, 9H), 1.10-1.20 (m, 1H), 1.20 (d, J=6.4, 3H), 1.30 (d, J=6.9, 3H), 1.36 (m, 2H), 1.40 (m, 2H), 1.44 (s, 9H), 1.48-1.72 (m, 2H), 1.72-1.78 (m, 1H), 1.83-1.88 (m, 1H), 2.01-2.17 (m, 3H), 2.27-2.29 (m, 1H), 2.47-2.53 (m, 1H), 2.53 (s, 3H), 2.93 (bs, 1H), 3.14-3.19 (m, 2H), 3.34-3.37 (dd, $J_1$=14.8, $J_2$=4.1, 1H), 3.54-3.56 (dd, $J_1$=10.5, $J_2$=4.1, 1H), 3.58-3.63 (m, 1H), 3.68-3.72 (m, 1H), 3.78 (s, 3H), 3.94-3.98 (m, 1H), 3.98 (q, J=7.5, 1H), 4.07-4.11 (3d, J=3.8, 1H), 4.57-4.61 (m, 2H), 4.77-4.81 (m, 1H), 4.97-4.98 (q, J=3.5, 1H), 5.02 (d, J=10.5, 1H), 5.18 (d, J=4.2, 1H), 6.81 (d, J=8.5, 2H), 7.05 (d, J=8.5, 2H), 7.19 (d, J=10.2, 1H), 7.64 (d, J=10.1, 1H). $^{13}C$ NMR (75 MHz, $CDCl_3$) δ 11.56, 14.68, 14.97, 15.27, 16.61, 18.45, 20.64, 23.50, 24.71, 24.78, 26.92, 27.73, 27.94, 31.55, 33.94, 33.94, 38.27, 38.52, 40.64, 46.86, 49.54, 49.65, 55.16, 55.19, 55.84, 57.12, 65.96, 67.30, 71.00, 80.27, 81.41, 114.02, 130.22, 158.53, 168.30, 169.31, 170.12, 170.29, 171.20, 172.38, 204.51. m/z (FAB) 938.9 [(M+Na)$^+$, 55], 916.9 [(M+H)$^+$, 100]; m/z (FABHRMS) 916.532 120, $C_{47}H_{73}N_5O_{13}$, requires (M+H)$^+$=916.528 300.

EXAMPLE 42

Synthesis of Cyclo-N(Me)-O(Me)-Tyr-O-(Boc-Thr)-Ist-Aip-Leu-Pro (SNPL5)

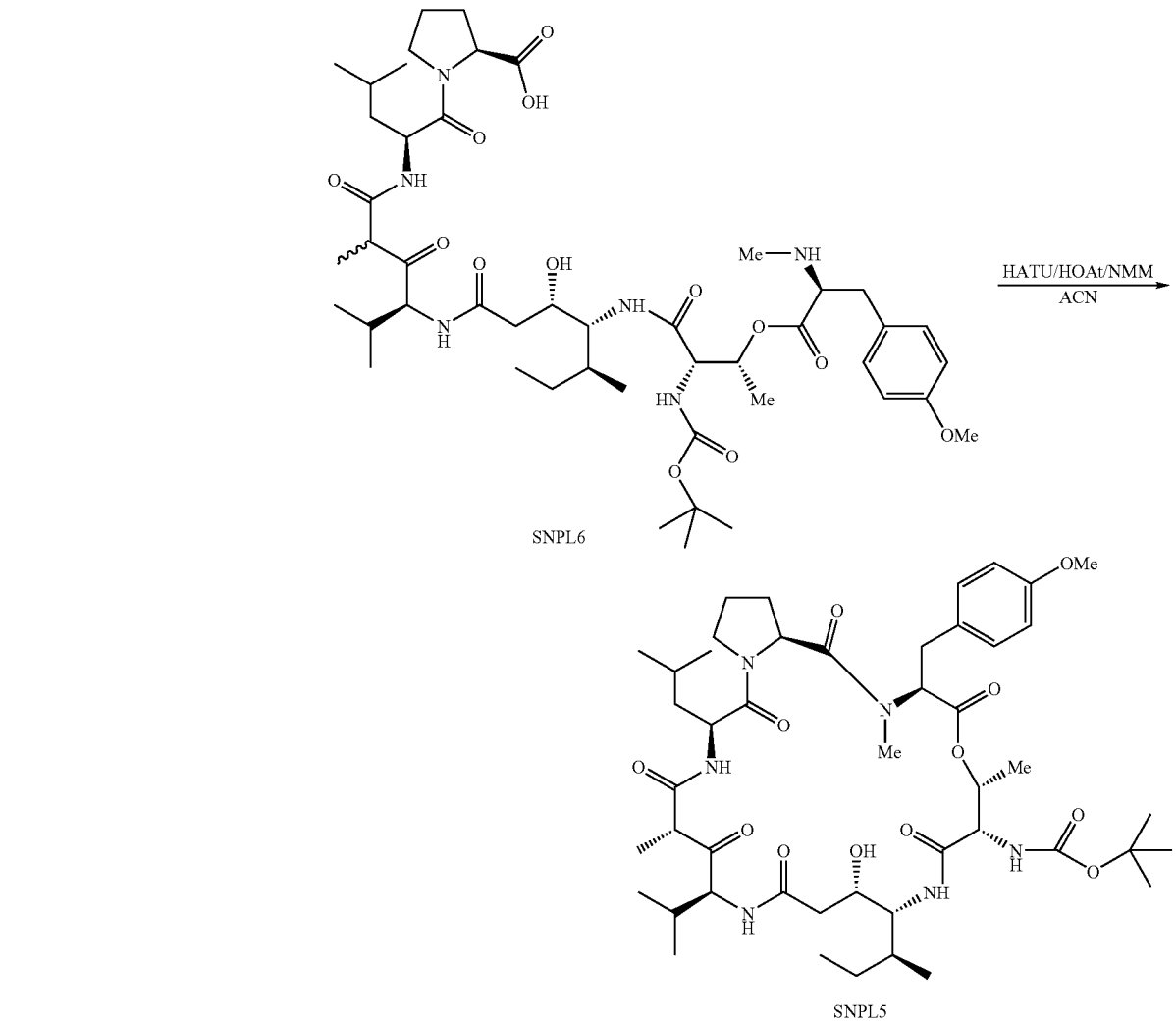

Following the procedure described for synthesis of SAPL5, starting from SNPL6 (100 mg, 0.11 mmol), the title compound (40 mg, 57%) was obtained as a white solid after flash LC (silica gel, EtOAc:hex 4:1 to EtOAc neat). Rf=0.4 (EtOAc).

$^1$H NMR (300 MHz, CDCl$_3$) δ 0.76 (d, J=6.8, 3H), 0.83-0.96 (m, 15H), 1.10-1.20 (m, 1H), 1.25 (d, J=6.4, 3H), 1.27 (d, J=6.3, 3H), 1.32 (d, J=6.8, 3H), 1.41 (m, 2H), 1.44 (s, 9H), 1.50-1.70 (m, 2H), 1.99-2.31 (m, 5H), 2.61 (s, 3H), 2.91-3.04 (m, 1H), 3.11-3.37 (m, 2H), 3.48-3.64 (m, 3H), 3.69-3.81 (m, 1H), 3.80 (s, 3H), 4.18 (m, 2H), 4.46-4.67 (m, 3H), 4.81 (t, J=10.7, 1H), 5.01 (m, 1H), 6.85 (d, J=8.3, 2H), 7.07 (d, J=8.3, 2H), 7.33 (d, J=8.7, 1H), 7.65 (d, J=9.2, 1H), 7.86 (d, J=10.7, 1H). ESI-MS Calcd for C$_{47}$H$_{74}$N$_6$O$_{12}$ 914.54. Found m/z 915.5 (M+H)$^+$.

EXAMPLE 43

Synthesis of Cyclo-N(Me)-O(Me)-Tyr-O-(Boc-Thr)-Ist-Hiv-Leu-Pro (SHPL5)

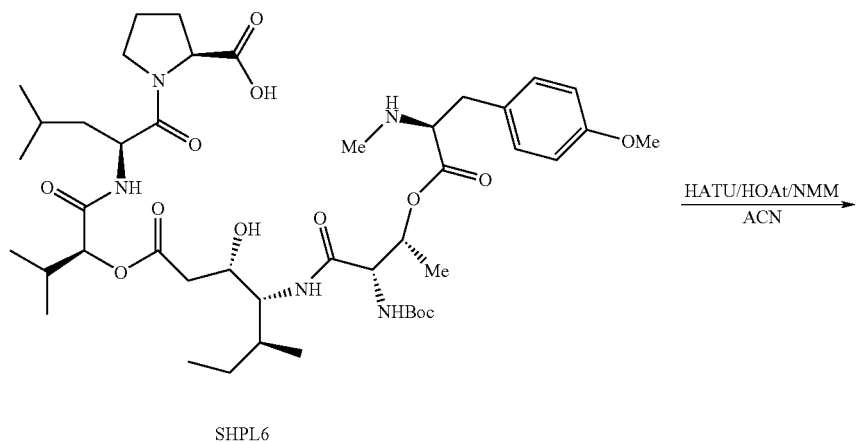

SHPL6

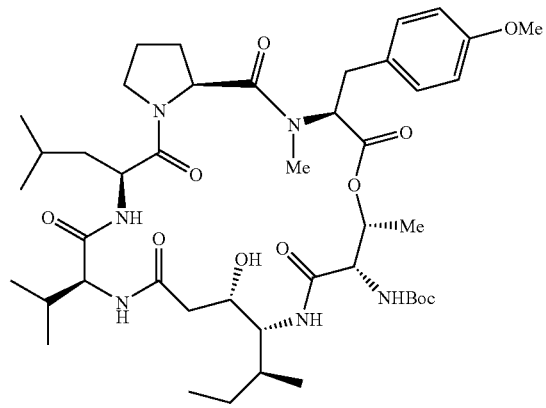

SHPL5

Following the procedure described for synthesis of SAPL5, starting from SHPL6 (2.45 g, 2.78 mmol), the title compound (2.1 g, 88%) was obtained as a white solid after cristalization of DCM/n-heptane (1:3). Rf=0.33 (hex-EtOAc 1:3).

$^1$H NMR (300 MHz, CDCl$_3$) δ 0.82-1.04 (m, 18H), 1.19 (m, 5H), 1.41 (s, 9H), 1.42 (m, 2H), 1.63 (m, 1H), 1.77 (m, 1H), 1.90 (m, 1H), 2.00-2.22 (m, 3H), 2.44 (m, 1H), 2.58 (s, 3H), 2.95 (m, 1H), 3.14 (m, 1H), 3.26 (m, 1H), 3.36 (m, 1H), 3.58 (m, 1H), 3.68 (m, 2H), 3.78 (s, 3H), 3.96 (m, 1H), 4.12 (m, 1H), 4.30 (m, 1H), 4.61 (m, 1H), 4.87 (m, 1H), 4.94 (m, 1H), 5.03 (m, 1H), 6.84 (d, J=8.3, 2H), 7.07 (d, J=8.3, 2H), 7.54 (d, J=7.3, 1H), 7.69 (d, J=6.4, 1H). $^{13}$C NMR (75 MHz, CDCl$_3$) δ 11.38, 14.57, 15.15, 18.11, 18.45, 20.67, 23.40, 24.70, 26.91, 27.89, 30.20, 33.57, 33.90, 38.51, 39.07, 46.62, 48.13, 55.16, 56.05, 56.23, 56.94, 65.67, 68.60, 71.13, 79.41, 80.01, 113.97, 129.69, 130.25, 155.75, 158.49, 168.51, 169.57, 170.24, 170.94, 171.06, 173.59. ESI-MS: Calcd for C$_{44}$H$_{69}$N$_5$O$_{12}$ 859.49. Found m/z 860.4 (M+H)$^+$.

EXAMPLE 44

Synthesis of Cyclo-N(Me)-O(Me)-Tyr-O-(Boc-Thr)-Ist-Val-Lou-Pro (SVPL5)

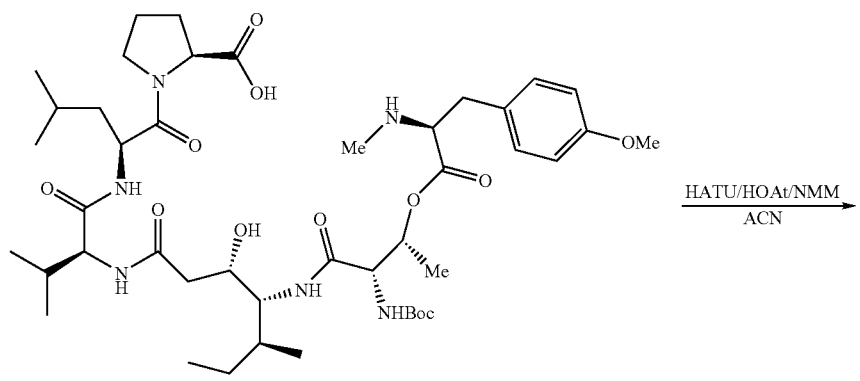

SVPL6

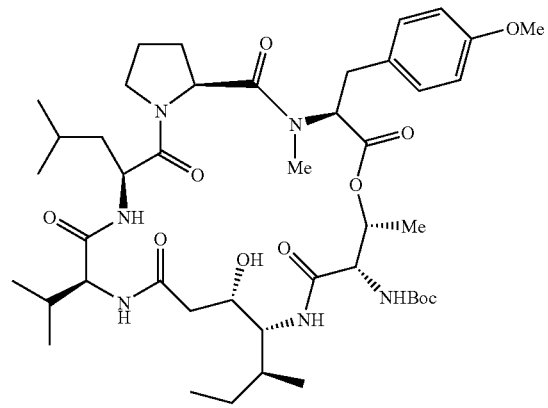

SVPL5

Following the procedure described for synthesis of SAPL5, starting from SVPL6 (90 mg, 0.1 mmol), 30 mg (35%) of the title compound was obtained as a white solid after purification by flash LC (silica, gradient hex-EtOAc from 1:4 to 1:10). Rf=0.35 (EtOAc).

$^1$H NMR (300 MHz, CDCl$_3$): δ, 0.85-1.00 (m, 18H), 1.14-1.38 (m, 8H), 1.44 (s, 9H), 1.57 (m, 2H), 1.76-1.95 (m, 2H), 2.01-2.21 (m, 2H), 2.33 (dd, J$_1$=7.3, J$_2$=14.7, 1H), 2.53 (m, 1H), 2.57 (s, 3H), 3.17 (dd, J$_1$=10.7, J$_2$=14.7, 1H), 3.35 (dd, J$_1$=4.4, J$_2$=14.2, 1H), 3.56 (dd, J$_1$=3.9, J$_2$=10.3, 1H), 3.59-3.77 (m, 4H), 3.78 (s, 3H), 4.06 (d, J$_1$=3.9, J$_2$=9.3, 1H), 4.33 (dd, J$_1$=2.9, J$_2$=9.3, 1H), 4.38 (dd, J$_1$=6.8, J$_2$=10.3, 1H), 4.58 (dd, J$_1$=5.4, J$_2$=7.3, 1H), 4.79 (t, J=10.3, 1H), 4.98 (d, J=9.3, 1H), 5.03 (dd, J$_1$=2.4, J$_2$=6.3, 1H), 6.81 (bs, 1H), 6.84 (d, J=8.3, 2H), 7.08 (d, J=8.3, 2H), 7.24 (d, J=9.8, 1H), 7.54 (d, J=9.8, 1H). $^{13}$C NMR (75 MHz, CDCl$_3$) δ 11.48, 14.50, 15.20, 18.86, 19.44, 21.03, 23.64, 24.83, 24.96, 26.97, 28.01, 28.135, 30.21, 33.53, 33.96, 38.56, 38.61, 41.05, 41.66, 46.84, 48.53, 55.24, 55.51, 56.31, 57.14, 59.75, 65.85, 70.60, 80.52, 114.11, 129.75, 130.33, 156.77, 158.67, 168.53, 170.21, 170.29, 170.73, 171.02, 174.34. ESI-MS Calcd for C$_{44}$H$_{70}$N$_6$O$_{11}$: 858.51. Found (m/z): 859.5 (M+H)$^+$.

EXAMPLE 45

Synthesis of Cyclo-N(Me)-O(Me)-Tyr-O-(Thr)-Ist-Hip-Leu-Pro (SAPL4)

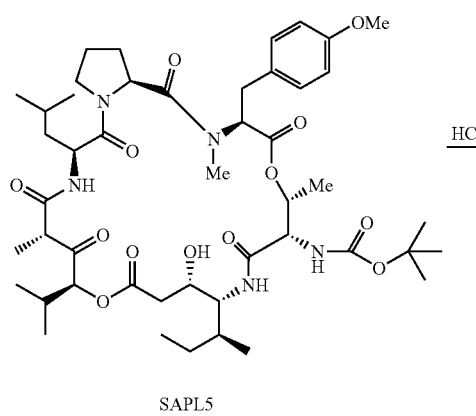

SAPL5

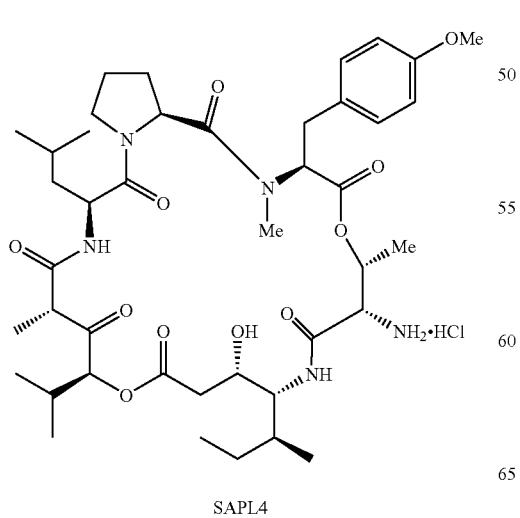

SAPL4

To a flask containing SAPL5 (8.79 g, 9.6 mmol) in anh. dioxane (93 mL), a solution of hydrochloric acid in anh. dioxane (5.3 N, 122 mL, 647 mmol) was added. The resulting solution was stirred at room temperature for 8 h or until complete disappearance of the starting material. When the reaction was completed, the solution was concentrated under reduced pressure. The residue was diluted with CHCl$_3$ (100 ml) and concentrated again. The white foam crude was coevaporated with CHCl$_3$/hex to give SAPL4 (8.17 g, 100% yield) as a white solid.

m/z (FAB) 838.3 [(M+Na)$^+$, 28], 816.3 [(M+H)$^+$, 100].

EXAMPLE 46

Synthesis of Cyclo-N(Me)-O(Me-Tyr-O-(Thr)-Ist-Aip-Leu-Pro (SNPL4)

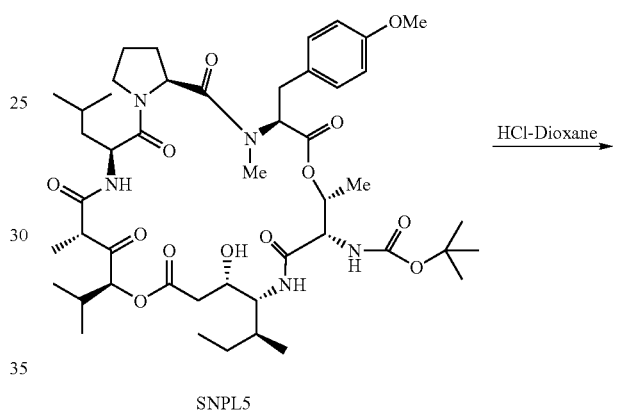

SNPL5

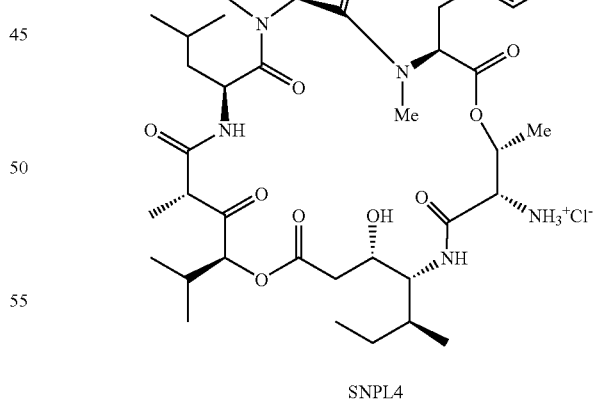

SNPL4

Following the procedure described for the synthesis of SAPL4, starting from SNPL5 (40 mg, 43 μmol), the title compound (36 mg, quant.) was obtained as a white solid after precipitation with Et$_2$O.

ESI-MS: Calcd for C$_{42}$H$_{65}$N$_5$O$_{11}$ 815.47. Found m/z 815.5 (M)$^+$.

EXAMPLE 47

Synthesis of Cyclo-N(Me)-O(Me-)Tyr-O-(Thr)-Ist-Niv-Leu-Pro (SHPL4)

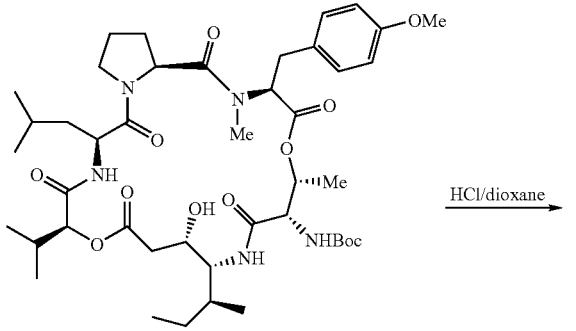

SHPL5

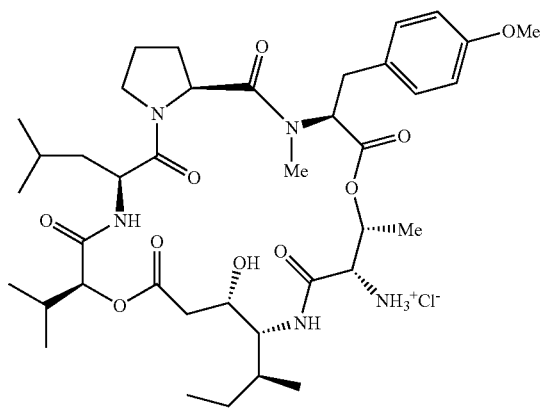

SHPL4

Following the procedure described for synthesis of SAPL4, starting from SVPL5 (25 mg, 29 μmol). The title compound (22 mg, quant.) was obtained as a white solid after coevaporation with MTBE.

ESI-MS: Calcd for $C_{39}H_{61}N_5O_{10}$ 759.44. Found m/z 760.4 (M+H)$^+$.

EXAMPLE 48

Synthesis of Cyclo-N(Me)-O(Me)-Tyr-O(Thr)-Ist-Val-Leu-Pro (SVPL4)

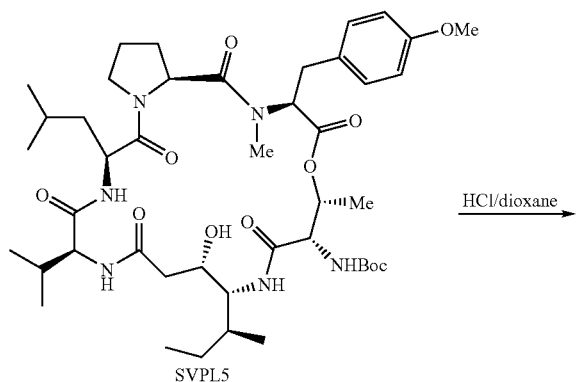

SVPL5

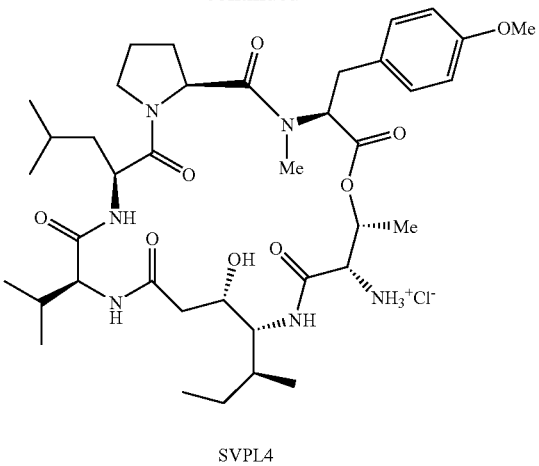

SVPL4

Following the procedure described for synthesis of SAPL4, starting from SVPL5 (25 mg, 29 □mol). The title compound (22 mg, quant.) was obtained as a white solid after coevaporation with MTBE.

ESI-MS Calcd for $C_{39}H_{62}N_6O_9$: 758.5. Found (m/z): 759.5 [(M+H)]$^+$.

EXAMPLE 49

Z-N-Methyl-D-Leucine (H1)

Ref: Coggins, J. R.; Benoiton, N. L. Can. J. Chem 1971, 49, 1968.

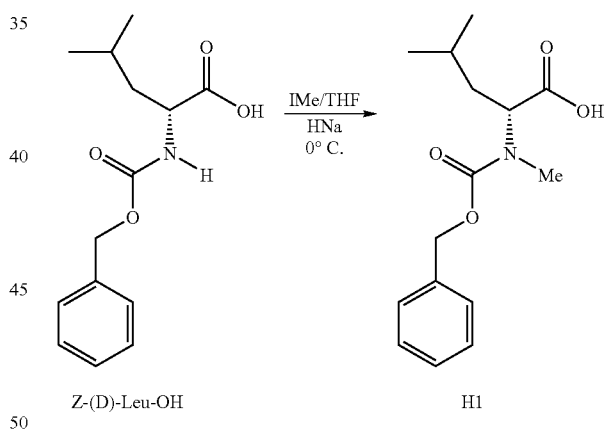

Z-(D)-Leu-OH      H1

To a stirred solution of Z-D-Leu-OH (10.32 g, 38.9 mmol) in anh. THF (120 mL) at 0° C. under Ar, Iodomethane (8.55 mL, 136.1 mmol) was added dropwise by syringe. Then, sodium hydride (4.80 g, 120.6 mmol, 60% dispersion in mineral oil) was added in portions while maintaining the temperature at 0° C. The reaction mixture was stirred at room temperature for 24 h. The solvent was eliminated under reduced pressure and the residue was dissolved in EtOAc (120 mL) and extracted with aq. NaHCO$_3$ (300 mL, sat). The aqueous phase was washed with EtOAc (2×100 ml), The aquous phase was cooled down, solid cytric acid was added up to pH 1-2, and the solution was extracted with EtOAc (4×250 mL), dried (Na$_2$SO$_4$), filtered and concentrated. The product was crystallized in EtOAc-Heptane (1:3) to obtain H1 (7.84 g, 72%) as a white cristalline solid. Mp: 71-72° C. $[\alpha]_D^{25}$ +23 (c 1, EtOH).

EXAMPLE 50

Synthesis of Z-Didemnin A (SAPL3)

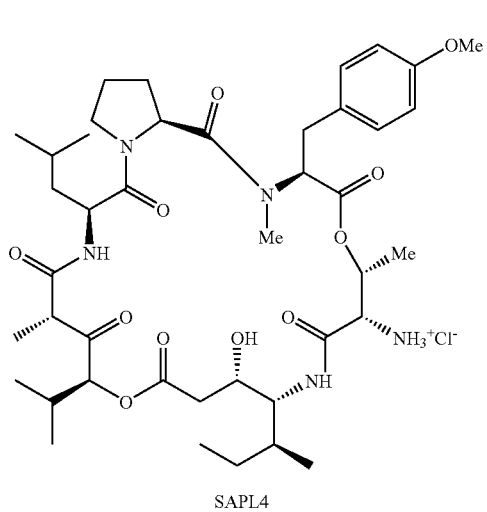

SAPL4

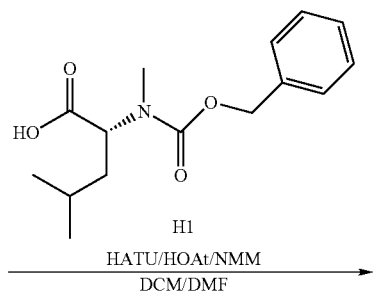

H1
HATU/HOAt/NMM
DCM/DMF

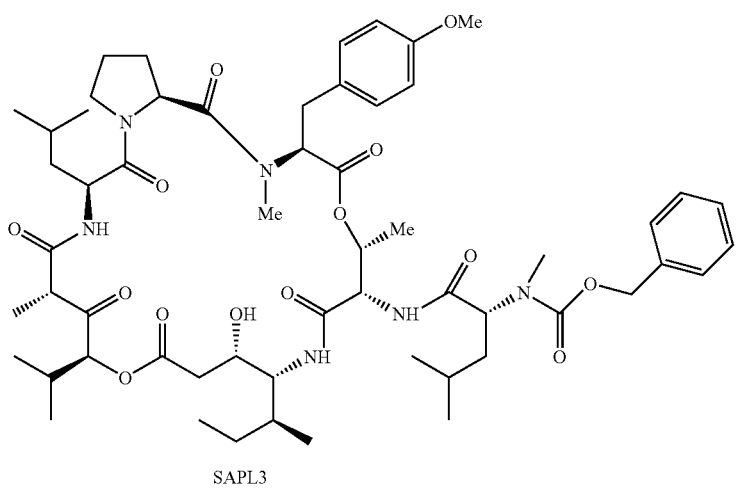

SAPL3

To a flask containing HATU (8.76 g, 23.0 mmol), HOAt (3.17 g, 23.1 mmol) SAPL4 (7.09 g, 15.8 mmol) and H1 (3.486 g, 12.5 mmol), anh. DCM (100 mL) and anh. DMF (50 mL) were added under Ar and the solution was stirred at −5° C. (ice bath). NMM (2.3 ml, 21.0 mmol) was added dropwise by syringe, while maintaining the temperature at −5° C. The resulting mixture reaction was stirred at −5° C. for 2 h, then allowed to reach room temperature for additional 14 h. The solvent was evaporated under reduced pressure. The crude was chased with EtOAc (100 ml) and the solution was filtered off to remove some precipitate, The solution was washed successively with aq. $KHSO_4$ (2×100 ml, 10%), brine (100 ml), aq. $NaHCO_3$ (100 ml, sat.) and rinse with brine (100 ml). The organic phase was dried ($Na_2SO_4$) and concentrated under reduced pressure to afford a yellow solid that was purified by flash LC (silica gel, gradient hex:EtOAc 2:1 to 1:1) to give SAPL3 (7.98 g, 89% yield) as a white solid. Rf=0.18 (hex/EtOAc 1:1).

$^1$H NMR (300 MHz, $CDCl_3$) δ 0.79-1.00 (m, 24H), 1.10-2.25 (m, 10H), 1.18 (d, J=6.3, 3H), 1.25 (s, 3H), 1.32 (d, J=6.8, 3H), 2.28-2.34 (m, 1H), 2.49 (dd, $J_1$=10.7, $J_2$=17.0, 1H), 2.54 (s, 3H), 2.83 (s, 3H), 2.95 (m, 1H), 3.02-3.24 (m, 2H), 3.31-3.40 (dd, $J_1$=3.9, $J_2$=14.1, 1H), 3.53-3.64 (m, 2H), 3.65-3.75 (m, 1H), 3.78 (s, 3H), 3.92-4.20 (m, 3H), 4.58 (t, J=4.8, 1H), 4.75-4.85 (m, 3H), 5.00 (m, 1H), 5.12-5.26 (m, 3H), 6.84 (d, J=8.3, 2H), 6.86 (bs, 1H), 7.07 (d, J=8.3, 2H), 7.21-7.44 (m, 6H), 7.92 (d, J=8.3,

1H). $^{13}$C NMR (75 MHz, CDCl$_3$) δ 11.57, 14.05, 15.18, 16.73, 18.52, 20.83, 22.62, 22.96, 23.66, 24.55, 24.81, 25.03, 25.28, 26.90, 27.86, 28.95, 31.28, 31.81, 33.91, 34.02, 38.51, 38.61, 47.03, 49.61, 55.21, 55.38, 55.50, 57.28, 66.10, 67.65, 67.93, 70.47, 81.44, 114.09, 127.83, 128.46, 129.74, 130.29, 158.60, 168.36, 169.59, 170.28, 171.20, 172.22, 204.80. ESI-MS Calcd for C$_{57}$H$_{84}$N$_6$O$_{14}$ 1076.60. Found m/z 1077.6 (M+H)$^+$.
EXAMPLE 51
Synthesis of [Aip]$^a$ Didemnin A (SNPL3)
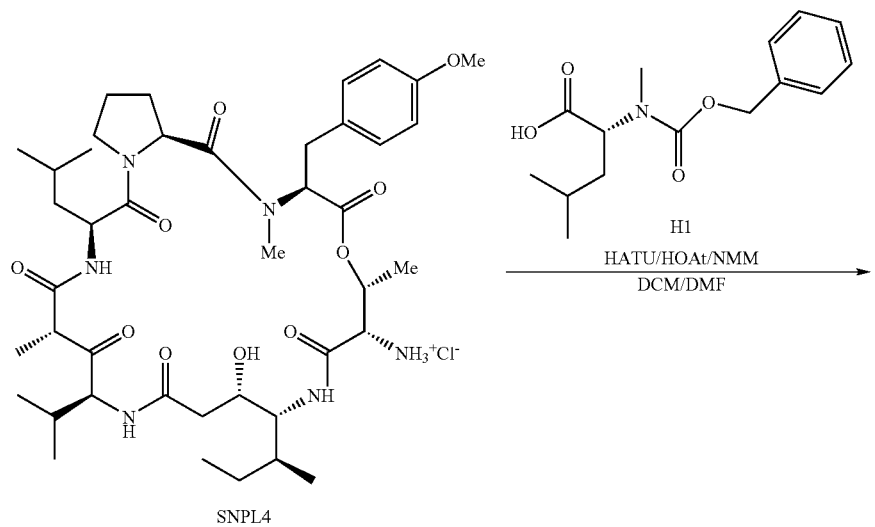
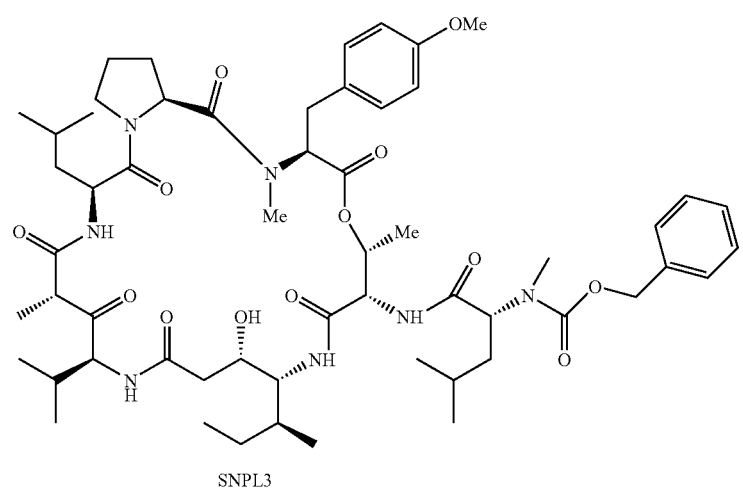

Following the procedure described for the synthesis of SAPL3, starting from SNPL4 (35 mg, 41 μmol) and H1 (17 mg, 61 μmol), the title compound (36 mg, 81%) was obtained as a white solid after purification by flash LC (silica gel, gradient hex-EtOAc from 1:4 to EtOAc neat). Rf=0.30 (EtOAc).

$^1$H NMR (300 MHz, CDCl$_3$) δ 0.74 (d, J=6.3, 3H), 0.80-1.00 (m, 21H), 1.10-2.25 (m, 10H), 1.21 (d, J=5.8, 3H), 1.24 (s, 3H), 1.34 (d, J=6.3, 3H), 2.61 (s, 3H), 2.86 (s, 3H), 3.12-3.25 (dd, J$_1$=11.2, J$_2$=14.1, 1H), 3.27-3.36 (dd, J$_1$=4.3, J$_2$=14.1, 1H), 3.52-3.63 (m, 3H), 3.69-3.81 (m, 2H), 3.80 (s, 3H), 4.09 (m, 3H), 4.47-4.63 (m, 3H), 4.76-4.92 (m, 2H), 5.00 (m, 1H), 5.08 (m, 1H), 5.18 (s, 2H), 6.85 (d, J=8.3, 2H), 6.97 (d, J=6.97, 1H), 7.07 (d, J=8.3, 2H), 7.35 (bs, 5H), 7.48 (d, J=8.3, 1H), 7.67 (d, J=8.3, 1H), 7.87 (d, J=10.2, 1H). ESI-MS Calcd for C$_{57}$H$_{85}$N$_7$O$_{13}$: 1075.62. Found m/z: 1076.6 (M+H)$^+$.

EXAMPLE 52

Synthesis of [Hiv]$^3$ Z-Didemnin A (SHPL3)

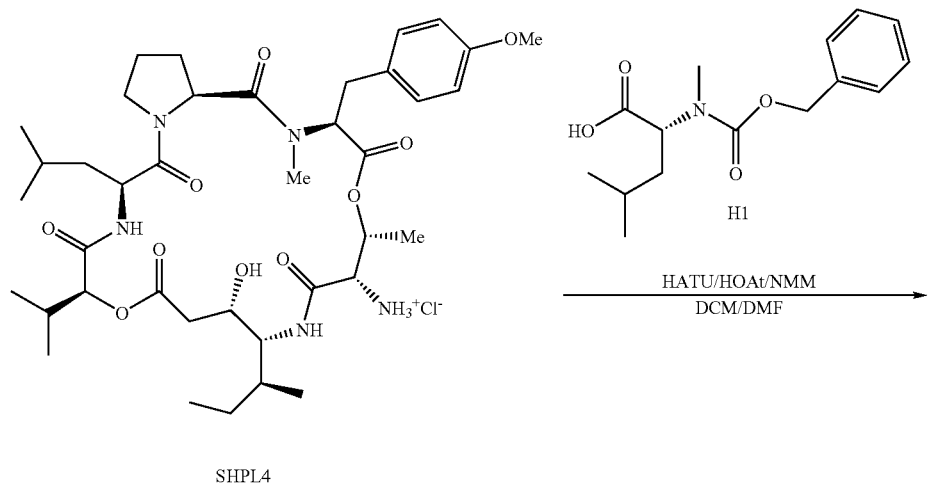

SHPL4

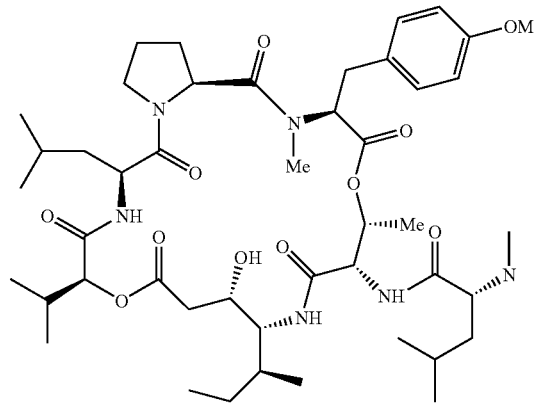

SHPL3

Following the procedure described for the synthesis of SAPL3, starting from SHPL4 (116 mg, 0.15 mmol) and H1 (63 mg, 0.23 mmol), the title compound (86 mg, 52%) was obtained as a white solid after purification by flash LC (silica gel, gradient hex-EtOAc from 1:1 to 1:2). Rf=0.27 (hex-EtOAc 1:2).

$^1$H NMR (300 MHz, CDCl$_3$) δ 0.80-1.08 (m, 24H), 1.18 (m, 3H), 1.21 (m, 4H), 1.58 (m, 2H), 1.74 (m, 1H), 1.80-2.42 (m, 6H), 2.56 (s, 3H), 2.80 (s, 3H), 2.88 (m, 1H), 3.15 (m, 1H), 3.32 (m, 1H) 3.60 (m, 3H), 3.78 (s, 3H), 3.83 (m, 1H), 3.98 (m, 1H), 4.42 (m, 1H), 4.58 (m, 1H), 4.75 (m, 1H), 4.84 (m, 1H), 4.92 (d, J=3.8, 1H), 5.00 (m, 1H), 5.20 (m, 2H), 6.65 (d, J=6.3, 1H), 6.84 (d, J=8.3, 2H), 7.07 (d, J=8.3, 2H), 7.34 (m, 5H), 7.50 (d, J=6.7, 1H), 7.75 (d, J=7.2, 1H). $^{13}$C NMR (75 MHz, CDCl$_3$) δ 11.58, 14.21, 15.39, 17.64, 18.63, 20.74, 21.88, 22.84, 23.48, 24.22, 24.75, 27.05, 27.84, 29.34, 29.99, 33.42, 33.86, 35.81, 38.52, 39.37, 46.63, 48.14, 55.13, 55.47, 55.53, 55.87, 56.92, 65.68, 67.72, 68.60, 70.61, 79.09, 113.95, 127.71, 127.86, 128.35, 129.63, 130.22, 158.48, 168.46, 169.36, 169.84, 170.29, 170.93, 171.00, 173.73. ESI-MS: Calcd for C$_{54}$H$_{80}$N$_6$O$_{13}$ 1020.58. Found m/z 1021.5 (M+H)$^+$.

EXAMPLE 53
Synthesis of [Val]$^3$ Z-Didemnin A (SVPL3)

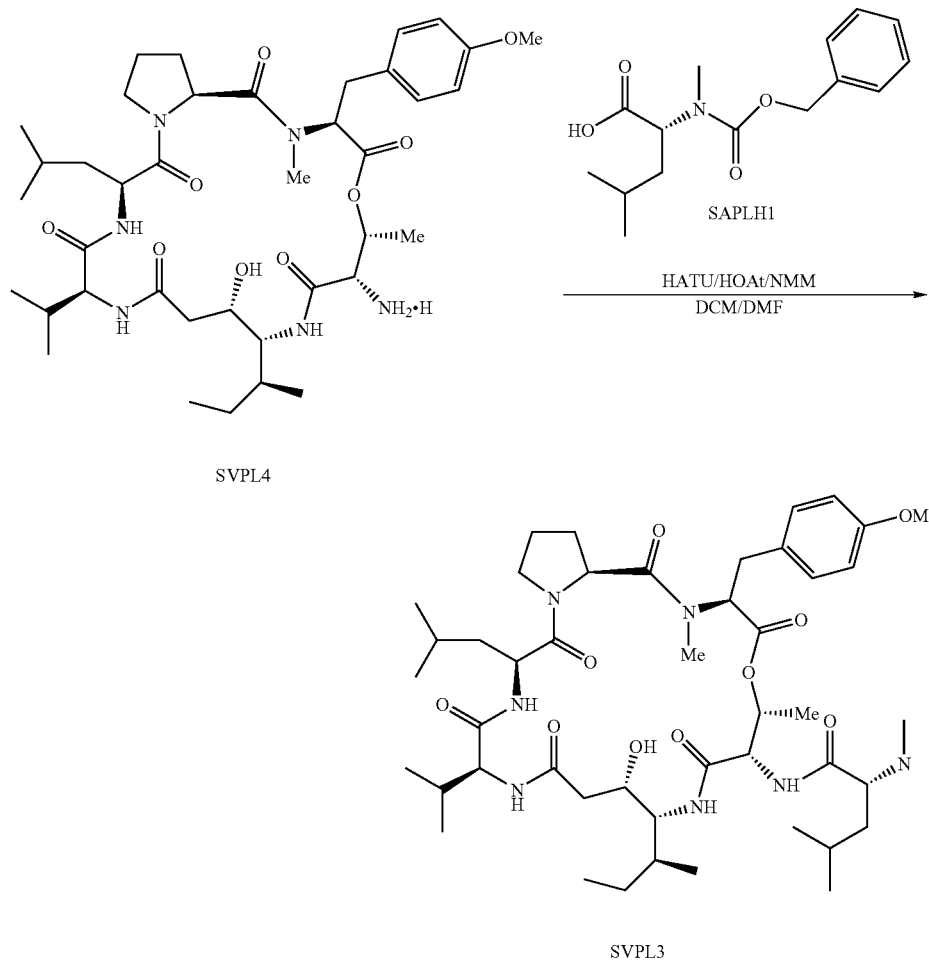

Following the procedure described for the synthesis of SAPL3, starting from SVPL4 (20 mg, 25 μmol) and SAPLH1 (11 mg, 37.5 μmol), the title compound (19 mg, 72%) was obtained as a white solid after purification by flash LC (silica gel, gradient hex-EtOAc from 1:1 to 1:5). Rf=0.44 (EtOAc).

$^1$H NMR (300 MHz, CDCl$_3$): δ 0.85-1.06 (m, 21H), 1.10-1.4 (m, 5H), 1.16 (d, J=6.6, 3H), 1.50-1.63 (m, 6H), 1.72-1.87 (m, 2H), 1.88-2.40 (m, 6H), 2.58 (s, 3H), 2.86 (s, 3H), 3.17 (dd, J$_1$=10.5, J$_2$=14.2, 1H), 3.36 (dd, J$_1$=3.9, J$_2$=14.2, 1H), 3.43 (bs, 1H), 3.51-3.72 (m, 4H), 3.79 (s, 3H), 3.98-4.16 (m, 1H), 4.40-4.47 (m, 2H), 4.58 (dd, J$_1$=5.7, J$_2$=7.8, 1H), 4.67-4.85 (m, 2H), 4.80-5.09 (m, 1H), 5.16 (d, J=12.4, 1H), 5.24 (d, J=12.4, 1H), 6.84 (d, J=8.4, 1H), 6.90-6.94 (bs, 1H), 7.09 (d, J=8.4, 1H), 7.28-7.50 (m, 6H). $^{13}$C NMR (75 MHz, CDCl$_3$) δ 11.99, 14.37, 15.70, 18.55, 19.82, 21.40, 21.99, 22.81, 23.17, 23.98, 24.62, 25.00, 25.24, 27.28, 28.26, 29.93, 30.23, 33.58, 34.10, 36.16, 38.78, 41.98, 47.10, 48.79, 54.73, 55.45, 56.62, 57.40, 59.51, 66.02, 68.18, 70.37, 71.03, 114.30, 128.00, 128.27, 128.72, 129.86, 130.56, 136.49, 158.28, 158.85, 168.75, 169.27, 170.40, 170.75, 171.04, 173.91, 175.03. ESI-MS Calcd for $C_{54}H_{81}N_7O_{12}$: 1019.59. Found (m/z): 1020.5 $(M+H)^+$.
EXAMPLE 54
Synthesis of Didemnin A (SAPL2)
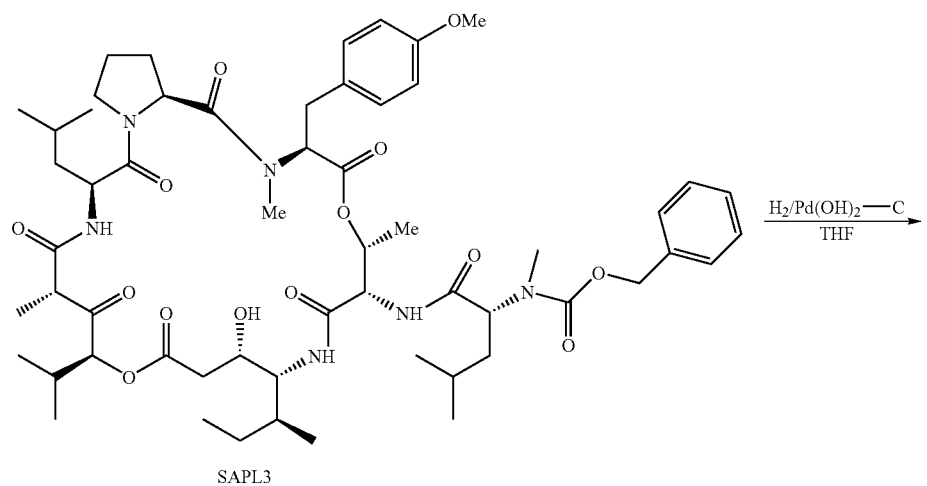
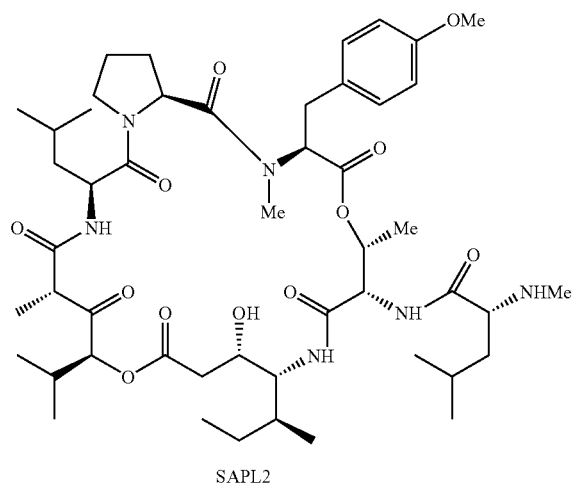

To a solution of SAPL3 (6.59 g, 6.1 mmol) in THF (free of stabilizer, 262 ml) degassed and surged with argon, Pd(OH)$_2$—C (20%, 3.29 g, 50% w/w) was added. The mixture was stirred under H$_2$ (1 atm) for 20 h, then filtered over a 0.45 μm teflon filter and concentrated under reduced pressure to give a white solid CHCl$_3$ (2×25 ml) was added, and the mixture was concentrated again under reduced pressure to give SAPL2 (5.51 g, 96%) as a white solid. Rf=0.22 (CHCl$_3$:tBuOH 90:10).

$^1$H NMR (500 MHz, CDCl$_3$) δ 0.82-0.92 (m, 24H), 1.11-1.19 (m, 1H), 1.22 (d, J=6.9, 3H), 1.32 (d, J=6.8, 3H), 1.30-1.35 (m, 1H), 1.35-1.63 (m, 6H), 1.71-1.81 (m, 2H), 1.93-2.07 (m, 1H), 2.07-2.18 (m, 2H), 2.28-2.34 (m, 1H), 2.49-2.52 (dd, J$_1$=11, J$_2$=10.5, 1H), 2.54 (s, 3H), 2.72 (bs, 3H), 2.79 (bs, 3H), 2.86-2.94 (bs, 1H), 2.72-2.79 (bd, J=10.5, 1H), 3.15-3.18 (dd, J$_1$=14.5, J$_2$=10.5, 1H), 3.33-3.36 (dd, J$_1$=14.5, J$_2$=4.5, 1H), 3.54-3.57 (dd, J$_1$=10.5, J$_2$=4.5, 1H), 3.56-3.61 (m, 1H), 3.78 (s, 3H), 3.96-4.00 (m, 1H), 4.03-4.08 (m, 1H), 4.11-4.80 (bs, 1H), 4.56-4.62 (m, 1H), 4.68-4.81 (m, 3H), 4.99-5.01 (q, J=3.5, 1H), 5.16 (bs, 1H), 6.83 (d, J=8.5, 2H), 6.95 (bs, 1H), 7.07 (d, J=8.5, 2H), 7.21-7.25 (bs, 1H), 7.95 (bs, 1H). $^{13}$C NMR (75 MHz, CDCl$_3$) δ 11.55, 14.95, 15.26, 16.82, 18.56, 20.89, 22.00, 23.08, 23.76, 24.58, 24.85, 25.10, 27.12, 29.35, 29.35, 29.65, 29.69, 31.36, 33.96, 34.14, 38.51, 38.64, 40.14, 55.38, 55.56, 57.31, 66.17, 67.85, 70.58, 80.96, 80.98, 81.57, 114.12, 130.33, 158.63, 168.41, 169.33, 169.70, 170.38, 171.24, 172.28, 172.28, 172.93, 204.83. m/z (FAB) 944.2 [(M+H)$^+$, 100].

EXAMPLE 55

Synthesis of [Aip]$^3$-Didemnin A (SNPL2)

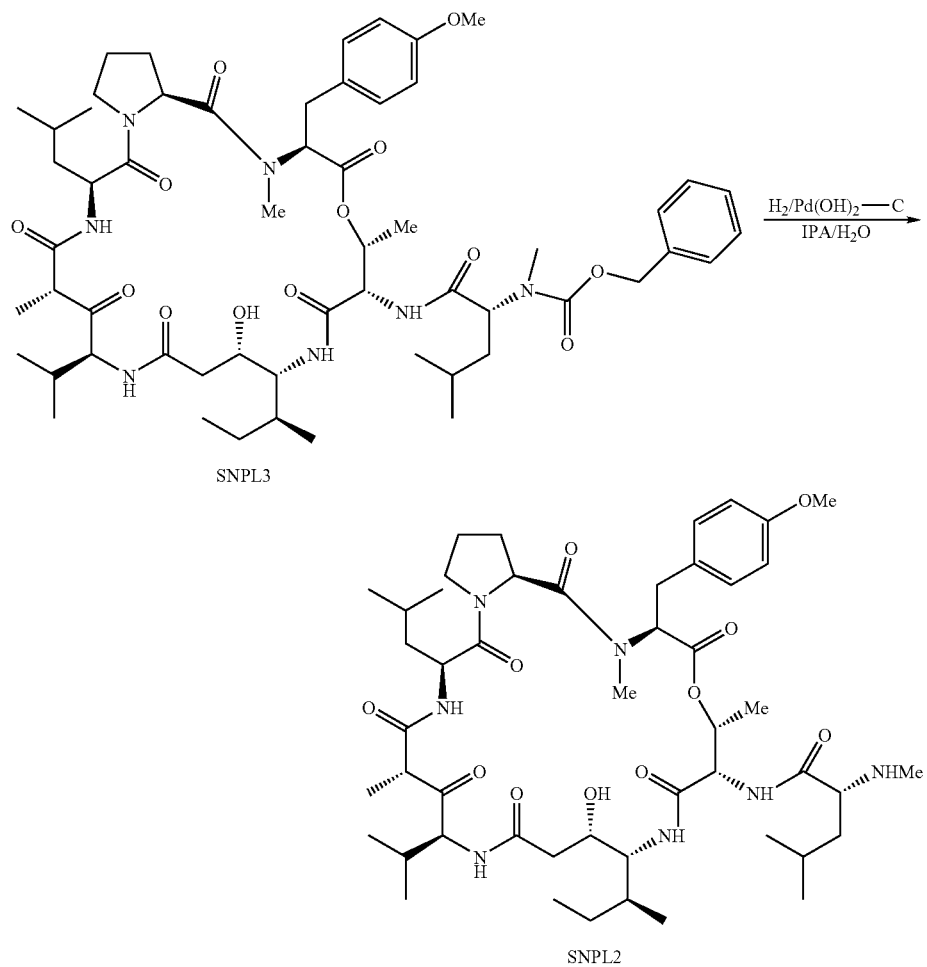

To a solution of SNPL3 (33 mg, 35 μmol) in a mixture of IPA/H$_2$O (2 ml:1 ml) degassed and purged with argon, Pd(OH)$_2$—C (20%, 20 mg, 60% w/w) was added. The mixture was stirred under H$_2$ (1 atm) for 20 h, then filtered over a 0.45 μm teflon filter and concentrated under reduced pressure to give a white solid. IPA (2×5 mL) was added, and the solution was concentrated again under reduced pressure to give SNPL2 (32 mg, 97%) as a white solid.

$^1$H NMR (300 MHz, CDCl$_3$) δ 0.78 (d, J=6.8, 3H), 0.82-0.92 (m, 21H), 1.11-2.58 (m, 21H), 2.41 (s, 3H), 2.62 (s, 3H), 2.75-3.00 (m, 4H), 3.15-3.18 (dd, J$_1$=10.7, J$_2$=14.7, 1H), 3.33-3.36 (dd, J$_1$=14.5, J$_2$=4.2, 1H), 3.51-3.78 (m, 3H), 3.78 (s, 3H), 3.92 (m, 1H), 4.01-4.20 (m, 2H), 4.50 (t, J=4.8, 1H), 4.59 (t, J=6.3, 1H), 4.75-4.91 (m, 2H), 5.05 (m, 1H), 6.84 (d, J=8.3, 2H), 7.07 (d, J=8.3, 2H), 7.70 (d, J=5.8, 1H), 7.78 (d, J=9.7, 1H), 7.89 (d, J=6.3, 1H), 8.14 (d, J=7.8, 1H). ESI-MS Calcd for C$_{49}$H$_{79}$N$_7$O$_{11}$ 941.58. Found m/z 942.7 (M+H)$^+$.

EXAMPLE 56

Synthesis of [Hiv]$^3$. Didemnin A (SHPL2)

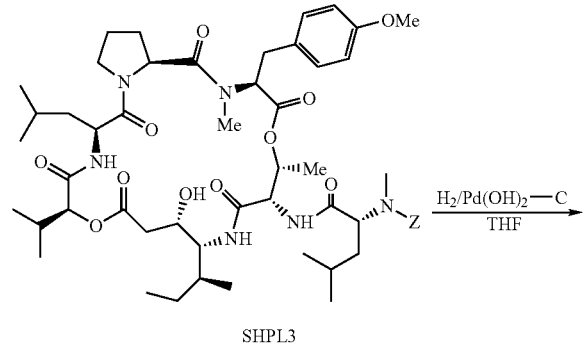

SHPL3

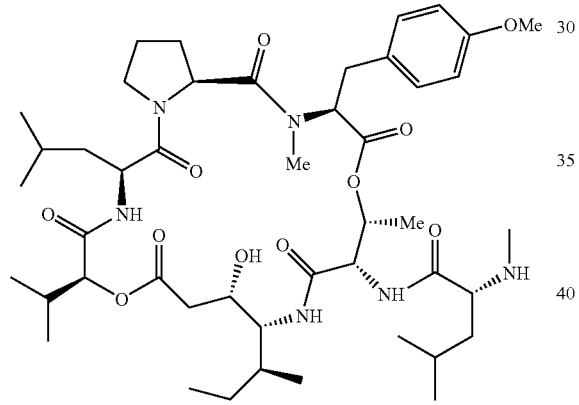

SHPL2

Following the procedure described for the synthesis of SAPL2, starting from SHPL3 (86 mg, 0.08 mmol), the title compound (73 mg, 97%) was obtained as a white solid. Rf=0.36 (CHCl$_3$/MeOH 95:5).

$^1$HNMR (300 MHz, CDCl$_3$) δ 0.82-1.02 (m, 24H), 1.12-2.42 (m, 16H), 2.54 (s, 3H), 2.64 (s, 3H), 2.95 (m, 1H), 3.15 (m, 1H), 3.35 (m, 1H), 3.52-3.90 (m, 5H), 3.78 (s, 3H), 4.04 (m, 1H), 4.38 (m, 1H), 4.48 (m, 1H), 4.57 (m, 1H), 4.88 (m, 1H), 4.91 (d, J=5.3, 1H), 5.22 (m, 1H), 6.84 (d, J=8.3, 2H), 7.07 (d, J=8.3, 2H), 7.54 (d, J=9.2, 1H), 7.60 (d, J=9.4, 1H), 8.68 (d, J=6.2, 1H). $^{13}$C NMR (75 MHz, CDCl$_3$) δ 11.78, 14.07, 16.13, 17.90, 18.56, 20.98, 21.74, 22.94, 23.60, 24.44, 24.78, 25.06, 27.17, 27.92, 30.09, 33.34, 33.89, 38.71, 40.30, 46.86, 48.22, 54.99, 55.23, 56.97, 57.21, 65.81, 68.53, 70.37, 79.47, 114.03, 129.76, 130.29, 158.57, 168.18, 169.40, 169.86, 170.20, 170.92, 174.16. ESI-MS Calcd for C$_{46}$H$_{74}$N$_6$O$_{11}$ 886.54. Found m/z 887.2 (M+H)$^+$.

EXAMPLE 57

Synthesis of [Val]$^3$-Didemnin A (SVPL2)

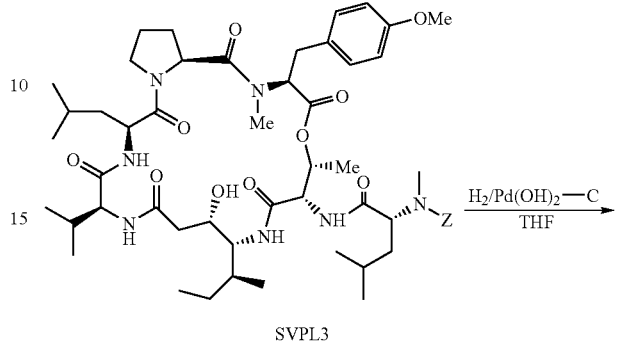

SVPL3

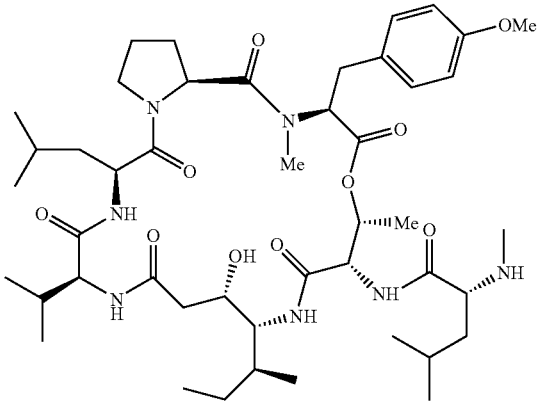

SVPL2

Following the procedure described for the synthesis of SAPL2, starting from SVPL3 (19 mg, 18 μmol), the title compound (16 mg, 97%) was obtained as a white solid. Rf=0.36 (CHCl$_3$/MeOH 95:5).

$^1$H NMR (300 MHz, CDCl$_3$): δ -0.82-1.02 (m, 21H), 1.85-1.32 (m, 9H), 1.42-1.83 (m, 7H), 1.87-2.23 (m, 8H), 2.34 (bs, 3H), 2.60 (bs, 1H), 2.85 (dd, J$_1$=5.7, J$_2$=7.8, 1H), 3.16 (dd, J$_1$=10.8, J$_2$=14.2, 1H), 3.37 (dd, J$_1$=4.2, J$_2$=14.2, 1H), 3.48 (bs, 1H), 3.57-3.68 (m, 4H), 3.79 (s, 3H), 3.95-4.15 (m, 2H), 4.45-4.52 (m, 2H), 4.61 (dd, J$_1$=4.8, J$_2$=7.8, 1H), 4.77 (t, J=9.9, 1H), 5.02-5.15 (m, 1H), 6.84 (d, J=8.4, 1H), 7.09 (d, J=8.4, 1H), 7.59-7.62 (m, 2H), 7.78-7.81 (m, 2H). $^{13}$C NMR (75 MHz, CDCl$_3$) δ 11.98, 14.46, 16.14, 18.50, 19.83, 21.50, 22.55, 22.81, 22.95, 23.46, 23.98, 27.33, 28.27, 28.33, 29.94, 33.71, 34.16, 38.94, 41.93, 42.11, 45.72, 47.18, 48.94, 53.64, 55.03, 55.50, 56.72, 57.55, 59.22, 59.56, 66.16, 70.71, 114.36, 118.53, 120.85, 130.02, 130.58, 168.71, 169.74, 170.23, 171.18, 175.10. ESI-MS Calcd for C$_{46}$H$_{75}$N$_7$O$_{10}$: 885.56. Found (m/z): 856.5 (M+H)$^+$.

EXAMPLE 58

Synthesis of Pyr-Pro-OBn (F2)

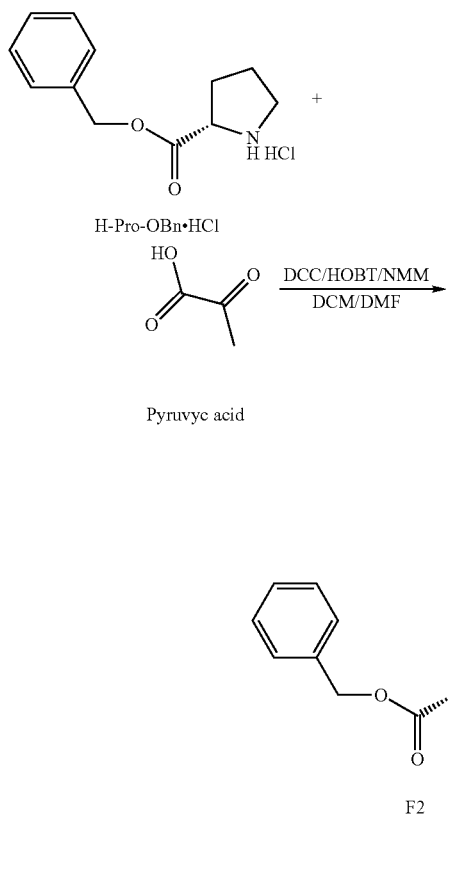

To a solution of H-Pro-OBn-HCl (10.0 g, 41.3 mmol) in anh DMF (50 mL) at 0° C. under Ar, NMM (4.55 mL, 43.8 mmol) was added dropwise by syringe while maintaining the temperature at 0° C. HOBt (18.98 g, 124 mmol) was then added in portions. After 15 min. pyruvic acid (8.61 g, 97.79 mmol) dissolved in anh DCM (10 mL) was added dropwise by syringe while maintaining the temperature below 3° C. Finally, DCC (22.17 g, 107.46 mmol) dissolved in DCM (80 mL) was added dropwise with a compensated funnel. The mixture was allowed to reach room temperature (2 h) and stirred for another 12 h. The reaction mixture was filtered to remove the precipitate and the solution was concentrated under reduced pressure. The residue was dissolved in EtOAc (500 mL) and washed successively with aq. KHSO$_4$ (100 mL, 10%), aq. NaHCO$_3$ (400 mL, sat.), brine (400 mL), dried (Na$_2$SO$_4$) and filtered. The solvent was eliminated under reduced pressure and the residue was chased with ACN (100 mL), cooled at −30° C. for 2 h and filtered to removed the excess of N,N-dicyclohexylurea. The resulting brown oil (15.82 g) was purified by flash LC (silica gel, grad. hex to hex:EtOAc 2:1) to afford F2 (9.06 g, 66% yield) as a white solid. Rf=0.25 (hex:EtOAc 2:1).

IR (film, DCM) ν 3035, 2956, 2884, 1744, 1717, 1645, 1499, 1443, 1383, 1352, 1273, 1175, 1092 cm$^{-1}$. $^1$H NMR (200 MHz, CDCl$_3$) δ 1.75-2.40 (m, 4H), 2.37 (s, 3H), 2.44 (s, 3H), 3.45-3.82 (m, 2H), 4.52-4.61 (m, 1H), 4.88-4.97 (m, 1H), 5.14-5.15 (m, 2H), 5.17-5.20 (m, 2H), 7.34 (bs, 5H). $^{13}$C NMR (50 MHz, CDCl$_3$) δ 22.11, 25.22, 26.5, 27.10, 28.53, 31.48, 47.53, 44.81, 59.76, 67.02, 67.31, 128.11, 128.64, 135.24, 170.1, 170.2, 198.0. m/z (CI) 293 [(M+NH$_4$)$^+$, 100]. Anal. Calcd for C$_{15}$H$_{17}$NO$_4$: C, 65.44; H, 6.22; N, 5.08. Found: C, 65.04; H, 6.01; N, 5.11.

EXAMPLE 59

Synthesis of Pyr-Pro-OH (F1)

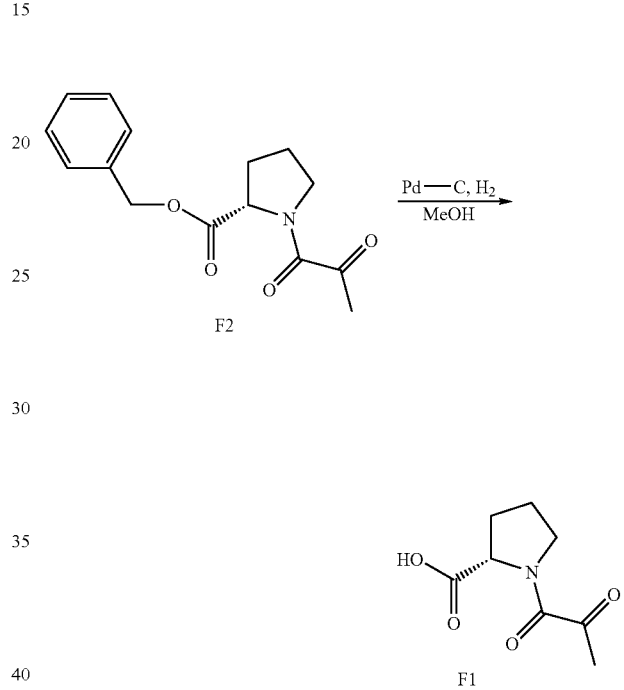

A solution of F2 (8.63 g, 31.34 mmol) and palladium on activated charcoal (10%, 86 mg, 10% w/w) in degassed MeOH (125 mL) was placed in a high pressure Parr reactor and purged with nitrogen gas (2×30 psi). The reaction mixture was sealed under hydrogen (30 psi) and stirred at 23° C. for 4.5 h. The mixture was filtered through a 0.45 □m teflon filter and concentrated at reduced pressure. The residue (6.29 g) was coated in SiO$_2$ and loaded onto the top of a column (LC 5.5×10.0 cm) and eluted with hex:EtOAc 1:2 to yield F1 (4.64 g, 80%) as a white solid. Rf=0.22 (hex: EtOAc 1:1). [α]$_D^{20}$ −92.4 (c 0.12, CHCl$_3$). M.p. 67-69° C.

IR (film) DCM ν 3450-3000, 2961-2870, 1719, 1643, 1615, 1452, 1354, 1205, 1175, 1094, 1018 cm$^{-1}$. $^1$H NMR (200 MHz, CDCl$_3$) δ 1.85-2.45 (m, 4H), 2.43 and 2.47 (s, 3H), 3.42-3.85 (m, 2H), 4.52-4.61 (m, 1H), 4.88-4.97 (m, 1H), 7.21-7.40 (bs, 1H). $^{13}$C NMR (75 MHz, CDCl$_3$) δ 22.03, 25.23, 26.48, 27.00, 28.23, 31.44, 47.57, 48.37, 59.61, 59.39, 162.47, 162.52, 175.04, 176.29, 197.18. m/z (CI) 220 [(M+N$_2$H$_7$)$^+$, 15], 203 [(M+NH$_4$)$^+$, 100], 186 [(M+H)$^+$, 16]. Anal. Calcd for C$_8$H$_{11}$NO$_4$: C, 51.88; H, 5.99; N, 7.56. Found: C, 52.13; H. 5.85; N, 7.65

EXAMPLE 60

Synthesis of Aplidine (SAPL1)

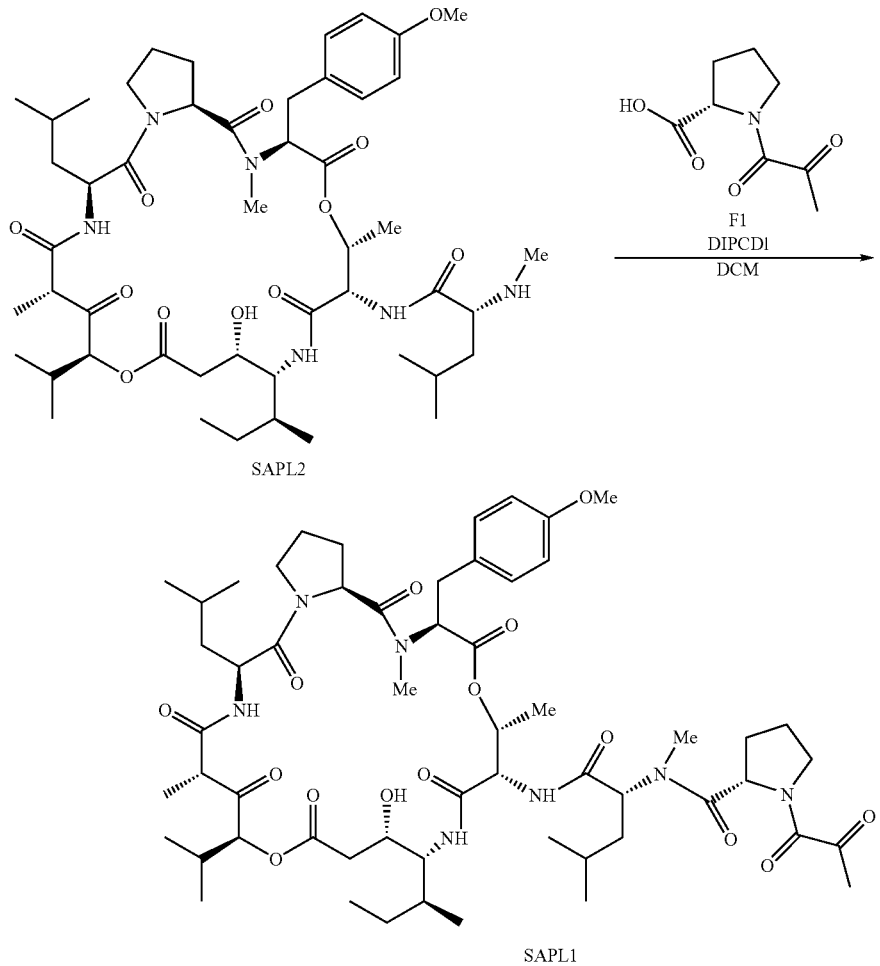

To a cold (3° C.) solution of F1 (4.908 g, 26.5 mmol) in anh. DCM (40 mL), was added, under nitrogen, a solution of DIPCDI (1.806 mg, 14.3 mmol) in DCM (10 ml) and the solution was stirred at 3° C. for 60 min. Then, a solution of SAPL2 (5.0 g, 5.3 mmol) in DCM (50 ml) was transferred via cannula to the previous solution under nitrogen pressure. After 90 h (4 days) at this temperature, aq HCl (50 ml, 0.1N) was added, and the reaction mixture was stirred for 15 min. Then, the organic layer was decanted and partitioned between aq. $KHSO_4$ (50 mL, 5%), aq. $NaHCO_3$ (50 mL, 5%) and brine (25 mL). The organic phase was dried ($Na_2SO_4$), filtered and concentrated, under reduced pressure. The resulting pale yellow solid was purified by flash LC (Lichroprep RP-18, 40-63 □m, gradient $MeOH:H_2O:TFA$ from 70:30:0.1 to 90:10:0.1) to yield SAPL1 (5.4 g, 93%) (mixture of rotamers). Rf=0.40 and 0.28 (DCM:AcOEt, 2:3), 0.52 and 0.45 ($CHCl_3$-MeOH, 9.5:0.5); $[\alpha]_D$ −95.9 (c 1.8, $CHCl_3$).

$^1$H NMR (500 MHz, $CDCl_3$) δ 0.84-0.93 (m, 24H), 1.16-1.70 (m, 9H), 1.72-1.81 (m, 1H), 1.81-1.90 (m, 1H), 1.90-2.24 (m, 6H), 2.30-2.39 (m, 1H), 2.49 (s, 3H) 2.51 (s, 3H), 2.55 (s, 3H), 2.52-2.64 (m, 1H), 2.85 (bs, 1H), 2.94 (bs, 1H), 3.09 (s, 3H), 3.13 (s, 5H), 3.15-3.18 (m, 1H), 3.21-3.26 (dd, $J_1$=15.8, $J_2$=6.1, 1H), 3.32-3.36 (dd, $J_1$=14.5, $J_2$=4.1, 1H), 3.54-3.60 (m, 1H), 3.66-3.72 (m, 1H), 3.78 (s, 3H), 3.80-3.87 (m, 1H), 3.96-3.99 (m, 1H), 4.03-4.11 (m, 2H), 4.15-4.23 (2q, J=7.5, 1H), 4.55-4.57 (2d, $J_1$=5.5, $J_2$=2.2, 1H), 4.59-4.62 (t, 1H), 4.56-4.64 (dd, $J_1$=6.5, $J_2$=2.5, 1H), 4.68-4.71 (t, 1H), 4.76-4.81 (t, 1H), 5.10-5.18 (m, 1H), 5.17 (d, J=3.5, 1H), 5.18 (d, J=3.5, 1H), 5.27-5.31 (m, 2H), 6.82 (d, J=8.5, 2H), 6.83 (d, J=8.5, 2H), 7.05 (d, J=8.5, 2H), 7.06 (d, J=8.5, 2H), 7.02 (d, J=7.1, 1H), 7.16 (d, J=9.5, 1H), 7.17 (d, J=9.5, 1H), 7.59 (d, J=5.5, 1H), 7.77 (d, J=9.5, 1H), 7.83 (d, J=9.4, 1H). $^{13}$C NMR (75 MHz, $CDCl_3$) δ 11.63, 11.68, 14.1, 14.70, 15.26, 15.30, 16.00, 16.20, 16.88, 16.93, 18.62, 18.85, 20.89, 20.94, 21.62, 21.36, 23.44, 23.57, 23.84, 23.93, 24.66, 24.77, 24.85, 25.02, 26.22, 26.34, 27.09, 27.6, 27.06, 27.30, 27.95, 27.99, 29.33, 29.69, 31.31-31.37, 33.97, 34.06, 36.02, 36.45, 38.68, 38.76, 41.01, 41.15, 47.00, 48.42, 48.48, 48.86, 49.20, 49.51, 54.65, 54.75, 55.26, 55.58, 55.61, 57.14, 57.27, 57.47, 57.79, 66.24, 67.80, 67.99, 70.34, 70.67, 81.0, 81.52, 114.10, 130.31, 156.0, 158.65, 161.1, 161.60, 168.20, 169.53, 169.59, 170.45, 171.25, 171.80, 171.95, 172.26, 172.33, 197.5, 204.80, 204.85. m/z (FAB) 1132.6 [(M+Na)$^+$, 42], 1110.8 [(M+H)$^+$, 100].
EXAMPLE 61
Synthesis of [Aip]$^3$-Aplidine (SNPL1)
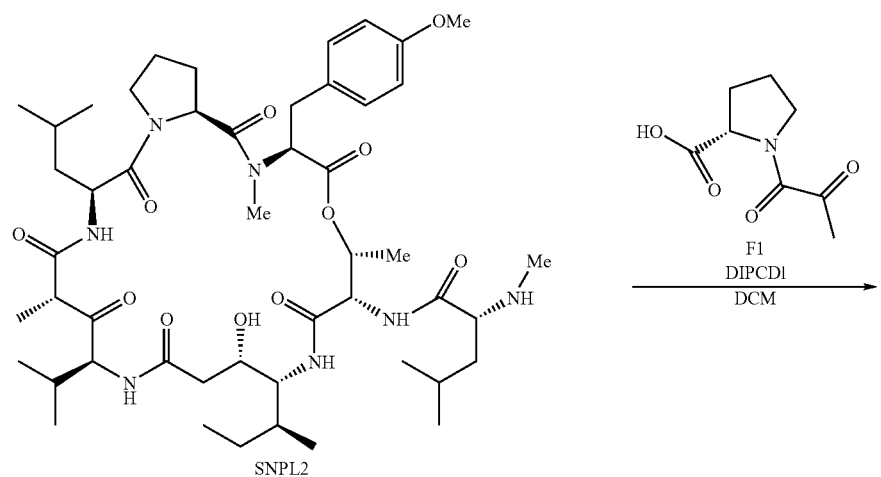
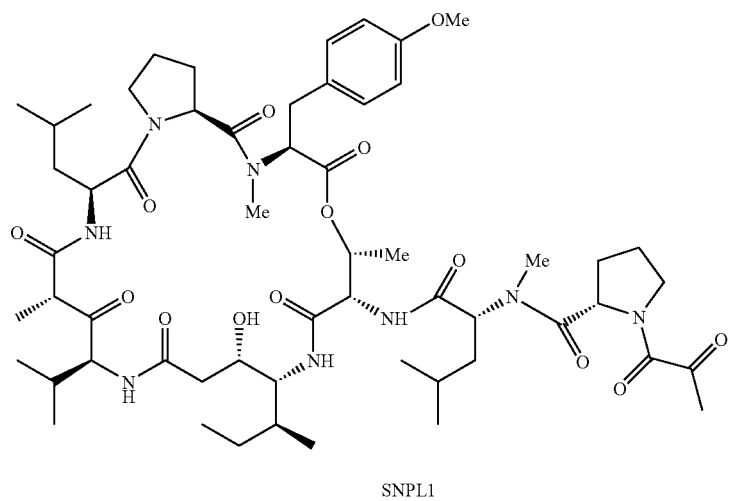

Following the procedure described for the synthesis of SAPL1, starting from SNPL2 (10 mg, 10.6 μmol) and F1 (10 mg, 54 μmol). The title compound (8 mg, 68%) was obtained as a white solid after purification by HPLC (HyperPrep PEP 100 C18, isocratic ACN/H$_2$O 85:15 (flow: 7 ml/min, 250×21 mm, at 270 nm, $t_R$=10.5 and 12.0 min).

$^1$H NMR (300 MHz, CDCl$_3$) δ 0.80-1.03 (m, 24H), 1.11-1.70 (m, 9H), 1.72-1.81 (m, 1H), 1.81-1.90 (m, 1H), 1.90-2.24 (m, 6H), 2.30-2.39 (m, 1H), 2.53 (s, 3H) 2.55 (s, 3H), 2.65 (s, 3H), 2.52-2.66 (m, 2H), 2.94 (m, 1H), 3.07 (s, 3H), 3.11 (s, 3H), 3.15-3.18 (m, 1H), 3.22-3.31 (dd, J$_1$=4.3, J$_2$=15.1, 1H), 3.54-3.60 (m, 2H), 3.67-3.92 (m, 2H), 3.80 (s, 3H), 3.98 (m, 1H), 4.13-4.29 (m, 3H), 4.45-4.75 (m, 4H), 4.81 (t, J=9.7, 1H), 5.09 (m, 1H), 5.18 (m, 1H), 5.26-5.44 (m, 3H), 6.84 (d, J=8.3, 2H), 7.07 (d, J=8.3, 2H), 7.30 (d, J=8.3, 1H), 7.36 (d, J=8.3, 1H), 7.68 (d, J=9.7, 1H), 7.87 (d, J=4.3, 1H), 8.09 (d, J=9.7, 1H), 8.28 (d, J=10.2, 1H). ESI-MS Calcd for C$_{57}$H$_{88}$N$_8$O$_{14}$: 1108.64. Found (m/z): 1110.3 (M+H)$^+$.

EXAMPLE 62

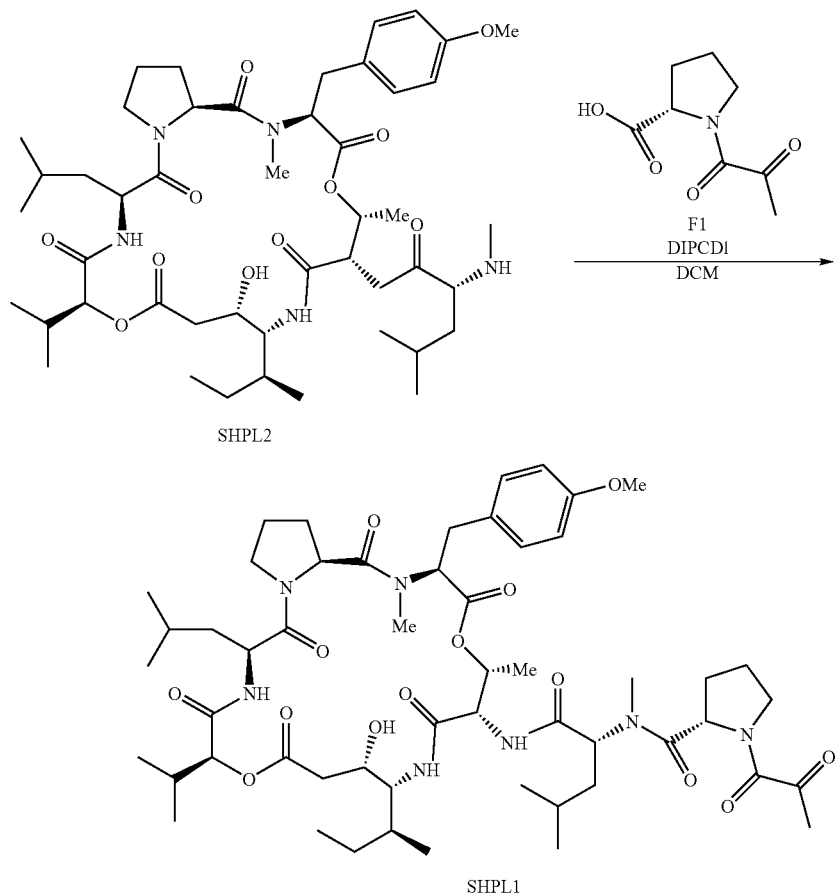

Following the procedure described for the synthesis of SAPL1, starting from SHPL2 (72 mg, 0.081 mmol) and F1 (75 mg, 0.405 mmol). The title compound (68 mg, 79%) was obtained as a white solid after purification by flash LC (Lichroprep RPC18, gradient ACN/H$_2$O/TFA from 70:30:0.5 to 90:10:0.5). Rf=0.49 (ACN/H$_2$O/TFA 90:10:1).

$^1$H NMR (300 MHz, CDCl$_3$) δ 0.80-1.10 (m, 24H), 1.12-1.50 (m, 18H), 1.50-2.30 (m, 6H), 2.42 (m, 1H), 2.53 (s, 3H) 2.55 (s, 3H), 2.57 (s, 3H), 2.96-3.40 (m, 3H), 3.05 (s, 3H), 3.10 (s, 3H), 3.63 (m, 5H), 3.78 (s, 3H), 3.90 (m, 1H), 4.01 (m, 1H) 4.30 (m, 1H), 4.63 (m, 1H), 4.69 (m, 1H), 4.86 (m, 1H), 5.02 (d, J=4.8, 1H), 5.09 (m 1H), 5.20 (m, 1H), 5.30 (m, 1H), 6.83 (d, J=8.3, 2H), 6.89 (d, J=6.3, 1H), 7.07 (d, J=8.3, 2H), 7.29 (d, J=9.7, 1H), 7.34 (m, 2H), 7.43 (d, J=5.3, 1H), 7.74 (d, J=9.7, 1H), 7.80 (d, J=10.2, 1H). $^{13}$C NMR (75 MHz, CDCl$_3$) δ 12.06, 14.22, 14.30, 16.49, 16.76, 17.84, 19.17, 21.08, 21.41, 21.54, 22.54, 23.79, 23.94, 24.05, 24.16, 24.82, 24.96, 25.05, 25.98, 26.45, 27.37, 27.57, 28.21, 28.59, 30.31, 30.83, 31.56, 31.62, 33.74, 34.24, 36.02, 36.25, 38.91, 38.96, 39.46, 39.86, 46.92, 48.44, 48.71, 49.06, 54.95, 55.49, 57.16, 57.68, 58.23, 59.13, 66.16, 66.28, 69.10, 70.83, 71.14, 79.12, 114.31, 129.96, 130.12, 130.59, 158.86, 168.69, 168.81, 169.75, 169.82, 170.18, 170.45, 170.52, 170.69, 170.84, 171.21, 171.28, 172.47, 173.17, 174.66, 174.82, 197.63, 201.38. ESI-MS Calcd for C$_{54}$H$_{83}$N$_7$O$_{14}$: 1053.60. Found (m/z): 1054.9 (M+H)$^+$.

EXAMPLE 63

Synthesis of [Val]³-Aplidine (SVPL1)

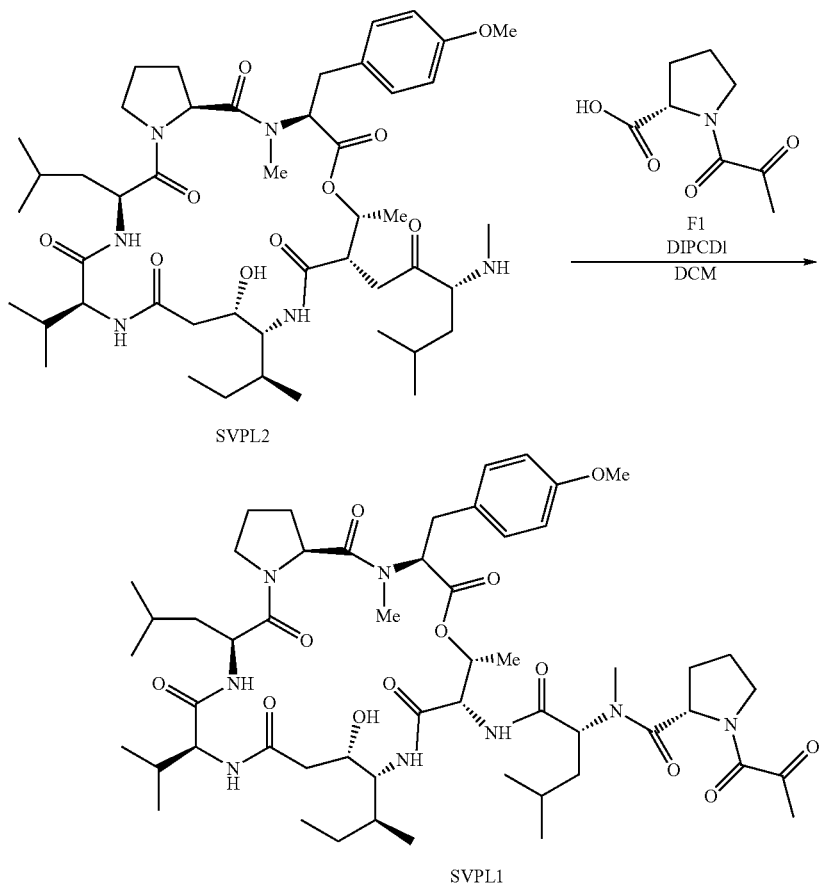

Following the procedure described for the synthesis of SAPL1, starting from SVPL2 (10 mg, 11 µmol) and F1 (10.5 mg, 57 µmol). The title compound (8 mg, 69%) was obtained as a white solid after purification by HPLC (HyperPrep PEP 100 C18, isocratic ACN/H₂O 85:15 (flow: 7 ml/min, 250×21 mm, at 270 mm, $t_R$=10.9 and 12.3 min).

$^1$H NMR (300 MHz, CDCl₃) δ 0.82-1.02 (m, 24H), 1.13-1.38 (m, 9H), 1.55 (m, 2H), 1.67-1.81 (m, 4H), 1.95-2.02 (m, 3H), 2.10-2.17 (m, 2H), 2.26-2.39 (m, 2H), 2.56 (s, 3H), 2.57 (s, 3H), 2.58 (s, 3H), 2.74-2.92 (m, 1H), 3.10 (s, 3H), 3.15 (s, 3H), 3.20 (m, 1H), 3.36 (dd, $J_1$=4.4, $J_2$=14.2, 1H), 3.49-3.72 (m, 5H), 3.79 (s, 3H), 3.97-4.13 (m, 2H), 4.38 (dd, $J_1$=4.6, $J_2$=14.2, 1H), 4.49 (m, 1H), 4.60 (m, 1H), 4.68-4.81 (m, 2H), 5.11 (m, 1H), 5.26-5.30 (m, 1H), 5.33-5.40 (m, 1H), 6.84 (d, J=7.8, 2H), 7.08 (d, J=8.3, 2H), 7.36-7.52 (m, 2H), 7.48 (d, J=9.6, 1H), 7.61 (d, J=6.8, 1H). ESI-MS Calcd for $C_{54}H_{84}N_8O_{13}$ 1052.62. Found (m/z): 1053.6 (M+H)⁺.

EXAMPLE 64

Synthesis of [Hiv]³-[isobutyryl]⁸-didemnin A (SISHPL1)

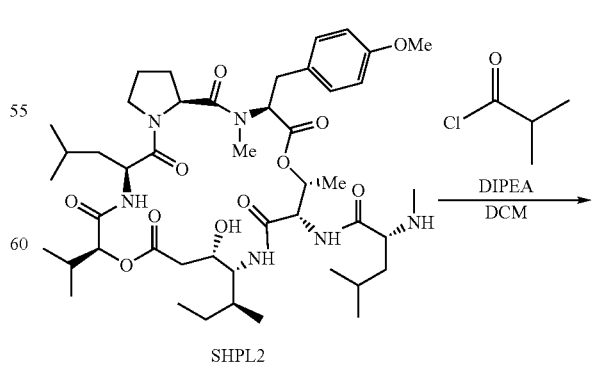

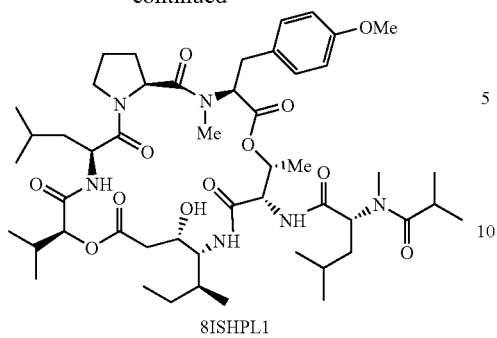

8ISHPL1

To a solution of SHPL2 (10 mg, 11.2 μmol) in DCM (200 μl) at 0° C. under Ar, was added DIPEA (3 μl, 16.8 μmol) and isobutyryl chloride (1.4 μl, 13.4 μmol). After 3 h at 22° C., DCM (3 ml) was added and the mixture was washed successively with aq. HCl (2 ml, 0.1N), aq. NaHCO$_3$ (2 ml, sat.) and brine (2 ml), dried (Na$_2$SO$_4$), filtered and concentrated in vacuo. Purification of the residue by HPLC (HyperPrep PEP 100 C18, isocratic ACN/H$_2$O 85:15 (flow: 7 ml/min, 250×21 mm, at 270 nm, t$_R$=19 min) afforded the title compound (10 mg, 94%) as a white solid.

$^1$H NMR (300 MHz, CDCl$_3$) δ 0.82-1.10 (24H, m), 1.13-1.65 (18H, m), 1.72-2.58 (6H, m), 2.56 (s, 3H), 2.89 (s, 3H), 2.92 (m, 2H), 3.13 (m, 2H), 3.36 (dd, J$_1$=4.6, J$_2$=15.6, 1H), 3.54-3.73 (m, 3H), 3.78 (s, 3H), 3.91 (m, 2H), 4.40 (m, 1H), 4.60 (m, 1H), 4.89 (m, 1H), 4.99 (d, J=5.3, 1H), 5.03 (m, 1H), 5.20 (m, 1H), 6.73 (d, J=9.3, 1H), 6.84 (d, J=9.6, 2H), 7.08 (d, J=9.6, 2H), 7.55 (d, J=8.6, 1H), 7.82 (d, J=11, 1H), $^{13}$C NMR (75 MHz, CDCl$_3$) δ 11.78, 14.63, 15.69, 17.92, 19.03, 19.31, 19.66, 21.03, 22.29, 23.19, 23.85, 24.71, 25.14, 27.27, 28.22, 30.39, 30.51, 31.15, 33.80, 34.25, 35.61, 38.85, 39.63, 46.98, 48.51, 53.29, 53.65, 55.49, 56.01, 56.35, 57.26, 66.07, 69.07, 70.94, 79.33, 114.31, 130.08, 130.60, 158.84, 168.79, 169.75, 170.34, 170.68, 171.36, 171.73, 174.02, 179.84. ESI-MS Calcd for C$_{50}$H$_{80}$N$_6$O$_{12}$, 956.58. Found (m/z): 957.5 (M+H)$^+$.

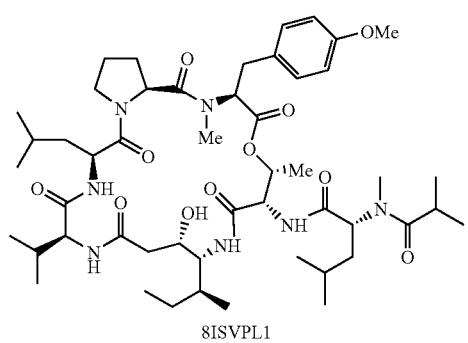

8ISVPL1

Following the procedure described for the synthesis of 8ISHPL1, starting from SVPL2 (20 mg, 22.6 μmol). The title compound (19 mg, 88%) was obtained after purification by HPLC (HyperPrep PEP 100 C18, isocratic ACN/H$_2$O 85:15, flow: 7 ml/min, 250×21 mm, at 270 nm, t$_R$=19 min).

$^1$H NMR (300 MHz, CDCl$_3$): δ 0.81-1.02 (m, 24H), 1.14-1.38 (m, 5H), 1.15 (d, J=6.6, 3H), 1.19 (d, J=6.6, 3H), 1.38-1.80 (m, 7H), 1.80-2.40 (m, 6H), 2.57 (s, 3H), 2.58-2.64 (m, 1H), 2.85-2.92 (m, 1H), 2.93 (s, 3H), 3.16 (dd, J$_1$=10.5, J$_2$=14.4, 1H), 3.36 (dd, J$_1$=4.5, J$_2$=14.4, 1H), 3.39 (bs, 1H), 3.56 (dd, 1H, J=4.5, 10.8), 3.59-3.72 (m, 3H), 3.78 (s, 3H), 4.01 (td, J$_1$=3.3, J$_2$=10.2, 1H), 4.39-4.47 (m, 2H), 4.58 (dd, J$_1$=5.7, J$_2$=7.5, 1H), 4.79 (t, J=9.9, 1H), 5.03-5.14 (m, 2H), 6.84 (d, J=8.4, 2H), 7.04 (d, J=7.8, 1H), 7.08 (d, J=8.4, 1H), 7.36 (d, J=9.0, 1H), 7.45 (d, J=10.2, 1H), 7.51 (d, J=10.2, 1H). $^{13}$C NMR (75 MHz, CDCl$_3$) δ 180.24, 175.10, 173.18, 171.14, 170.72, 170.42, 169.38, 168.73, 158.87, 130.60, 130.02, 114.33, 71.31, 70.50, 66.11, 59.47, 57.42, 56.56, 55.51, 54.93, 53.84, 48.83, 47.13, 41.94, 38.94, 35.67, 34.17, 33.63, 31.32, 31.10, 29.96, 28.32, 27.25, 25.30, 25.05, 24.82, 24.01, 23.22, 21.42, 19.88, 19.72, 11.25, 18.51, 15.60, 14.32, 11.96. ESI-MS Calcd for C$_{50}$H$_{81}$N$_7$O$_{11}$: 955.60. Found 956.8 (M+H)$^+$.

EXAMPLE 65

Synthesis of [Val]$^3$-[Isobutyryl]$^8$-didemnin A (8IS-VPL1)

EXAMPLE 66

Synthesis of [Hiv]$^3$[Butyryl]$^8$-didemnin A (8BSHPL1)

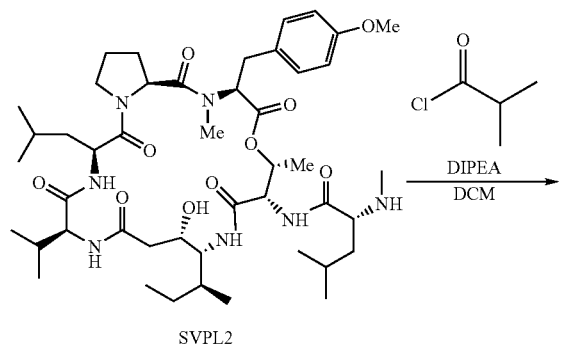

SVPL2

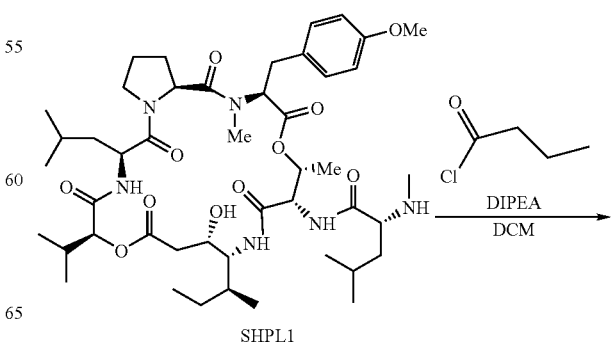

SHPL1

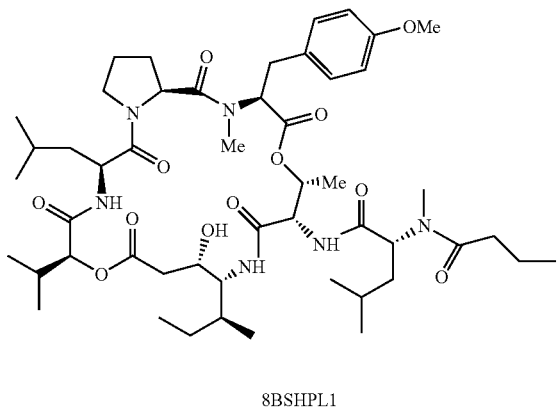

8BSHPL1

Following the procedure described for the synthesis of 8ISHPL1, starting from SHPL2 (10 mg, 11.2 μmol). The title compound (9 mg, 84%) was obtained as a white solid after purification by HPLC (HyperPrep PEP 100 C18, isocratic ACN/$H_2O$ 85:15, flow: 7 ml/min, 250×21 mm, at 270 nm, $t_R$=18.6 min).

$^1$H NMR (300 MHz, $CDCl_3$) δ 0.82-1.10 (m, 24H), 1.11-1.72 (m, 18H), 1.75-2.51 (m, 6H), 2.56 (s, 3H), 2.84 (s, 3H), 2.92 (m, 2H), 3.15 (m, 2H), 3.35 (dd, $J_1$=5.0, $J_2$=15.6, 1H), 3.54-3.77 (m, 3H), 3.79 (s, 3H), 3.91 (m, 2H), 4.40 (m, 1H), 4.60 (m, 1H), 4.89 (m, 1H), 4.98 (d, $J_1$=6.0, 1H), 5.04 (m, 1H), 5.20 (m, 1H), 6.78 (d, $J_1$=9.6, 1H), 6.84 (d, $J_1$=9.6, 2H), 7.08 (d, $J_1$=9.6, 2H), 7.54 (d, $J_1$=9.6, 1H), 7.82 (d, $J_1$=10.6, 1H). $^{13}$C NMR (75 MHz, $CDCl_3$) δ 11.82, 14.15, 14.55, 15.72, 17.96, 18.67, 19.01, 21.05, 22.37, 23.13, 23.84, 24.71, 25.14, 27.30, 28.21, 29.92, 30.38, 30.63, 33.78, 34.25, 35.69, 35.97, 38.85, 39.61, 46.98, 48.52, 53.27, 55.49, 55.99, 56.25, 57.27, 66.07, 69.07, 70.96, 79.40, 114.31, 130.08, 130.59, 158.85, 168.78, 169.73, 170.42, 170.64, 171.36, 171.65, 174.07, 175.79. ESI-MS Calcd for $C_{50}H_{80}N_6O_{12}$: 956.60. Found (m/z): 957.8 $(M+H)^+$.

EXAMPLE 67

Synthesis of [Hiv]$^3$-[hexanoyl]$^8$-didemnin A (8HS-HPL1)

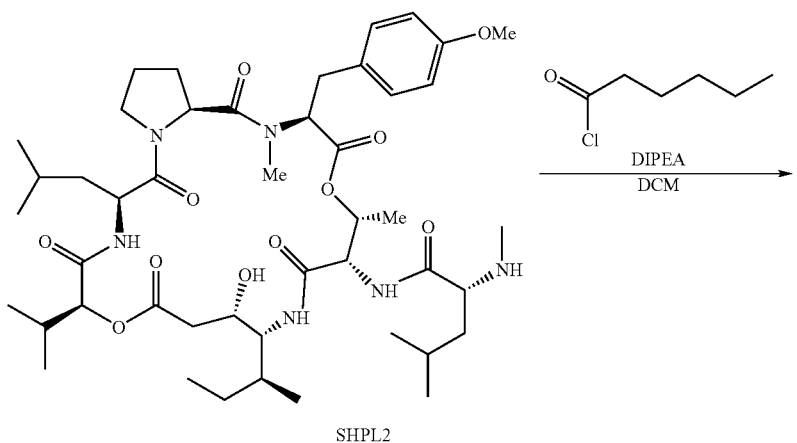

SHPL2

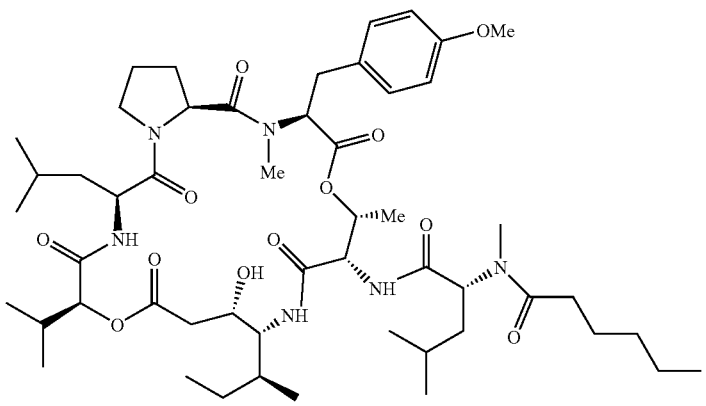

8HSHPL1

Following the procedure described for the synthesis of 8ISHPL1, starting from SHPL2 (10 mg, 11.2 μmol), the title compound (9 mg, 82%) was obtained as a white solid, after purification by HPLC (HyperPrep PEP 100 C18, isocratic ACN/H$_2$O 85:15, flow: 7 ml/min, 250×21 mm, at 270 nm, $t_R$=27.8 min).

$^1$H NMR (300 MHz, CDCl$_3$) δ 0.82-1.10 (m, 24H), 1.11-1.72 (m, 22H), 1.80-2.51 (m, 6H), 2.56 (s, 3H), 2.84 (s, 3H), 2.93 (m, 2H), 3.14 (m, 2H), 3.35 (dd, J$_1$=4.4, J$_2$=14.1, 1H), 3.54-3.76 (m, 3H), 3.79 (s, 3H), 3.91 (m, 2H), 4.41 (m, 1H), 4.60 (m, 1H), 4.88 (m, 1H), 4.98 (d, J$_1$=5.3, 1H), 5.03 (m, 1H), 5.19 (m, 1H), 6.76 (d, J$_1$=8.7, 1H), 6.84 (d, J$_1$=8.7, 2H), 7.08 (d, J$_1$=8.7, 2H), 7.51 (d, J$_1$=8.8, 1H), 7.81 (d, J$_1$=9.7, 1H), $^{13}$C NMR (75 MHz, CDCl$_3$) δ 11.59, 13.94, 14.34, 15.49, 17.73, 18.77, 20.81, 22.14, 22.46, 22.90, 23.60, 24.47, 24.69, 24.90, 27.08, 27.97, 30.14, 30.40, 31.54, 33.53, 33.76, 34.02, 35.47, 38.62, 39.40, 46.76, 48.28, 53.04, 55.26, 55.78, 55.90, 57.04, 65.84, 6882, 70.72, 79.17, 114.07, 129.84, 130.36, 158.61, 168.54, 169.51, 170.15, 170.41, 171.12, 171.42, 173.86, 175.75. ESI-MS Calcd for C$_{52}$H$_{84}$N$_6$O$_{12}$; 984.61. Found (m/z): 985.8 (M+H)$^+$.

EXAMPLE 68

Synthesis of Isobutyryl-Pro-OBn

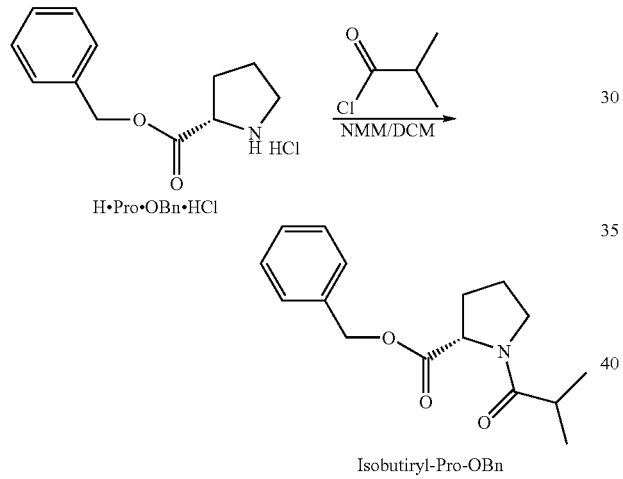

To a solution of H-Pro-OBn.HCl (500 mg, 2.07 mmol) in DCM (10 ml) at 0° C., NMM (680 μl, 6.21 mmol) was added under argon. After 10 min, isobutyryl chloride (240 μl, 2.27 mmol) was added and the reaction mixture was allowed to warm to 20° C. and stirred for 5 h. The mixture was filtered and the filtrate washed successively wit aq. HCl (15 ml, 1N), aq NaHCO$_3$ (10 ml, sat.), and brine (10 ml), then dried (Na$_2$SO$_4$), filtered and concentrated under reduced pressure to afford 560 mg (98%) of the title compound. Rf=0.42 (hex:EtOAc 1:1).

$^1$H-NMR (300 MHz, CDCl$_3$) δ 1.20-1.40 (2d, 6H), 1.90-2.35 (m, 4H), 2.35 (q, 1H), 3.40-3.80 (m, 2H), 4.30 (m, 1H), 5.20 (m, 2H), 7.40 (m, 5H).

EXAMPLE 69

Synthesis of Isobutyryl-Pro-OH

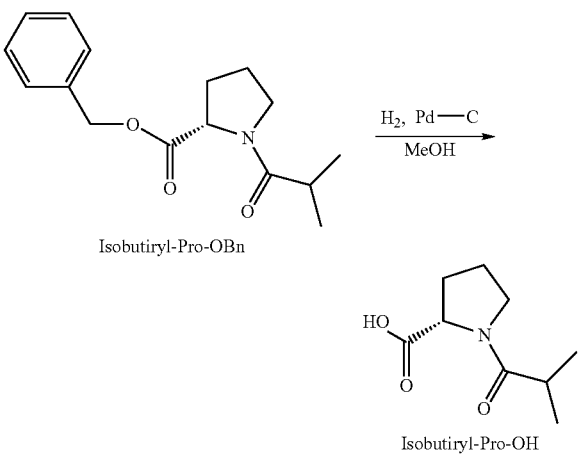

To a solution of Isobutyryl-Pro-OBn (430 mg, 1.56 mmol) in degassed MeOH was added Pd/C (10%) (43 mg, 10% w/w) and then flushed successively with Ar and bubbled with hydrogen. The mixture was stirred under H$_2$ for 14 h and then degassed and filtered. The solution was concentrated and the residue crystallized with MTBE/hex to give 140 mg (48%) of the title compound as a white solid.

$^1$H-NMR (300 MHz, CDCl$_3$) δ 1.20 (m, 6H), 1.90-2.10 (m, 3H), 2.50 (m, 1H), 2.70 (q, 1H), 3.40-3.70 (m, 2H), 4.60 (dd, 1H). ESI-MS Calcd for C$_9$H$_{15}$NO$_3$: 185.11, Found (m/z): 186.1 (M+H)$^+$.

EXAMPLE 70

Synthesis of [Hiv]$^3$-[Isobutyryl]$^9$-aplidine (9ISHPL1)

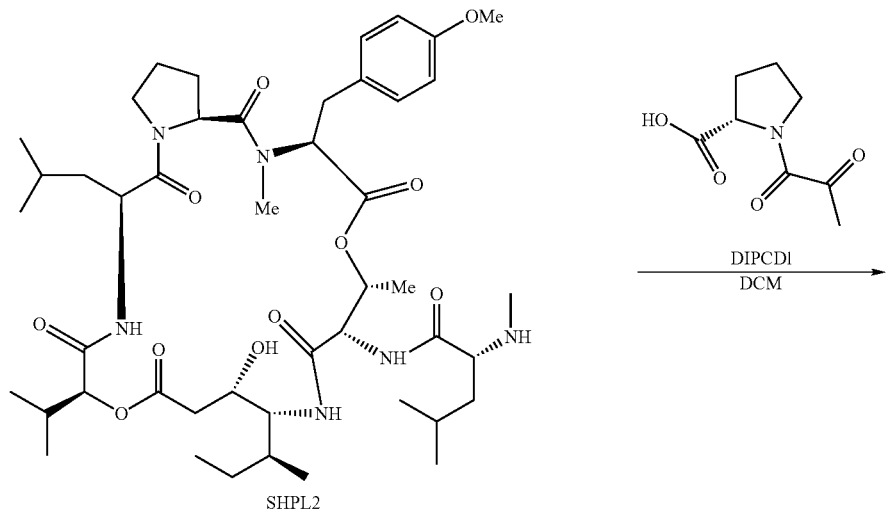

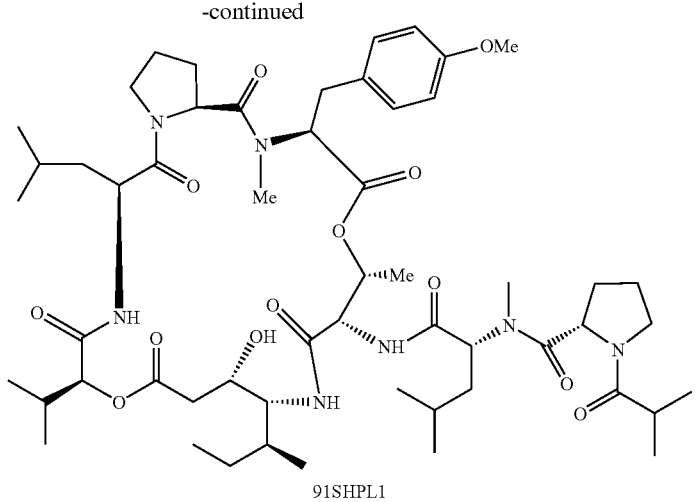

91SHPL1

To a solution of Isobutyryl-Pro-OH (10 mg, 54 μmol) in DCM (150 μl) at 0° C., was added DIPCDI (5 μl, 32 μmol). Stirring was continued for 60 min and then, the mixture was transferred to a flask containing SHPL2 (10 mg, 11.2 μmol) in DCM (150 μl). After 4d at 2-4° C. the mixture was diluted with DCM (2 ml) and washed successively with aq HCl (1 ml, 0.1 N), aq. NaHCO$_3$ (1 ml, sat.) and brine (1 ml), the organic phase was dried (Na$_2$SO$_4$), filtered and concentrated. The residue was purified by HPLC (HyperPrep PEP 100 C18, isocratic ACN/H$_2$O 85:15 (flow: 7 ml/min, 250×21 mm, at 270 nm, t$_R$=13 and 14 min) to afford 9ISHPL1 (9 mg, 72%) as a white solid.

$^1$H NMR (300 MHz, CDCl$_3$) δ 0.82-1.10 (m, 24H), 1.12-1.50 (m, 18H), 1.52-2.70 (m, 10H), 2.56 (s, 3H), 3.00-3.44 (m, 4H), 3.08 (s, 3H), 3.55-3.72 (m, 5H) 3.78 (s, 3H), 4.00 (m, 3H), 4.26 (m, 1H), 4.62 (m, 2H), 4.86 (m, 1H), 5.02 (d, J=5.3, 1H), 5.30 (m, 2H), 6.84 (d, J=9.0, 2H), 7.07 (d, J=9.0, 2H), 7.29 (d, J=11.0, 1H), 7.80 (d, J=9.0, 1H); 7.88 (d, J=11, 1H). $^{13}$C NMR (75 MHz, CDCl$_3$) δ 12.04, 14.44, 16.91, 17.94, 18.96, 19.03, 19.15, 21.07, 21.59, 23.87, 24.10, 24.89, 25.08, 26.04, 27.54, 28.21, 28.87, 30.33, 31.61, 32.64, 33.77, 34.24, 36.19, 39.07, 39.33, 39.81, 46.87, 47.52, 48.45, 54.74, 55.49, 56.20, 57.08, 58.50, 66.41, 69.13, 71.48, 79.16, 114.27, 130.30, 130.59, 158.80, 168.55, 169.88, 170.86, 171.06, 171.22, 173.63, 174.92, 176.19. ESI-MS Calcd for C$_{55}$H$_{87}$N$_7$O$_3$: 1053.64, Found (m/z): 1054.6 (M+H)$^+$.

EXAMPLE 71

Synthesis of [Val]$^3$-[Isobutyryl]$^9$-aplidine (9IS-VPL1)

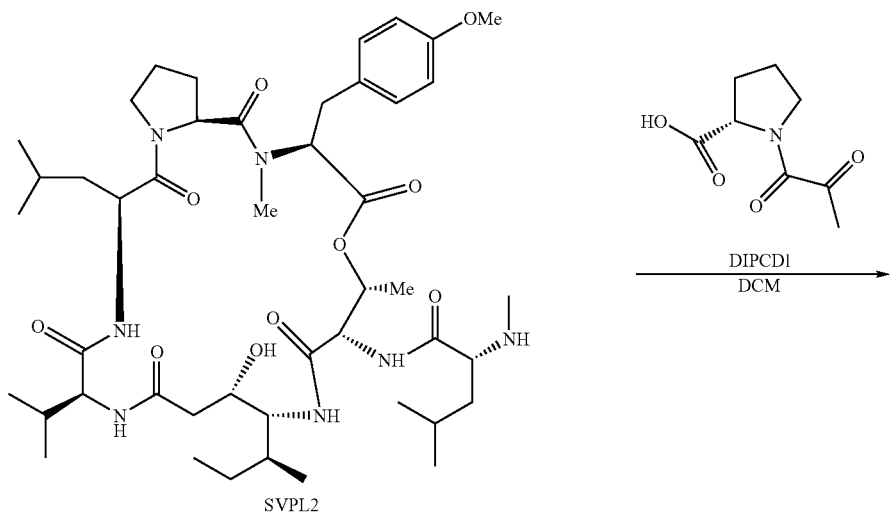

SVPL2

-continued

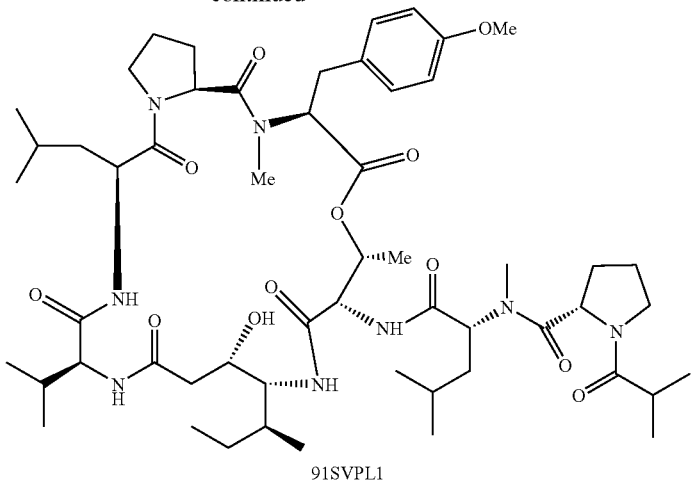

91SVPL1

Following the procedure described for the synthesis of 9ISHPL1, starting from SVPL2 (10 mg, 11.2 µmol), the title compound (9 mg, 77%) was obtained as a white solid after purification by HPLC (HyperPrep PEP 100 C18, isocratic ACN/H$_2$O 85:15 (flow: 7 ml/min, 250×21 nun, at 270 nm, $t_R$=15.3 min).

$^1$H NMR (300 MHz, CDCl$_3$): δ 0.82-1.01 (m, 24H), 1.14-1.37 (m, 12H), 1.148-2.35 (m 8H), 2.55 (s, 3H), 2.57-2.68 (m, 1H), 2.77-2.83 (m, 1H), 3.12 (s, 3H), 3.19-3.23 (m, 1H), 3.35-3.41 (m, 2H), 3.52-3.56 (m, 1H), 3.58-3.70 (m, 3H), 3.78 (s, 3H), 4.03-4.13 (m, 1H), 4.33-4.35 (m, 1H), 4.44-4.48 (m, 1H), 4.55-4.66 (m, 2H), 4.70-4.83 (m, 1H), 5.35-5.39 (m, 2H), 6.82 (d, J=8.4, 2H), 7.06 (d, J=8.4, 2H), 7.25 (bs, 2H), 7.37 (d, 10.5, 1H), 7.46 (d, J=8.7, 1H), 7.60 (d, J=9.3, 1H), 8.07 (bs, 1H). $^{13}$C NMR (75 MHz, CDCl$_3$) δ 12.10, 14.44, 16.84, 18.63, 18.95, 19.92, 21.31, 21.61, 23.91, 24.05, 24.86, 25.00, 25.30, 26.06, 27.41, 28.33, 28.93, 30.00, 31.76, 32.65, 33.59, 31.16, 36.21, 39.17, 41.71, 42.19, 47.08, 47.57, 48.88, 54.37, 54.65, 55.50, 56.15, 57.33, 58.70, 59.33, 66.45, 70.92, 71.54, 114.29, 130.28, 130.59, 158.82, 168.41, 170.08, 170.52, 170.69, 171.03, 172.65, 173.80, 175.68, 176.42. ESI-MS Calcd for C$_{55}$H$_{88}$N$_8$O$_{12}$: 1052.65. Found (m/z): 1053.8 (M+H)$^+$.

EXAMPLE 72

Synthesis of Z-NVa-Pro-OMe

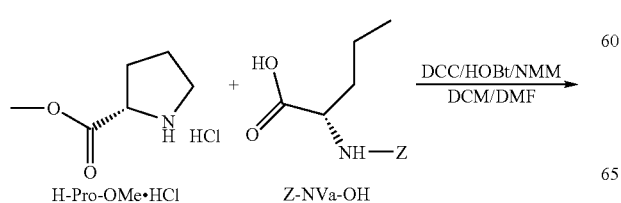

H-Pro-OMe·HCl     Z-NVa-OH

-continued

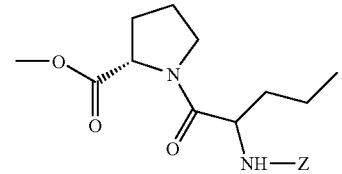

Z-NVa-Pro-OMe

Following the procedure described for the synthesis of F2, from Z-NVa-OH (261 mg, 1.04 mmol), H-Pro-OMe.HCl (156.6 mg, 0.94 mmol), the title compound (315 mg, 87%) was obtained as a colourless oil after purification by LC-silica (hex-EtOAc, gradient 3:1 to 1:1). R$_f$=0.42 (hex-EtOAc 1:1).

$^1$H NMR (300 MHz, CDCl$_3$): δ 0.97 (t, J=6.9, 2H), 1.44 (six, J=7.5, 2H), 1.53-1.65 (m, 1H), 1.68-1.77 (m, 1H), 1.82-2.09 (m, 3H), 2.17-2.24 (m, 1H), 3.43-3.80 (m, 2H), 3.71 (s, 3H), 4.45-4.55 (m, 2H), 5.07 (s, 2H), 5.51 (d, J=8.4, 1H), 7.32-7.35 (m, 5H).

EXAMPLE 73

Synthesis of NVa-Pro-OH

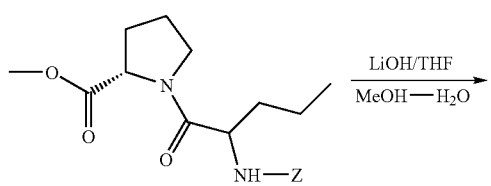

Z-NVa-Pro-OMe

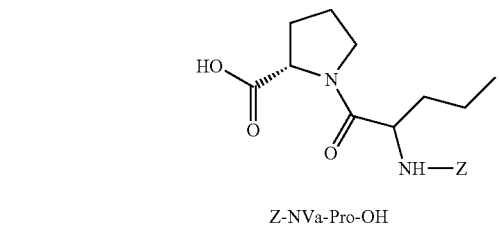

Z-NVa-Pro-OH

To a solution of Z-NVa-Pro-OMe (36 mg, 99 μmol) in a mixture of THF and MeOH (130 μl:130 μl) at 0° C., aq LiOH (130 μl, 15% w/w) was added. After 6 h of stirring the reaction mixture was partitioned between $H_2O$ (3 ml) and diethyl ether (3×2 ml). The organic phase was then extracted with $NaHCO_3$ (3×2 ml). The combined aqueous phases were neutralized (pH=5) with aq. HCl (0.1 N) and partitioned with $Et_2O$ (3×3 ml). The organic phase was dried ($Na_2SO_4$), filtered and concentrated to give the title compound (36 mg, quant) as a colourless oil.

$^1$H NMR (300 MHz, $CDCl_3$) δ 0.96 (t, J=6.9, 2H), 1.41 (six, J=7.4, 2H), 1.53-1.65-1.77 (m, 2H), 1.82-2.10 (m, 3H), 2.17-2.24 (m, 1H), 3.52-3.81 (m, 2H), 4.45-4.58 (m, 2H), 5.07 (bs, 2H), 5.81 (d, J=8.4, 1H), 7.30-7.35 (m, 5H), 7.41 (bs, 1H). ESI-MS Calcd for $C_{18}H_{24}N_2O_5$: 348.17. Found (m/z): 349.2 $(M+H)^+$.

EXAMPLE 74

Synthesis of [ZNVa-Pro]$^9$-aplidine (9NVSAPL2)

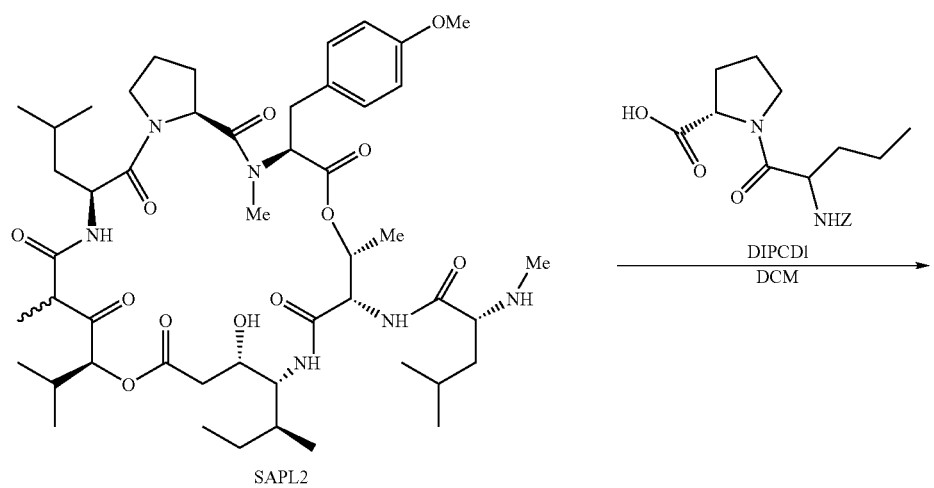

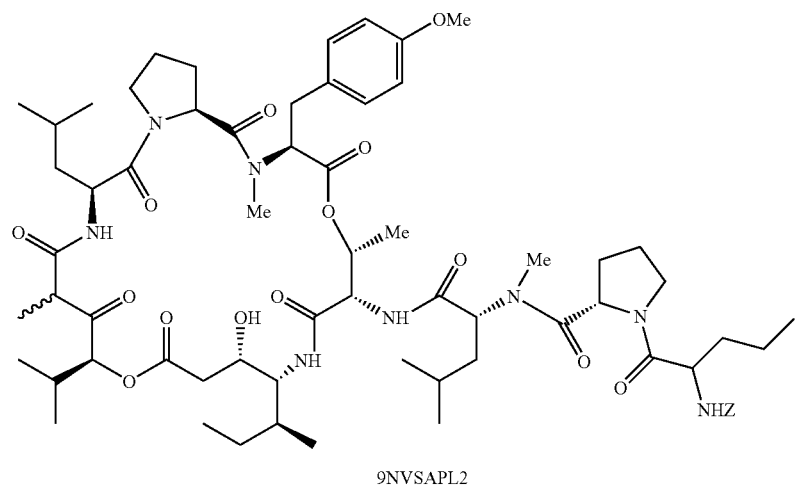

Following the procedure described for the synthesis of SAPL1, starting from SAPL2 (18 mg, 19 μmol) and Z-NVa-Pro-OH (34 mg, 97 μmol), the title compound (16 mg, 66%) was obtained as a white solid after purification by HPLC (HyperPrep PEP 100 C18, isocratic ACN/H$_2$O 85:15 (flow: 7 ml/min, 250×21 mm, at 270 nm, t$_R$=29 min).

$^1$H NMR (300 MHz, CDCl$_3$): δ 0.84-0.96 (m, 27H), 1.12-1.85 (m, 19H), 2.00-2.25 (m, 7H), 2.30-2.40 (m, 1H), 2.54 (s, 3H), 2.62 (dd, J$_1$=10.5, J$_2$=17.7, 1H), 2.93 (d, 4.2, 1H), 3.14 (s, 3H), 3.14-3.20 (m, 1H), 3.28-3.34 (m, 2H), 3.50-3.67 (m, 4H), 3.77-3.80 (m, 1H), 3.79 (s, 3H), 3.82-3.91 (m, 1H), 4.00-4.17 (m, 2H), 4.27 (dd, J$_1$=6.3, J$_2$=13.2, 1H), 4.43-4.51 (m, 2H), 4.58-4.63 (m, 1H), 4.69-4.75 (m, 1H), 4.77-4.82 (m, 1H), 5.07 (d, 1H, J=12.9, 2H), 5.13 (d, J=12.9, 1H), 5.32-5.41 (m, 2H), 6.07 (d, J=8.7, 1H), 6.83 (d, J=8.4, 2H), 7.06 (d, J=8.4, 2H), 7.17 (d, J=9.9, 1H), 7.32 (m, 5H), 7.83 (d, J=9.0, 1H). $^{13}$C NMR (75 MHz, CDCl$_3$) δ 11.68, 13.74, 14.56, 15.24, 16.39, 16.85, 18.61, 20.94, 21.26, 23.34, 23.70, 24.76, 24.90, 25.02, 26.00, 27.17, 27.81, 28.54, 31.29, 31.40, 33.30, 33.85, 33.86, 36.19, 38.62, 38.84, 41.31, 46.91, 47.21, 49.38, 49.49, 52.50, 54.96, 55.24, 55.25, 56.50, 57.17, 57.96, 62.53, 66.40, 67.93, 70.64, 81.37114.04, 127.89, 127.77, 128.32, 129.97, 130.29, 136.84, 156.72, 158.55, 168.48, 169.36, 169.58, 170.52, 171.27, 171.71, 172.54, 173.22, 205.08. ESI-MS Calcd for C$_{67}$H$_{100}$N$_8$O$_{16}$: 127.73. Found (m/z): 1273.7 (M+H)$^+$.

EXAMPLE 75

Synthesis of [Hiv]$^3$-[Z-NVa-Pro]$^9$-aplidine (9NVSHPL2)

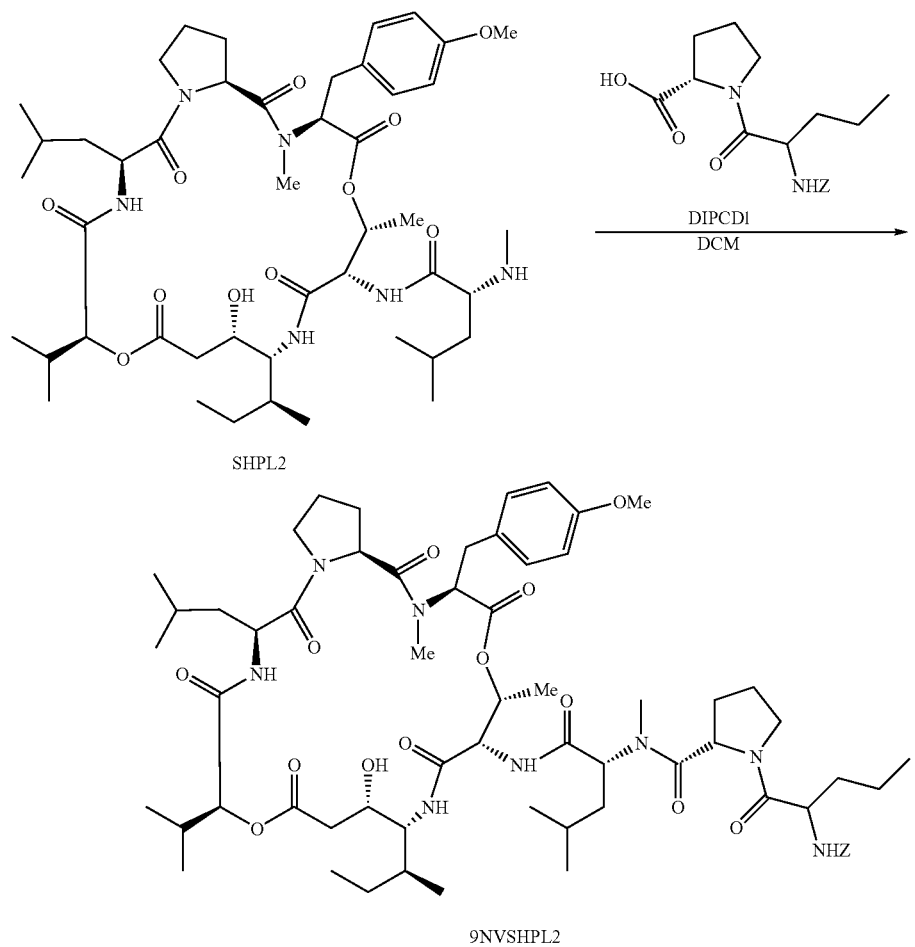

Following the procedure described for the synthesis of SAPL1, starting from SHPL2 (10 mg, 11.2 μmol), and Z-NVa-Pro-OH (20 mg, 56 μmol), the title compound (8 mg, 60%) was obtained as a white solid after purification by HPLC (HyperPrep PEP 100 C18, isocratic ACN/H$_2$O 85:15 (flow: 7 ml/min, 250×21 mm, at 270 nm, t$_R$=26.7 min).

$^1$H NMR (300 MHz, CDCl$_3$) δ 0.82-1.10 (m, 24H), 1.12-1.80 (m, 22H), 1.82-2.35 (m, 6H), 2.42 (m, 1H), 2.56 (s, 3H), 2.96-3.38 (m, 4H), 3.10 (s, 3H), 3.48-3.72 (m, 5H), 3.78 (s, 3H), 3.88 (m, 1H), 4.01 (m, 1H), 4.18 (m, 1H), 4.47 (m, 1H), 4.68 (m, 2H), 4.87 (m, 1H), 5.02 (d, J$_1$=5.3, 1H), 5.08 (m, 2H), 5.28 (m, 1H), 5.42 (m, 1H), 6.10 (d, J=8.3, 1H), 6.84 (d, J=8.3, 2H), 7.07 (d, J=8.3, 2H), 7.31 (m, 6H), 7.72 (d, J=4.3, 1H), 7.78 (d, J=8.7, 1H). $^{13}$C NMR (75 MHz, CDCl$_3$) δ 12.06, 13.88, 14.22, 16.85, 17.76, 18.89, 19.18, 21.12, 21.47, 23.72, 23.98, 25.08, 26.25, 27.57, 28.15, 28.79, 30.32, 31.61, 33.45, 33.72, 34.07, 35.95, 38.92, 39.59, 39.90, 46.87, 47.44, 48.46, 52.76, 55.21, 55.49, 56.77, 57.17, 58.37, 66.41, 66.65, 69.22, 71.14, 79.07, 114.24, 127.87, 128.00, 128.56, 130.25, 130.55, 157.00, 158.79, 168.82, 169.86, 170.36, 170.58, 170.77, 171.30, 171.86, 173.28, 174.94. ESI-MS Calcd for $C_{64}H_{96}N_8O_{15}$ 1216.7. Found m/z: 1217.5 $(M+1)^+$.
EXAMPLE 76
Synthesis of [NVa-Pro]$^9$-aplidine (9NVSAPL1)
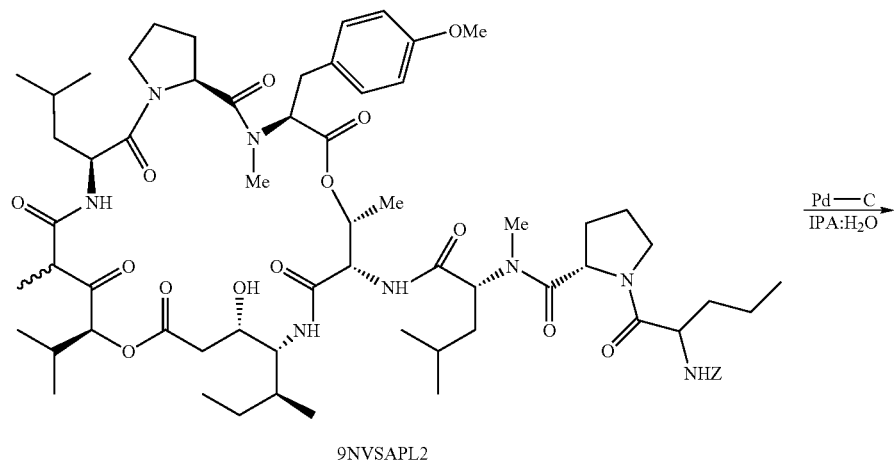
9NVSAPL2
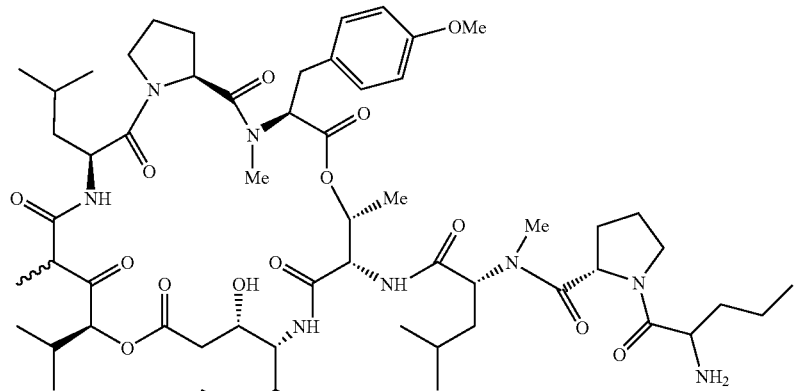
9NVSAPL1

A degassed mixture of 9NVSAPL2 (10 mg, 7.8 μmol) and Pd/C (10%, 5 mg) in IPA:H$_2$O (0.2 ml:0.1 ml), was saturated (and maintained at 1 atm) with hydrogen gas while stirring for 14 h. Then, the mixture was filtered (teflon 0.45 μm) and concentrated under vacuum to yield the title compound (8.8 mg, quant) as a white solid.

$^1$H NMR (300 MHz, CDCl$_3$): δ 0.85-0.95 (m, 27H), 1.18-1.51 (m, 18H), 1.50-2.45 (m, 7H), 2.59-2.83 (m, 1H), 2.57 (s, 3H), 2.57-2.80 (m, 3H), 2.81-2.95 (m, 1H), 3.14 (s, 3H), 3.15-3.40 (m, 3H), 3.52-3.79 (m, 4H), 3.79 (s, 3H), 4.45-4.52 (m, 1H), 4.61-4.65 (m, 1H), 4.70-4.85 (m, 2H), 5.17 (d, J=3.3, 1H), 5.36-5.39 (m, 2H), 6.84 (d, J=8.1, 2H), 7.86 (d, J=8.7, 2H), 7.19 (d, J=10.2, 1H), 7.82 (d, J=9.0, 1H), 7.80-7.85 (m, 1H). ESI-MS Calcd for C$_{59}$H$_{40}$N$_8$O$_{14}$: 1138.69. Found (m/z): 1139.7 [(M+H)]$^+$.

EXAMPLE 77

Synthesis of [Hiv]$^3$-[NVa-Pro]$^9$-aplidine (9NVSHPL1)

Following the procedure described for the synthesis of 9NVSAPL1, starting from 9NVSHPL2 (10 mg, 8.2 μmol), the title compound (8 mg, quant) was obtained as a white solid.

$^1$H NMR (300 MHz, CDCl$_3$) δ 0.82-1.10 (m, 30H), 1.12-1.85 (m, 22H), 1.92-2.35 (m, 6H), 2.42 (m, 1H), 2.56 (s, 3H), 3.10-3.45 (m, 4H), 3.10 (s, 3H), 3.50-3.70 (m, 5H), 3.78 (s, 3H), 3.82 (m, 1H), 4.01 (m, 1H), 4.26 (m, 1H), 4.65 (m, 1H), 4.64 (m, 1H), 4.88 (m, 1H), 5.02 (d, J=5.3, 1H), 5.32 (m, 2H), 6.84 (d, J=8.3, 2H), 7.07 (d, J=8.3, 2H), 7.38 (d, J=8.7, 1H), 7.60 (d, J=4.3, 1H), 7.80 (d, J=9.3, 1H). $^{13}$C NMR (75 MHz, CDCl$_3$) δ 12.03, 14.13, 14.30, 16.80, 17.81, 18.72, 19.15, 21.09, 21.55, 23.73, 23.96, 25.07, 26.16, 27.55, 28.17, 28.72, 29.91, 30.33, 31.52, 33.80, 34.17, 36.00, 38.94, 39.51, 39.84, 46.88, 47.51, 48.45, 55.01, 55.49, 56.91, 57.15, 58.10, 66.37, 69.17, 71.10, 79.12, 114.29, 130.21, 130.57, 158.82, 163.66, 168.91, 169.86, 170.38, 170.75, 170.82, 171.30, 173.22, 174.79. ESI-MS Calcd for C$_{56}$H$_{90}$N$_8$O$_{13}$ 1082.66. Found m/z: 1083.7 (M+H)$^+$.

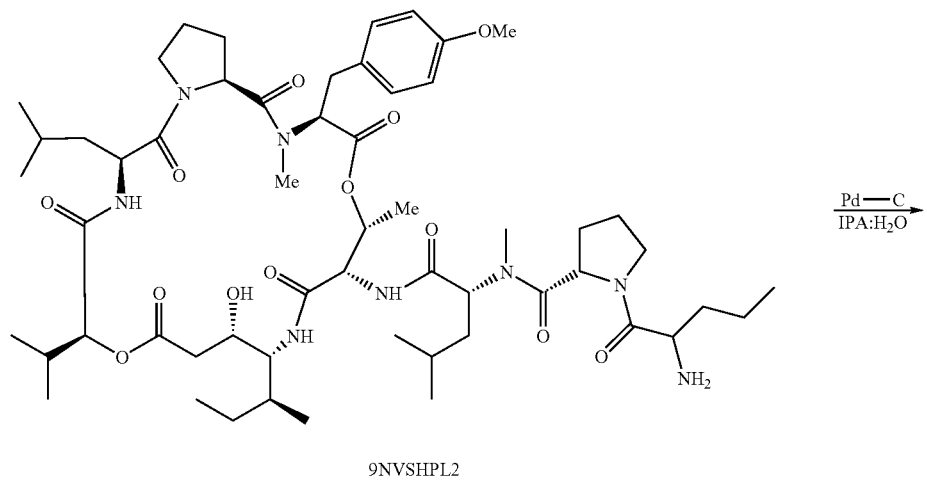

9NVSHPL2

9NVSHPL1

EXAMPLE 78

Synthesis of [Hiv]³-[L-Lac(OTBDMS)]⁹-aplidine [9LSHPL2(L)]

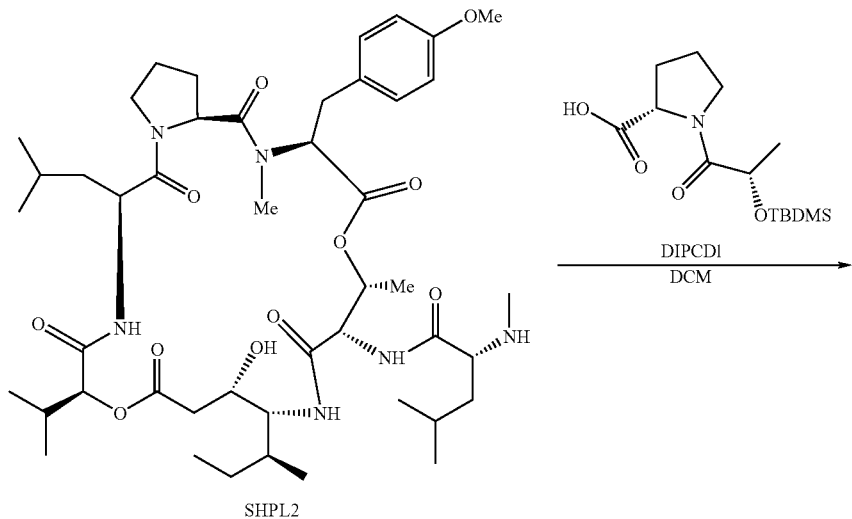

SHPL2

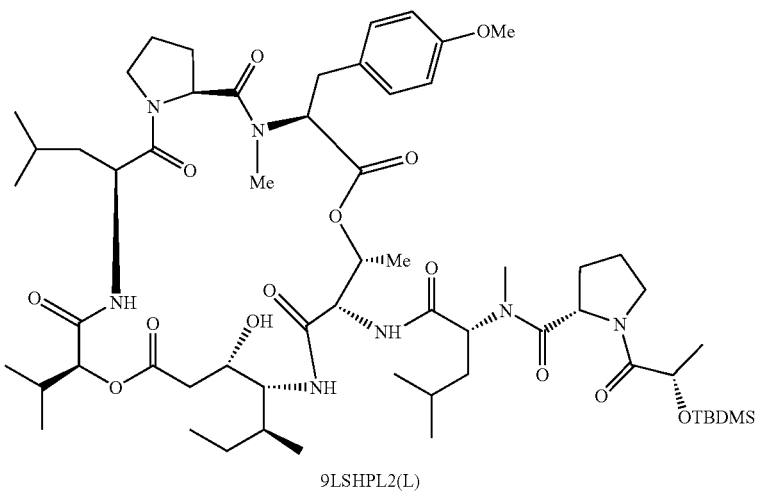

9LSHPL2(L)

Following the procedure described for the synthesis of SAPL1, starting from SHPL2 (10 mg, 11.2 μmol) and (L)-Lac(OTBDMS)-Pro-OH (17 mg, 56 μmol), the title compound (9 mg, 68%) was obtained as a white solid after purification by HPLC (HyperPrep PEP 100 C18, gradient ACN/H$_2$O 85:15-100:0 in 10 min. (flow: 7 nm/min, 250×21 mm, at 270 nm, t$_R$=30.1 min).

$^1$H NMR (300 MHz, CDCl$_3$) δ 0.08 (s, 3H), 0.10 (s, 3H), 0.82-1.10 (m, 24H), 1.11-1.72 (m, 18H), 1.75-2.51 (m, 6H), 2.41 (m, 1H), 2.56 (s, 3H), 3.00-3.40 (m, 5H), 3.11 (s, 3H), 3.53-3.82 (m, 3H), 3.79 (s, 3H), 3.91 (m, 2H), 4.02 (m, 1H), 4.27 (m, 1H), 4.50 (m, 1H), 4.63 (m, 2H), 4.87 (m, 1H), 5.01 (d, J=4.8, 1H), 5.27 (m, 2H), 6.84 (d, J=8.7, 2H), 7.07 (d, J=8.7, 2H), 7.29 (d, J=9.7, 1H), 7.63 (d, J=5.8, 1H), 7.88 (d, J=9.7, 1H). $^{13}$H NMR (75 MHz, CDCl$_3$) δ −4.26, −4.12, 12.04, 14.40, 16.91, 17.97, 19.14, 20.60, 21.11, 21.66, 23.82, 24.11, 24.96, 25.08, 26.11, 26.37, 27.53, 28.18, 28.37, 30.33, 31.69, 33.75, 34.19, 36.23, 39.00, 39.36, 39.81, 46.87, 47.64, 48.45, 54.91, 55.37, 55.48, 56.81, 57.08, 58.37, 66.38, 69.14, 69.89, 71.42, 79.19, 82.66, 114.23, 130.36, 130.59, 158.77, 168.43, 469.86, 170.72, 171.01, 171.21, 172.03, 173.62, 174.91. ESI-MS Calcd for C$_{60}$H$_{99}$N$_7$O$_{14}$Si: 1169.7. Found m/z: 1170.9 (M+H)$^+$.

EXAMPLE 79

Synthesis of [Hiv]³-[D-Lac(OTEDMS)]⁹-aplidine [9LSHPL2(D)]

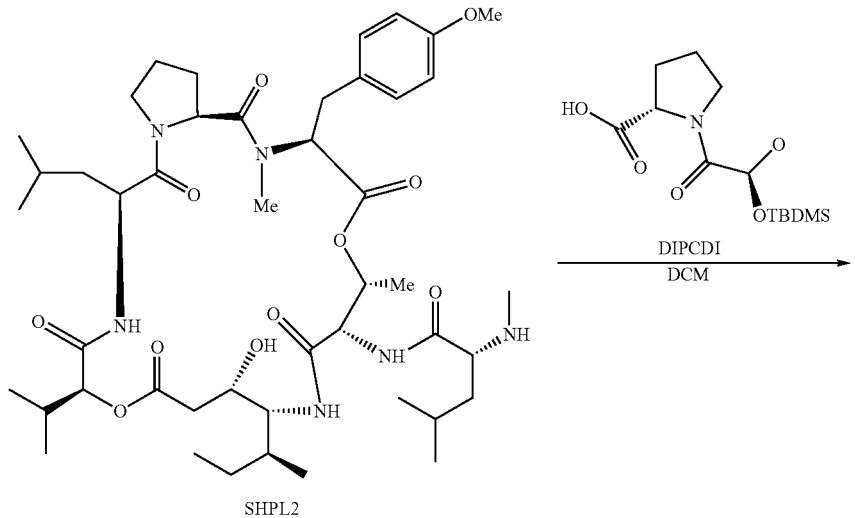

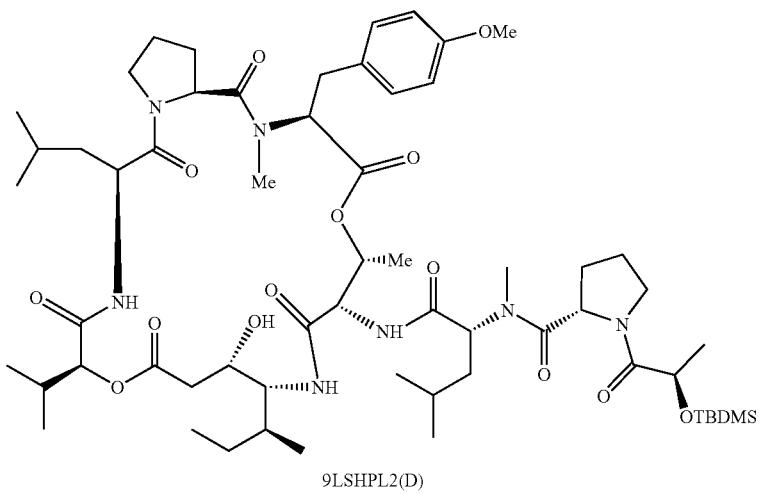

9LSHPL2(D)

Following the procedure described for the synthesis of SAPL1, starting from SHPL2 (10 mg, 11.2 μmol) and (D)-Lac(OTBDMS)-Pro-OH (17 mg, 56 μmol), the title compound (9 mg, 68%) was obtained as a white solid after purification by HPLC (HyperPrep PEP 100 C18, gradient ACN/H$_2$O 85:15-100:0 in 10 min (flow: 7 ml/min, 250×21 mm, at 270 nm, t$_R$=30.4 min).

$^1$H NMR (300 MHz, CDCl$_3$) δ 0.03 (m, 3H), 0.06 (m, 3H) 0.87 (s, 9H), 0.82-1.10 (m, 24H), 1.11-1.72 (m, 18H), 1.75-2.30 (m, 6H), 2.41 (m, 1H), 2.56 (s, 3H), 3.00-3.40 (m, 5H), 3.06 (s, 3H), 3.56 (m, 1H), 3.65 (m, 2H), 3.78 (s, 3H), 3.90 (m, 1H), 4.01 (m, 1H), 4.17 (m, 1H), 4.25 (m, 1H), 4.39 (m, 1H), 4.61 (m, 2H), 4.86 (m, 1H), 5.00 (d, J=4.8, 1H), 5.25 (m, 2H), 6.84 (d, J=8.3, 2H), 7.07 (d, J=8.3, 2H), 7.29 (d, J=9.7, 1H), 7.74 (d, J=5.3, 1H), 7.87 (d, J=9.7, 1H). $^{13}$C NMR (75 MHz, CDCl$_3$) δ −4.87, −4.84, 12.04, 14.38, 16.89, 17.94, 19.14, 20.24, 21.08, 21.60, 23.85, 24.12, 24.90, 25.06, 25.13, 26.01, 26.53, 27.53, 27.83, 28.20, 30.33, 31.51, 33.76, 34.20, 36.16, 38.99, 39.35, 39.82, 46.87, 47.02, 48.46, 54.79, 55.42, 55.48, 57.08, 57.18, 58.28, 66.39, 69.11, 71.43, 72.61, 79.18, 114.25, 130.29, 130.59, 158.79, 168.45, 169.86, 170.77, 170.81, 170.97, 171.20, 172.53, 173.67, 174.84. ESI-MS Calcd for C$_{60}$H$_{99}$N$_7$O$_{14}$Si: 1169.7. Found m/z: 1170.8 (M+H)$^+$.

EXAMPLE 80

Synthesis of [Val]³-[L-Lac(OTBDMS)]⁹-aplidine [9LSVPL2(L)]

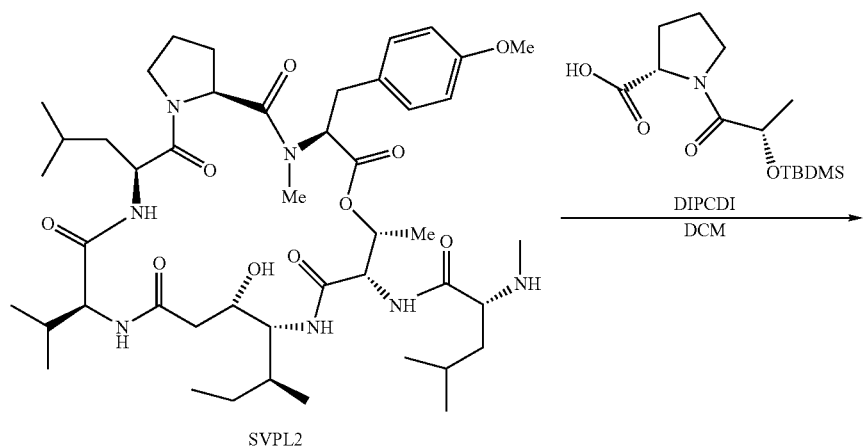

SVPL2

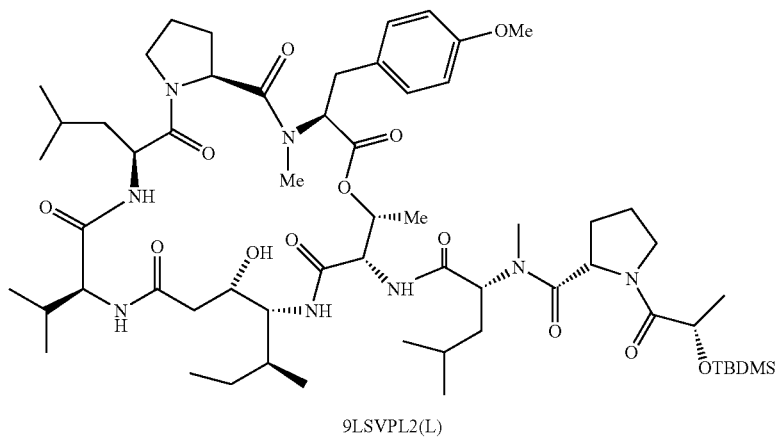

9LSVPL2(L)

Following the procedure described for the synthesis of SAPL1, starting from SVPL2 (10 mg, 11.2 µmol) and (L)-Lac(OTBDMS)-Pro-OH (17 mg, 56 µmol), the title compound (9 mg, 68%) was obtained as a white solid after purification by HPLC (HyperPrep PEP 100 C18, isocratic ACN/H₂O 85:15 (flow: 7 ml/min, 250×21 mm, at 270 nm, $t_R$=17.8 min).

¹H NMR (300 MHz, CDCl₃): δ 0.14 (s, 6H), 0.71-1.06 (m, 27H), 1.10-1.42 (m, 10H), 1.43-1.84 (m, 8H), 1.85-2.40 (m, 11H), 2.57 (s, 3H), 2.80 (d, J=14.7, 1H), 3.15 (s, 3H), 3.15-3.23 (m, 1H), 3.33-3.42 (m, 2H), 3.54 (dd, $J_1$=4.2, $J_2$=10.8, 1H), 3.58-3.69 (m, 3H), 3.79 (s, 3H), 3.88-3.90 (m, 1H), 4.05-4.12 (bt, 1H), 4.32 (bs, 1H), 4.43-4.68 (m, 4H), 4.77 (t, J=10.5, 1H), 5.31-5.35 (m, 2H), 6.83 (d, J=8.4, 2H), 7.08 (d, J=8.7, 2H), 7.39 (d, J=9.9, 1H), 7.45 (d, J=9.0, 1H), 7.60 (d, J=10.5, 1H), 7.83 (d, J=4.5, 1H). ¹³C NMR (75 MHz, CDCl₃) δ −4.67, −4.49, 11.84, 14.13, 16.67, 18.19, 18.41, 19.68, 20.48, 21.15, 21.40, 23.61, 23.92, 24.72, 24.80, 25.06, 25.88, 26.24, 27.17, 28.04, 28.13, 29.78, 31.57, 33.33, 33.81, 35.99, 38.84, 41.56, 41.95, 46.83, 47.52, 48.68, 54.09, 54.64, 55.26, 56.63, 57.13, 58.36, 59.12, 66.20, 70.10, 70.57, 71.27, 77.20, 114.01, 130.13, 130.36, 158.55, 168.09, 169.76, 170.07, 170.48, 170.77, 172.21, 172.33, 173.58, 175.45. ESI-MS Cald. for $C_{59}H_{40}N_8O_{14}$: 1168.72. Found (m/z): 1169.8 (M+H)⁺.

EXAMPLE 81

Synthesis of [Hiv]³-[L-Lac]⁹-aplidine [9LSHPL1(L)]: Tamandarine A

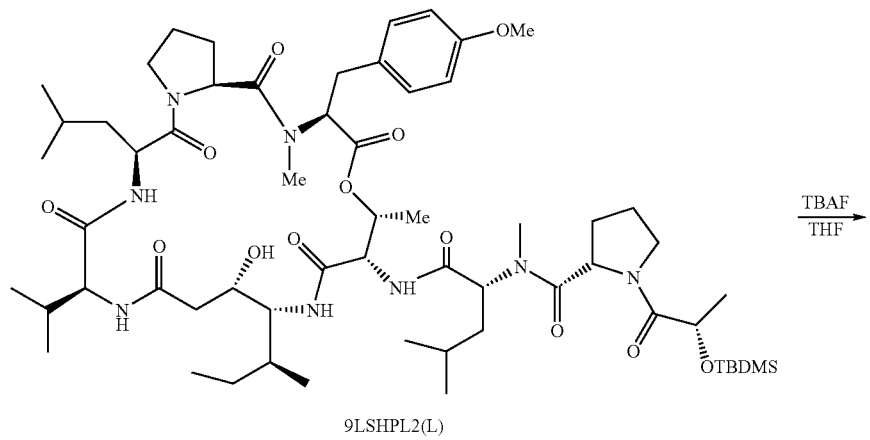

9LSHPL2(L)

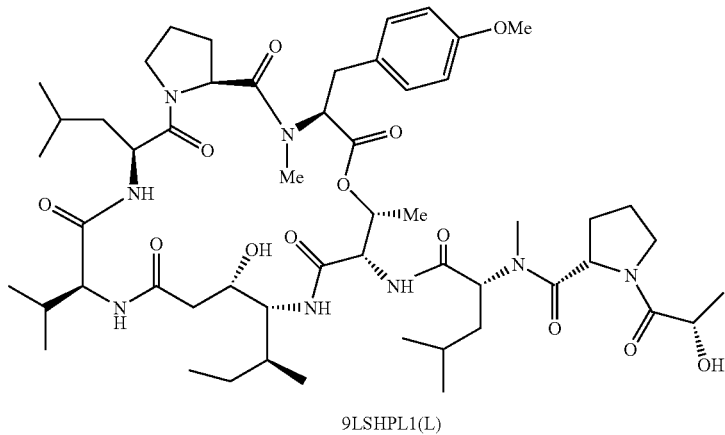

9LSHPL1(L)

To a solution of 9LSHPL2(L) (16 mg, 14 μmol) in THF (500 μml, anh.) at 0° C. under Ar, was added TBAF (50 μl, 1M in THF). After 1 h at 22° C. the mixture was concentrated in vacuo and the crude was purified by flash LC (silica gel, grad DCM:MeOH 1% to 5%) to yield the title compound 813 mg, 88%) as a white solid.

Experimental data were published: Fenical, W. et al., *J. Org. Chem.* 2000, 65, 782-792.

$^1$H NMR (300 MHz, CDCl$_3$): δ 0.82-0.96 (m, 18H), 1.02 (d, J=3.4, 3H), 1.04 (d, J=3.4, 3H), 1.14-2.28 (m, 14H), 1.24 (s, 3H), 1.34 (d, J=6.8, 3H), 1.43 (d, J=6.8, 3H), 2.44 (dd, J$_1$=7.8, J$_2$=17.1, 1H), 2.58 (s, 3H), 3.00 (bs, 1H), 3.10 (s, 3H), 3.14-3.31 (m, 2H), 3.37-3.43 (m, 2H), 3.56-3.72 (m, 5H), 3.79 (s, 3H), 3.90 (t, J=7.8, 1H), 4.02 (dt, J$_1$=3.4, J$_2$=9.8, 1H), 4.25 (d, J=3.9, 1H), 4.30 (t, J=6.8, 1H), 4.37 (dd, J$_1$=7.3, J$_2$=8.3, 1H), 4.65 (m, 1H), 4.71 (t, J=7.4, 1H), 4.87 (t, J=11.2, 1H), 5.03 (d, J=4.9, 1H), 5.29 (dd, J$_1$=3.4, J$_2$=11.7, 1H), 5.42 (m, 1H), 6.83 (d, J=8.3, 2H), 7.07 (d, J=8.3, 2H), 7.34 (d, J=9.8, 1H), 7.48 (d, J=5.4, 1H), 7.76 (d, J=9.8, 1H). ESI-MS Calcd for C$_{54}$H$_{85}$N$_7$O$_{14}$: 1055.6. Found; 1056.7 (M+H)$^+$.

EXAMPLE 82

Synthesis of [Hiv]³-[D-Lac]⁹-aplidine [9LSHPL1(D)]

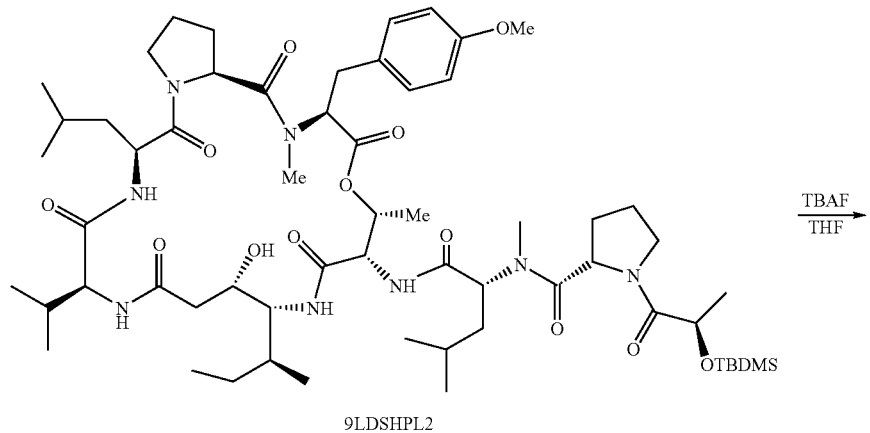

9LDSHPL2

TBAF / THF →

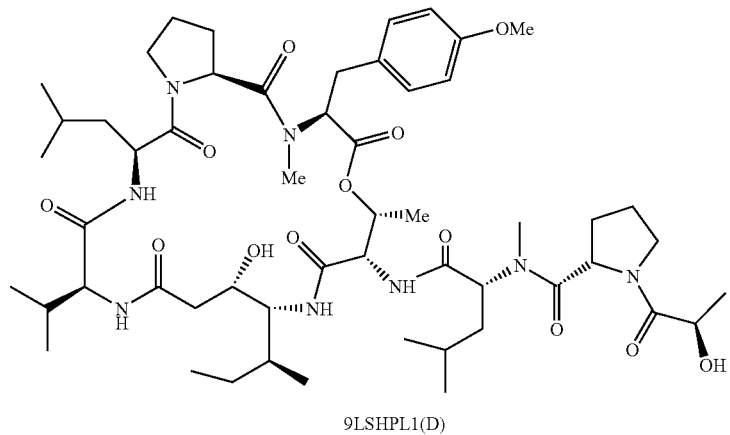

9LSHPL1(D)

Following the procedure described for the synthesis of 9LSHPL1(L), starting from 9LSHPL2(D) (20 mg, 17 μmol) and TBAF (50 μl, 1M in THF), afforded the litle compound (14 mg, 78%) as a white solid, after purification by flash LC (silica gel, grad DCM:MeOH 1% to 5%).

$^1$H NMR (300 MHz, CDCl$_3$): δ 0.78-1.08 (m, 18H), 1.02 (d, J=3.9, 3H), 1.04 (d, J=3.4, 3H), 1.10-2.36 (m, 14H), 1.20 (d, J=6.3, 3H), 1.34 (d, J=6.3, 3H), 1.37 (d, J=6.3, 3H), 2.38-2.50 (dd, J$_1$=7.8, J$_2$=17.5, 1H), 2.56 (s, 3H), 3.10 (s, 3H), 3.13-3.20 (m, 1H), 3.22-3.28 (m, 1H), 3.37-3.42 (dd, J$_1$=3.9, J$_2$4.3, 1H), 4.61-4.68 (m, 3H), 3.69-3.76 (m, 3H), 3.77 (m, 1H), 3.78 (s, 3H), 3.90 (t, J=7.8, 1H), 3.97-4.07 (m, 1H), 4.26 (m, 1H), 4.41 (q, J=6.3, 1H), 4.63 (m, 1H), 4.71 (m, 1H), 4.86 (t, J=10.7, 1H), 5.01 (d, J=4.8, 1H), 5.21-5.37 (m, 2H), 6.83 (d, J=8.3, 2H), 7.06 (d, J=8.3, 2H), 7.41 (m,

2H), 7.77 (d, J=9.2, 1H). ESI-MS Calcd for $C_{54}H_{85}N_7O_{14}$: 1055.62. Found. 1056.6 $(M+H)^+$.

EXAMPLE 83
Synthesis of $[Val]^3$-$[L-Lac]^9$-aplidine [9LSVPL1(L)]

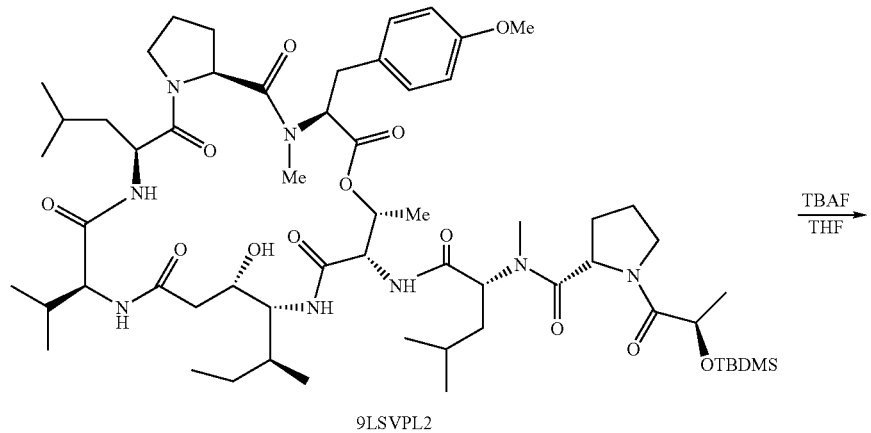

9LSVPL2

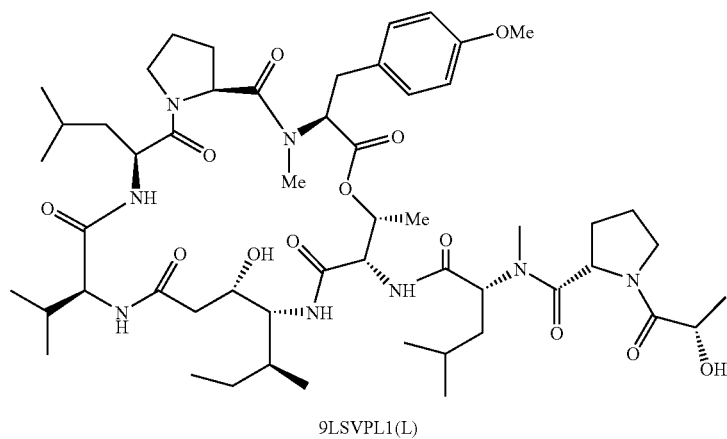

9LSVPL1(L)

Following the method described for the synthesis of 9LSHPL1, starting from 9LSVPL2 (5 mg, 4.3 μmol), afforded the little compound (4 mg, 88%) as a white solid, after purification by flash LC (silica gel, grad DCM:MeOH 1% to 5%).

$^1$H NMR (300 MHz, CDCl$_3$): δ 0.82-1.02 (m, 18H), 1.16-1.42 (m, 4H), 1.32 (d, J=3.0, 3H), 1.40 (d, J=6.6, 3H), 1.56-1.83 (m, 8H), 1.95-2.34 (m, 11H), 2.58 (s, 3H), 2.84 (d, J=14.7, 1H), 3.15 (s, 3H), 3.15-3.23 (m, 1H), 3.36-3.42 (m, 1H), 3.55 (dd, J$_1$=9.0, J$_2$=10.5, 2H), 3.64-3.66 (m, 3H), 3.95 (dd, J$_1$=3.3, J$_2$=9.9, 1H), 4.08 (td, J$_1$=7.5, J$_2$=17.1, 1H), 4.32 (bs, 1H), 4.41 (dd, J$_1$=6.6, J$_2$=9.9, 1H), 4.48 (dd, J$_1$=5.1, J$_2$=10.5, 1H), 4.61 (dd, J$_1$=6.0, J$_2$=6.6, 1H), 4.69-4.80 (m, 2H), 5.29-5.35 (m, 1H), 5.57 (m, 1H), 6.84 (d, J=8.1, 2H), 7.08 (d, J=8.7, 2H), 7.37 (d, J=3.9, 1H), 7.40 (d, J=5.4, 1H), 7.60 (d, J=10.8, 1H), 7.72 (d, J=3.9, 1H). ESI-MS Calcd for $C_{54}H_{86}N_8O_{13}$: 1054.63. Found: 1055.8 $(M+H)^+$.

181
Synthesis of the Spiro[4,4]nonane Unit

EXAMPLE 84

Synthesis of N-[(2R)-2-ally-N-(tert-butoxycarbonyl)prolyl]D-leucine (9)

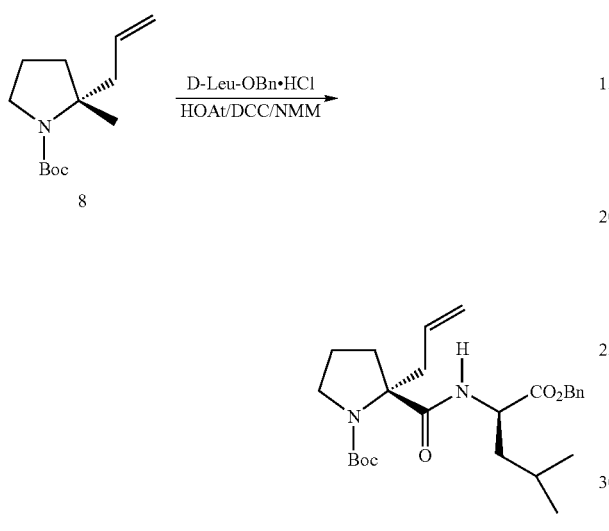

182

EXAMPLE 85

Synthesis of (5R,8RS)-1-(tert-butoxycarbonyl)-7-[(1R)-1-benzyloxycarbonyl-3-methylbutyl]-8-hydroxy-6-oxo-1,7-diazaspiro[4,4]nonane (10)

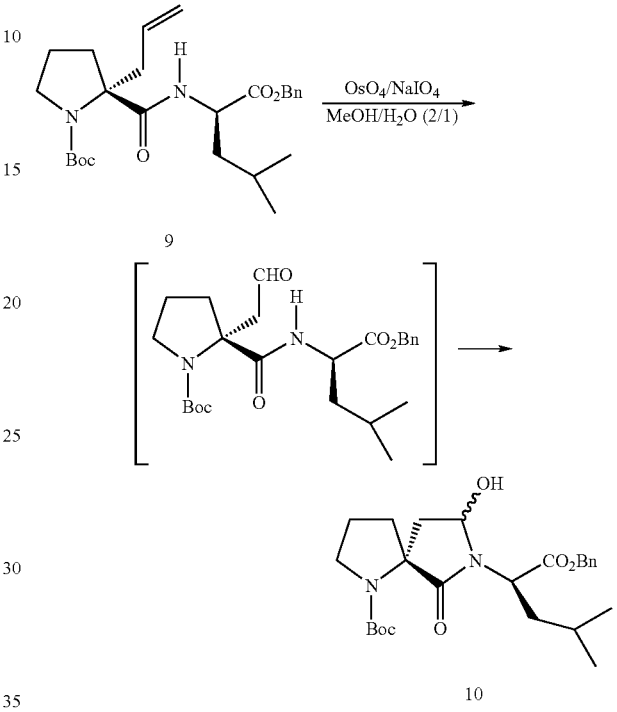

To a cooled (0° C.) solution of 8 (1.53 g, 6 mmol) in anh DCM (33 ml) under argon, was added: HOAt (980 mg, 7.2 mmol), D-Leu-OBn.pTsOH (2.65 g, 12 mmol), NMM (1.21 g, 12 mmol) and DCC (1.48 g, 7.2 mmol). The mixture was stirred 2 h at 0° C. and then 12 h at r.t.; additional D-Leu-OBn.pTsOH (0.66 g, 3 mmol) and NMM (0.30 g, 3 mmol) were added, and the mixture was stirred 3 h more. The mixture was filtered and the solvent was concentrated in vacuo. The residue was dissolved in EtOAc (30 ml) and washed successively with $NaHCO_3$ (2×25 ml, sat), citric acid (2×25 ml, 10%) and brine (25 ml). The organic solution was dried ($Na_2SO_4$) and concentrated under reduced pressure. The residue was purified by LC-silica (hex-EtOAc, 6:1) to afford 9 (2.63 g, 96%) as a colourless oil. $[\alpha]_D^{20}$ 12.4° (c 1, MeOH). HPLC (column Bondapack $C_{18}$ (Waters), 10 m, 3.9×300 mm, flow: 1 ml/min, at 214 nm, eluent ACN/0.05% TFA (40:60)] $t_R$=9.08 min].

$^1$H-NMR (300 MHz, DMSO-$d_6$) δ 0.86 (m, 6H), 1.37 (s, 9H), 1.55-1.72 (m, 5H), 2.00 (m, 2H), 2.64 (m, 1H), 2.86 (m, 1H), 3.15 (m, 1H), 3.55 (m, 1H), 4.41 (m, 1H), 5.05-5.11 (m, 4H), 5.63-5.72 (m, 1H), 7.28-7.35 (m, 5H). $^{13}$C-MNR (75 MHz, acetone-$d_6$) δ 21.6, 22.8, 24.6, 28.3, 34.7, 38.2, 41.3, 49.38, 51.0, 66.9, 69.7, 80.1, 119.1, 128.3, 132.7, 153.9, 172.8.

Ref. Synthesis of 8: a) Seebach, D. et al. *J. Am. Chem. Soc* 1983, 105, 5390-5398. b) Genin, M. J. et al. *J. Org. Chem.* 1993, 58, 2334-2337.

To a solution of 9 (1.56 g, 3.42 mmol) in MeOH/$H_2O$ (2:1, 108 ml) under argon, a solution of $OsO_4$ (2.5% w/w, 2.9 ml) in tert-butanol was added. Stirring was continued for 10 min and $NaIO_4$ (2.195 g, 10.3 mmol) was added. After 24 h of stirring the reaction mixture diluted with $H_2O$ (100 m) and extracted with EtOAc (3×50 ml). The combined organic extracts were washed with brine (50 ml), dried ($Na_2SO_4$) and concentrated under reduced pressure. The residue was purified by LC-silica (hex-EtOAc, gradient 80:20 to 0:100%) to afford diastereomers 10a and 10b (combined: 1.17 g, 76%) as a white solid.

10a: HPLC [Column Novapack $C_{18}$ (Waters), 3.9×150 mm, Φ=1 ml/min, λ=214 nm, eluent: $CH_3CN$/0.05% TFA, (40/60)] $t_R$=14.45 min. m.p.: 140-141° C. $[\alpha]_D^{20}$ −4° (c 1, MeOH). $^1$H-NMR (300 MHz, acetone-$d_6$) δ0.90 (m, 6H), 1.29 (s, 9H), 1.64-2.30 (m, 9H); 2.68 (dd, 1H, $J_1$=6, $J_2$=13, 1H), 3.37 (m, 2H), 4.51 (dd, 1H), 5.13 (d, J=15, 2H), 5.79 (t, J=5, 2H), 7.40 (m, 5H). $^{13}$C-MNR (75 MHz, acetone-$d_6$) δ 21.8, 23.8, 24.1, 24.9, 28.5, 39.6, 40.8, 41.5, 48.5, 66.8, 79.4, 79.8, 81.2, 129.1, 129.3, 128.6, 171.7, 172.0. ESI-MS: Calcd for $C_{25}H_{36}N_2O_6$: 460.26. Found m/z; 483.4 (M+Na)$^+$.

10b: HPLC [Column Novapack $C_{18}$ (Waters), 3.9×150 mm, Φ=1 ml/min, λ=214 nm, eluent: $CH_3CN$/0.05% TFA, (40/60)] $t_R$=18.75 min. M.p.: 134-135° C. $[\alpha]_D^{20}$+26 (c 1.2, MeOH). $^1$H-NMR (300 MHz, $CDCl_3$) δ 0.90 (6H, m), 1.40 (9H, s), 1.50-2.60 (9H, m), 3.40 (2H, m), 4.20-5.40 (5H, m), 7.40 (5H, m). $^{13}$C-MNR (75 MHz, acetone-$d_6$) δ 21.3, 23.2, 24.1, 24.9, 28.3, 38.9, 40.2, 42.5, 47.9, 53.2, 66.8, 77.5, 79.4, 80.6, 129.1, 171.2, 174.1. ESI-MS Calcd for $C_{25}H_{36}N_2O_6$: 460.26. Found m/z: 483.5 (M+Na)$^+$.

EXAMPLE 86

Synthesis of (5R)-7-[(1R)-1-benzyloxycarbonyl-3-methylbutyl]-6-oxo-1,7-diazaspiro[4.4]nonane as trifluoracetate salt (11)

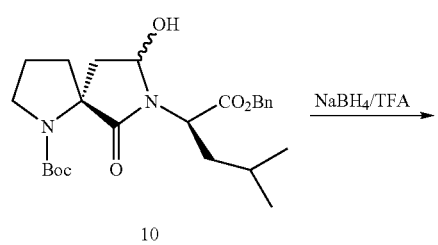

10

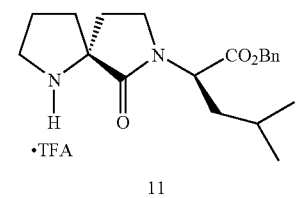

11 ·TFA

To a solution of 10 (430 mg, 0.93 mmol) in TFA (10 ml), NaBH$_4$ (106 mg, 2.8 mmol) was added. The mixture was stirred for 2 h and then, the reaction was concentrated under reduced pressure. The residue was partitioned between H$_2$O (5 ml) and DCM (20 ml). The organic phase was dried (Na$_2$SO$_4$) and concentrated in vacuo to afford 11 as an orange oil (318 mg, quant.). $[\alpha]^{20}_D$ +15 (c 1, MeOH).

$^1$H-NMR (300 MHz, acetone-d$_6$) 0.91 (m, 6H), 1.50 (m, 1H), 1.66-1.94 (m, 2H), 2.11-2.72 (m, 6H), 3.48-3.72 (m, 4H), 4.74 (dd, J$_1$=6, J$_2$=15, 1H), 5.18 (s, 2H), 7.37 (m, 5H). $^{13}$C-MNR (75 MHz, acetone-d$_6$) δ 21.2, 23.2, 23.9, 25.5, 30.2, 34.6, 38.0, 42.2, 46.6, 53.9, 67.6, 69.6, 129.3, 161.1, 161.6, 170.9, 172.6. ESI-MS Calcd for C$_{20}$H$_{28}$N$_2$O$_3$: 344.21. Found m/z; 345.3 (M+H)$^+$.

EXAMPLE 87

Synthesis of (5R)-1-(tert-butoxycarbonyl)-7-[(1R)-1-carboxy-3-methylbutyl]-6-oxo-1,7-diazaspiro[4.4]nonane (12)

To a solution of 11 (150 mg, 0.44 mmol) in ACN (5 ml), tetramethylammonium hydroxyde pentahydrate (158 mg, 0.87 mmol) and Boc$_2$O (144 mg, 0.66 mmol) were added while stirring. After 6 h, additional TMAH. 5 H$_2$O (158 mg) and Boc$_2$O (192 mg) were added. The reaction was stirred for 2d and then, it was partitioned between H$_2$O (10 ml) and DCM (25 ml). The aqueous phase was liophilyzed and purified by LC-silica (DCM-MeOH, gradient 92:8 to 60:40) to yield 12 (100 mg, 64%) as a white solid.

EXAMPLE 88

Synthesis of (5R)-1-(isobutyryl)-7-[(1R)-1-benzyloxycarbonyl-3-methylbutyl]-6-oxo-1,7-diazaspiro[4.4]nonane (13)

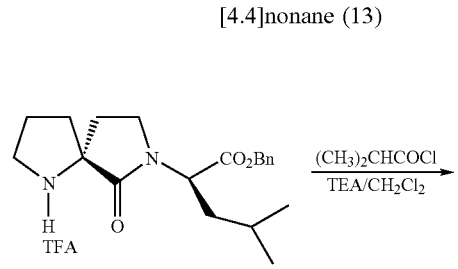

To a solution of 11 (169 mg, 0.49 mmol) in anh DCM (10 ml) at 0° C. under argon, were added TEA (199 mg, 1.96 mmol), DMAP (6 mg, 0.049 mmol) and dropwise isobutyl chloride (104 mg, 0.98 mmol). The reaction mixture was allowed to warm to room temperature and stirred for 24 h. The crude was partitioned between H$_2$O (10 ml) and DCM (10 ml). The organic phase was washed with brine (10 ml), dried (NaSO$_4$) and concentrated in vacuo. Pure compound 13 (150 mg, 74%) as a white solid, was obtained after LC-silica (hex-EtOAc, gradient 60:40 to 0:100).

HPLC [Column Novapack C$_{18}$ (Waters), 3.9×150 mm, Φ=1 ml/min, λ=214 nm, eluent: CH$_3$CN/0.05% TFA, (50/50)] t$_R$=4.50 min. M.p.: 87° C. [□□$^{20}_D$ +9.6 (c 1.4, MeOH). $^1$H-NMR (300 MHz, CDCl$_3$) δ 0.90 (2d, J=7, 6H), 1.09-1.12 (2d, 6H), 1.37 (septuplet, J=6, 1H), 1.61-2.10 (m, 7H), 2.64 (m, 2H), 3.14 (dd, J$_1$=9, J$_2$=17, 1H), 3.64 (m, 3H), 4.85 (dd, J$_1$=5, J$_2$=10, 1H), 5.14 (d, J=6, 2H), 7.32 (m, 5H). $^{13}$C-NMR (300 MHz, CDCl$_3$) δ 18.6, 18.7, 21.2, 23.1, 24.0, 24.8, 29.5, 32.5, 35.7, 37.6, 40.5, 47.8, 52.7, 66.7, 76.3, 170.8, 174.3, 174.9. ESI-MS Calcd for C$_{24}$H$_{34}$N$_2$O$_4$: 414.25. Found m/z: 415.4 (M+H)$^+$.

EXAMPLE 89

Synthesis of (5R)-1-(pyruvyl)-7-[(1R)-1-benzyloxy-carbonyl-3-methylbutyl]-6-oxo-1,7-diazaspiro[4.4]nonane (14)

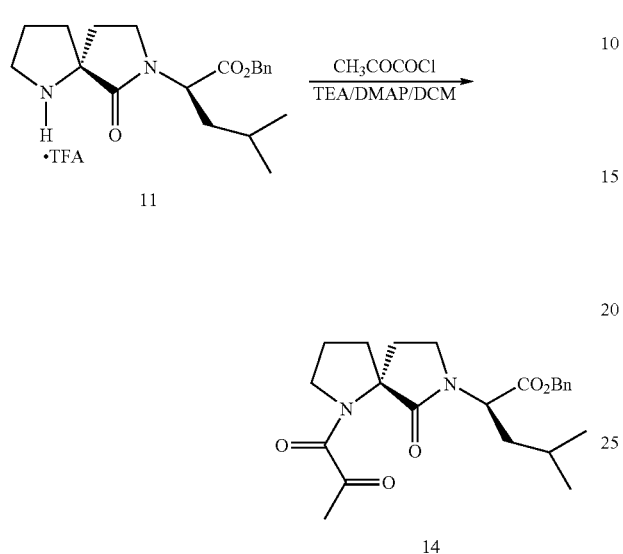

Pyruvil chloride was prepared according to the method described in the literature, Pansare, S. V.; Gnana R. R. "Asymmetric Allylation and reduction on an Ephedrine-Derived Template: Stereoselective Synthesis of α-Hydroxy Acids and Derivatives" J. Org. Chem. 1998, 63, 4120-4124, α,α-dichloromethyl methyl ether (188 mg, 1.57 mmol) was added to pyruvic acid (115 mg, 1.31 mmol). The reaction mixture was stirred for 20 min and the resulting solution was warmed to 50-55° C. and then, stirred for further 30 ml. The reaction mixture was allowed to cool to room temperature and DCM (3 ml) was added.

To a solution of 11 (150 mg, 0.33 mmol) in anh DCM (4 ml) at 0° C. under argon, were added TEA (200 mg, 1.98 mmol) and DMAP (4 mg, 0.033 mmol) to the freshly solution of pyruvil chloride at 0° C. The reaction mixture was allowed to warm to room temperature and stirred for 6 h. The crude was washed successively with citric acid (5 ml, 10%), aq. NaHCO$_3$ sat. (5 ml) and brine (5 ml). The organic phase was dried (Na$_2$SO$_4$) and concentrated. Pure compound 14 (77 mg, 56%) as an oil, was obtained after LC-silica (hex-EtOAc, 1:3).

HPLC [Column Novapack C$_{18}$ (Waters), 3.9×150 mm, Φ=1 ml/min, λ=214 nm, eluent: ACN/0.05% TFA, (50/50)) t$_R$=5.87 and 6.72 min. $^1$H-MNR (200 MHz, CDCl$_3$) δ 0.92 and 0.95 (2d, J=6, 6H); 1.42 (m, 1H); 1.61-2.39 (m, 7H); 2.44 (s, 3H), 2.77 (m, 1H), 3.22 (m, 1H), 3.56-3.78 (m, 2H), 3.92 (m, 1H), 4.67 and 4.85 (dd, J$_1$=6, J$_2$=10, 1H), 5.21 (s, 2H), 7.34 (m, 5H). $^{13}$C-MNR (75 MHz, CDCl$_3$) δ 21.2, 23.0, 24.4, 24.8, 26.4, 29.3, 35.6, 37.3, 40.7, 48.9, 53.0, 66.8, 68.6, 135.0, 166.0, 170.8, 173.0, 198.0. ESI-MS Calcd for C$_{23}$H$_{30}$N$_2$O$_5$: 414.22. Found m/z: 415.4 (M+H)$^+$.

EXAMPLE 90

Synthesis of (5R)-1-(2-methylacryloyl)-7-[(1R)-1-benzyloxycarbonyl-3-methylbutyl]-6-oxo-1,7-diazaspiro[4.4]nonane (15)

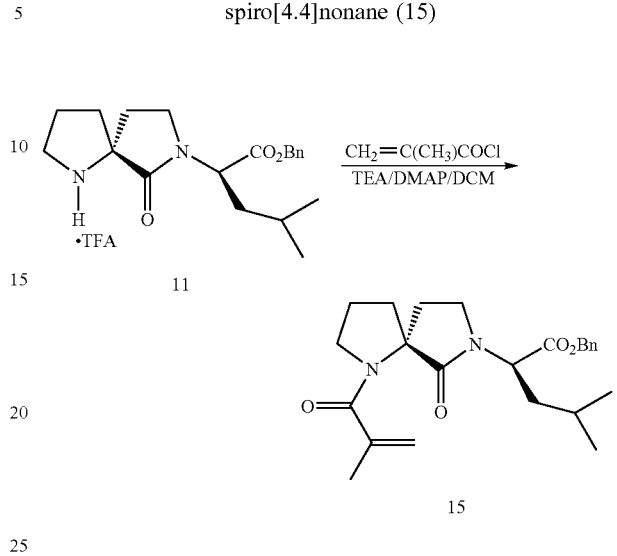

Following the procedure described for the synthesis of 13, starting from 11 (200 mg, 0.43 mmol) and methylacryloyl chloride (89 mg, 0.86 mmol), the title compound (70 mg, 50%) was obtained as a colourless oil, after purification by LC (silica ge, hex-EtOAc, 2:1). HPLC [Column Novapack C$_{18}$ (Waters), 3.9×150 mm, Φ=1 ml/min, λ=214 nm, eluent: ACN/0.05% TFA, (25/75)] Rt=6.38 min.

$^1$H-MNR (200 MHz, CDCl$_3$) δ 0.91 (t, J=6, 6H), 1.44 (m, 1H), 1.64-1.93 (m, 5H), 1.93 (s, 3H), 1.96-2.12 (m, 2H), 2.78 (m, 1H), 3.20 (m, 1H), 3.56-3.68 (m, 3H), 4.80 and 4.77 (2d, J=10, 1H), 5.16 (s, 2H), 5.19 (d, J=9, 2H), 7.32 (m, 5H), $^{13}$C-MNR (75 MHz, CDCl$_3$) δ 19.8, 21.4, 23.0, 24.2, 24.9, 29.9, 37.1, 37.7, 41.1, 50.2, 53.2, 66.6, 67.4, 116.9, 128.1, 128.3, 128.4, 135.0, 141.7, 170.7, 174.1. ESI-MS Calcd for C$_{24}$H$_{32}$N$_2$O$_4$: 412.24. Found: 413.3 (M+H)$^+$.

EXAMPLE 91

Synthesis of (5R)-1-(isobutiryl)-7-[(1R)-1-carboxy-3-methylbutyl]-6-oxo-1,7-diazaspiro[4.4]nonane (16)

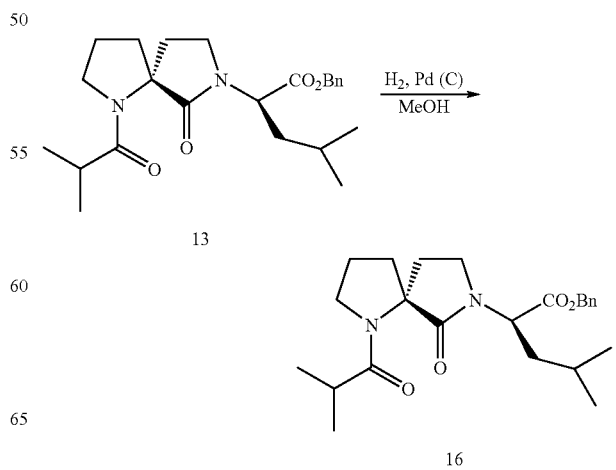

A degassed solution of 13 (134 mg, 0.32 mmol) in methanol containing 10% Pd/C (27 mg) was hydrogenated under 16 psi for 24 h. The mixture was filtered through a pad of celite and the filtered solution was concentrated under reduced pressure to afford 16 (100 mg, 95%) as a colourless oil. M.p. 68-69° C. $[\alpha]^{20}_D$ −2° (c 1.1, MeOH)

$^1$H-NMR [300 MHz, acetone-$d_6$] δ 0.87-0.91 (2d, J=7, 6H), 1.09-1.12 (2d, 6H), 1.46 (m, 1H), 1.70 (m, 2H), 1.90-2.10 (m, 5H), 2.49 (m, 1H), 2.70 (m, 1H), 3.30 (m, 1H), 3.49 (dt, $J_1$=8, $J_2$=10, 1H), 3.61-3.75 (m, 2H), 4.71 (dd, $J_1$=5, $J_2$=11, 1H). $^{13}$C-NMR (75 MHz, CDCl$_3$) δ 16.4, 16.6, 21.1, 23.0, 24.3, 25.0, 30.8, 32.6, 36.6, 36.9, 40.6, 48.0, 53.4, 67.5, 171.8, 174.2, 176.2. ESI-MS Calcd for $C_{17}H_{28}N_2O_4$: 324.20. Found: 323.3 (M−1)$^+$.

EXAMPLE 92

Synthesis of (5R)-1-(pyruvil)-7-[(1R)-1-carboxy-3-methybutyl]-6-oxo-1,7-diazaspiro[4.4]nonane (17)

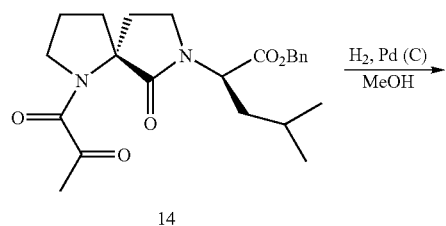

14

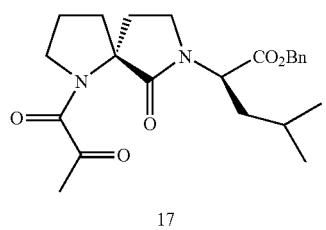

17

A degassed solution of 14 (79 mg, 0.26 mmol) in methanol (20 ml) containing Pd-C (10%, 22 mg) was hydrogenated under atmospheric pressure for 45 min. The filtered solution was concentrated under reduced pressure to afford 17 (79 mg, 95%) as a a white solid. HPLC [Column Novapack $C_{18}$ (Waters), 3.9×150 mm, Φ=1 ml/min, λ=214 nm, eluent: ACN/0.05% TFA, (20/80)] Rt=13.14 min.

$^1$H-MNR (200 MHz, CDCl$_3$) δ 0.93 (m, 6H), 1.43 (m, 1H), 1.71-2.22 (m, 7H), 2.34 (s, 3H), 2.41 (s, 3H), 2.74 (m, 1H), 3.31 (m, 1H), 3.74 (m, 2H), 3.92 (m, 1H), 4.80 (dd, $J_1$=6, $J_2$=10, 1H), 7.07 (bs, 1H). $^{13}$C-MNR (200 MHz, CDCl$_3$) δ 21.3, 23.2, 24.7, 25.1, 27.1, 29.9, 36.0, 37.0, 41.0, 49.3, 53.6, 69.1, 162.1, 172.7, 173.7, 197.5. ESI-MS Calcd for $C_{23}H_{30}N_2O_5$: 324.17. Found m/z 325.1 (M+H)$^+$.

EXAMPLE 93

Synthesis of (5R)-1-(2-methylacryloyl)-7-[(1R)-1-carboxy-3-methylbutyl]-6-oxo-1,7-diazaspiro[4.4]nonane (18)

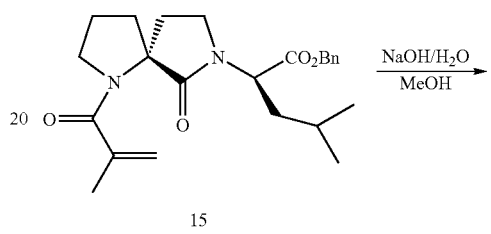

15

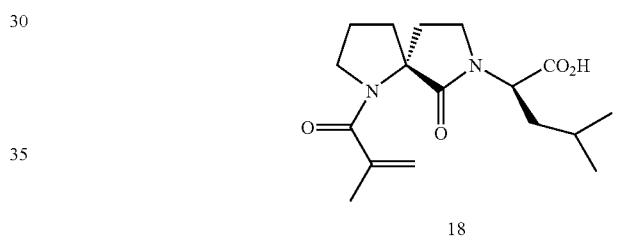

18

To a solution of 15 (65 mg, 0.16 mmol) in methanol (2.5 ml) were added aq. NAOH (1.6 ml, 1N) and H$_2$O (1.6 ml) and the mixture was stirred at room temperature for 1 h. The resulting mixture was concentrated at reduced pressure, and the residue was partitioned between H$_2$O (20 ml) and DCM (20 ml). The aqueous phase was acidified to pH=2 with aq HCl (10 ml, 0.1 N) and extracted with DCM (3×20 ml). The combined organic phases were washed with brine (25 ml), dried (Na$_2$SO$_4$) and concentrated at reduced pressure to afford 18 (44 mg, 85%) as a white solid. HPLC [Column Novapack $C_{18}$ (Waters), 3.9×150 mm, Φ=1 ml/min, λ=214 nm, eluent: ACN/0.05% TFA, (25/75)] Rt=6.38 min.

$^1$H-MNR (300 MHz, CDCl$_3$) δ 0.86 (d, J=5, 3H), 0.89 (d, J=5, 3H), 1.42 (m, 1H), 1.55-2.25 (m, 8H), 2.56 (m, 1H), 3.19-3.44 (m, 2H), 3.57-3.67 (m, 2H), 4.78 (d, J=11, 1H), 4.82 (d, J=11, 1H), 5.18 (d, J=6, 2H). $^{13}$C-MNR (75 MHz, CDCl$_3$) δ 19.5, 21.2, 23.1, 24.2, 25.1, 30.9, 36.5, 37.6, 40.9, 50.5, 53.7, 67.5, 117.5, 140.6, 170.8, 174.2. ESI-MS Calcd for $C_{17}H_{26}N_2O_4$: 322.19. Found: 323.2 (M+H)$^+$.

EXAMPLE 94

Synthesis of [(5R)-1-(tert-buthoxycarbonyl]-7-[(1R)-1-carboxy-3-methylbutyl]-6-oxo-1,7-diaza-spiro[4.4]nonane]$^{7-9}$-aplidine (9SBSAPL1)

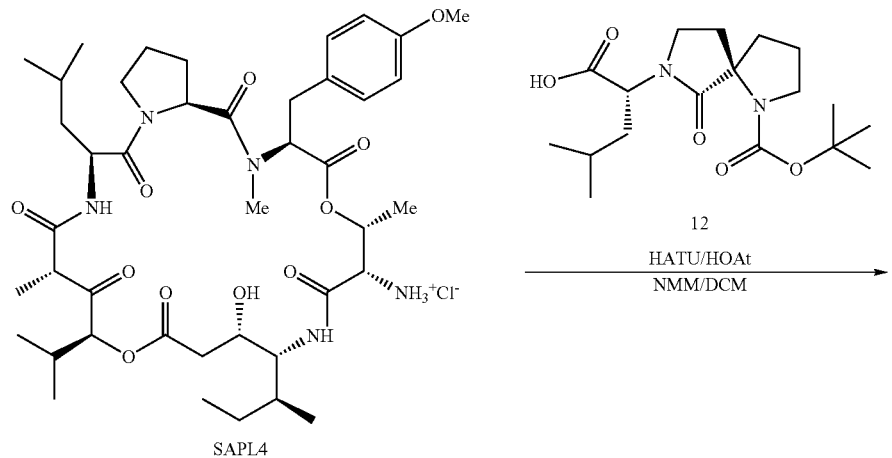

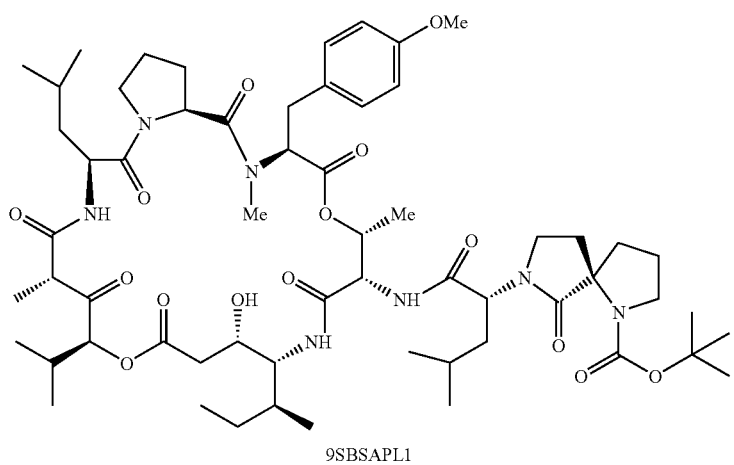

Following the procedure described for the synthesis of SAPL3, starting from SAPL4 (10 mg, 13 μmol), 12 (5 mg, 14 μmol), HATU (12.4 mg), HOAt (4.5 mg), NMM (3.3 μl), DCM (140 μl) and DMF (70 μl), the title compound (11 mg, 73%) was obtained as a white solid after purification by HPLC (HyperPrep PEP 100 C18, isocratic ACN/H$_2$O 85:15 (flow: 7 ml/min, 250×21 mm, at 270 nm, Rt=30 min).

$^1$H NMR (300 MHz, CDCl$_3$): δ 0.85-0.97 (m, 24H), 1.19-1.34 (m, 18H), 1.48 (s, 9H), 1.50-2.20 (m, 6H), 2.32-2.36 (m, 1H), 2.54 (s, 3H), 2.58-2.72 (m, 2H), 2.97-3.08 (m, 1H), 3.10-3.22 (m, 3H), 3.34 (dd, 1H, J=3.9, 13.8), 3.46-3.79 (m, 6H), 3.79 (s, 3H), 4.03-4.12 (m, 2H), 4.28 (dd, 1H, J=6.6, 13.2), 4.57-4.63 (m, 2H), 4.79-4.88 (m, 2H), 5.15 (d, 1H, J=3.3), 5.21-5.23 (m, 1H), 6.84 (d, 2H, J=8.4), 7.07 (d, 2H, J=8.7), 7.28 (d, 1H, J=10.8), 7.79 (d, 1H, J=6.6), 7.82 (d, 1H, J=9.9), $^{13}$C NMR (75 MHz, CDCl$_3$) δ 11.66, 15.21, 15.43, 16.79, 17.23, 18.69, 18.77, 21.24, 23.67, 23.95, 24.10, 24.90, 25.10, 25.38, 27.04, 28.23, 28.75, 29.93, 31.61, 34.50, 33.88, 34.16, 36.20, 36.57, 38.76, 39.09, 39.78, 41.29, 47.27, 47.76, 49.60, 49.96, 52.66, 55.50, 56.26, 57.38, 58.18, 66.74, 66.86, 68.34, 70.53, 80.75, 81.93, 114.33, 130.23, 130.54, 168.08, 169.83, 170.18, 170.80, 171.43, 172.55, 175.04, 205.04. ESI-MS Calcd for C$_{60}$H$_{93}$N$_7$O$_{15}$ 1151.7. Found m/z: 1152.4 (M+H)$^+$

EXAMPLE 95

Synthesis of [Hiv]³-[(5R)-1-(tert-buthoxycarbonyl)-7-[(1R)-1-carboxy-3-methylbutyl]-6-oxo-1,7-diaza-spiro[4.4]nonane]⁷⁻⁹-aplidine (9SBSHPL1)

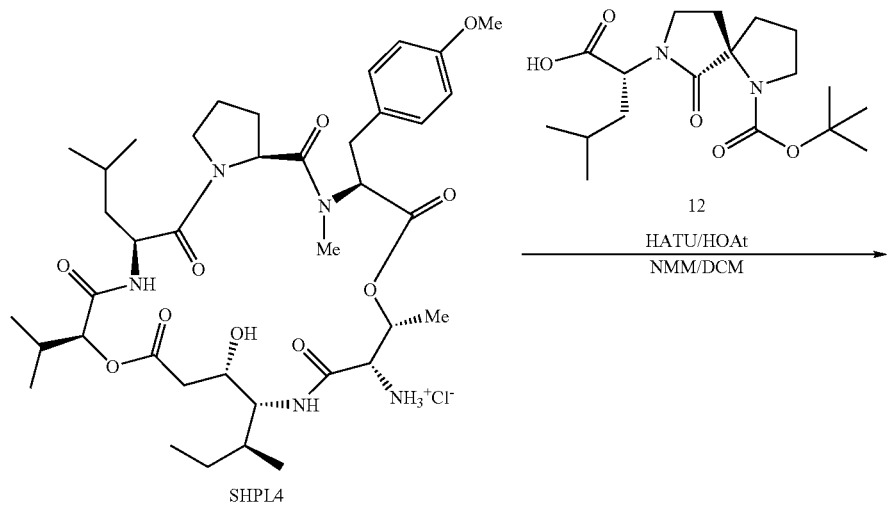

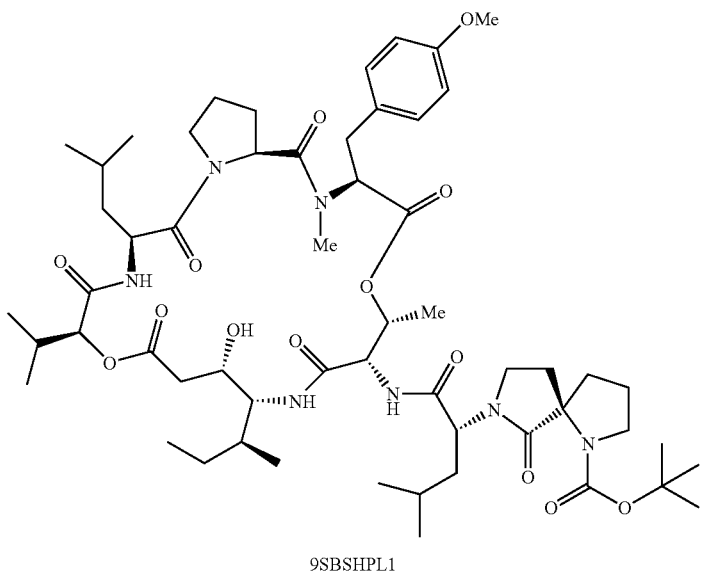

9SBSHPL1

Following the procedure described for the synthesis of SAP3, starting from SHPL4 (10 mg, 13 μmol), 12 (5 mg, 14 μmol), HATU (14 mg), HOAt (5 mg), NMM (6 μl), DCM (150 μl) and DMF (50 μl), the title compound (10 mg, 70%) was obtained as a white solid after purification by HPLC (HyperPrep PEP 100 C18, isocratic ACN/H₂O 85:15 (flow: 7 ml/min, 250×21 min, at 270 nm, Rt=28.1 min).

$^1$H NMR (300 MHz, CDCl$_3$) δ 0.80-1.07 (m, 24H), 1.08-1.67 (m, 12H), 1.48 (s, 9H), 1.68-2.30 (m, 10H), 2.41 (m, 1H), 2.55 (s, 3H), 2.68 (m, 1H), 2.94 (m, 1H), 3.07-3.40 (m, 4H), 3.42-3.72 (m, 6H), 3.78 (s, 3H), 3.90 (m, 1H), 4.01 (m, 1H), 4.29 (m, 1H) 4.63 (m, 1H), 4.77 (m, 1H), 4.87 (m, 1H), 5.02 (d, J=4.8, 1H), 5.25 (m, 1H), 6.84 (d, J=8.3, 2H), 7.07 (d, J=8.3, 2H), 7.31 (d, J=9.7, 1H), 7.50 (d, J=5.8, 1H), 7.85 (d, J=9.7, 1H). $^{13}$C NMR (75 MHz, CDCl$_3$) δ 12.07, 14.25, 17.12, 17.92, 19.15, 21.11, 21.18, 23.80, 24.00, 24.06, 24.86, 25.08, 25.15, 27.58, 28.21, 28.82, 30.33, 31.18, 33.78, 34.28, 35.77, 36.65, 39.07, 39.45, 39.86, 46.91, 48.14, 48.47, 52.62, 55.49, 57.13, 58.42, 66.36, 66.80, 69.14, 70.84, 79.19, 80.55, 114.27, 130.29, 130.59, 154.12, 158.81, 168.25, 169.84, 170.72, 170.80, 170.90, 171.25, 174.89. ESI-MS Calcd for C$_{57}$H$_{89}$N$_7$O$_{14}$ 1095.6. Found m/z: 1096.9 (M+H)⁺.

EXAMPLE 96

Synthesis of [(5R)-1-(isobutiryl)-7-[(1R)-1-carboxy-3-methylbutyl]-6-oxo-1,7-diazaspiro[4.4]nonane][7-9]-Aplidine (9SISAPL1)

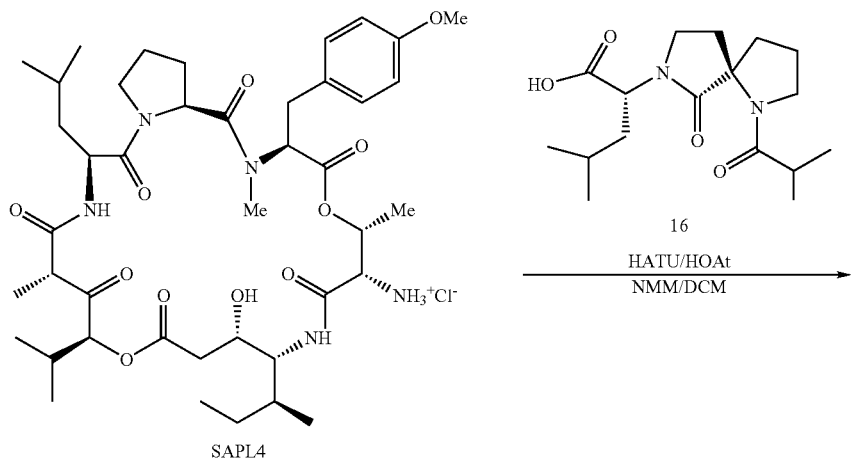

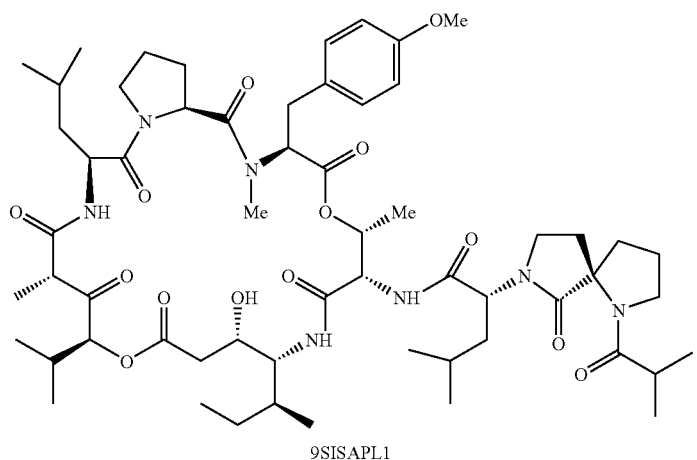

Following the procedure described for the synthesis of SAPL3, starting from SAPL4 (11 mg, 12.9 µmol), 16 (5 mg, 15.4 µmol), HATU (14 mg), HOAt (5 mg), NMM (3.6 µl), DCM (155 µl) and DMF (78 µl), the title compound (10 mg, 69%) was obtained as a white solid after purification by HPLC (HyperPrep PEP 100 C18, isocratic ACN/H$_2$O 85:15 (flow: 7 ml/min, 250×21 mm, at 270 nm, $t_R$=19 min).

$^1$H NMR (300 MHz, CDCl$_3$): δ 0.86-1.00 (m, 24H), 1.12 (d, J=6.9, 3H), 1.18 (d, J=6.6, 3H), 1.34 (t, J=6.6, 2H), 0.90-1.30 (m, 7H), 1.56-2.25 (m, 16H), 2.30-2.80 (m, 3H), 2.55 (s, 3H), 2.95-3.06 (m, 1H), 3.15-3.25 (m, 3H), 3.65 (dd, 1H) 3.52-3.79 (m, 6H), 3.79 (s, 3H), 3.98-4.15 (m, 1H), 4.28 (dd, J$_1$=6.6, J$_2$=10.3, 1H), 4.59 (m, 2H), 4.79-4.85 (m, 2H), 5.17 (d, J=3.6, 1H), 5.40-5.44 (m, 1H), 6.84 (d, J=8.4, 2H), 7.06 (d, J=8.7, 2H), 7.24 (d, J=11.1, 1H), 7.90 (d, J=9.3, 1H), 8.56 (d, J=5.1, 1H). $^{13}$C NMR (75 MHz, CDCl$_3$) δ: 11.50, 14.92, 15.22, 16.68, 16.95, 18.50, 18.59, 18.81, 20.94, 23.42, 23.80, 24.49, 24.68, 24.90, 25.11, 26.91, 27.98, 30.93, 31.30, 35.58, 33.88, 34.16, 35.85, 36.24, 38.64, 38.84, 39.71, 41.29, 47.01, 47.76, 49.42, 49.62, 52.66, 55.26, 55.73, 57.12, 58.21, 66.57, 67.40, 68.10, 70.79, 81.57, 114.07, 130.05, 130.31, 158.57, 168.12, 169.66, 170.08, 170.56, 171.13, 171.96, 172.37, 174.04, 175.41, 205.04. ESI-MS Calcd for $C_{59}H_{91}N_7O_{14}$:1121.66. Found: 1122.8 $(M+H)^+$.
EXAMPLE 97
Synthesis Of [Hiv]$^3$-[(5R)-1-(isobutyryl)-7-[(1R)-1-carboxy-3-methylbutyl]-6-oxo-1,7-diazaspiro[4.4]nonane]$^{7-9}$-aplidine (9SISHPL1)
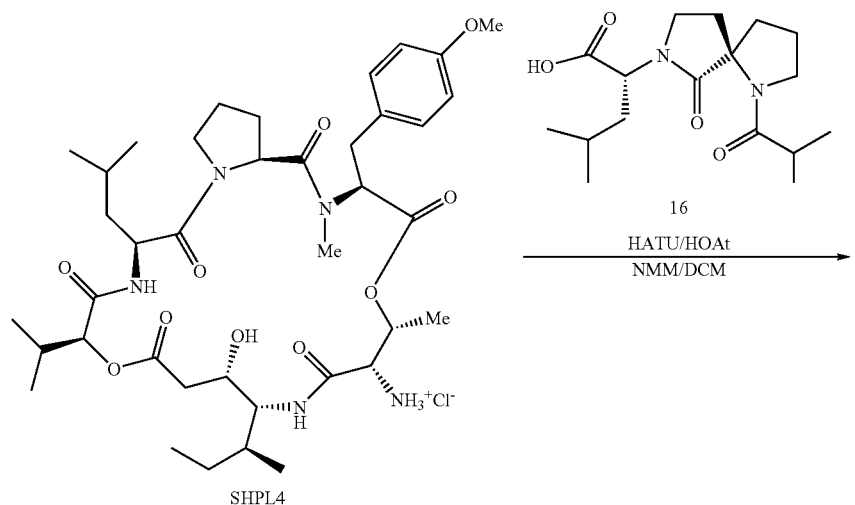
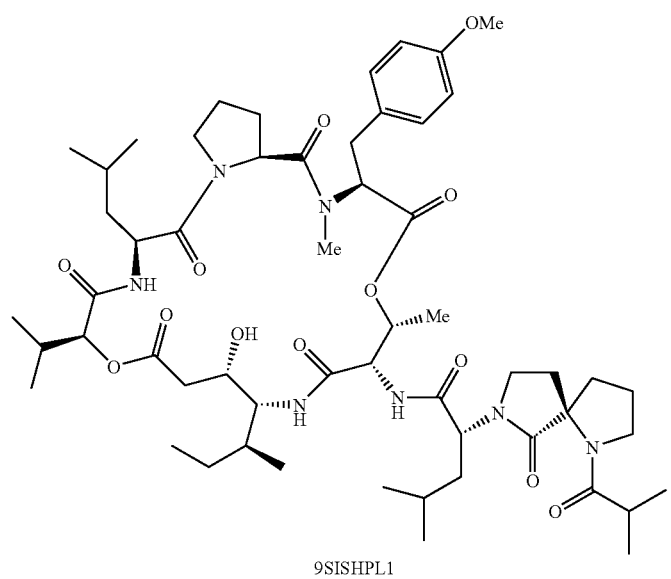

Following the procedure described for the synthesis of SAPL3, starting from SHPL4 (10 mg, 13 μmol), 16 (4.5 mg, 14 μmol), HLTU (14 mg), HOAt (5 mg), NMM (6 μl), DCM (150 μl) and DMF (50 μl), the title compound (10 mg, 72%) was obtained as a white solid after purification by HPLC (HyperPrep PEP 100 C18, isocratic ACN/H$_2$O 85:15 (flow: 7 ml/min, 250×21 mm, at 270 nm, $t_R$=16.9 min).

$^1$H NMR (300 MHz, CDCl$_3$) δ 0.80-1.07 (m, 24H), 1.08-1.47 (m, 12H), 1.48-2.30 (m, 16H), 2.36 (m, 2H), 2.56 (s, 3H), 2.65 (m, 1H), 2.96 (m, 1H), 3.18 (m, 2H), 3.36 (m, 2H), 3.65 (m, 6H), 3.78 (s, 3H), 3.91 (m, 1H), 4.02 (m, 1H), 4.25 (m, 1H) 4.63 (m, 1H), 4.72 (m, 2H), 4.87 (m, 1H), 5.02 (d, J=4.8, 1H), 5.45 (m, 1H), 6.84 (d, J=8.7, 2H), 7.07 (d, J=8.7, 2H), 7.27 (d, J=4.8, 1H), 7.88 (d, J=9.7, 1H), 8.32 (d, J=4.8, 1H). ESI-MS Calcd for C$_{56}$H$_{87}$N$_7$O$_{13}$ 1065.6. Found m/z: 1066.7 (M+H)$^+$.

EXAMPLE 98

Synthesis of [(5R)-1-(pyruvyl)-7-[(1R)-1-carboxy-3-methylbutyl]-6-oxo-1,7-diazaspiro[4.4]nonane]$^{7-9}$-aplidine (9SPSAPL1)

Following the procedure described for the synthesis of SAPL3, starting from SAPL4 (10 mg, 11.7 μmol), 17 (5 mg, 15.4 μmol), HATU (12 mg), HOAt (5 mg), NMM (5 μl), DCM (140 μl) and DMF (70 μl), the title compound (9 mg, 63%) was obtained as a white solid after purification by HPLC (HyperPrep PEP 100 C18, isocratic ACN/H$_2$O 85:15 (flow: 7 mil/min, 250×21 mm, at 270 nm, $t_R$=14.4 min).

$^1$H NMR (300 MHz, CDCl$_3$). δ 0.90-1.00 (m, 24H), 1.05-1.40 (m, 12H), 1.40-2.25 (m, 16H), 2.27-2.41 (m, 1H), 2.42-2.70 (m, 3H), 2.54 (s, 3H), 2.92-2.98 (m, 1H), 3.12-3.38 (m, 4H), 3.54-3.78 (m, 4H), 3.79 (s, 3H), 4.01-4.12 (m, 2H), 4.20-4.26 (m, 2H), 4.57-4.62 (m, 2H), 4.77-4.82 (m, 2H), 535.18 (d, J=3.0, 2H), 5.37-5.42 (m, 1H), 6.84 (d, J=8.7, 2H), 7.07 (d, J=8.7, 2H), 7.20 (d, J=9.6, 1H), 7.85 (d, J=9.6, 1H), 98.04 (d, J=5.4, 1H). $^{13}$C NMR (75 MHz, CDCl$_3$) δ 11.86, 14.97, 15.47, 16.78, 17.12, 18.84, 21.20, 21.27, 23.62, 24.14, 15.03, 25.15, 25.30, 27.35, 27.51, 28.19, 30.46, 31.52, 34.27, 35.95, 39.01, 40.07, 41.59, 47.25, 49.72, 53.08, 55.51, 55.81, 57.38, 58.21, 66.66, 68.19, 69.23, 70.74, 81.69, 85.15, 114.33, 130.13, 130.56, 158.85, 161.12, 168.49, 169.81, 169.91, 170.81, 171.38, 171.69, 172.60, 173.34, 197.64, 205.19. ESI-MS Calcd for C$_{58}$H$_{87}$N$_7$O$_5$: 1121.63. Found 1122.3 (M+H)$^+$.

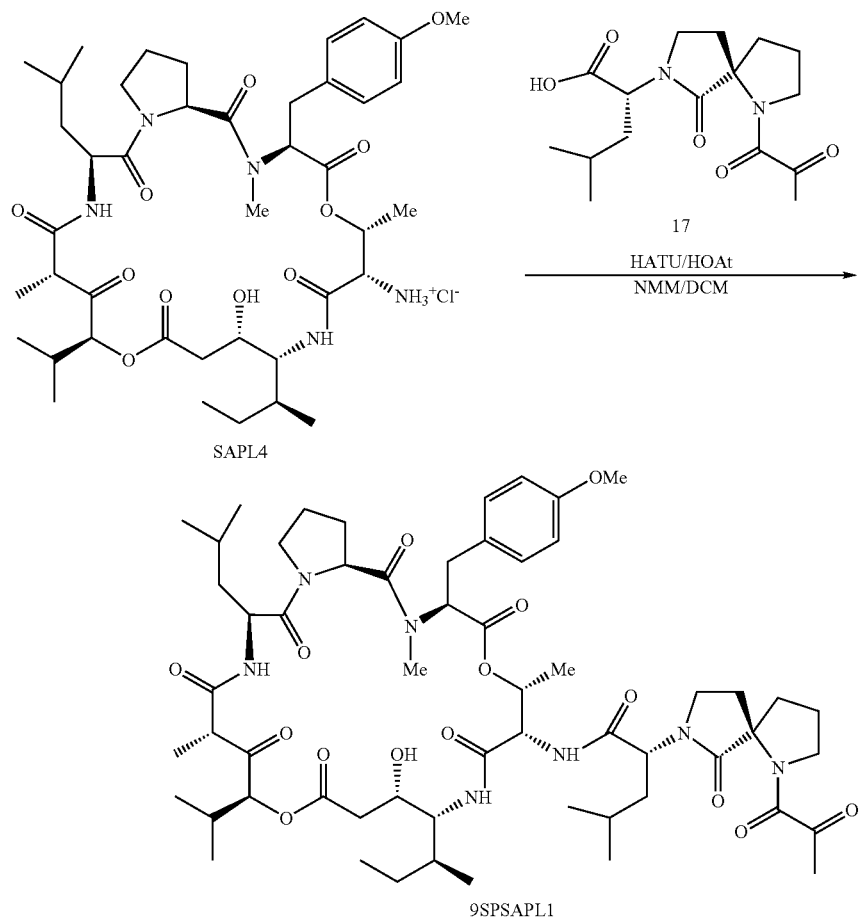

EXAMPLE 99

Synthesis of [Hiv]³-[(5R)-1-(pyruvyl)-7-[(1R)-1-carboxy-3-methylbutyl]-6-oxo-1,7-diazaspiro[4.4]nonane]⁷⁻⁹-aplidine (9SPSHPL1)

(HyperPrep PEP 100 C18, isocratic ACN/H₂O 85:15 (flow: 7 ml/min, 250×21 mm, at 270 nm, t_R=13.6 min).

¹H NMR (300 MHz, CDCl₃) δ 0.80-1.10 (24H, m), 1.11-1.80 (12H, m), 1.81-2.30 (10H, m), 2.45 (m, 1H), 2.55 (s, 3H), 2.57 (s, 3H), 3.07-3.43 (m, 6H), 3.52-3.77 (m, 6H), 3.78 (s, 3H), 3.91 (m, 1H), 4.03 (m, 1H), 4.29 (m, 1H) 4.63

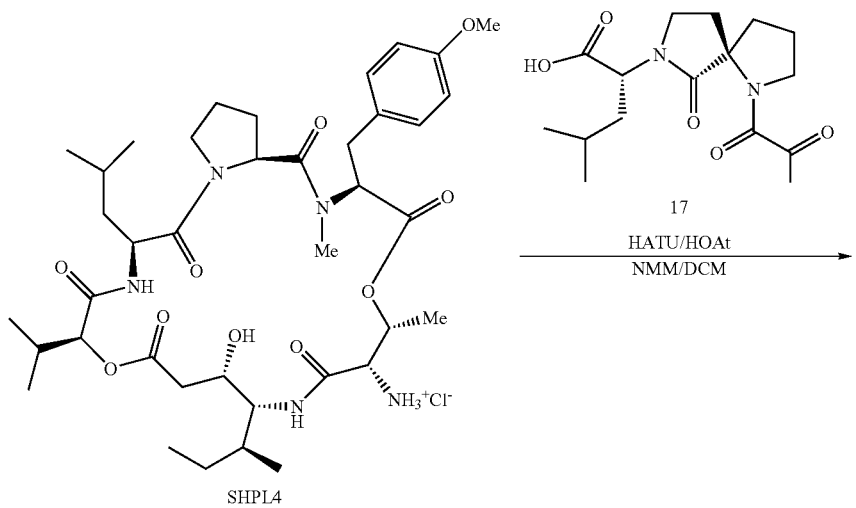

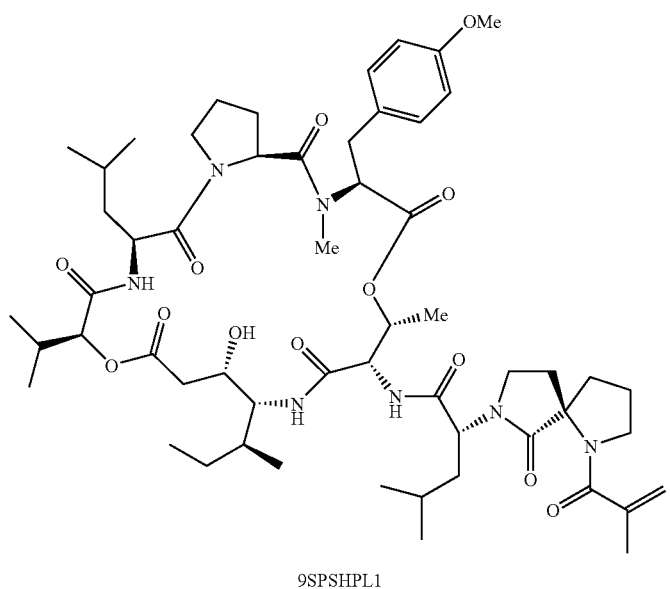

Following the procedure described for the synthesis of SAPL3, starting from SHPL4 (10 mg, 13 μmol), 17 (4.5 mg, 14 μmol), HATU (14 mg), HOAt (5 mg), NMM (6 μl), DCM (150 μl) and DMF (50 μl), the title compound (10 mg, 72%) was obtained as a white solid after purification by HPLC (m, 1H), 4.72 (m, 1H), 4.87 (m, 1H), 5.03 (d, J=4.3, 1H), 5.45 (m, 1H), 6.84 (d, J=8.3, 2H), 7.07 (d, J=8.3, 2H), 7.29 (d, J=8.7, 1H), 7.81 (d, J₁=9.2, 1H), 7.87 (d, J=4.8, 1H), ESI-MS Calcd for C₅₅H₈₃N₇O₁₄: 1065.6. Found 1066.4 (M+H)⁺.

EXAMPLE 100
Synthesis of [Hiv]³-[5R)-1-(acriloyl)-7-[(1R)-1-carboxy-3-methylbutyl]-6-oxo-1,7-diazaspiro[4.4]nonane]⁷⁻⁹-aplidine (9SASHPL1)
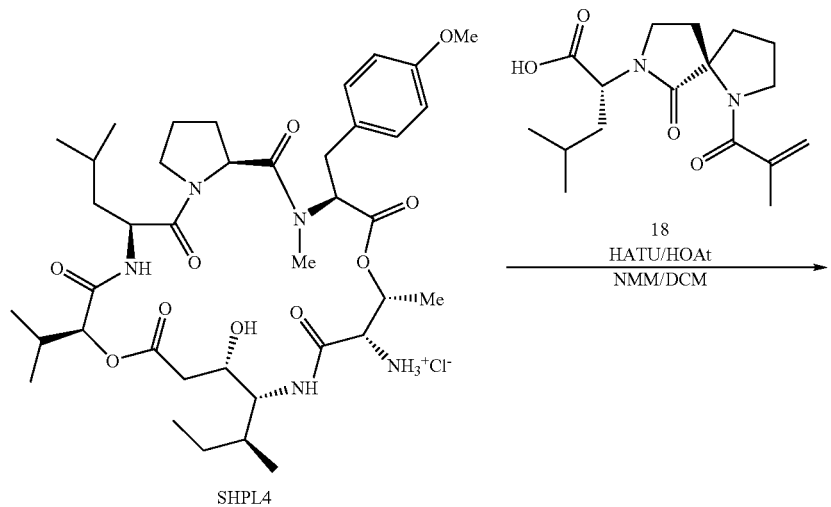
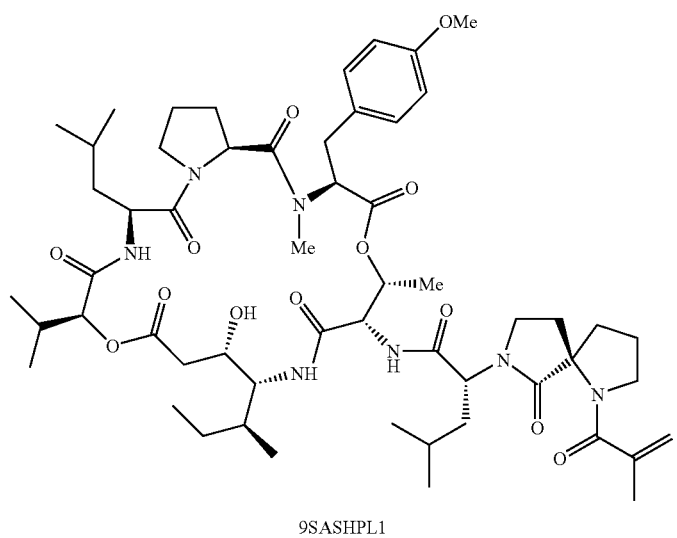

Following the procedure described for the synthesis of SAPL3, starting from SHPL4 (10 mg, 13 µmol), 18 (5.8 mg, 14 µmol), HATU (14 mg, HOAt (5 mg), NMM (6 µl), DCM (150 µl) ad DMF (50 µl), the title compound (10 mg, 72%) was obtained as a white solid after purification by HPLC (HyperPrep PEP 100 C18, isocratic ACN/H$_2$O 85:15 (flow: 7 ml/min, 250×21 mm, at 270 nm, t$_R$=16.4 min).

$^1$H NMR (300 MHz, CDCl$_3$) δ 0.85-0.96 (m, 18H), 1.02-1.05 (m, 6H), 1.14-1.45 (m, 12H), 1.49-1.64 (m, 4H), 1.68-1.77 (m, 1H), 1.89-2.05 (m, 3H), 1.99 (s, 3H), 2.10-2.28 (m, 4H), 2.43 (dd, J$_1$=7.8, J$_2$=17.1, 1H), 2.57 (s, 3H), 2.60-2.68 (m, 1H), 2.97 (bs, 1H), 3.13-3.40 (m, 4H), 3.54-3.77 (m, 5H), 3.79 (s, 3H), 3.89-4.07 (m, 2H), 4.27 (m, 1H), 4.64 (m, 1H), 4.73 (m, 1H), 4.88 (m, 1H), 5.03 (d, J=4.4, 1H), 5.30 (d, J=20, 1H), 5.30-5.39 (m, 1H), 6.84 (d, J=8.3, 2H), 7.08 (d, J=8.3, 2H), 7.29 (s, 1H), 7.88 (d, J=9.8, 1H), 8.23 (d, J=7.4, 1H). ESI-MS Calcd for C$_{56}$H$_{85}$N$_7$O$_{13}$: 1063.6. Found 1064.6 (M+H)$^+$.

EXAMPLE 101

Synthesis of [Hiv]$^8$-[Z-Ala]$^9$-aplidine (9ZASHPL2)

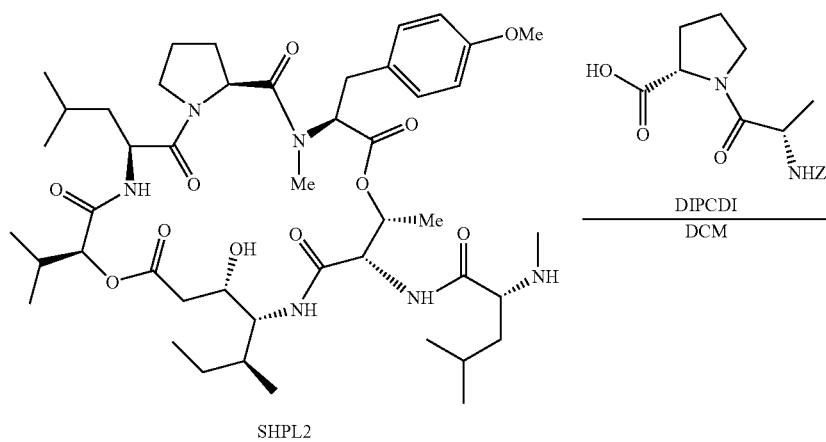

SHPL2

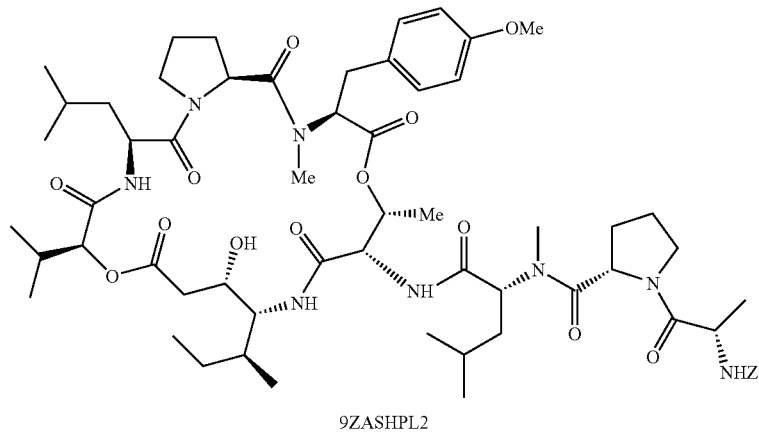

9ZASHPL2

To a flask containing Z-Ala-Pro-OH (36 mg, 112 μmol) in DCM (0.4 ml) at 0° C., under argon, DIPCDI (10 μl, 64 μmol) was added and the mixture was stirred for 60 min. Then, a solution of SHPL2 (20 mg, 22.5 μmol) in DCM (0.2 ml) was added and after 3d the reaction was quenched by addition of aq HCl (3 ml, 0.1 N). The mixture was stirred for 5 min and then, diluted with DCM (4 ml) and washed successively with aq. KHSO$_4$ (4 ml, 10%), aq. NaHCO$_3$ (4 ml, sat) and brine (4 ml). The organic phase was dried (Na$_2$SO$_4$), filtered and concentrated. Purification of the residue by HPLC (HyperPrep PEP 100 C18, isocratic ACN/H$_2$O 85:15 (flow: 7 ml/min, 250×21 mm, at 270 nm, t$_R$=18.2 min) afforded 9ZASHPL2 (30 mg, 67%) as a white solid.

$^1$H NMR (300 MHz, CDCl$_3$) δ 0.82-1.10 (m, 24H), 1.12-1.50 (m, 18H), 1.52-2.70 (m, 6H), 2.45 (m, 1H), 2.56 (s, 3H), 2.96-3.38 (m, 4H), 3.10 (s, 3H), 3.52-3.72 (m, 5H), 3.85 (m, 1H), 3.78 (s, 3H), 4.01 (m, 1H), 4.18 (m, 1H), 4.51 (m, 1H), 4.64 (m, 1H), 4.71 (m, 1H), 4.87 (m, 1H), 5.02 (d, J$_1$=5.3, 1H), 5.06 (m, 2H), 5.25 (m, 1H), 5.42 (m, 1H), 6.10 (d, J=8.3, 1H), 6.84 (d, J=8.3, 2H), 7.07 (d, J=8.3, 2H), 7.31 (m, 6H), 7.70 (d, J=4.3, 1H), 7.77 (d, J=9.7, 1H). $^{13}$C NMR (75 MHz, CDCl$_3$) δ 11.80, 13.97, 16.63, 17.02, 17.48, 18.93, 20.86, 21.15, 23.45, 23.76, 24.78, 25.96, 27.31, 27.92, 28.50, 30.06, 31.36, 33.44, 33.82, 35.66, 38.70, 39.38, 39.63, 46.54, 46.62, 46.98, 47.10, 48.19, 48.59, 54.89, 54.97, 55.22, 56.44, 56.90, 58.14, 66.16, 66.36, 68.95, 70.94, 78.78, 114.00, 127.75, 128.30, 129.90, 130.26, 156.31, 158.53, 168.67, 169.57, 170.06, 170.25, 170.65, 171.97, 173.08, 174.67. ESI-MS Calcd for C$_{62}$H$_{92}$N$_8$O$_{15}$ 1188.67. Found m/z 1189.7 (M+H)$^+$.

EXAMPLE 102

Synthesis of [Hiv]$^3$-[Boc-Ala]$^9$-aplidin (9BASHPL2)

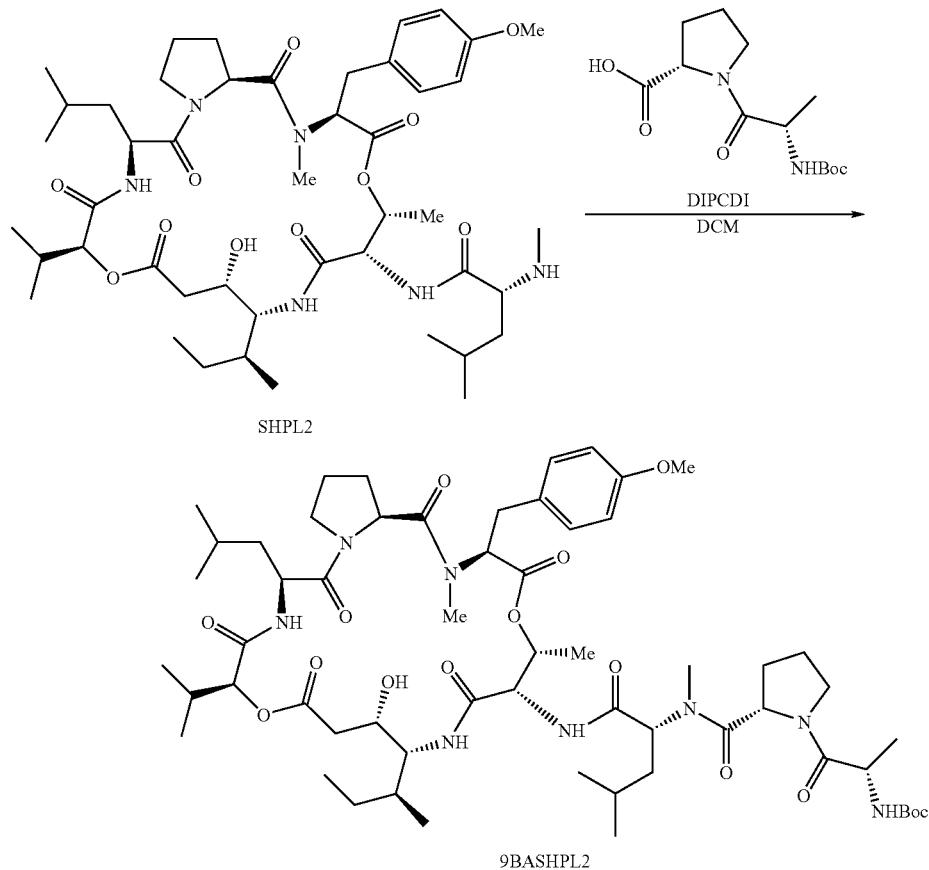

Following the procedure described for the synthesis of 9ZASHPL2, from SHPL2 (10 mg, 11.2 μmol), Boc-Ala-Pro-OH (17 mg, 57 μmol), DIPCDI (5 μl) and DCM (300 μl), the title compound (9 mg, 70%) was obtained as a white solid after purification by HPLC (HyperPrep PEP 100 C18, gradient ACN/H$_2$O 85:15-100:0 in 10 min (flow: 7 ml/min, 250×21 mm, at 270 nm, t$_R$=14.5 min).

$^1$H NMR (300 MHz, CDCl$_3$) δ 0.82-1.10 (m, 24H), 1.12-1.50 (m, 15H), 1.40 (s, 9H), 1.52-2.70 (m, 9H), 2.45 (m, 1H), 2.60 (s, 3H), 3.00-3.43 (m, 4H), 3.10 (s, 3H), 3.62 (m, 5H), 3.79 (s, 3H), 3.90 (m, 1H), 4.02 (m, 1H), 4.20 (m, 1H), 4.41 (m, 1H), 4.67 (m, 2H), 4.87 (m, 1H), 5.02 (d, J$_1$=4.3, 1H), 5.26 (m, 1H), 5.40 (m, 1H), 5.76 (d, J=7.8, 1H), 6.84 (d, J=8.3, 2H), 7.07 (d, J=8.3, 2H), 7.32 (d, J=9.7, 1H), 7.73 (d, J=4.8, 1H), 7.80 (d, J=9.7, 1H). $^{13}$C NMR (75 MHz, CDCl$_3$) δ 12.06, 14.34, 16.88, 17.20, 17.77, 19.17, 21.10, 21.41, 23.72, 24.03, 25.06, 26.17, 27.60, 28.19, 28.60, 30.31, 31.63, 33.74, 35.96, 38.96, 38.93, 39.59, 39.86, 46.86, 47.27, 48.29, 48.45, 55.18, 55.42, 55.49, 56.59, 57.16, 58.44, 66.43, 69.14, 71.30, 79.05, 79.40, 114.29, 130.21, 130.54, 156.06, 158.83, 168.80, 169.87, 170.51, 170.64, 170.94, 171.31, 172.59, 173.45, 174.92. ESI-MS Calcd for $C_{59}H_{94}N_8O_{15}$ 1154.68. Found m/z 1155.6 $(M+H)^+$.

EXAMPLE 103

Synthesis of $[Hiv]^3$-$[Ala]^9$ aplidine (9ASHPL1)

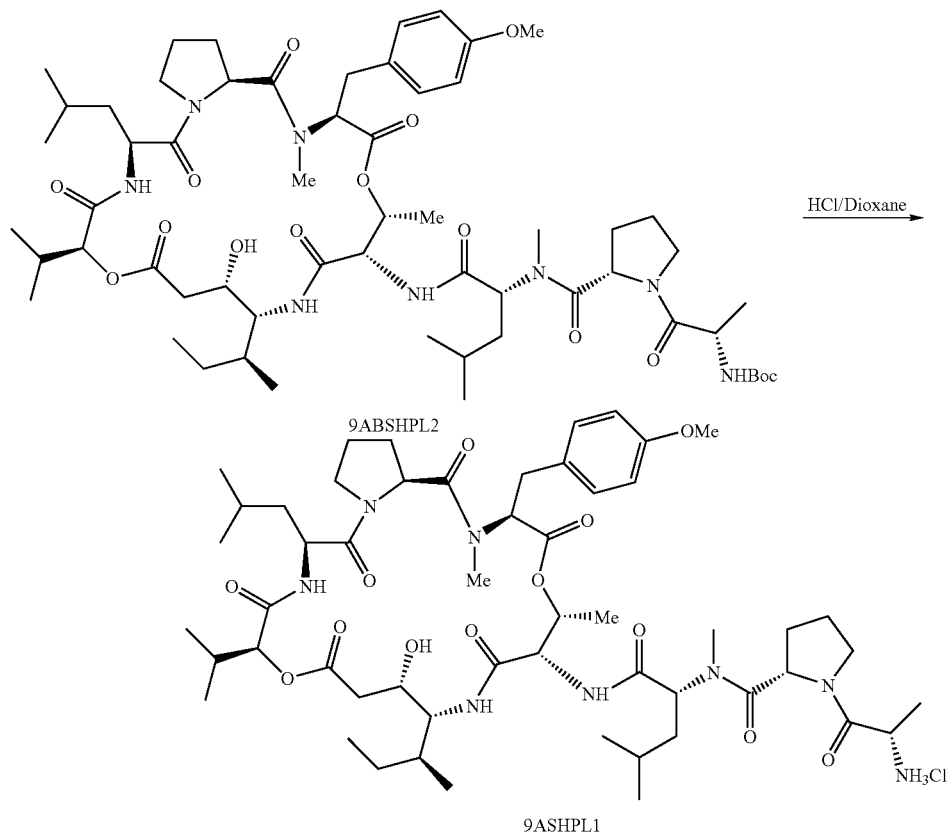

To a flask containing 9BASHPL2 (8 mg, 6.92 μmol), a solution of hydrochloric acid in anh. dioxane (1.5 ml, 5.3 N, 7.9 mmol) was added. The resulting solution was stirred at room temperature for 5 h or until complete disappearance of the starting material (TLC). Then, the solution was concentrated under reduced pressure and the residue was dissolved in DCM and concentrated again. The white foam crude was precipitated with DCM/hex (2 ml/4 ml) to yield 9ASHPL1 (7.2 mg, quant.) as a white solid.

ESI-MS Calcd for $C_{54}H_{86}N_8O_{13}$ 1054.6. Found m/z: 1055.6 $(M+H)^+$.

EXAMPLE 104

Synthesis of $[Hiv]^3$-$[Boc-Pro]^8$-didemnin A (8PSHPL2)

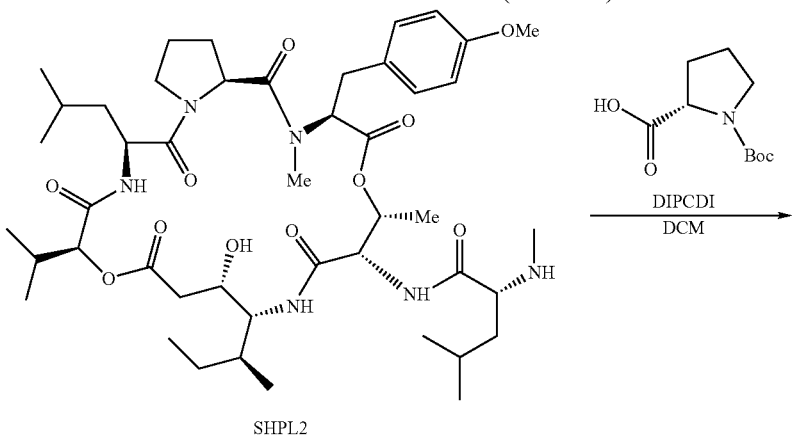

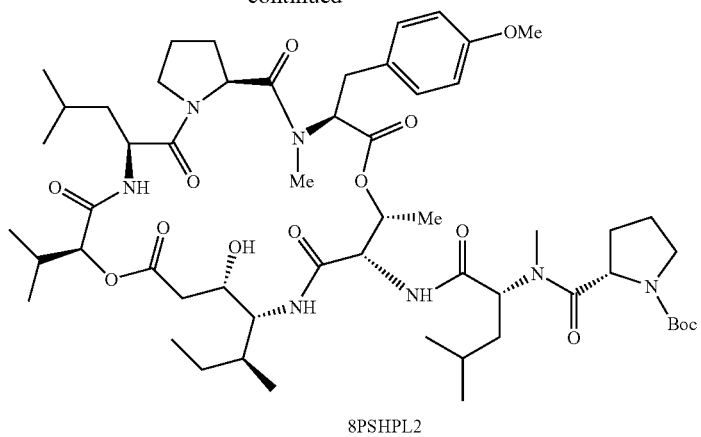

8PSHPL2

Following the procedure described for the synthesis of 9ZASHPL2, starting from SHPL2 (10 mg, 11.2 μmol), Boc-Pro-OH (13 mg, 57 μmol), DIPCDI (5 μl) and DCM (300 μl), the title compound (9 mg, 74%) was obtained as a white solid after purification by HPLC (HyperPrep PEP 100 C18, gradient ACN/H$_2$O 85:15-100:0 in 10 min (flow: 7 ml/min, 250×21 mm, at 270 nm, t$_R$=18.7 min).

$^1$H NMR (300 MHz, CDCl$_3$) δ 0.82-1.10 (m, 24H), 1.12-2.30 (m, 22H), 1.47 (s, 9H), 2.41 (m, 1H), 3.04 (s, 3H), 3.10-3.74 (m, 7H), 3.78 (s, 3H), 3.91 (m, 1H), 4.01 (m, 1H), 4.31 (m, 1H), 4.59 (m, 1H), 4.87 (m, 1H), 5.02 (d, J=4.8, 1H), 5.16 (m, 1H), 5.36 (m, 1H), 6.84 (d, J=8.3, 2H), 7.07 (d, J=8.3, 2H), 7.17 (d, J=6.3, 1H), 7.35 (d, J=9.7, 1H), 7.85 (d, J=9.7, 1H). $^{13}$C NMR (75 MHz, CDCl$_3$) δ 12.04, 14.41, 16.76, 17.97, 19.12, 21.03, 21.66, 23.92, 24.00, 24.77, 25.09, 25.20, 27.53, 28.21, 28.72, 29.67, 30.35, 31.23, 33.80, 34.30, 36.24, 39.05, 39.37, 39.80, 46.90, 47.33, 48.42, 54.48, 55.49, 55:58, 55.84, 57.12, 58.08, 66.31, 69.11, 71.05, 79.23, 80.28, 114.29, 130.23, 130.59, 154.91, 158.82, 168.37, 169.88, 170.66, 170.86, 171.28, 171.40, 174.10, 174.79. ESI-MS Calcd for C$_{56}$H$_{91}$N$_7$O$_{14}$: 1085.6. Found m/z: 1086.7 (M+H)$^+$.

EXAMPLE 105

Synthesis of [Hiv]$^3$-[Pro]$^8$-didemnin A (8PSHPL1)

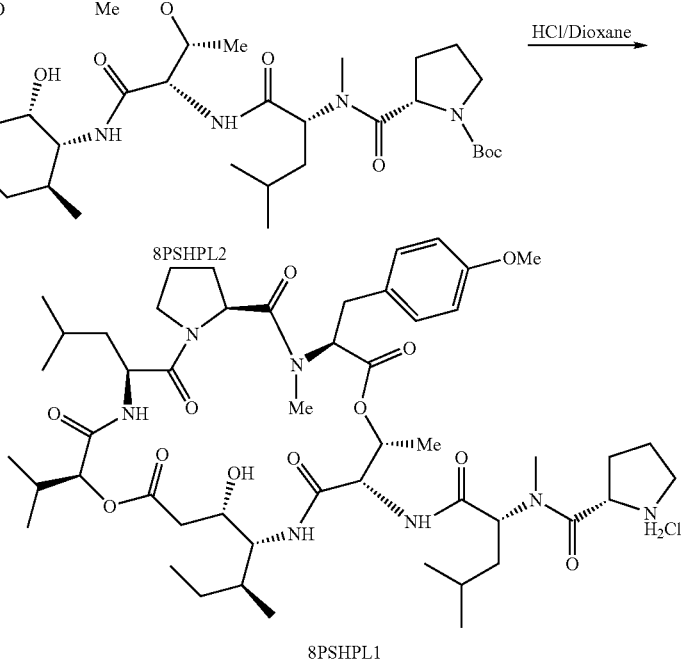

8PSHPL1

Following the procedure described for the synthesis of 9ASHPL1, starting from 8PSHPL2 (7 mg, 6.4 µmol), the title compound (6 mg, quant.) was obtained as a white solid.

ESI-MS Calcd for $C_{51}H_{81}N_7O_{12}$: 983.59. Found m/z: 984.6 (M+H)⁺.

EXAMPLE 106

Synthesis of [Hiv]³-Boc-Val⁸-didemnin A (8VSHPL2)

Following the procedure described for the synthesis of 9ZASHPL2, starting from SHPL2 (10 mg, 11.2 µmol), Boc-Val-OH (12 mg, 56 µmol), DIPCDI (5 µl) and DCM (300 µl), the title compound (9 mg, 82%) was obtained as a white solid after purification by HPLC (HyperPrep PEP 100 C18, gradient ACN/H₂O 85:15-100:0 in 10 min (flow: 7 ml/min, 250×21 mm, at 270 nm, $t_R$=22.1 min).

¹H NMR (300 MHz, CDCl₃) δ 0.82-1.10 (m, 30H), 1.12-1.82 (m, 12H), 1.45 (s, 9H), 1.84-2.40 (m, 6H), 2.56 (s, 3H), 2.96 (s, 3H), 2.97 (m, 3H), 3.13 (m, 1H), 3.35 (m, 1H), 3.56 (m, 1H), 3.65 (m, 2H), 3.79 (s, 3H), 3.85 (m, 1H), 4.03 (m, 1H), 4.24 (m, 1H), 4.41 (m, 1H), 4.61 (m, 1H), 4.88 (m, 1H), 4.99 (d, $J_1$=5.3, 1H), 5.07 (m, 1H), 5.19 (m, 1H), 5.60 (d, J=8.3, 1H), 6.84 (d, J=8.3, 2H), 7.03 (d, J=8.7, 2H), 7.07 (d, J=8.3, 2H), 7.46 (d, J=10.2, 1H), 7.84 (d, J=9.2, 1H). ESI-MS Calcd for $C_{56}H_{91}N_7O_{14}$: 1085.6. Found m/z: 1086.7 (M+H)⁺.

EXAMPLE 107

Synthesis of [Hiv]³-[Val]⁸-didemnin A (8VSHPL1)

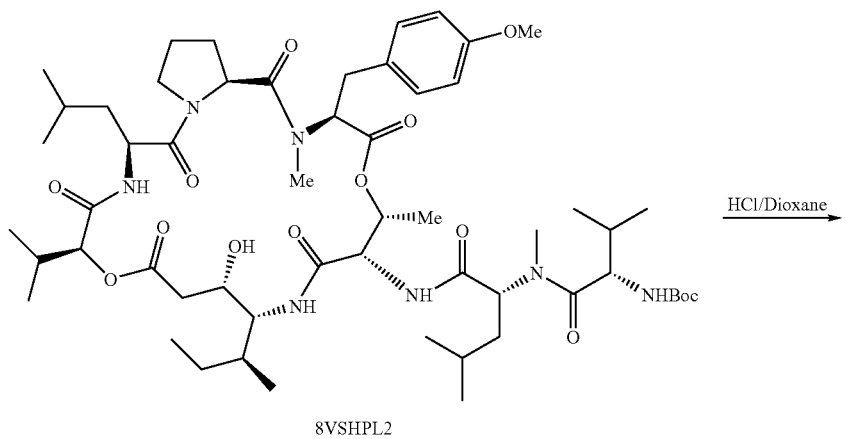
8VSHPL2
HCl/Dioxane →
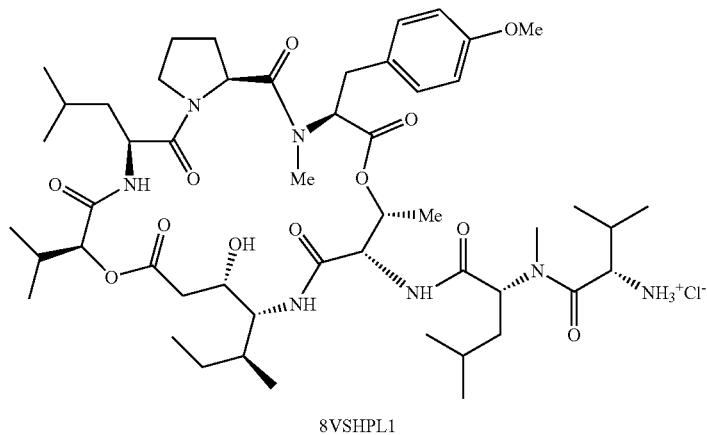
8VSHPL1
Following the procedure described for the synthesis of 9ASHPL1, starting from 8VSHPL2 (8 mg, 7.4 µmol), the title compound (7 mg, quant.) was obtained as a white solid.
ESI-MS Calcd for $C_{51}H_{83}N_7O_{12}$: 985.61. Found: (m/z): 986.6 (M+H)$^+$.
EXAMPLE 108
Synthesis of [Hiv]$^3$-[Val]$^8$-[Isobutyryl]$^9$-didemnin A (8V9ISHPL1)
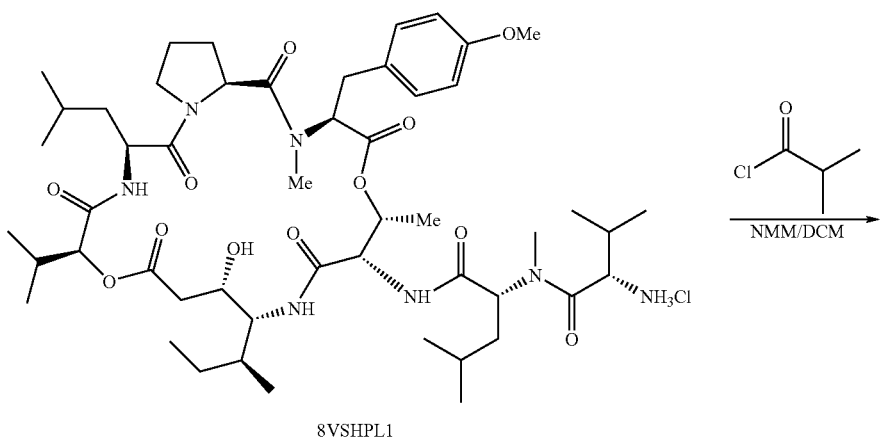
8VSHPL1

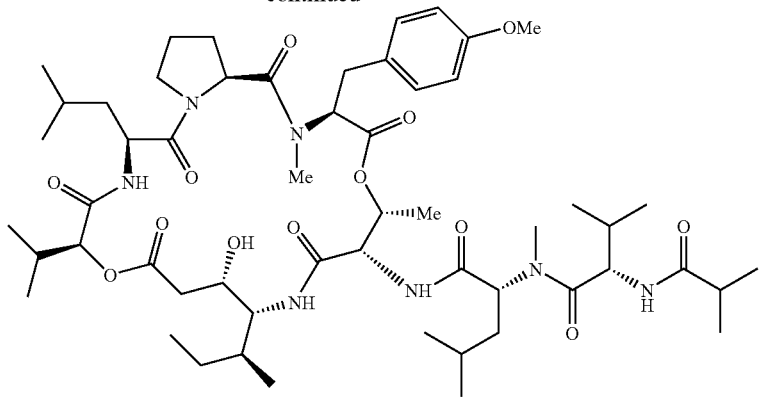

8V9ISHPL1

To a solution of 8VSHPL1 (6 mg, 5.8 μmol) in DCM (200 μml) at 0° C. under Ar, were added NMM (3.3 μl, 30 μmol) and isobutyryl chloride (2 μl, 19 μmol). After 5 h of stirring at r.t., the reaction mixture was diluted with DCM (5 ml) and washed successively with aq. $KHSO_4$ (5 ml, 10%), aq. $HCO_3Na$ (5 ml, sat) and brine (5 ml). The organic solution was dried ($Na_2SO_4$), filtered and concentrated at reduced pressure to yield 8V9ISHPL1 (6 mg, 97%) as a white solid.

$^1$H NMR (300 MHz, $CDCl_3$) δ 0.82-1.10 (m, 36H), 1.12-1.85 (m, 10H), 1.90-2.45 (m, 6H), 2.56 (s, 3H) 2.90 (m, 1H), 3.00 (s, 3H), 3.13 (m, 2H), 3.36 (dd, $J_1$=4.3, $J_2$=14.1, 1H), 3.64 (m, 6H), 3.78 (s, 3H), 3.87 (m, 1H), 3.97 (m, 1H), 4.21 (m, 1H), 4.34 (m, 2H), 4.61 (m, 1H), 4.87 (m, 1H), 4.98 (d, J=4.8, 1H), 5.17 (m, 2H), 6.24 (d, J=6.3, 1H), 6.84 (d, J=8.3, 2H), 7.07 (d, J=8.3, 2H), 7.32 (d, J=6.3, 1H), 7.35 (d, J=4.3, 1H), 7.81 (d, J=9.7, 1H). ESI-MS Calcd for $C_{55}H_{89}N_7O_{13}$, 1055.6. Found m/z: 1056.7 (M+H)$^+$.

EXAMPLE 109

Synthesis of [coumarin]$^8$-didemnin A (8CSAPL1)

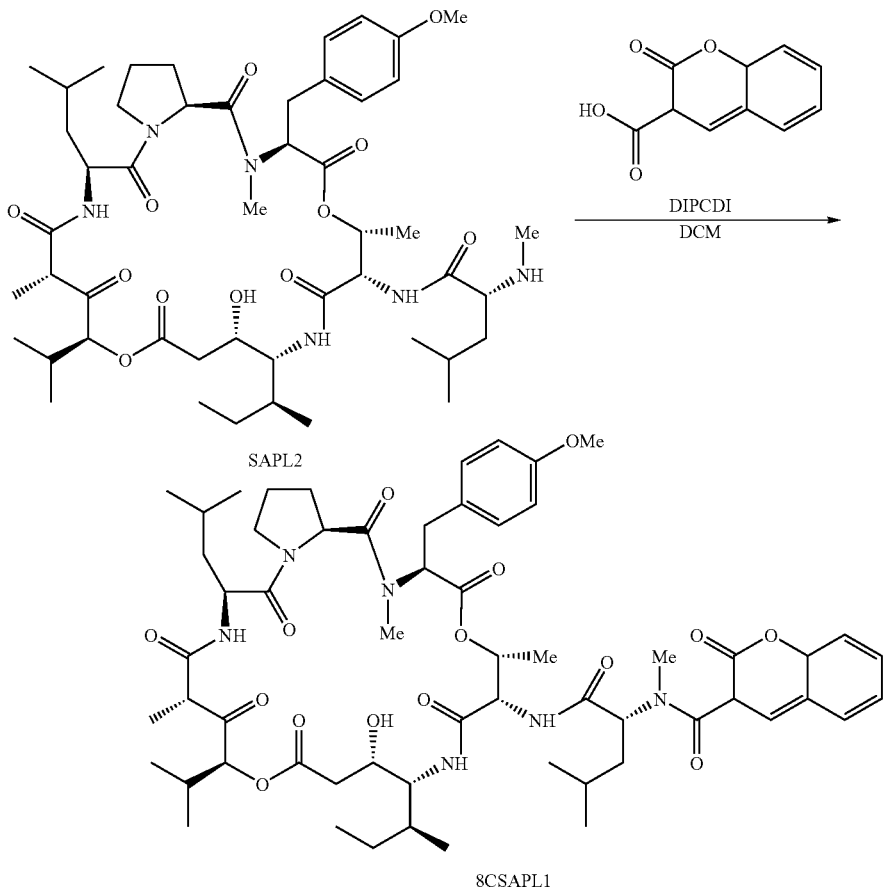

SAPL2

8CSAPL1

Following the procedure described for the synthesis of 9ZASHPL2, starting from SAPL2 (20 mg, 21 μmol) and coumarin-3-carboxylic acid (20 mg, 107 μmol), the title compound (18 mg, 76%) was obtained as a white solid after purification by HPLC (HyperPrep PEP 100 C18, isocratic ACN/H$_2$O 85:15 (flow: 7 ml/min, 250×21 mm, at 270 nm, $t_R$=16.5 min).

$^1$H NMR (300 MHz, CDCl$_3$) δ 0.78-1.00 (m, 24H), 1.20-2.50 (m, 22H), 2.56 (s, 3H), 2.92 (s, 3H), 3.08-3.25 (m, 2H), 3.90 (m, 1H), 3.60 (m, 2H), 3.70 (m, 1H), 3.79 (s, 3H), 3.92-4.25 (m, 3H), 4.60 (m, 1H), 4.80 (m, 2H), 5.15 (m, 1H), 5.18 (d, J=3.4, 1H), 5.28 (m, 1H), 6.84 (d, J=8.3, 2H), 7.08 (d, J=8.3, 2H), 7.20 (d, J=6.3, 1H), 7.37 (m, 2H), 7.45 (d, J=9.7, 1H), 7.58 (m, 2H), 7.96 (m, 1H), 8.23 (m, 1H). ESI-MS Calcd for C$_{59}$H$_{82}$N$_6$O$_{15}$: 1114.58. Found: 1116.3 (M+H)$^+$.

EXAMPLE 110

Synthesis of coumarin-3-carbonylamino-acetic Acid Methyl Ester (8G9C2)

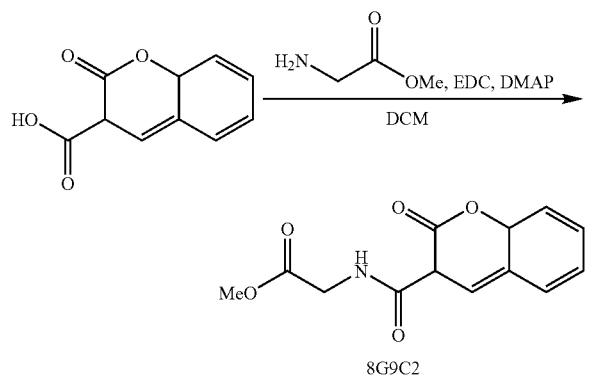

To a round bottom flask containing methyl-glycine (89 mg, 1.00 mmol), 3-carboxy coumarine, anh. DCM (25 ml), under Ar, N'-(3 Dimethylaminopropil)-N-ethyl-carbodiimid hydrochlorid (EDC) (479 mg, 2.50 mmol) and DMAP (489 mg, 4.00 mmol) were added at room temperature. The resulting mixture was stirred for 1 h 30 min (total conversion was observed by TLC). Then, DCM (20 ml) was added and the solution was washed successively with aq. NaHCO$_3$ (10 ml, sat) and brine (10 ml). The organic phase was dried (Na$_2$SO$_4$), filtered and concentrated. The resulting orange solid obtained was purified by flash LC (silica gel, grad hex:EtOAc 1:1 to 2:1) to give the title compound (445 mg, quant) as a colourless oil. Rf=0.08 (Hex/EtOAc 1:1).

$^1$H NMR (300 MHz, CDCl$_3$) δ 3.79 (s, 3H), 4.25 (d, J=5.4, 2H), 7.40 (m, 2H), 7.74 (d, J=7.3, 1H), 7.68 (m, 2H), 8.91 (s, 1H), 9.25 (s, 1H). ESI-MS Calcd for C$_{13}$H$_{11}$NO$_5$: 261.06. Found: 283.1 (M+Na)$^+$.

EXAMPLE 111

Synthesis of coumarin-3-carbonylamino-acetic acid (8G9C1)

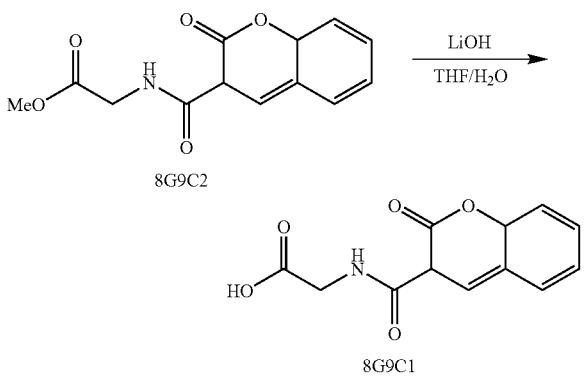

A solution of coumarin-3-carbonylamino-acetic acid methyl ester (312 mg, 1.19 mmol), in THF (12 ml) under Ar atmosphere, at 0° C. (ice bath), a solution of LiOH in H$_2$O (0.2 M) was added dropwise. The reaction mixture was stirred vigorously at room temperature until total conversion was observed by TLC (2 hours). The solution was partially concentrated and Et$_2$O was added (10 ml). The organic layer was washed with NaHCO$_3$ (10 ml, sat) and the combined aqueous layers were acidified with 10% KHSO$_4$ (pH=3-4) and extracted with ether (3×20 ml). The organic layer was concentrated at reduced pressure to afford 8G9C1 (280 mg, 95%) as a white solid.

$^1$H NMR (300 MHz, CDCl$_3$) δ 4.18 (d, J=5.3, 2H), 7.41 (m, 1H), 7.45 (d, J=7.8, 1H), 7.74 (d, J=7.3, 1H), 7.78 (t, J=8.3, 1H), 7.85 (d, J=7.8, 1H), 8.89 (s, 1H), 9.41 (m, 1H). ESI-MS Calcd for C$_{12}$H$_9$NO$_5$: 247.05. Found: 248.0 (M+H)$^+$.

EXAMPLE 112

Synthesis of [Gly]$^8$-[coumarin]$^9$-didemnin A (8G9CSAPL1)

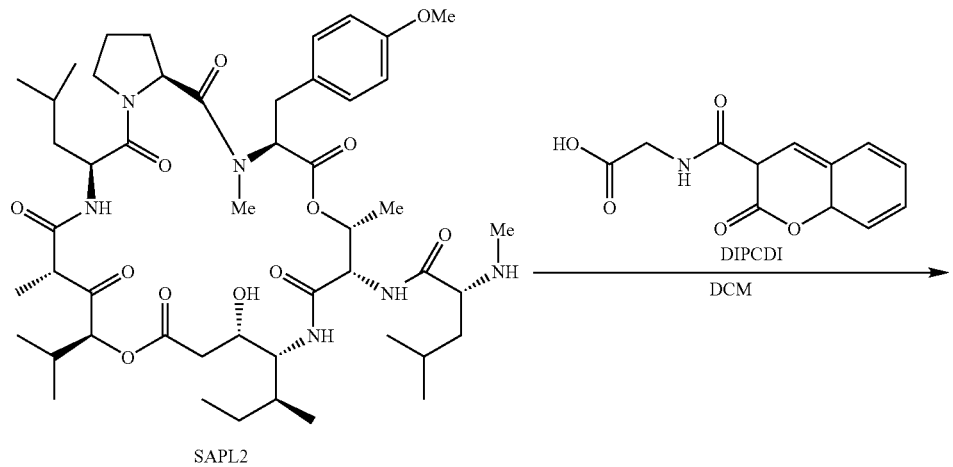

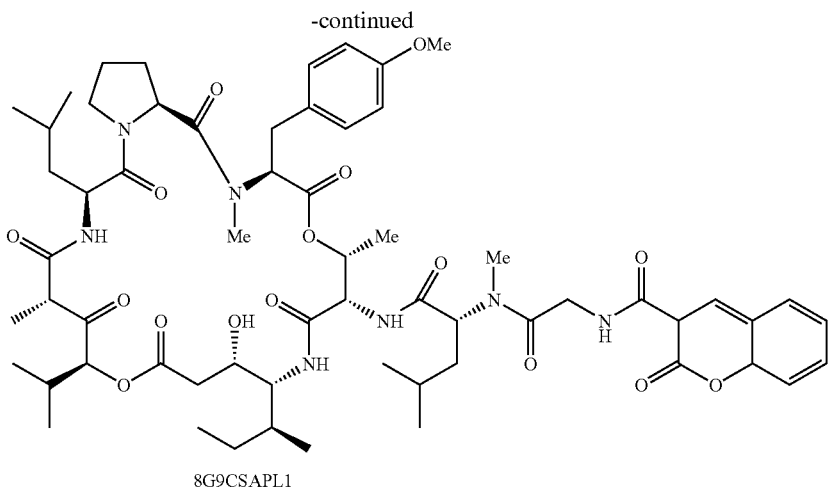

8G9CSAPL1

Following the procedure described for the synthesis of 9ZASHPL2, starting from SAPL2 (20 mg, 21 μmol) and coumarin-3-carbonylamino-acetic acid (26 mg, 105 μmol), the title compound (18 mg, 72%) was obtained as a white solid after HPLC (Symetry Prep™ C18, isocratic ACN/H$_2$O 60:40 (flow: 3 ml/min, 150×7.8 mm, at 270 nm, $t_R$=17.5 min).

$^1$H NMR (300 MHz, CDCl$_3$) δ 0.85-0.94 (m, 24H), 1.23-2.17 (m, 21H), 2.30-2.44 (m, 1H), 2.56 (s, 3H), 3.01 (s, 3H), 3.10-3.24 (m, 2H), 3.40 (dd, J$_1$=5.4, J$_2$=14.2, 1H), 3.59-3.74 (m, 3H), 3.79 (s, 3H), 3.99-4.21 (m, 4H), 4.37-4.44 (m, 1H), 4.60 (m, 1H), 4.68 (m, 1H), 4.81 (t, J=9.8, 1H), 5.18 (d, J=3.4, 1H), 5.25 (dd, J$_1$=2.9, J$_2$=5.9, 1H), 5.20-5.45 (m, 1H), 6.84 (d, J=8.3, 2H), 7.08 (d, J=8.3, 2H), 7.19-7.28 (m, 1H), 7.34-7.42 (m, 2H), 7.63-7.72 (m, 2H), 7.88 (d, J=8.3, 2H), 9.00 (s, 1H), 9.57 (m, 1H). ESI-MS Calcd for C$_{61}$H$_{85}$N$_7$O$_{16}$: 1171.61. Found: 1172.5 (M+H)$^+$.

EXAMPLE 113

Synthesis of N-methylsulphonyl-Pro-OBz (P2)

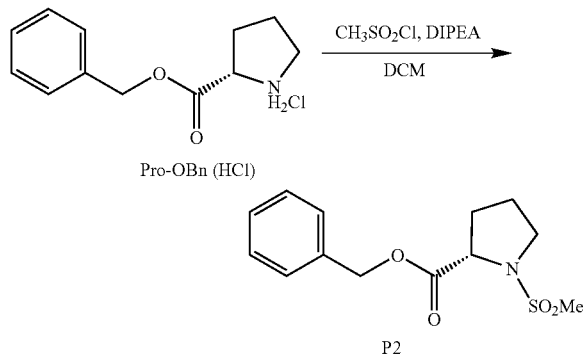

To a solution of Pro-OBn (HCl) (300 mg, 1.24 mmol) in DCM (25 ml, anh) at 0° C. under Ar, DIPEA (0.7 μl) and methanesulphonyl chloride (116 μl) were added dropwise by syringe. The reaction mixture was stirred at room temperature overnight. DCM (10 ml) was added and the solution was washed successively with aq, KHSO$_4$ (15 ml, 10%), aq. NaHCO$_3$ (15 ml, sat) and brine (15 ml) The organic phase was dried (Na$_2$SO$_4$), filtered and concentrated to reduce pressure to yield pure P2 (350 mg, 1.24 mmol, quant) as a white solid. Rf=0.55 (Hex/AcOEt 1:1).

$^1$H NMR (300 MHz, CDCl$_3$) δ 1.91-2.08 (m, 3H), 2.19-2.31 (m, 1H), 2.93 (s, 3H), 3.38-3.54 (m, 2H), 3.65 (s, 3H), 4.51 (dd, J$_1$=3.4, J$_2$=8.3, 1H), 5.11 (d, J=12.2, 1H), 5.18 (d, J=12.2, 1H), 7.31 (m, 5H). ESI-MS Calcd for C$_{13}$H$_{17}$NO$_4$S: 283.09. Found: 284.1 (M+H)$^+$.

EXAMPLE 114

Synthesis of N-methylsulphonyl-Pro-OH (P1)

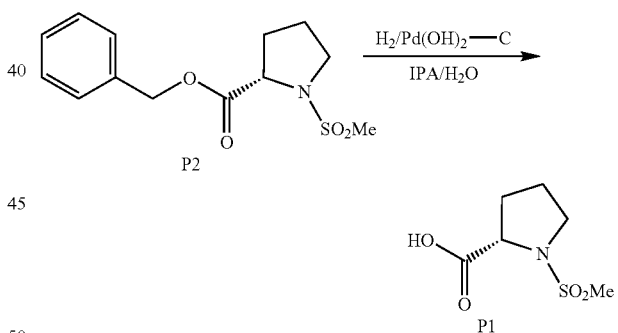

A degassed mixture of N-methylsulphonyl-Pro-OBz (P2) (250 mg, 0.88 mmol) and Pd(OH)$_2$/C (20% Pd, 100 mg, 40% w/w) in IPA:H$_2$O (26 ml:13 ml), was saturated with H$_2$ and maintained at 1 atm of hydrogen gas while stirring for 3 h. Then, the mixture was filtered through a Teflon filter (0.45 μm), and concentrated under vacuum to yield the title compound (128 mg, 75% yield) as a white solid with no further purification.

$^1$H NMR (300 MHz, CDCl$_3$) δ 1.94-2.03 (m, 2H), 2.07-2.14 (m, 1H), 2.22-2.35 (m, 1H), 2.96 (s, 3H), 3.44 (m, 2H), 4.44 (dd, J$_1$=3.9, J$_2$=8.8, 2H), 9.10 (m, 1H). $^{13}$C NMR (75 MHz, CDCl$_3$) δ 24.96, 31.08, 38.46, 48.06, 60.66, 174.75. ESI-MS Calcd for C$_6$H$_{11}$NO$_4$S: 193.22. Found: 194.0 (M+H)$^+$.

EXAMPLE 115
Synthesis of [Methylsulphonyl]⁹-aplidine (9MSAPL1)
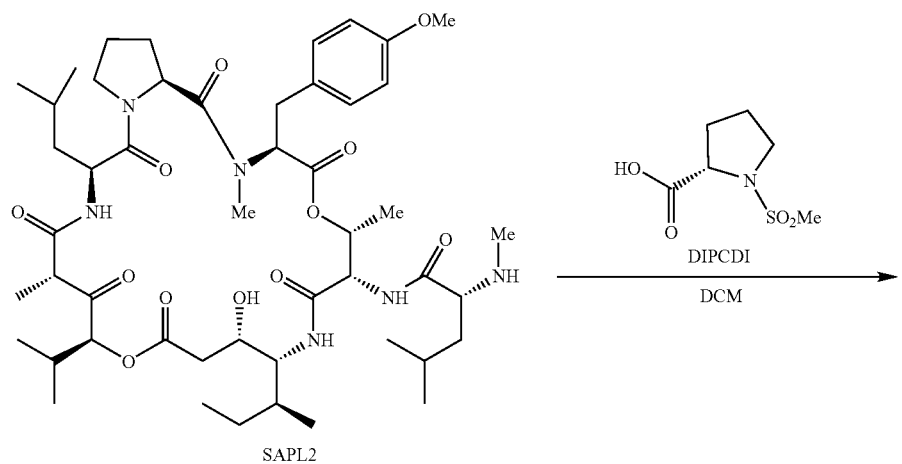
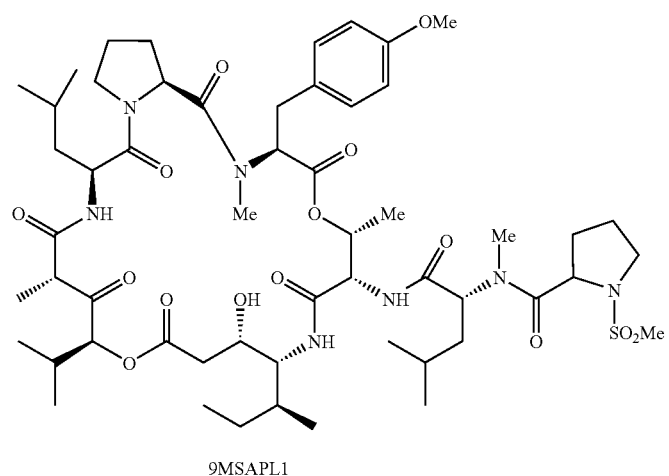

Following the procedure described for the synthesis of 9ZASHPL2, starting from SAPL2 (10 mg, 10.7 μmol) and N-methylsulphonyl-Pro-OH (10 mg, 53 μmmol), the title compound (9 mg, 74%) was obtained as a white solid after purification by HPLC (Symetry Prep C18, isocratic ACN/H$_2$O 60:40 (flow: 3 ml/ml, 150×7.8 mm, at 270 nm, t$_R$=9 min).

$^1$H NMR (300 MHz, CDCl$_3$) δ 0.78-1.00 (m, 24H), 1.20-2.50 (m, 26H), 2.56 (s, 3H), 2.93 (m, 1H), 3.04 (s, 3M), 3.06 (s, 3H), 3.08-3.25 (m, 2H), 3.28-3.50 (m, 2H), 3.60 (m, 2H), 3.70 (m, 1H), 3.79 (s, 3H), 4.05 (m, 2H), 4.17 (m, 1H), 4.60 (m, 2H), 4.81 (m, 2H), 5.10 (m, 1H), 5.19 (d, J=3.4, 1H), 5.33 (m, 1H), 6.84 (d, J=8.3, 2H), 6.86 (m, 1H), 7.07 (d, J=8.3, 2H), 7.09 (m, 1H), 7.82 (d, J=9.2, 1H). ESI-MS Calcd for C$_{55}$H$_{87}$N$_7$O$_{15}$S: 1117.60. Found: 1118.7 (M+H)$^+$.

EXAMPLE 116

Synthesis of [Methylsulphonyl]$^8$-didemnin A (8MSAPL1)

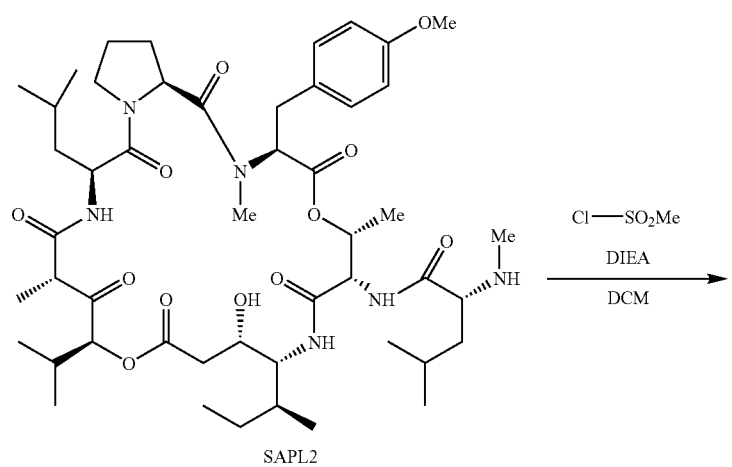

SAPL2

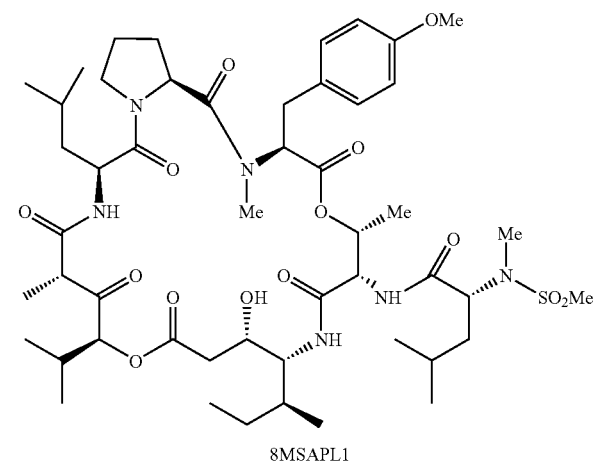

8MSAPL1

To a solution of SAPL2 (10 m g, 10.7 μmol) in DCM (200 μl, anh) at 0° C. under Ar, were added DIPEA (3 μl) and methanesulphonyl chloride (0.85 μl). The reaction mixture

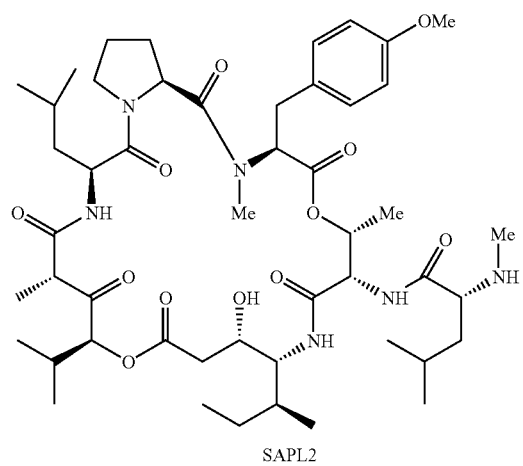

SAPL2

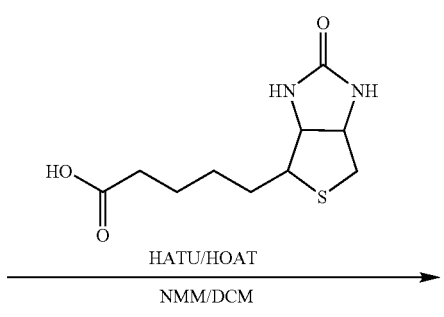

HATU/HOAT
NMM/DCM

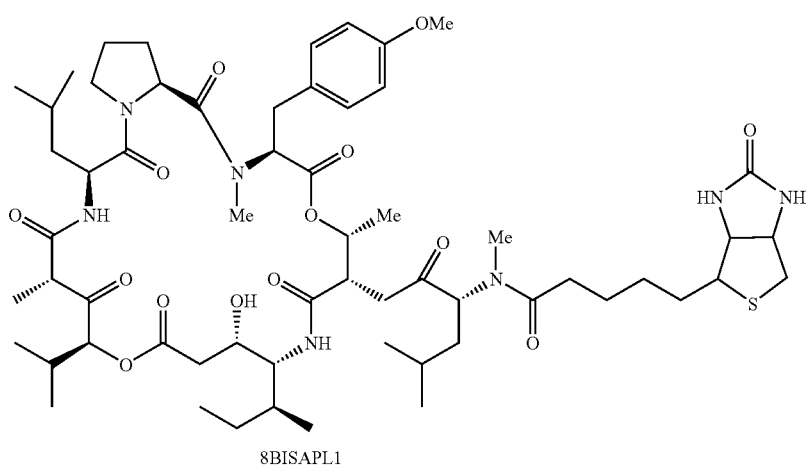

8BISAPL1 was stirred at 5° C. overnight. DCM (10 ml) was added and the solution was washed successively with aq. $KHSO_4$ (5 ml, 10%), aq. $NaHCO_3$ (5 ml, sat) and brine (5 ml). The organic phase was dried ($Na_2SO_4$), filtered and concentrated to reduce pressure to yield pure 8MSAPL1 (11 mg, quant) as a white solid.

$^1$H NMR (300 MHz, $CDCl_3$) δ 0.83-0.97 (m, 24H), 1.10-1.45 (m, 10H), 1.50-1.65 (m, 5H), 1.76-1.82 (m, 2H), 2.00-2.20 (m, 3H), 2.27-2.36 (m, 1H), 2.45-2.55 (m, 1H), 2.56 (s, 3H), 2.90 (s, 3H), 3.02 (s, 3H), 3.08 (d, J=16.6, 1H), 3.17 (dd, $J_1$=10.7, $J_2$=14.1, 1H), 3.37 (m, 1H), 3.60 (m, 2H), 3.70 (m, 1H), 3.79 (s, 3H), 3.99-4.11 (m, 3H), 4.49 (m, 1H), 4.59 (m, 1H), 4.78 (m, 2H), 5.06 (m, 1H), 5.19 (d, J=3.9, 1H), 6.68 (d, J=8.8, 1H), 6.84 (d, J=8.3, 2H), 7.07 (d, J=8.3, 2H), 7.33 (d, J=9.8, 1H), 7.61 (d, J=8.8, 1H). ESI-MS Calcd for $C_{50}H_{80}N_6O_{14}S$: 1020.55. Found: 1022.1 $(M+1H)^+$.

EXAMPLE 117
Synthesis of [Biotin]$^8$-didemnin A (8BISAPL1)

To a solution of HATU (24 mg, 61 μmol), HOAt (8 mg, 63 μmol), SAPL2 (20 mg, 21.4 μmol) and d-Biotin (7.8 mg, 32 μmol), in anh. DCM (400 μL) at 0° C. under Ar, NMM was added dropwise by syringe. The resulting mixture was stirred for 2 h at 0° C. and then, at room temperature for additional 14 h. DCM (10 ml) was added and the solution was washed successively with aq. $KHSO_4$ (5 ml, 10%), aq. $NaHCO_3$ (5 ml, salt.) and brine (5 ml). The organic phase was dried ($Na_2SO_4$), filtered and concentrated under reduced pressure. The title compound (18 mg, 72%) was obtained as a white solid after purification by HPLC (Symetry Prep C18, gradient ACN/$H_2O$ 60:40-100:0 in 10 min. (flow; 3 ml/min, 150×7.8 mm, at 270 nm, $t_R$=6 min).

$^1$H NMR (300 MHz, $CDCl_3$) δ 0.78-1.00 (m, 24H), 1.20-1.98 (m, 23H), 2.00-2.62 (m, 7H), 2.53 (s, 3H), 2.80-3.00 (m, 2H), 2.86 (s, 3H), 3.16 (m, 2H), 3.35 (m, 2H), 3.57 (m, 2H), 3.70 (m, 1H), 3.79 (s, 3H), 4.01 (m, 2H), 4.10 (m, 1H), 4.31 (m, 1H), 4.46 (m, 1H), 4.56 (m, 1H), 4.82 (m, 2H), 5.00 (m, 1H), 5.14 (m, 2H), 5.67 (s, 1H), 6.23 (s, 1H), 6.84 (d, J=8.3, 2H), 7.07 (d, J=8.3, 2H), 7.28 (d, J=8.5, 1H), 7.35 (d, J=7.8, 1H), 8.01 (d, J=8.7, 1H). ESI-MS Calcd for $C_{59}H_{92}N_8O_{14}S$: 1168.65. Found: 1169.6 $(M+H)^+$.

EXAMPLE 118

Synthesis of [Phenylurea]$^8$-didemnin A (8PUSAPL1)

$^1$H NMR (300 MHz, CDCl$_3$) δ 0.85-0.94 (m, 24H), 1.11-1.43 (m, 4H), 1.22 (d, J=6.8, 3H), 1.35 (d, J=6.8, 3H), 1.49-1.83 (m, 5H), 1.73 (s, 3H), 2.02 (m, 1H), 2.14 (m, 2H), 2.34 (dt, J$_1$=3.4, J$_2$=6.8, 1H), 2.54 (s, 3H), 2.91 (s, 3H), 3.04 (d, J=16.6, 1H), 3.17 (dd, J$_1$=11.2, J$_2$=14.6, 1H), 3.36 (dd, J$_1$=3.9, J$_2$=14.2, 1H), 3.57 (dd, J$_1$=4.4, J$_2$=10.7, 1H), 3.59-3.63 (m, 1H), 3.67-3.75 (m, 1H), 3.79 (s, 3H), 3.96-4.10 (m, 2H), 4.19 (q, J=6.8, 1H), 4.58 (m, 1H), 4.74 (dd, J$_1$=39, J$_2$8.8, 1H), 4.78-4.85 (m, 1H), 5.05 (m, 2H), 5.17 (d, J=3.4,

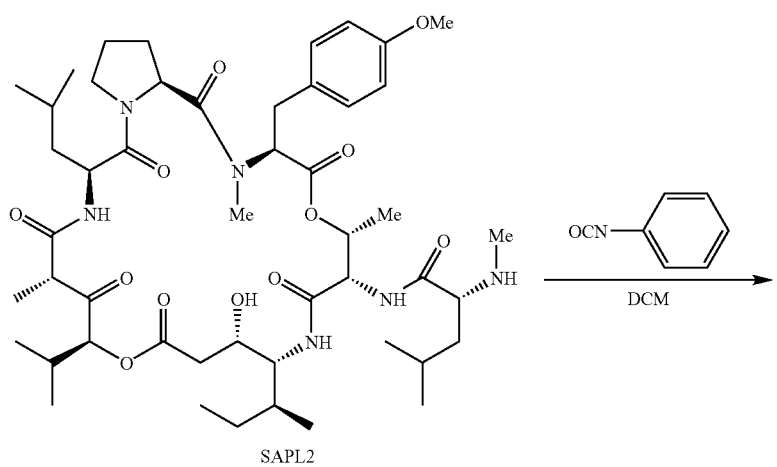

SAPL2

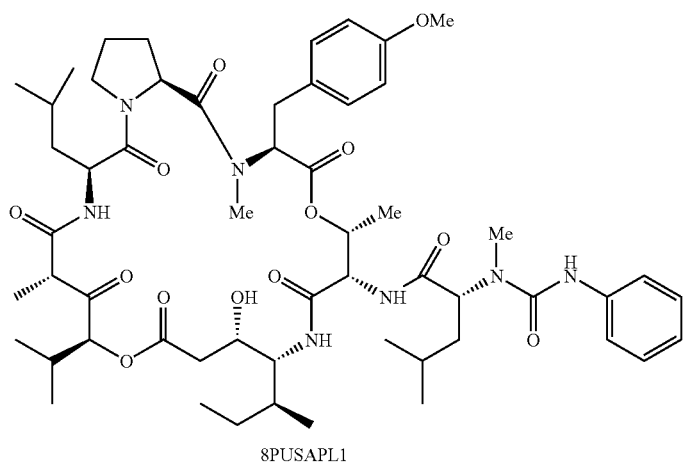

8PUSAPL1

To a solution of SAPL2 (10 mg, 10.7 μmol) in DCM (200 μl, anh) at 0° C. under Ar, phenyl isocyanate (1.3 μl, 12 μmol) was added and the reaction mixture was stirred at r.t. for 4 hours. DCM (10 ml) was added and the solution was washed successively with aq. KHSO$_4$ (5 ml, 10%), aq. NaHCO$_3$ (5 ml, sat) and brine (5 ml). The organic phase was dried (Na$_2$SO$_4$), filtered and concentrated to reduced pressure to yield pure 8PUSAPL1 (11 mg, 94%) as a white solid.

1H), 6.52 (s, 1H), 6.84 (d, J=8.3, 2H), 7.03-7.09 (m, 3H), 7.22-7.32 (m, 4H), 7.39 (d, J=8.3, 2H), 7.93 (d, J=8.8, 1H). $^{13}$C NMR (75 MHz, CDCl$_3$) δ 11.70, 15.51, 17.16, 18.74, 21.11, 22.41, 23.29, 23.98, 24.94, 25.10, 25.32, 26.97, 28.18, 30.36, 31.57, 34.44, 36.51, 38.86, 41.64, 45.23, 47.30, 49.80, 50.08, 54.60, 55.50, 56.06, 57.51, 62.77, 66.45, 68.17, 70.72, 81.93, 114.36, 120.76, 123.86, 129.12, 130.04, 130.57, 138.78, 141.00, 157.78, 158.87, 169.92, 170.68, 171.49, 172.43, 173.44, 181.47, 192.38, 204.93, 206.66. ESI-MS Calcd for $C_{56}H_{83}N_7O_{13}$; 1161.60. Found: 1062.6 (M+H)+.

EXAMPLE 119

Synthesis of [Phenylthiourea]⁸-didemnin A (8PTSAPL1)

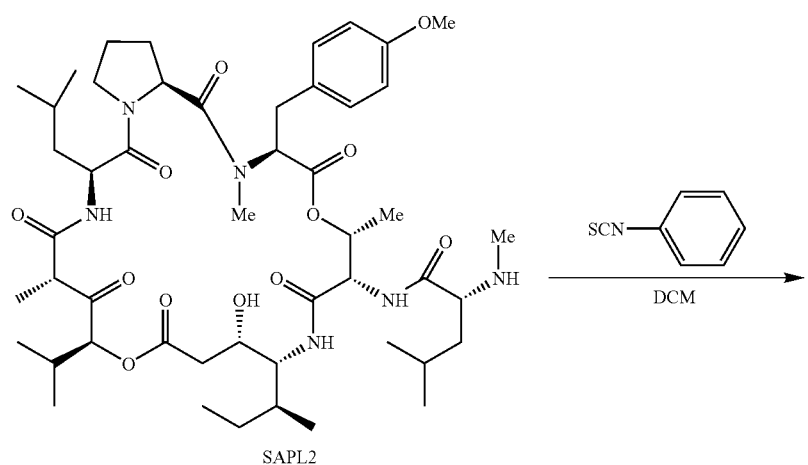

SAPL2

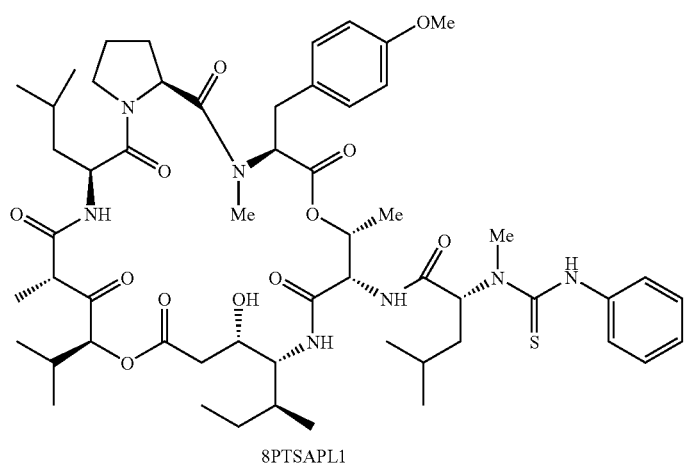

8PTSAPL1

Following the procedure for the synthesis of 8PUSAPL1, starting from SAPL2 (10 mg, 10.7 μmol) and phenyl thio-isocyanate (1.3 μl, 12 μmol), after 15 h of stirring the title compound (11 mg, 93%) was obtained as a white solid with no further purification.

$^1$H NMR (300 MHz, CDCl$_3$) δ 0.84-0.99 (m, 24H), 1.14-1.46 (m, 9H), 1.46-1.78 (m, 9H), 1.98-2.19 (m, 3H), 2.34 (m, 1H), 2.54 (s, 3H), 2.91 (m, 1H), 3.00 (s, 3H), 3.08-3.21 (m, 1H), 3.36 (dd, J$_1$=4.4, J$_2$=14.1, 1H), 3.55-3.64 (m, 2H), 3.66-3.74 (m, 1H), 3.79 (s, 3H), 3.96-4.12 (m, 2H), 4.21 (q, J=6.8, 1H), 4.59 (t, J=5.3, 1H), 4.75 (dd, J$_1$=3.4, J$_2$=8.3, 1H), 4.83 (t, J=10.3, 1H), 5.05-5.12 (m, 2H), 5.16 (d, J=3.4, 1H), 6.30 (t, J=7.3, 1H), 6.84 (d, J=8.3, 2H), 7.07 (d, J=8.3, 2H), 7.21-7.37 (m, 6H), 7.93 (d, J=8.8, 1H), 8.08 (d, J=8.8, 1H). $^{13}$C NMR (75 MHz, CDCl$_3$) δ 11.68, 15.28, 15.85, 17.15, 18.73, 21.12, 22.73, 23.66, 24.01, 25.13, 25.33, 26.62, 28.16, 29.92, 31.53, 32.42, 32.90, 34.41, 36.77, 38.86, 41.69, 47.28, 50.12, 55.50, 56.48, 57.51, 59.87, 66.47, 70.75, 81.91, 114.37, 125.25, 125.95, 126.57, 127.54, 129.12, 129.77, 130.06, 130.57, 135.43, 158.88, 168.54, 169.90, 170.70, 171.49, 172.38, 190.41. ESI-MS Calcd for $C_{56}H_{83}N_7O_{12}S$: 1077.58. Found: 1078.5 (M+H)+.

EXAMPLE 120

Synthesis of [Butylurea]⁸-didemnin A (8BUSAPL1)

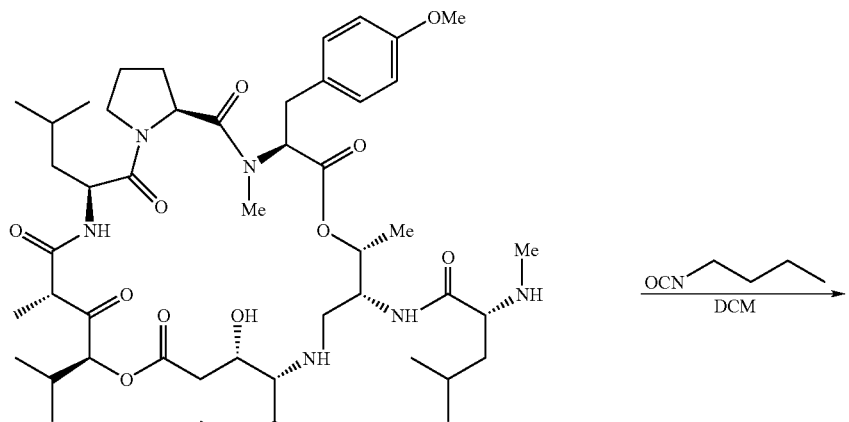

SAPL2

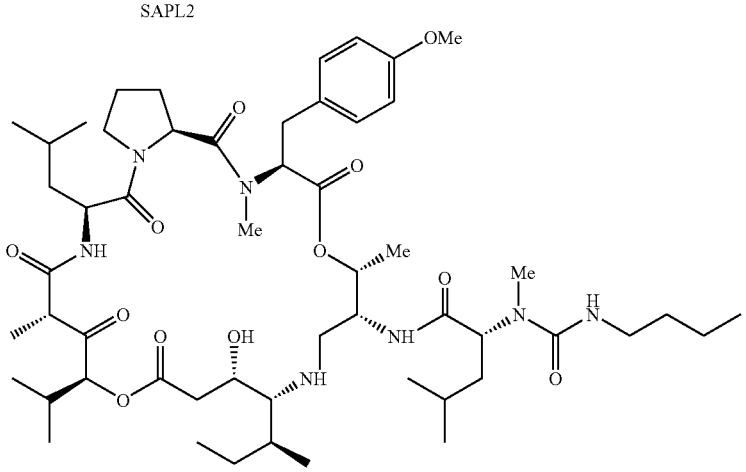

8BUSAPL1

Following the procedure for the synthesis of 8PUSAPL1, starting from SAPL2 (10 mg, 10.7 μmol) and butyl thioisocyanate (1.4 μl, 12 μmol), after 4 h of stirring the title compound (9 mg, 78%) was obtained as a white solid with no further purification.

$^1$H NMR (300 MHz, CDCl$_3$) δ 0.85-0.94 (m, 24H), 1.10-1.80 (m, 24H), 2.03 (m, 1H), 2.13 (m, 2H), 2.33 (m, 1H), 2.55 (s, 3H), 2.72 (s, 3H), 3.02 (d, J=16.1, 1H), 3.17 (dd, J$_1$=11.2, J$_2$=14.2, 1H), 3.23-3.40 (m, 3H), 3.62-3.78 (m, 3H), 3.79 (s, 3H), 4.03 (m, 2H), 4.19 (q, J=6.8, 1H), 4.58 (m, 2H), 4.71 (dd, J$_1$=3.4, J$_2$=8.3, 1H), 4.82 (m, 1H), 5.00 (m, 2H), 5.16 (d, J=3.4, 1H), 5.22-5.28 (m, 2H), 6.85 (d, J=8.8, 2H), 7.08 (d, J=8.3, 2H), 7.21-7.29 (m, 1H), 7.96 (d, J=9.2, 1H). ESI-MS Calcd for C$_{54}$H$_{87}$N$_7$O$_{13}$: 1041.64. Found. 1042.7 (M+H)$^+$.

EXAMPLE 121

Synthesis of [Butylthiourea]$^8$-didemnin A (8BTSAPL1)

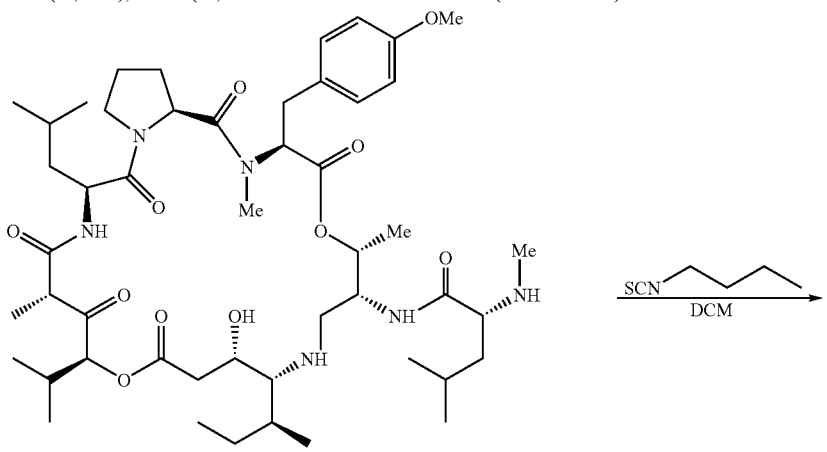

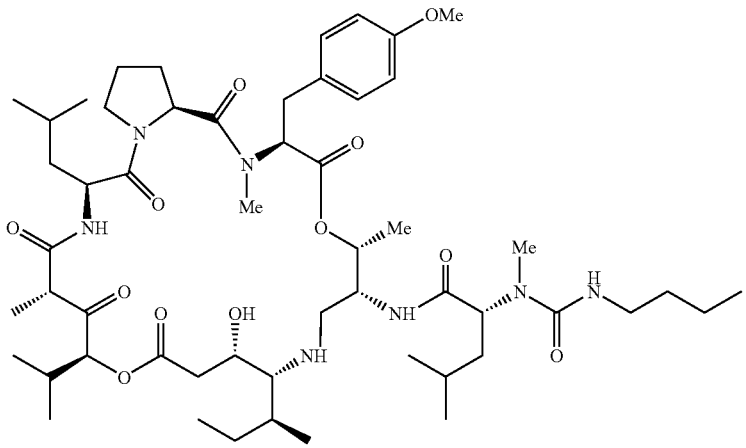

8BTSAPL1

Following the procedure for the synthesis of 8PUSAPL1, starting from SAPL2 (10 m g, 10.7 μmol) and butyl thioisocyanate (1.5 μl, 12 μmol), after 15 h of reaction the title compound (10 mg, 86%) was obtained as a white solid with no further purification.

$^1$H NMR (300 MHz, CDCl$_3$) δ 0.86-0.97 (m, 24H), 1.14-1.78 (m, 27H), 1.99-2.14 (m, 3H), 2.34 (m, 1H), 2.55 (s, 3H), 2.88 (s, 3H), 3.01 (d, J=16.6, 1H), 3.16 (dd, J$_1$=11.2, J$_2$=14.6, 1H), 3.36 (dd, J$_1$=4.4, J$_2$=14.2, 1H), 3.49-3.74 (m, 3H), 3.79 (s, 3H), 4.02 (d, J=6.8, 2H), 4.21 (q, J=6.8, 1H), 4.58 (m, 1H), 4.70 (dd, J$_1$=2.9, J$_2$=8.3, 1H), 4.82 (t, J=10.3, 1H), 5.07-5.12 (m, 2H), 5.09 (d, J=3.9, 1H), 5.60 (m, 1H), 6.36 (dd, J$_1$=5.4, J$_2$=8.3, 1H), 6.84 (d, J=8.8, 2H), 7.08 (d, J=38.8, 2H), 7.84 (d, J=8.3, 1H), 7.91 (d, J=9.3, 1H). ESI-MS Calcd for C$_{54}$H$_{87}$N$_7$O$_{12}$S: 1057.61. Found: 1080.7 (M+Na)$^+$.

The invention claimed is:

1. A compound of the formula:

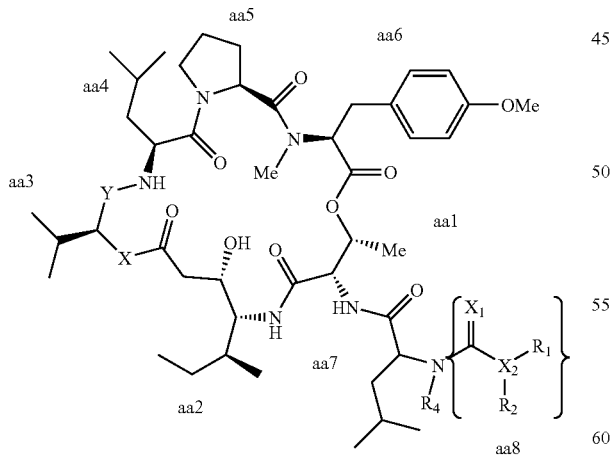

wherein:

X is independently —C(R)$_2$—, —O—, —S—, or —NR—, in which R is independently H or an organic group selected from an alkyl group, an alkenyl group, an aryl group, an aralkyl group, and their substituted derivatives substituted with one or more of a heterocyclic group, an alkoxy group, an hydroxy group, a mercapto group, an optionally protected amino group, a guanidino group, or a halogen group;

Y is CO or —COCHCH$_3$CO—;

R$_4$ is H or an organic group selected from a group RSO$_2$—, an amido group RCONH— or an acyl group RCO— where R is as defined, an alkyl group, an alkenyl group, an aryl group, an aralkyl group, and substituted derivatives substituted with one or more of a heterocyclic group, an alkoxy group, an hydroxy group, a mercapto group, an optionally protected amino group, a guanidino group, or a halogen group;

X$_1$ is O or S;

when Y is CO, then a) X$_2$ is CR, O (and R$_2$ is absent), S (and R$_2$ is absent), or N, in which R is independently H or an organic group selected from an alkyl group, an alkenyl group, an aryl group, an aralkyl group, and their substituted derivatives substituted with one or more of a heterocyclic group, an alkoxy group, an hydroxy group, a mercapto group, an optionally protected amino group, a guanidino group, or a halogen group; and R$_1$ and R$_2$ are each independently H or an organic group selected from an alkyl group, an alkenyl group, an aryl group, an aralkyl group, an amido group RCONH— or an acyl group RCO— where R is an alkyl group, an alkenyl group, an aryl group, an aralkyl group, and substituted derivatives substituted with one or more of an alkoxy group, an hydroxy group, a mercapto group, an optionally protected amino group, a guanidino group, or a halogen group, and R$_1$ or R$_2$ when X$_2$ is N can further be —SO$_2$R, where R is as defined; or b) R$_1$ and R$_2$ with X$_2$ form an optionally substituted cycloalkyl; an optionally substituted aryl; or an optionally substituted heterocyclic group selected from the group consisting of coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazol, tetrahydrofuranyl, tetrahydropyranyl, piperidinyl, and morpholino; where the optional substituents are selected from alkyl group, alkenyl group, aryl group, aralkyl group, and substituted derivatives substituted with one or more of a carbonyl group, an hydroxy group, a mercapto group, an optionally protected amino group, a guanidino group, or a halogen group; or c) aa8 is replaced by an organic group selected from an aryl group, an aralkyl group, a group $RSO_2$— or an acyl group RCO— where R is an alkyl group, an aryl group, an aralkyl group, and substituted derivatives substituted with one or more of a carbonyl group, an alkoxy group, an hydroxy group, a mercapto group, an amino group, a guanidino group, or a halogen group;

when Y is —$COCHCH_3CO$—, then a) $X_2$ is N, and $R_1$ and $R_2$ are each independently H or an organic group selected from an alkyl group, an alkenyl group, an aryl group, an aralkyl group, an amido group RCONH—, a group —$SO_2R$ or an acyl group RCO— where R is an alkyl group, an alkenyl group, an aryl group, an aralkyl group, and substituted derivatives substituted with one or more of a heterocyclic group, an alkoxy group, an hydroxy group, a mercapto group, an optionally protected amino group, a guanidino group or a halogen group, or b) $R_1$ and $R_2$ with $X_2$ form an optionally substituted cycloalkyl; an optionally substituted aryl; or an optionally substituted heterocyclic group selected from the group consisting of coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazol, tetrahydrofuranyl, tetrahydropyranyl, piperidinyl, and morpholino; where the optional substituents are selected from alkyl group, alkenyl group, aryl group, aralkyl group, and substituted derivatives substituted with one or more of a carbonyl group, an hydroxy group, a mercapto group, an optionally protected amino group, a guanidino group, or a halogen group; or c) aa8 is replaced by an organic group selected from an aryl group, an aralkyl group or a group $RSO_2$— where R is an alkyl group, an aryl group, an aralkyl group, and substituted derivatives substituted with one or more of an alkoxy group, an hydroxy group, a mercapto group, an amino group, a guanidino group, or a halogen group;

and pharmaceutically acceptable salts thereof.

2. A compound according to claim 1, wherein X is —NR—, in which R is as defined.

3. A compound according to claim 2, wherein X is —NH— or —NMe-.

4. A compound according to claim 3, wherein X is —NH—.

5. A compound according to claim 1, wherein X is —O—.

6. A compound according to claim 1, wherein Y is —CO—.

7. A compound according to claim 1, wherein X is —NH— or —O— and Y is —$COCHCH_3CO$— or —CO—.

8. A compound according to claim 1, wherein $R_4$ is methyl.

9. A compound according to claim 1, wherein $X_1$ is O.

10. A compound according to claim 1, wherein $X_2R_1$ is an optionally substituted aralkyloxy group.

11. A compound according to claim 10, wherein $X_2R_1$ is a benzyloxy group.

12. A compound according to claim 7, wherein $X_2R_1R_2$ is an optionally substituted amino group.

13. A compound according to claim 12, wherein $X_2R_1R_2$ is a group —$NHR_1$, where $R_1$ is an optionally substituted alkyl group, alkenyl group, aryl group, or aralkyl group.

14. A compound according to claim 13, wherein $R_1$ is an alkyl group or an aryl group.

15. A compound according to claim 14, wherein $R_1$ is a phenyl group or a butyl group.

16. A compound according to claim 1, wherein $X_2R_1$ is an optionally substituted alkyl group.

17. A compound according to claim 16, where $X_2R_1$ is a propyl group, isopropyl group, pentyl group or biotin group.

18. A compound according to claim 1, wherein —$C(=O)X_2R_1R_2$ forms an optionally substituted amino acid acyl group.

19. A compound according to claim 1, wherein $X_1$ is S and $X_2R_1R_2$ is a group —$NHR_1$, where $R_1$ is an optionally substituted alkyl group, alkenyl group, aryl group, or aralkyl group.

20. A compound according to claim 19, wherein $R_1$ is an alkyl group or an aryl group.

21. A compound according to claim 20, wherein $R_1$ is a phenyl group or a butyl group.

22. A compound according to claim 1, wherein $R_1$ and $R_2$ with $X_2$ form an optionally substituted heterocyclic group selected from the group consisting of coumarinyl, quinolinyl, pyridyl, pyrazinyl, pyrimidyl, furyl, pyrrolyl, thienyl, thiazolyl, oxazolyl, imidazolyl, indolyl, beazofuranyl, benzothiazol, tetrahydrofuranyl, tetrahydropyranyl, piperidinyl, and morpholino.

23. A compound according to claim 22, wherein the heterocyclic group is coumarinyl.

24. A compound according to claim 1, wherein aa8 is replaced by an organic group $RSO_2$—, where R is as defined.

25. A compound according to claim 24, wherein R is methyl.

26. A compound according to claim 1, which is selected from:

8-[Phenylurea]-didemnin A,
8-[Butylurea]-didemnin A,
3-[hiv]-8-[isobutyryl]-didemnin A,
8-[Phenylthiourea]-didemnin A,
8-[Coumarin]-didemnin A,
8-[Butylthiourea]-didemnin A,
8-[Methylsulphonyl]-didemnin A,
3-[val]-Z-didemnin A,
3-[Hiv]-8-[Val]-didemnin A,
3-[Hiv]-Z-didemnin A,
3[Hiv]-8-[hexanoyl]-didemnin A,
3-[val]-8-[isobutyryl]-didemnin A,
3-[Hiv]-8-[butyryl]-didemnin A,
3-[Hiv]-8-[Boc-Val]-didemnin A, or
3[Hiv]-8-[Val]-9-[Isobutyryl]-didemnin A, or a pharmaceutically acceptable salt thereof.

27. A compound according to claim 1, in the form a pharmaceutically acceptable salt.

28. A method of making a didemnin analog comprising the coupling of the didemnin analog having the structure

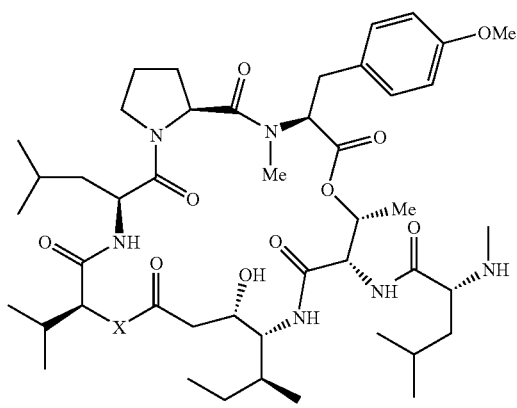

and the fragment having the structure

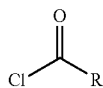

to yield the didemnin analog having the structure

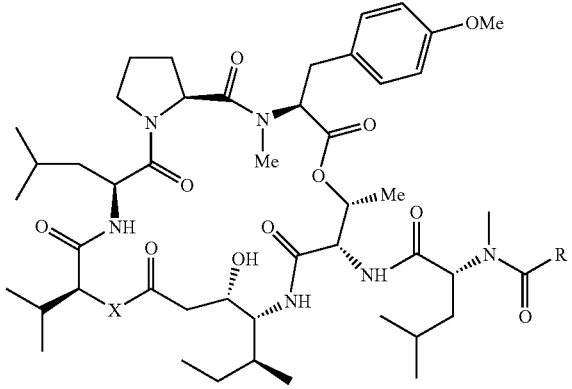

wherein X is —NH—, and R is i-Propyl; or
X is —O—, and R is i-Propyl, n-Propyl, or n-Pentyl.

29. A method of making a didemnin analog comprising the coupling of a didemnin analog having the structure:

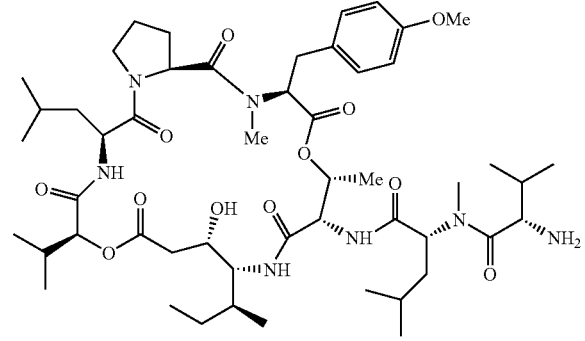

and isobutyryl chloride to yield the didemnin analog having the structure

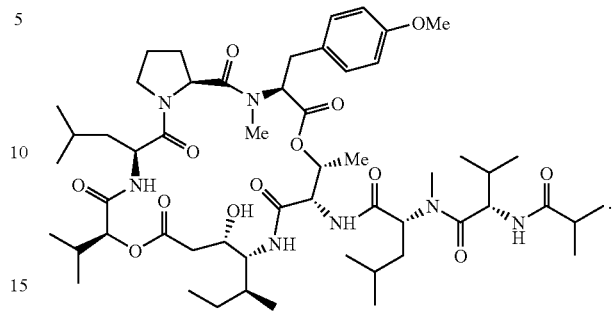

30. A method of making a didemnin analog comprising the coupling of the didemnin analog having the structure

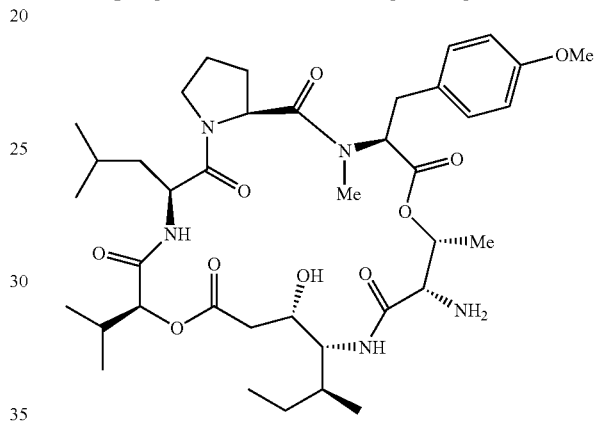

and the fragment having the structure

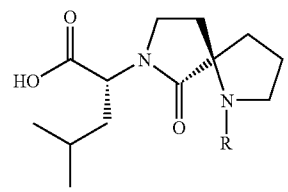

to yield the didemnin analog having the structure

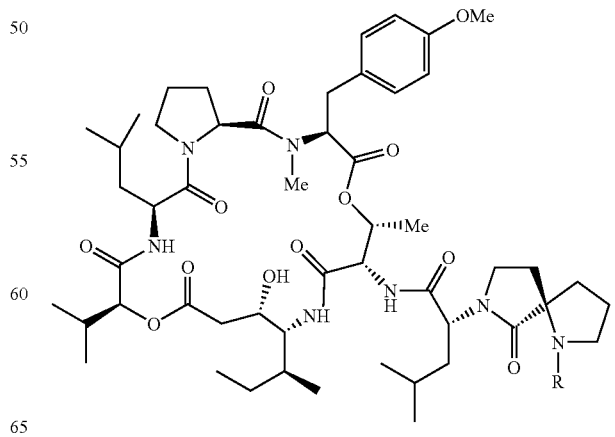

wherein R is Boc, isobutyryl, pyruvyl, or acriloyl.

31. A method of making a didemnin analog comprising the coupling of the didemnin analog having the structure

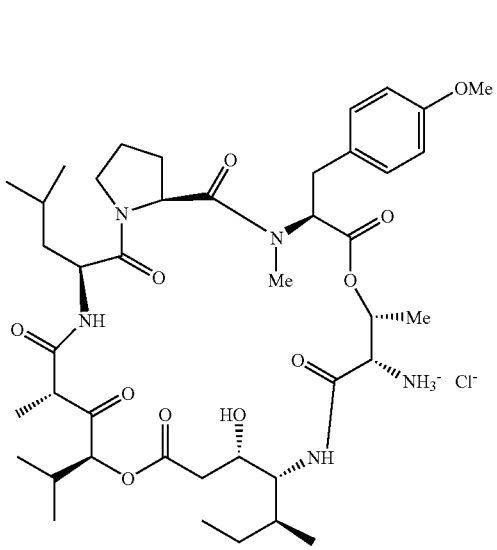

and the fragment having the structure

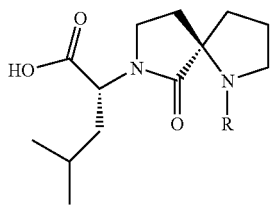

to yield the didemnin analog having the structure

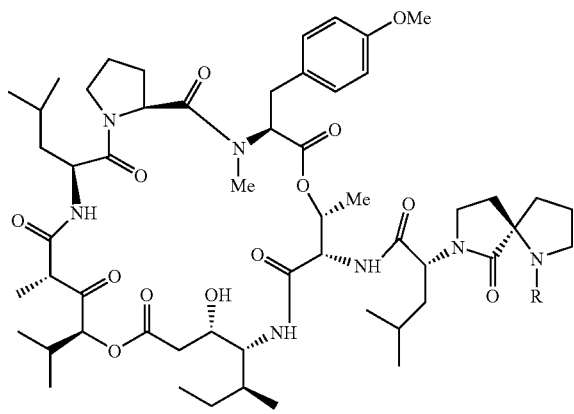

wherein R is Boc, isobutyryl, or pyruvyl.

32. A method of making a didemnin analog comprising the coupling of the didemnin analog having the structure

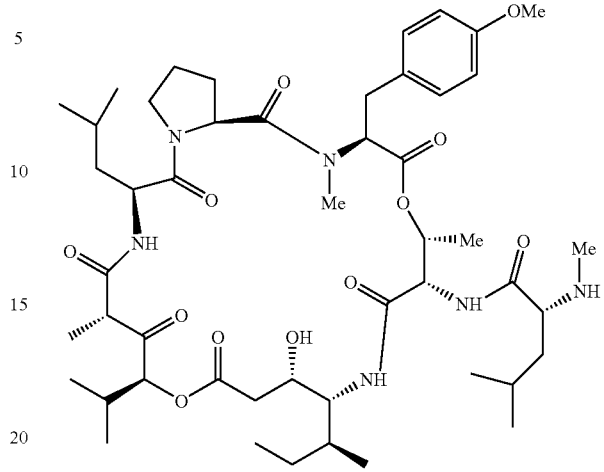

and the fragment having the structure

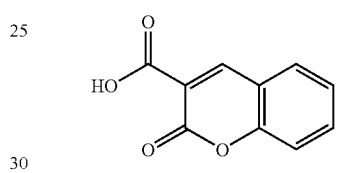

to yield the didemnin analog having the structure

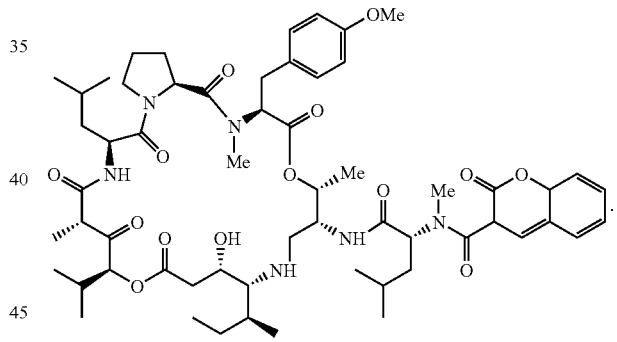

33. A method of making a didemnin analog comprising the coupling of the didemnin analog having the structure

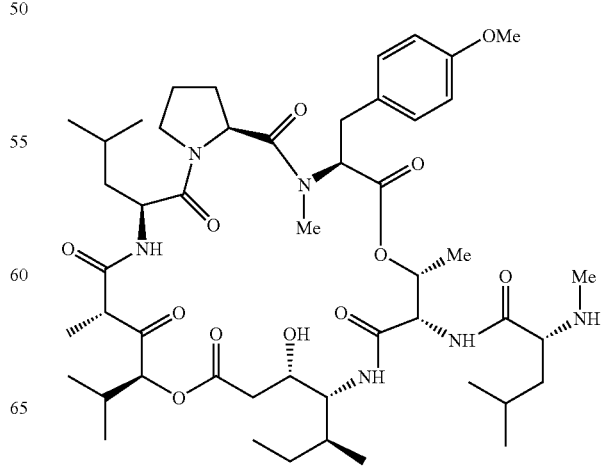

and methylsulphonyl chloride, to yield the didemnin analog having the structure

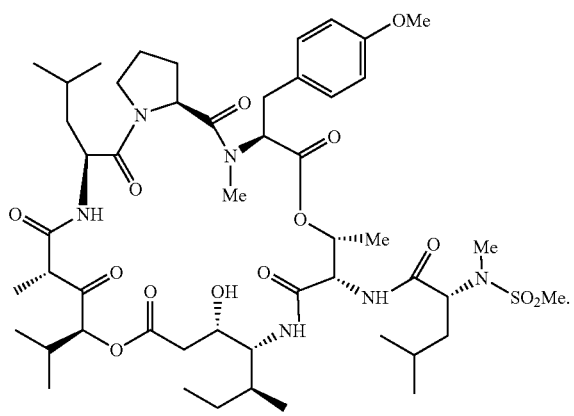

34. A method of making a didemnin analog comprising the coupling of the didemnin analog having the structure

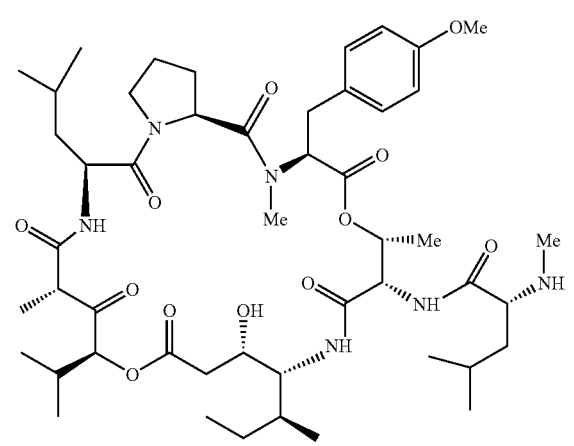

and the fragment having the structure

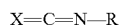

to yield the didemnin analog having the structure

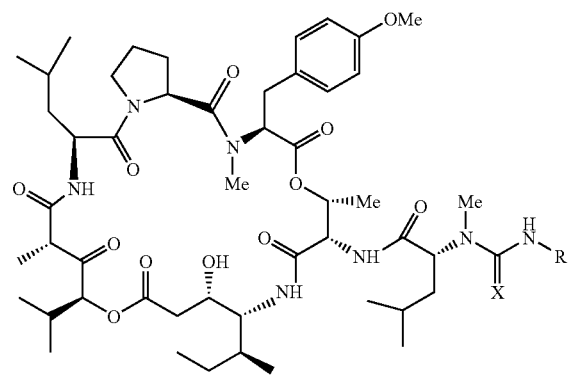

wherein X is O, and S; wherein R is butyl, and phenyl.

35. Substantially pure 3-[Hiv]-Z-didemnin A.

36. A pharmaceutical composition comprising 3-[Hiv]-Z-didemnin A and a pharmaceutically acceptable carrier.

37. The compound of claim 26, wherein the compound is 8-[Phenylurea]-didemnin A or a pharmaceutically acceptable salt thereof.

38. A compound of the formula:

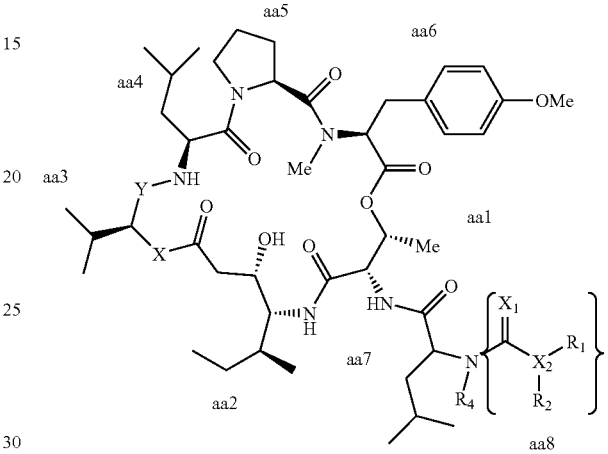

wherein:
X is independently —C(R)$_2$—, —O—, —S—, or —NR—, in which R is independently H or an organic group selected from an alkyl group, an alkenyl group, an aryl group, an aralkyl group, and their substituted derivatives substituted with one or more of a heterocyclic group, an alkoxy group, an hydroxy group, a mercapto group, an optionally protected amino group, a guanidino group, or a halogen group;

Y is CO or —COCHCH$_3$CO—;

X$_1$ is O; and

X$_1$ and the carbon bearing X$_1$, R$_1$, R$_2$, X$_2$, R$_4$ and the nitrogen bearing R$_4$ form an oxadiazaspiroalkane N-substituted with R$_5$, where R$_5$ is independently:

(i) H; or (ii) an organic group selected from a group RSO$_2$— or an acyl group RCO where R is H or an organic group selected from an alkyl group, an alkenyl group, an aryl group, an aralkyl group, and their substituted derivatives substituted with one or more of a heterocyclic group, an alkoxy group, an hydroxy group, a mercapto group, an optionally protected amino group, a guanidino group, or a halogen group; or (iii) an organic group selected from an alkyl group, an aryl group, an aralkyl group, and substituted derivatives substituted with one or more of a carbonyl group, an alkoxy group, an hydroxy group, a mercapto group, an amino group, a guanidino group, or a halogen group; and pharmaceutically acceptable salts thereof.

39. The compound of claim 38, wherein R₅ is H.

40. The compound of claim 38, wherein the N-substituted oxadiazaspiroalkane is an N-substituted 6-oxa-1,7-diazaspiro[4.4]nonane of the formula:

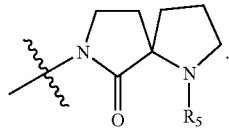

41. The compound of claim 38, wherein the compound is:
[(5R)-1-(pyruvyl)-7-[(1R)-1-carboxy-3-methylbutyl]-6-oxo-1,7-diazaspiro[4.4]nonane]$^{7-9}$-aplidine,
[(5R)-1-(tert-butoxycarbonyl)-7-[(1R)-1-carboxy-3-methylbutyl]-6-oxo-1,7-diazaspiro[4.4]nonane]$^{7-9}$-aplidine,
[Hiv]$^3$-[(5R)-1-(pyruvyl)-7-[(1R)-1-carboxy-3-methylbutyl]-6-oxo-1,7-diazaspiro[4.4]nonane]$^{7-9}$-aplidine,
[Hiv]$^3$-[(5R)-1-(isobutyryl)-7-[(1R)-1-carboxy-3-methylbutyl]-6-oxo-1,7-diazaspiro[4.4]nonane]$^{7-9}$-aplidine, or
[Hiv]$^3$-[(5R)-1-(acryloyl)-7-[(1R)-1-carboxy-3-methylbutyl]-6-oxo-1,7-diazaspiro[4.4]nonane]$^{7-9}$-aplidine.

* * * * *

UNITED STATES PATENT AND TRADEMARK OFFICE
CERTIFICATE OF CORRECTION

| | | |
|---|---|---|
| PATENT NO. | : 7,348,310 B2 | Page 1 of 2 |
| APPLICATION NO. | : 10/312341 | |
| DATED | : March 25, 2008 | |
| INVENTOR(S) | : Ignacio Rodriguez et al. | |

It is certified that error appears in the above-identified patent and that said Letters Patent is hereby corrected as shown below:

In Claim 22, Col. 236, line 30, delete "beazofuranyl," and insert -- benzofuranyl, --;

In Claim 26, Col. 236, line 46, delete "[hiv]" and insert -- [Hiv] --;

In Claim 26, Col. 236, line 61, delete "3[Hiv]" and insert -- 3-[Hiv] --;

In Claim 27, Col. 236, line 64, after "form" insert -- of --;

In Claim 30, Col. 238, line 67, delete "acriloyl." and insert -- acryloyl. --;

UNITED STATES PATENT AND TRADEMARK OFFICE
CERTIFICATE OF CORRECTION

PATENT NO.      : 7,348,310 B2
APPLICATION NO. : 10/312341
DATED           : March 25, 2008
INVENTOR(S)     : Ignacio Rodriguez et al.

Page 2 of 2

It is certified that error appears in the above-identified patent and that said Letters Patent is hereby corrected as shown below:

In Claim 31, Col. 239, lines 5-25, delete "

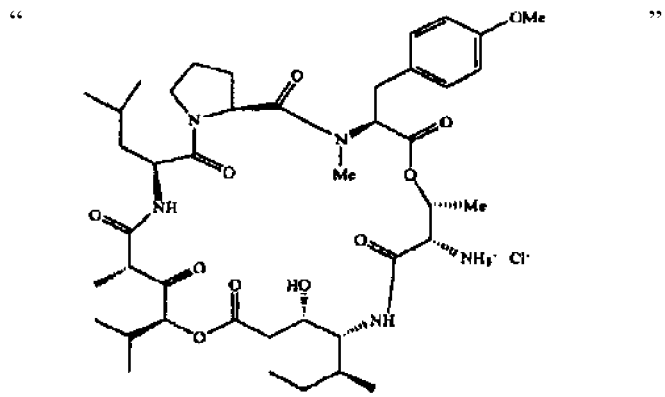

"

and insert --

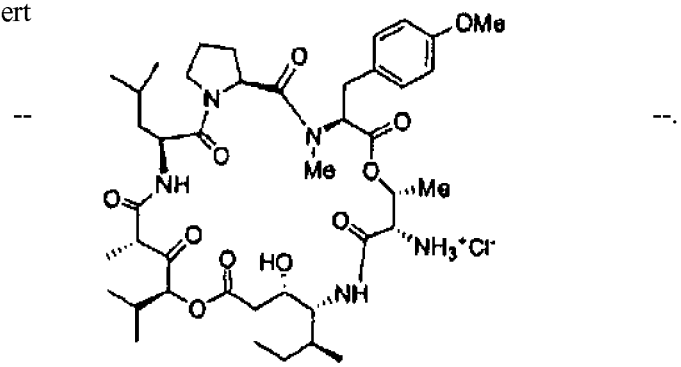

--.

Signed and Sealed this

Twenty-third Day of September, 2008

JON W. DUDAS
*Director of the United States Patent and Trademark Office*